US010023579B2

(12) United States Patent
Augelli-Szafran et al.

(10) Patent No.: US 10,023,579 B2
(45) Date of Patent: Jul. 17, 2018

(54) PYRROLOPYRIMIDINE COMPOUNDS, USE AS INHIBITORS OF THE KINASE LRRK2, AND METHODS FOR PREPARATION THEREOF

(71) Applicant: Southern Research Institute, Birmingham, AL (US)

(72) Inventors: Corinne E. Augelli-Szafran, Homewood, AL (US); Mark Suto, Birmingham, AL (US); Robert Galemmo, San Francisco, CA (US); Omar Moukha-Chafiq, Birmingham, AL (US); Vandana Gupta, Birmingham, AL (US); Subramaniam Ananthan, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 15/382,213

(22) Filed: Dec. 16, 2016

(65) Prior Publication Data

US 2017/0174694 A1    Jun. 22, 2017

Related U.S. Application Data

(60) Provisional application No. 62/268,393, filed on Dec. 16, 2015.

(51) Int. Cl.
*C07D 487/14*    (2006.01)

(52) U.S. Cl.
CPC .................. *C07D 487/14* (2013.01)

(58) Field of Classification Search
None
See application file for complete search history.

(56) References Cited

U.S. PATENT DOCUMENTS

| 5,089,500 A | 2/1992 | Daluge |
| 9,212,173 B2 | 12/2015 | Baker-Glenn et al. |
| 2011/0237607 A1 | 9/2011 | Eriksen et al. |

FOREIGN PATENT DOCUMENTS

| WO | WO-2000/041531 A2 | 7/2000 |
| WO | WO-2009/032694 A1 | 3/2009 |
| WO | WO-2009/127642 A2 | 10/2009 |
| WO | WO-2010/090764 A1 | 8/2010 |
| WO | WO-2011/141756 A1 | 11/2011 |
| WO | WO-2014/078578 A1 | 5/2014 |
| WO | WO-2014/135473 A1 | 9/2014 |
| WO | WO-2014/170248 A1 | 10/2014 |
| WO | WO-2015/113451 A1 | 8/2015 |
| WO | WO-2015/113452 A1 | 8/2015 |
| WO | WO-2017/087905 A1 | 5/2017 |

OTHER PUBLICATIONS

Alexander et al., (Acyloxy)alkyl Carbamates as Novel Bioreversible Prodrugs for Amines: Increased Permeation Through Biological Membranes. J Med Chem. 1988; 31(2): 318-22.
Bosgraaf et al., Roc, a Ras/GTPase Domain in Complex Proteins. Biochim Biophys Acta. 2003; 1643(1-3): 5-10.
Cardoso et al., Leprosy Susceptibility: Genetic Variations Regulate Innate and Adaptive Immunity, and Disease Outcome. Future Microbiol. 2011; 6(5): 533-49.
Chan et al., Discovery of a Highly Selective, Brain-Penetrant Aminopyrazole LRRK2 Inhibitor. ACS Med Chem Lett. 2013; 4(1): 85-90.
Farrer et al., LRRK2 Mutations in Parkinson Disease. Neurology. 2005; 65(5): 738-40.
Greggio et al., Kinase Activity is Required for the Toxic Effects of Mutant LRRK2/dardarin. Neurobiol Dis. 2006; 23(2): 329-41.
Hatcher et al., Discovery of a Pyrrolopyrimidine (JH-II-127), a Highly Potent, Selective, and Brain Penetrant LRRK2 Inhibitor. ACS Med Chem Lett. 2015; 6(5):584-9.
Looyeng et al., Chromosomal Amplification of Leucine-Rich Repeat Kinase-2 (LRRK2) is Required for Oncogenic MET Signaling in Papillary Renal and Thyroid Carcinomas. Proc Natl Acad Sci USA. 2011; 108(4): 1439-44.
Manning et al., The Protein Kinase Complement of the Human Genome. Science. 2002; 298(5600):1912-34.
Marin, The Parkinson Disease Gene LRRK2: Evolutionary and Structural Insights. Mol Biol Evol. 2006; 23(12):2423-33.
Mata et al., LRRK2 in Parkinson's Disease: Protein Domains and Functional Insights. Trends Neurosci. 2006; 29(5):286-93.
Moehle et al., LRRK2 Inhibition Attenuates Microglial Inflammatory Responses. J Neurosci. 2012; 32(5):1602-11.
Paisán-Ruiz et al., Cloning of the Gene Containing Mutations that Cause PARK 8-Linked Parkinson's Disease. Neuron. 2004; 4(4):595-600.
Taylor et al., LRRK2: a Common Pathway for Parkinsonism, Pathogenesis and Prevention? Trends Mol Med. 2006; 12(2):76-82.
West et al., Parkinson's Disease-Associated Mutations in Leucine-Rich Repeat Kinase 2 Augment Kinase Activity. Proc Natl Acad Sci USA. 2005; 102(46):16842-7.
Zabetian et al., A Clinic-Based Study of the LRRK2 Gene in Parkinson Disease Yields New Mutations. Neurology. 2005; 65(5):741-4.
International Search Report and Written Opinion dated Mar. 22, 2017 by the International Searching Authority for International Patent Application No. PCT/US2016/067359, which was filed on Dec. 12, 2016 (Inventor—Augelli-Szafran et al.) Applicant—Southern Research Institute; (17 pages).
U.S. Appl. No. 62/268,393, filed Dec. 16, 2015, Augelli-Szafran et al.
PCT/US2016/067359, Dec. 16, 2016, Augelli-Szafran et al.
U.S. Appl. No. 62/258,244, De Vicente Fidalgo.
U.S. Appl. No. 62/259,165, De Vicente Fidalgo.

*Primary Examiner* — Brian J Davis
(74) *Attorney, Agent, or Firm* — Ballard Spahr LLP

(57) ABSTRACT

The present disclosure is concerned with certain pyrrolopyrimidine compounds that are capable of inhibiting certain protein kinases, and especially the leucine-rich repeat kinase 2 (LRRK2) protein. Compounds of the present disclosure can be used to treat a number of disorders caused by or associated with abnormal LRRK2 kinase activity. Compounds of the present disclosure can be used to treat disorders including neurodegenerative diseases such as Parkinson's disease; precancerous conditions and cancer; autoimmune disorders such as Crohn's disease, rheumatoid arthritis and psoriasis; and leprosy (Hansen's disease). This abstract is intended as a scanning tool for purposes of searching in the particular art and is not intended to be limiting of the present invention.

30 Claims, No Drawings

PYRROLOPYRIMIDINE COMPOUNDS, USE AS INHIBITORS OF THE KINASE LRRK2, AND METHODS FOR PREPARATION THEREOF

CROSS-REFERENCE TO RELATED APPLICATIONS

This application claims the benefit of U.S. Provisional Application No. 62/268,393, filed on Dec. 16, 2015, which is incorporated herein by reference in its entirety.

BACKGROUND

The LRRK2 gene encodes a protein kinase and it has been disclosed that missense mutations in this gene can lead to a number of diseases such as various neurodegenerative diseases including Parkinson's disease. Additionally, LRRK2 is genetically linked to precancerous conditions and cancer; autoimmune disorders such as Crohn's disease, rheumatoid arthritis and psoriasis, and leprosy. For instance, it has been suggested that certain mutations in LRRK2 can lead to Parkinson's disease through the up-regulation of the kinase activity of the protein kinase. It is suspected that this protein kinase may be over-active in Parkinson's disease.

There has been much interest raised by the recent discovery that different autosomal dominant point mutations within the gene encoding for LRRK2 predispose humans to develop late-onset Parkinson's disease (OMIM accession number 609007), with a clinical appearance indistinguishable from idiopathic Parkinson's disease. See Paisan-Ruiz et al. (2004), "Cloning of the gene-containing mutations that cause PARK 8-linked Parkinson's disease." Neuron. 44, 595-600; Mata et al. (2006), "LRRK2 in Parkinson's disease: protein domains and functional insights." Trends Neurosci. 29, 286-293; Taylor et al. (2006), "LRRK2: a common pathway for Parkinsonism, pathogenesis and prevention?" Trends Mol. Med. 12, 76-82. The genetic analysis undertaken to date indicates that mutations in LRRK2 are relatively frequent, not only accounting for 5-10% of familial Parkinson's disease, but also being found in a significant proportion of sporadic Parkinson's disease cases. See Farrer et al. (2005), "LRRK2 mutations in Parkinson disease." Neurology 65, 738-740; and Zabetian et al. (2005), "A clinic-based study of the LRRK2 gene in Parkinson disease yields new mutations." Neurology 65, 741-744.

Little is known about how LRRK2 is regulated in cells, what its physiological substrates are, and how mutations cause or increase risk of Parkinson's disease. The domain structure of LRRK2 is depicted in WO 2011/141756 A1, the disclosure of which is incorporated herein by reference. See FIG. 1 therein, which also shows mutations which have been reported in patients with Parkinson's disease. The defining feature of the LRRK2 enzyme is a leucine rich repeat (LRR) motif (residues 1010-1291), a Ras-like small GTPase (residues 1336-1510), a region of high amino acid conservation that has been termed the C-terminal of Ras complex (COR) domain (residues 1511-1878), a protein kinase catalytic domain (residues 1879-2132) and a C-terminal WD40 motif (2231-2276). See Bosgraaf et al. (2003), "Roc, a Ras/GTPase domain in complex proteins." Biochim. Biophys. Acta. 1643, 5-10; and Marin (2006), "The Parkinson disease gene LRRK2: evolutionary and structural insights." Mol. Biol. Evol. 23, 2423-2433.

The protein kinase domain of LRRK2 belongs to the tyrosine-like serine threonine protein kinases and is most similar to the kinase RIP (Receptor Interacting Protein), which play key roles in innate immunity signaling pathways. See Manning et al. (2002), "The protein kinase complement of the human genome." Science 298, 1912-1934. Almost 40 single amino acid substitution mutations have been linked to autosomal-dominant Parkinson's disease. Mata et al., supra; Taylor et al., supra; WO 2011/141756 A1. It has also been reported that the most prevalent mutant form of LRRK2 accounting for approximately 6% of familial Parkinson's disease and 3% of sporadic Parkinson's disease cases in Europe, comprises an amino acid substitution of Gly2019 to a Ser residue. Gly2019 is located within the conserved DYG-Mg'-binding motif, in subdomain-VII of the kinase domain. Mata et al., supra. More recent reports suggest that this mutation enhances the autophosphorylation of LRRK2, as well as its ability to phosphorylate myelin basic protein 2-3-fold. West et al. (2005), "Parkinson's disease-associated mutations in leucine-rich repeat kinase 2 augment kinase activity." Proc. Natl. Acad. Sci. USA 102, 16842-16847; and Greggio et al. (2006), "Kinase activity is required for the toxic effects of mutant LRRK2ldardarin." Neurobiol. Dis. 23, 329-341. These observations suggest that over-activation of LRRK2 predisposes humans to develop some forms of Parkinson's disease.

As discussed in "Chromosomal amplification of leucine-rich repeat kinase-2 (LRRK2) is required for oncogenic MET signaling in papillary renal and thyroid carcinomas", Looyeng et al., Proceedings of the National Academy of Sciences of the United States of America (2011), 108(4), 1439-1444, S1439/1-S1439/10; language: English; database: CAPLUS, DOI:10.1073/pnas.1012500108; the receptor tyrosine kinase MET is frequently amplified in human tumors, resulting in high cell surface densities and constitutive activation even in the absence of growth factor stimulation by its endogenous ligand, hepatocyte growth factor (HGF). LRRK2 was identified and shown to be amplified and overexpressed in papillary renal and thyroid carcinomas. Down-regulation of LRRK2 in cultured tumor cells compromises MET activation and selectively reduces downstream MET signaling to mTOR and STAT3. Loss of these critical mitogenic pathways induces cell cycle arrest and cell death due to loss of ATP production, indicating that MET and LRRK2 cooperate to promote efficient tumor cell growth and survival in these cancers.

Missense mutations in LRRK2, as discussed above, cause late-onset Parkinson's disease (PD). In addition, common genetic variation in LRRK2 modifies susceptibility to Crohn's disease and leprosy. See "LRRK2 inhibition attenuates microglial inflammatory responses", Moehle et al., Journal of Neuroscience (2012), 32(5), 1602-1611. Language: English, Database: CAPLUS, DOI:10.1523/JNEUROSCI.5601-11.2012.

Included among the genes identified as being associated with leprosy susceptibility or resistance, PARK2 and LRRK2 have been discussed as participating in the regulation of host-cell apoptosis. See "Leprosy susceptibility: genetic variations regulate innate and adaptive immunity, and disease outcome," Cardoso et al., Future Microbiology (2011), 6(5), 533-549. Cardoso et al. further report that the same genes associated with leprosy are also associated with autoimmune (Crohn's disease, rheumatoid arthritis, psoriasis) or neurodegenerative diseases (Parkinson's and Alzheimer's).

Despite the discovery of the causal relationship between missense mutations within the gene encoding for LRRK2 and late-onset Parkinson's disease, the development of

3

LRRK2 selective inhibitors has remained elusive. Thus, there remains a need for small molecule inhibitors of LRRK2.

SUMMARY

In accordance with the purpose(s) of the invention, as embodied and broadly described herein, the invention, in one aspect, relates to pyrrolopyrimidine compounds that inhibit LRRK2, and therefore find utility in the treatment of a number of disorders including, but not limited to, neurodegenerative diseases such as Parkinson's disease, precancerous conditions and cancer, autoimmune disorders such as Crohn's disease, rheumatoid arthritis and psoriasis, and leprosy.

The present disclosure relates to compounds having a structure represented by a formula:

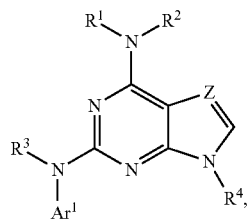

wherein Z is selected from N and $CR^{20}$, wherein each occurrence of $R^{20}$, when present, is independently selected from hydrogen, —CN, —F, —Cl, —$CF_3$, and C1-C4 alkyl; wherein $R^1$ is selected from $Cy^1$, $Ar^2$,—$CR^{21a}R^{21b}Cy^2$, and $CR^{21a}R^{21b}Ar^2$; wherein each of $R^{21a}$ and $R^{21b}$, when present, are independently selected from hydrogen and C1-C4 alkyl; wherein $Cy^1$, when present, is selected from C3-C5 cycloalkyl and 2,3-dihydroindene and substituted with 0, 1, or 2 groups independently selected from halogen, C1-C4 alkyl, C1-C4 monohaloalkyl, and C1-C4 polyhaloalkyl; wherein $Cy^2$, when present, is selected from C3-C6 cycloalkyl, C2-C5 heterocycloalkyl, and 2,3-dihydroindene and substituted with 0, 1, or 2 groups independently selected from halogen, C1-C4 alkyl, C1-C4 monohaloalkyl, and C1-C4 polyhaloalkyl; wherein $Ar^2$, when present, is selected from C5-C6 aryl and C4-C5 heteroaryl and substituted with 0, 1, or 2 groups independently selected from halogen, C1-C4 alkyl, C1-C4 monohaloalkyl, and C1-C4 polyhaloalkyl; and wherein each of $R^2$, $R^3$, and $R^4$ are independently selected from hydrogen and C1-C4 alkyl; wherein $Ar^1$ is a structure selected from:

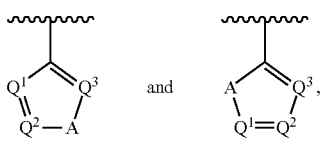

wherein A is selected from $NR^{22}$ and $CR^{23a}R^{23b}$; wherein $R^{22}$, when present, is selected from hydrogen, halogen, C1-C8 alkyl, C1-C8 monohaloalkyl, C1-C8 polyhaloalkyl, C1-C8 hydroxyalkyl, C1-C8 alkoxyalkyl, —(C1-C8 alkyl)$NH_2$, —(C1-C8 alkyl)NH(C1-C8alkyl), —(C1-C8 alkyl)N(C1-C8 alkyl)(C1-C8 alkyl), C1-C8 alkylacid, —(C1-C4 alkyl)$CONH_2$, —(C1-C4 alkyl)CONH(C1-C4 alkyl), —(C1-C4 alkyl)CON(C1-C4 alkyl)(C1-C4 alkyl), —(C1-C4 alkyl)(C=O)$Cy^3$, and $Cy^3$; wherein each occurrence of

4

$Cy^3$, when present, is independently selected from C3-C6 cycloalkyl and C2-C5 heterocycloalkyl and substituted with 0, 1, or 2 groups independently selected from halogen, C1-C4 alkyl, C1-C4 monohaloalkyl, and C1-C4 polyhaloalkyl; wherein each of $R^{23a}$ and $R^{23b}$, when present, is independently selected from hydrogen, halogen, C1-C8 alkyl, C1-C8 monohaloalkyl, C1-C8 polyhaloalkyl, C1-C8 hydroxyalkyl, C1-C8 alkoxyalkyl, C1-C8 alkylacid, —(C1-C4 alkyl)(C=O)$Cy^1$, —(C1-C4 alkyl)$CONH_2$, —(C1-C4 alkyl)CONH(C1-C4 alkyl), —(C1-C4 alkyl)CON(C1-C4 alkyl)(C1-C4 alkyl), and $Cy^3$; wherein each of $Q^1$, $Q^2$, and $Q^3$ is independently selected from N and $CR^{24}$; and wherein each occurrence of $R^{24}$, when present, is independently selected from hydrogen, halogen, C1-C8 alkyl, C1-C8 monohaloalkyl, C1-C8 polyhaloalkyl, C1-C8 alkoxyalkyl, —(C1-C4 alkyl)$CONH_2$, —(C1-C4 alkyl)CONH(C1-C4 alkyl), —(C1-C4 alkyl)CON(C1-C4 alkyl)(C1-C4 alkyl), provided that two or three of A, $Q^1$, $Q^2$, and $Q^3$ are N, and provided that if $Ar^1$ is a structure represented by a formula:

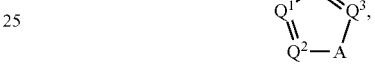

wherein each of Z, $Q^1$, and $Q^3$ are CH, $Q^2$ is N, A is $NR^{22}$, $R^{22}$ is C1-C8 alkyl, and each of $R^2$, $R^3$, and $R^4$ are hydrogen, then $R^1$ is selected from $Ar^2$,—$CR^{21a}R^{21b}Cy^2$, and —$CR^{21a}R^{21b}Ar^2$; or a pharmaceutically acceptable salt thereof.

Also disclosed are compounds having a structure represented by a formula:

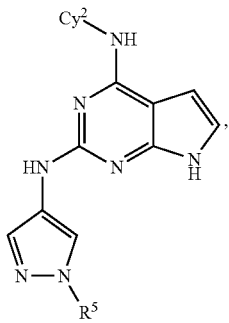

wherein $Cy^2$, when present, is selected from C3-C5 cycloalkyl and 2,3-dihydroindene and substituted with 0, 1, or 2 groups independently selected from halogen, C1-C4 alkyl, C1-C4 monohaloalkyl, and C1-C4 polyhaloalkyl; and wherein $R^5$ is C1-C8 alkyl, or a pharmaceutically acceptable salt thereof.

Also disclosed are pharmaceutical compositions comprising a therapeutically effective amount of at least one disclosed compound, or a pharmaceutically acceptable salt thereof, and a pharmaceutically acceptable carrier.

Also disclosed are methods for inhibiting LRRK2 kinase activity in a mammal, the method comprising the step of administering to the mammal a therapeutically effective amount of at least one disclosed compound, or a pharmaceutically acceptable salt thereof.

Also disclosed are methods for inhibiting LRRK2 kinase activity in at least one cell, the method comprising the step of contacting the at least one cell with an effective amount of at least one disclosed compound, or a pharmaceutically acceptable salt thereof.

Also disclosed are methods for the treatment of a disorder associated with LRRK2 kinase dysfunction in a mammal, the method comprising the step of administering to the mammal an effective amount of at least one disclosed compound, or a pharmaceutically acceptable salt thereof.

Also disclosed are methods for the treatment of a disorder associated with LRRK2 kinase dysfunction in a mammal, the method comprising the step of administering to the mammal an effective amount of at least one compound having a structure represented by a formula:

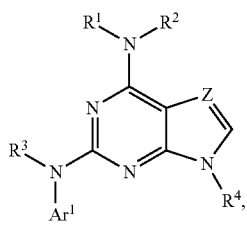

wherein Z is selected from N and $CR^{20}$, wherein each occurrence of $R^{20}$, when present, is independently selected from hydrogen, —CN, —F, —Cl, —$CF_3$, and C1-C4 alkyl; wherein $R^1$ is selected from $Cy^1$, $Ar^2$, —$CR^{21a}R^{21b}Cy^2$, and —$CR^{21a}R^{21b}Ar^2$; wherein each of $R^{21a}$ and $R^{21b}$, when present, are independently selected from hydrogen and C1-C4 alkyl; wherein $Cy^1$, when present, is selected from C3-C5 cycloalkyl and 2,3-dihydroindene and substituted with 0, 1, or 2 groups independently selected from halogen, C1-C4 alkyl, C1-C4 monohaloalkyl, and C1-C4 polyhaloalkyl; wherein $Cy^2$, when present, is selected from C3-C6 cycloalkyl, C2-C5 heterocycloalkyl, and 2,3-dihydroindene and substituted with 0, 1, or 2 groups independently selected from halogen, C1-C4 alkyl, C1-C4 monohaloalkyl, and C1-C4 polyhaloalkyl; wherein $Ar^2$, when present, is selected from C5-C6 aryl and C4-C5 heteroaryl and substituted with 0, 1, or 2 groups independently selected from halogen, C1-C4 alkyl, C1-C4 monohaloalkyl, and C1-C4 polyhaloalkyl; and wherein each of $R^2$, $R^3$, and $R^4$ are independently selected from hydrogen and C1-C4 alkyl; wherein $Ar^1$ is a structure selected from:

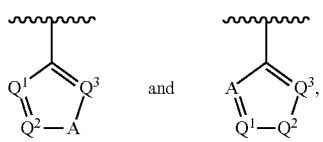

wherein A is selected from $NR^{22}$ and $CR^{23a}R^{23b}$; wherein $R^{22}$, when present, is selected from hydrogen, halogen, C1-C8 alkyl, C1-C8 monohaloalkyl, C1-C8 polyhaloalkyl, C1-C8 hydroxyalkyl, C1-C8 alkoxyalkyl, —(C1-C8 alkyl)$NH_2$, —(C1-C8 alkyl)NH(C1-C8alkyl), —(C1-C8 alkyl)N(C1-C8 alkyl)(C1-C8 alkyl), C1-C8 alkylacid, —(C1-C4 alkyl)$CONH_2$, —(C1-C4 alkyl)CONH(C1-C4 alkyl), —(C1-C4 alkyl)CON(C1-C4 alkyl)(C1-C4 alkyl), —(C1-C4 alkyl)(C=O)$Cy^3$, and $Cy^3$; wherein each occurrence of $Cy^3$, when present, is independently selected from C3-C6 cycloalkyl and C2-C5 heterocycloalkyl and substituted with 0, 1, or 2 groups independently selected from halogen, C1-C4 alkyl, C1-C4 monohaloalkyl, and C1-C4 polyhaloalkyl; wherein each of $R^{23a}$ and $R^{23b}$, when present, is independently selected from hydrogen, halogen, C1-C8 alkyl, C1-C8 monohaloalkyl, C1-C8 polyhaloalkyl, C1-C8 hydroxyalkyl, C1-C8 alkoxyalkyl, C1-C8 alkylacid, —(C1-C4 alkyl)(C=O)$Cy^1$, —(C1-C4 alkyl)$CONH_2$, —(C1-C4 alkyl)CONH(C1-C4 alkyl), —(C1-C4 alkyl)CON(C1-C4 alkyl)(C1-C4 alkyl), and $Cy^3$; wherein each of $Q^1$, $Q^2$, and $Q^3$ is independently selected from N and $CR^{24}$; and wherein each occurrence of $R^{24}$, when present, is independently selected from hydrogen, halogen, C1-C8 alkyl, C1-C8 monohaloalkyl, C1-C8 polyhaloalkyl, C1-C8 alkoxyalkyl, —(C1-C4 alkyl)$CONH_2$, —(C1-C4 alkyl)CONH(C1-C4 alkyl), —(C1-C4 alkyl)CON(C1-C4 alkyl)(C1-C4 alkyl), provided that two or three of A, $Q^1$, $Q^2$, and $Q^3$ are N, or a pharmaceutically acceptable salt thereof, wherein the disorder is selected from a neurodegenerative disorder and leprosy.

Also disclosed are pharmaceutical compositions comprising at least one of the above identified compounds or derivatives, and a pharmaceutically acceptable carrier.

Also disclosed are methods for treating a patient having a disease caused by or associated with abnormal LRRK2 kinase activity, which comprises administering to the patient an effective treatment amount of at least one of the above identified compounds or derivatives.

Also disclosed are methods for treating a patient having a neurodegenerative disease, and especially Parkinson's disease, which comprises administering to the patient an effective treatment amount of at least one of the above identified compounds or derivatives.

Also disclosed are methods for treating a patient having an autoimmune disease such as Crohn's disease, rheumatoid arthritis and psoriasis, which comprises administering to the patient an effective treatment amount of at least one of the above identified compounds or derivatives.

Also disclosed are methods for treating a patient for a precancerous condition or cancer, which comprises administering to the patient an effective treatment amount of at least one of the above identified compounds or derivatives.

Also disclosed are methods for treating a patient having leprosy, which comprises administering to the patient and effective treatment amount of at least one of the above identified compounds or derivatives.

Also disclosed are methods for enhancing the blood brain barrier transmission of the above-disclosed compounds by modifying the compounds and/or employing the compounds along with another component capable of enhancing transmission of the compound through the blood brain barrier.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders prior to the administering step. In various aspects, the one or more disorders are selected from neurodegenerative diseases such as Parkinson's disease; precancerous conditions and cancer; autoimmune disorders such as Crohn's disease, rheumatoid arthritis and psoriasis; and leprosy.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of neurodegenerative diseases such as Parkinson's disease; precancerous conditions and cancer; autoimmune disorders such as Crohn's disease, rheumatoid arthritis and psoriasis; and leprosy prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "comprising" (and its grammatical variations) as used herein is used in the inclusive sense of "having" or "including" and not in the exclusive sense of "consisting of."

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Accordingly, the deuterated forms contain heavy hydrogen including deuterium. The carbon labeled forms may contain carbon-13. Examples of radio-actively labeled forms include compounds labeled with tritium, phosphorous-32, iodine-129, carbon-11, fluorine-18, and the like.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A''$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a-$, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A', $S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; $N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$;

—(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

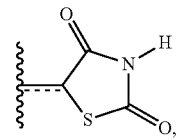

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkyl sulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}$H, $^{3}$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

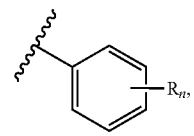

which is understood to be equivalent to a formula:

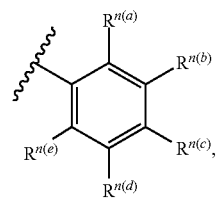

wherein n is typically an integer. That is, $R^n$ is understood to represent five independent substituents, $R^{n(a)}$, $R^{n(b)}$, $R^{n(c)}$, $R^{n(d)}$, $R^{n(e)}$. In each such case, each of the five $R^n$ can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further aspects, a structure of a compound can be represented by a formula:

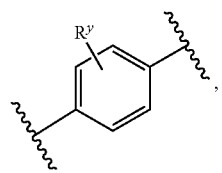

wherein $R^y$ represents, for example, 0-2 independent substituents selected from $A^1$, $A^2$, and $A^3$, which is understood to be equivalent to the groups of formulae:

wherein $R^y$ represents 0 independent substituents

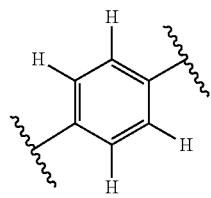

wherein $R^y$ represents 1 independent substituent

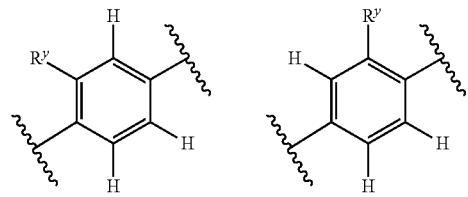

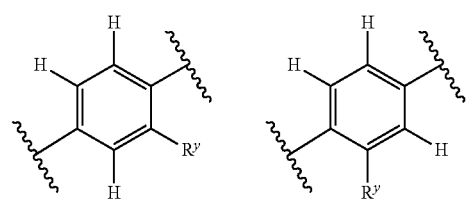

wherein $R^y$ represents 2 independent substituents

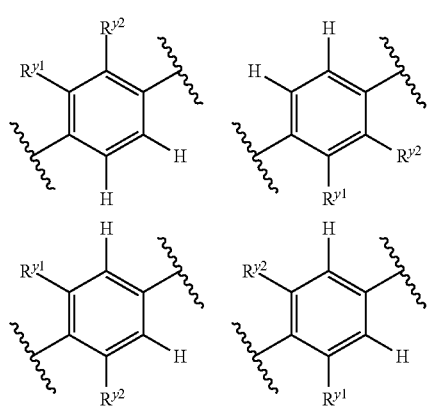

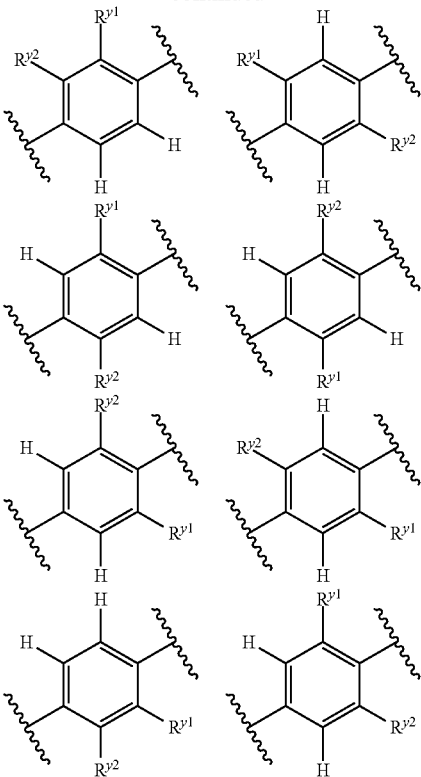

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

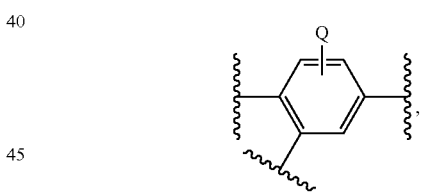

wherein, for example, Q comprises three substituents independently selected from hydrogen and A, which is understood to be equivalent to a formula:

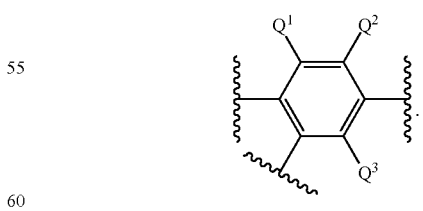

Again, by "independent substituents," it is meant that each Q substituent is independently defined as hydrogen or A, which is understood to be equivalent to the groups of formulae:

wherein Q comprises three substituents independently selected from H and A wherein Q comprises three substituents independently selected from H and A

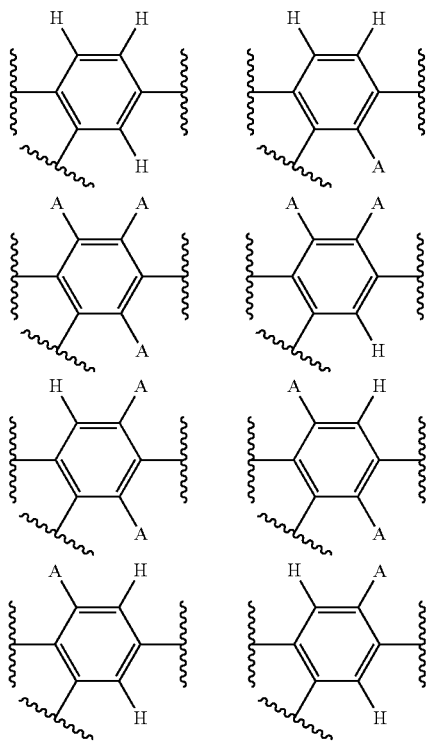

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful in treating disorders associated with LRRK2 kinase dysfunction, in particular neurological disorders, such as Parkinson's disease, cancers, such as renal cancer and thyroid cancer, autoimmune disorders, such as Crohn's disease, rheumatoid arthritis, and psoriasis, and leprosy.

In one aspect, the disclosed compounds exhibit antagonism of LRRK2.

In one aspect, the compounds of the invention are useful in inhibiting LRRK2 kinase activity in a mammal. In a further aspect, the compounds of the invention are useful in inhibiting LRRK2 kinase activity in at least one cell.

In one aspect, the compounds of the invention are useful in the treatment of disorders associated with LRRK2 dysfunction, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

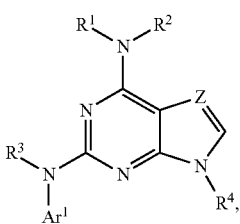

wherein Z is selected from N and CR[20]; wherein each occurrence of R[20], when present, is independently selected from hydrogen, —CN, and C1-C4 alkyl; wherein R[1] is selected from Cy[1], Ar[2], CR[21a]R[21b]Cy[2], and —CR[21a]R[21b]Ar[2]; wherein each of R[21a] and R[21b], when present, are independently selected from hydrogen and C1-C4 alkyl; wherein Cy[1], when present, is selected from C3-C5 cycloalkyl and 2,3-dihydroindene and substituted with 0, 1, or 2 groups independently selected from halogen, C1-C4 alkyl, C1-C4 monohaloalkyl, and C1-C4 polyhaloalkyl; wherein Cy[2], when present, is selected from C3-C6 cycloalkyl, C2-C5 heterocycloalkyl, and 2,3-dihydroindene and substituted with 0, 1, or 2 groups independently selected from halogen, C1-C4 alkyl, C1-C4 monohaloalkyl, and C1-C4 polyhaloalkyl; wherein Ar[2], when present, is selected from C5-C6 aryl and C4-C5 heteroaryl and substituted with 0, 1, or 2 groups independently selected from halogen, C1-C4 alkyl, C1-C4 monohaloalkyl, and C1-C4 polyhaloalkyl; and wherein each of R[2], R[3], and R[4] are independently selected from hydrogen and C1-C4 alkyl; wherein Ar[1] is a structure selected from:

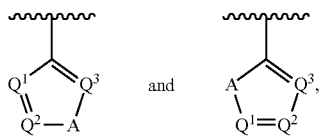

wherein A is selected from NR[22] and CR[23a]R[23b]; wherein R[22], when present, is selected from hydrogen, halogen, C1-C8 alkyl, C1-C8 monohaloalkyl, C1-C8 polyhaloalkyl, C1-C8 hydroxyalkyl, C1-C8 alkoxyalkyl, —(C1-C8 alkyl)NH$_2$, —(C1-C8 alkyl)NH(C1-C8alkyl), —(C1-C8 alkyl)N(C1-C8 alkyl)(C1-C8 alkyl), C1-C8 alkylacid, —(C1-C4 alkyl)CONH$_2$, —(C1-C4 alkyl)CONH(C1-C4 alkyl), —(C1-C4 alkyl)CON(C1-C4 alkyl)(C1-C4 alkyl), —(C1-C4 alkyl)(C=O)Cy[3], and Cy[3]; wherein each occurrence of Cy[3], when present, is independently selected from C3-C6 cycloalkyl and C2-C5 heterocycloalkyl and substituted with 0, 1, or 2 groups independently selected from halogen, C1-C4 alkyl, C1-C4 monohaloalkyl, and C1-C4 polyhaloalkyl; wherein each of R[23a] and R[23b], when present, is independently selected from hydrogen, halogen, C1-C8 alkyl, C1-C8 monohaloalkyl, C1-C8 polyhaloalkyl, C1-C8 hydroxyalkyl, C1-C8 alkoxyalkyl, C1-C8 alkylacid, —(C1-C4 alkyl)(C=O)Cy[1], —(C1-C4 alkyl)CONH$_2$, —(C1-C4 alkyl)CONH(C1-C4 alkyl), —(C1-C4 alkyl)CON(C1-C4 alkyl)(C1-C4 alkyl), and Cy[3]; wherein each of Q[1], Q[2], and Q[3] is independently selected from N and CR[24]; and wherein each occurrence of R[24], when present, is independently selected from hydrogen, halogen, C1-C8 alkyl, C1-C8 monohaloalkyl, C1-C8 polyhaloalkyl, C1-C8 alkoxyalkyl, —(C1-C4 alkyl)CONH$_2$, —(C1-C4 alkyl)CONH(C1-C4 alkyl), —(C1-C4 alkyl)CON(C1-C4 alkyl)(C1-C4 alkyl), provided that two or three of A, Q[1], Q[2], and Q[3] are N, and provided that if Ar[1] is a structure represented by a formula:

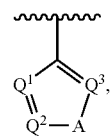

wherein each of Z, Q[1], and Q[3] are CH, Q[2] is N, A is NR[22], R[22] is C1-C8 alkyl, and each of R[2], R[3], and R[4] are hydrogen, then R[1] is selected from Ar[2], CR[21a]R[21b]Cy[2], and CR[21a]R[21b]Ar[2]; or a pharmaceutically acceptable salt thereof.

In one aspect, disclosed are compounds having a structure represented by a formula:

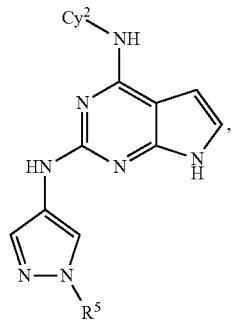

wherein Cy[2], when present, is selected from C3-C5 cycloalkyl and 2,3-dihydroindene and substituted with 0, 1, or 2 groups independently selected from halogen, C1-C4 alkyl, C1-C4 monohaloalkyl, and C1-C4 polyhaloalkyl; and wherein R[5] is C1-C8 alkyl, or a pharmaceutically acceptable salt thereof.

In a further aspect, the compound has a structure represented by a formula selected from:

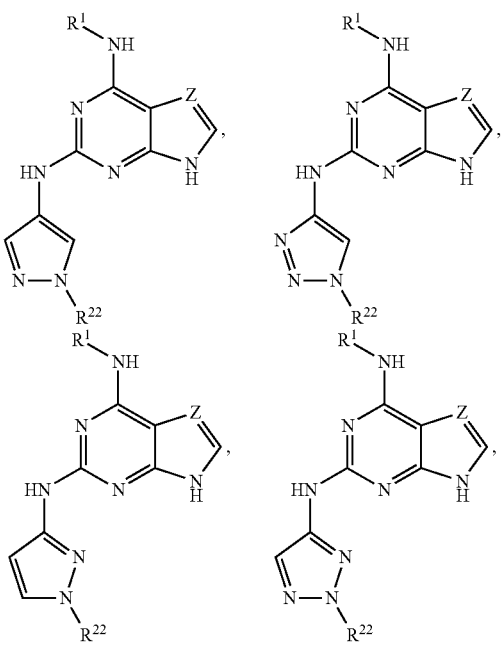

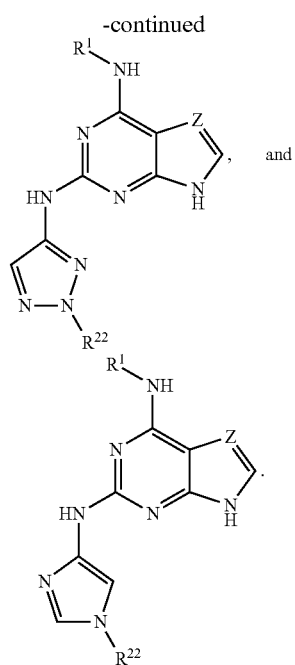
In a further aspect, the compound has a structure represented by a formula:
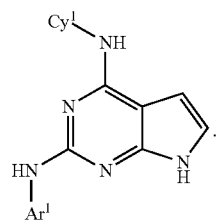
In a further aspect, the compound has a structure represented by a formula:
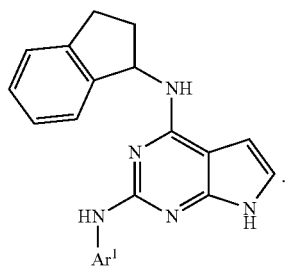
In a further aspect, the compound has a structure represented by a formula:
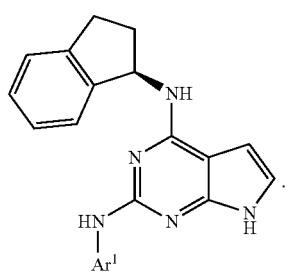
In a further aspect, the compound has a structure selected from:
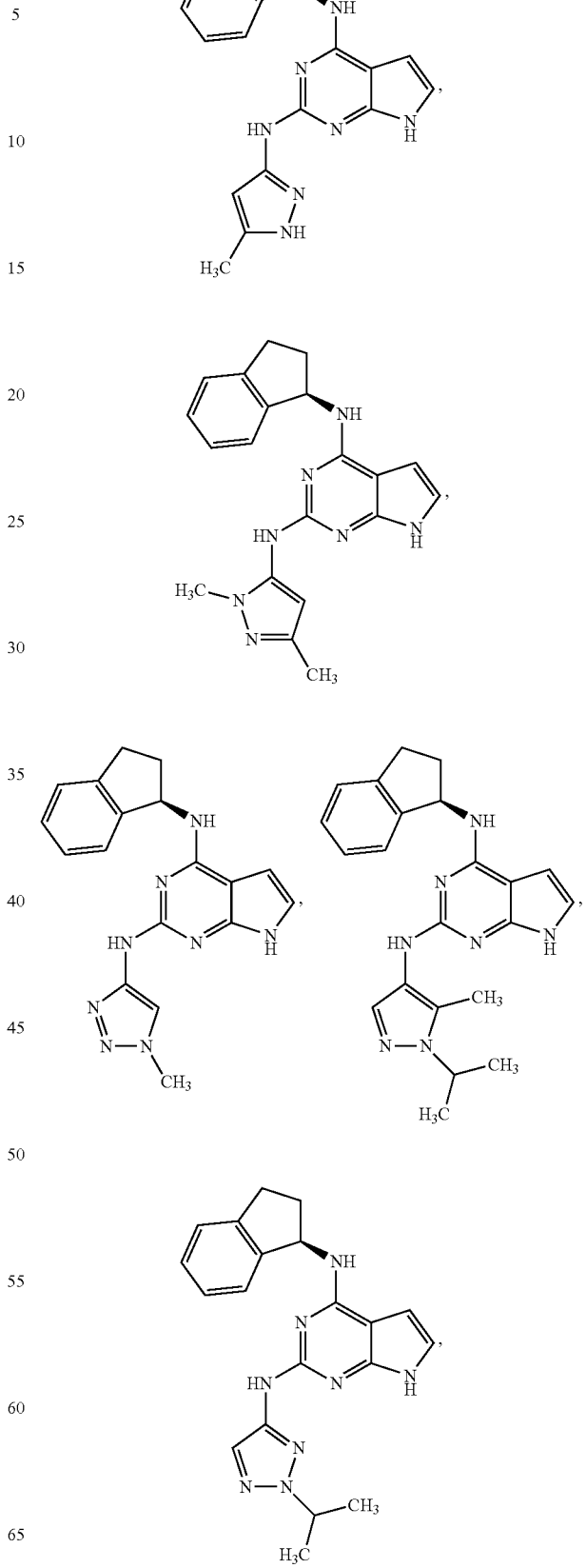

-continued
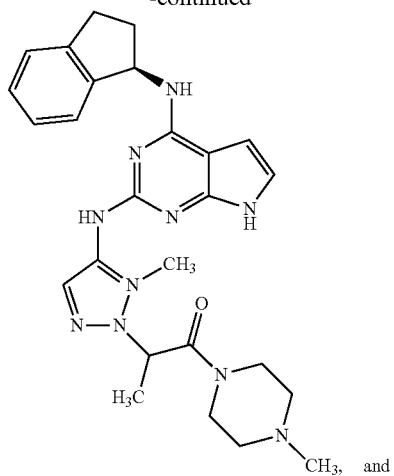
and
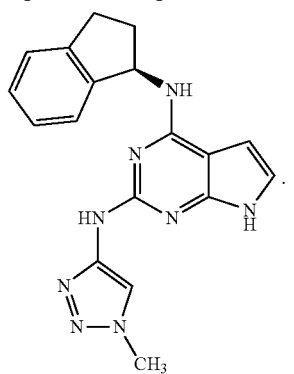
In a further aspect, the compound has a structure:
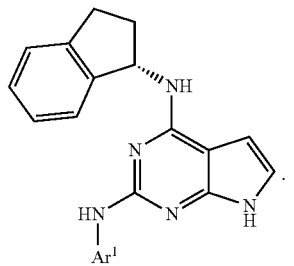
In a further aspect, the compound has a structure represented by a formula:
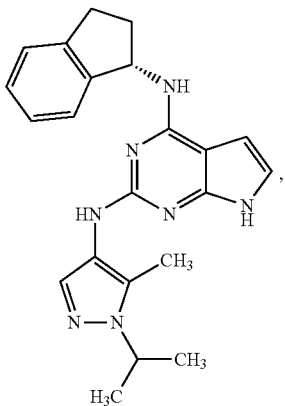
In a further aspect, the compound has a structure selected from:
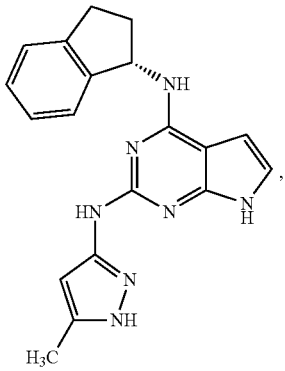
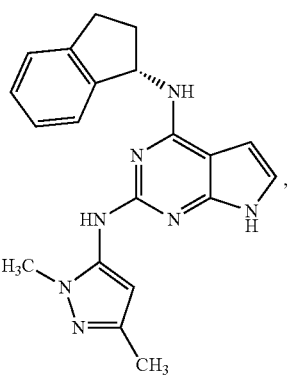
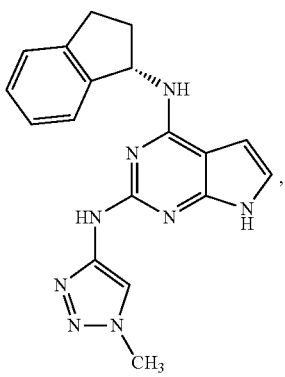 [SMILES: Cn1cc(Nc2nc(N[C@H]3CCc4ccccc43)c3cc[nH]c3n2)nn1]

-continued

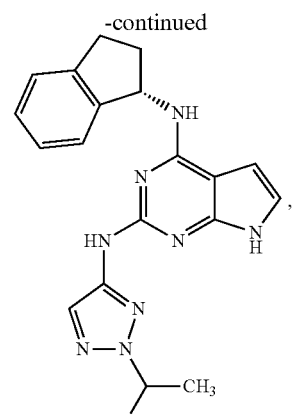

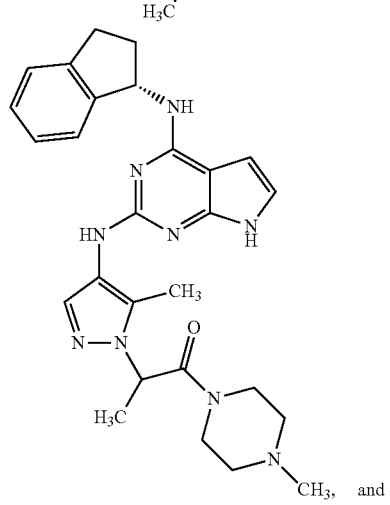

and

In a further aspect, the compound has a structure:

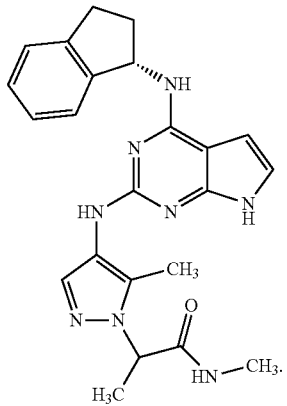

In a further aspect, the compound has a structure represented by a formula:

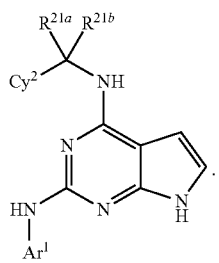

In a further aspect, the compound has a structure represented by a formula:

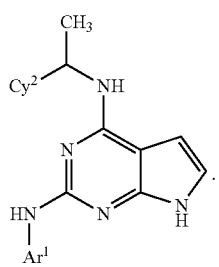

In a further aspect, the compound has a structure represented by a formula:

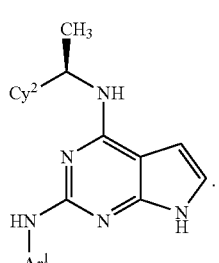

In a further aspect, the compound has a structure represented by a formula:

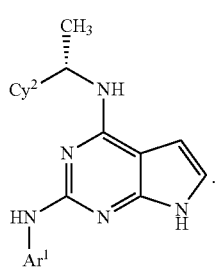

In a further aspect, the compound has a structure represented by a formula:

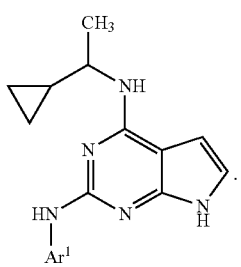
In a further aspect, the compound has a structure represented by a formula:
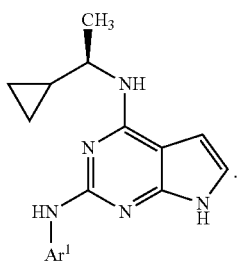
In a further aspect, the compound has a structure selected from:
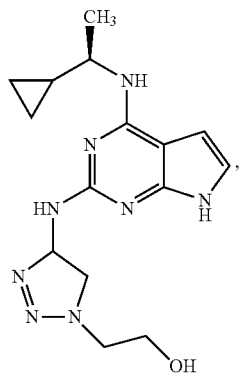
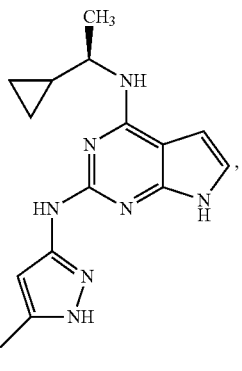
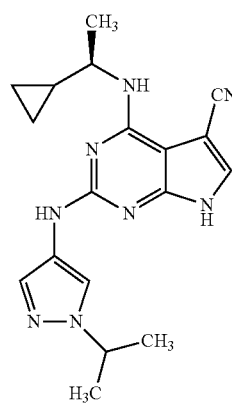
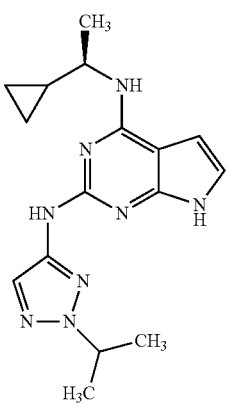
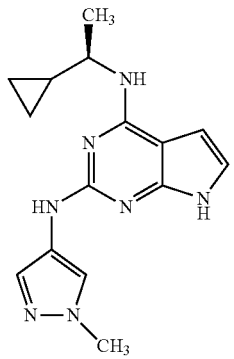
-continued
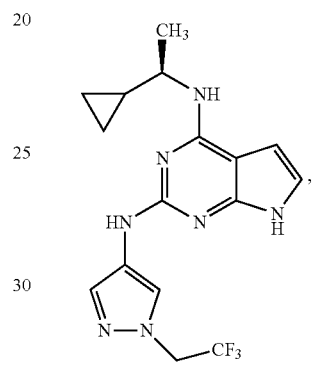
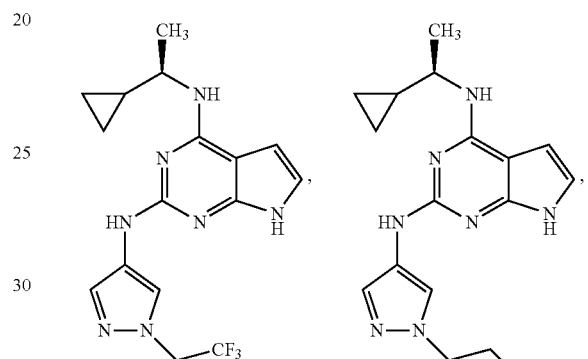
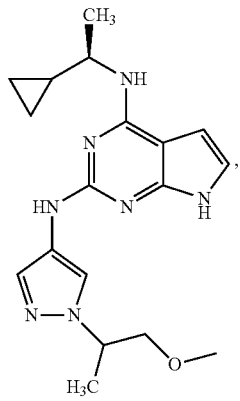
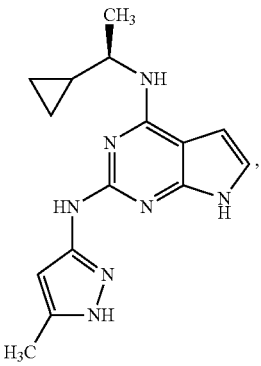
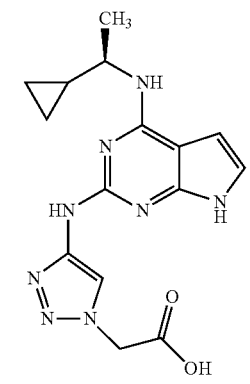
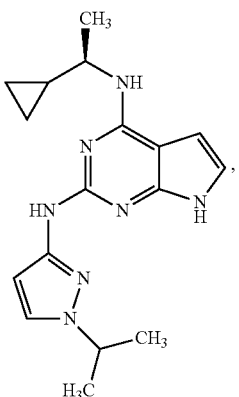

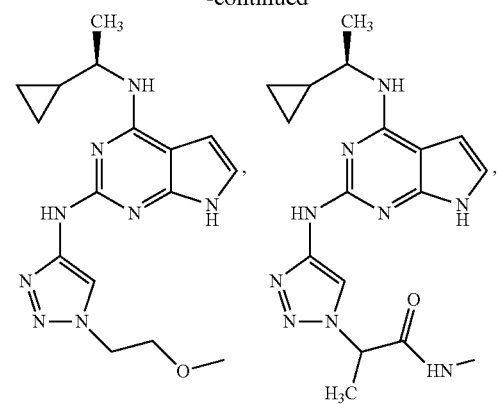
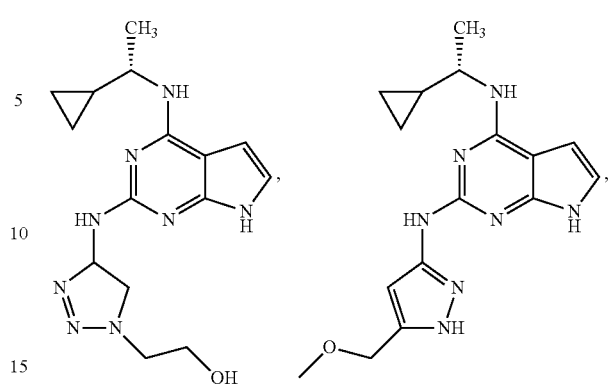
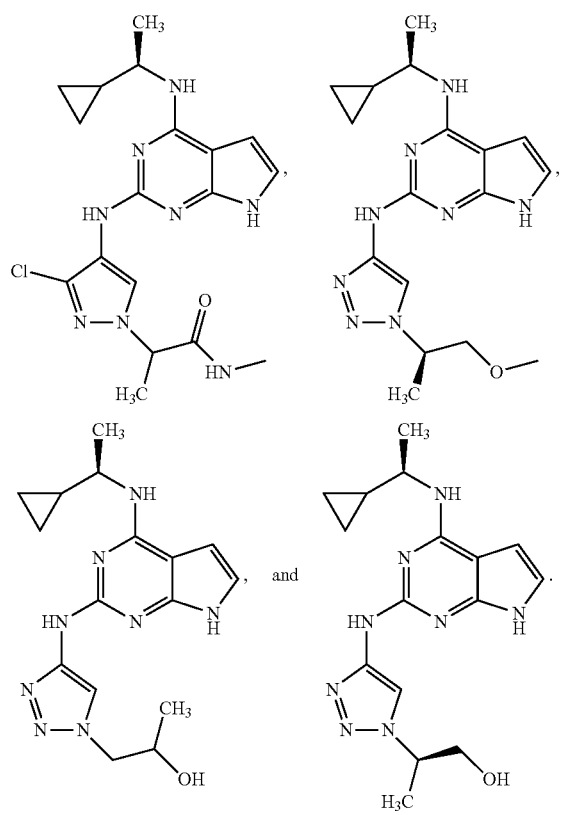
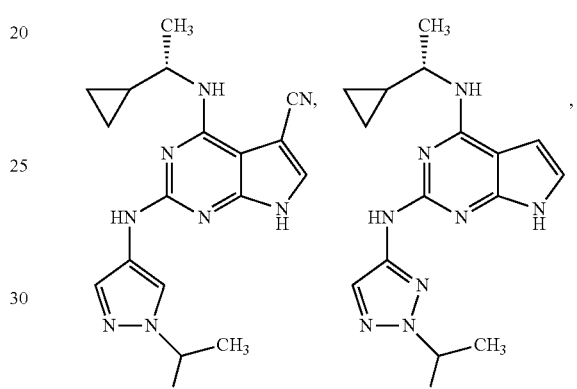
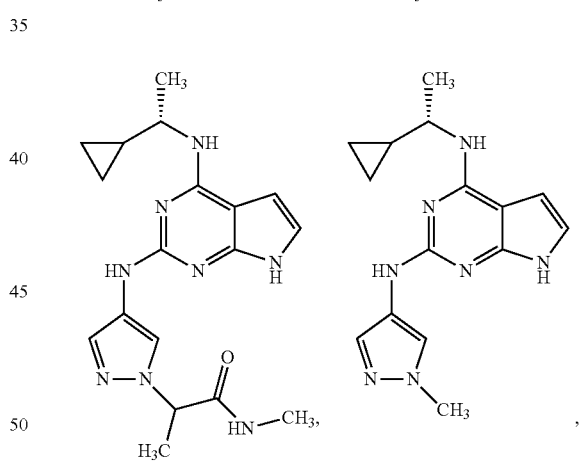
In a further aspect, the compound has a structure represented by a formula:
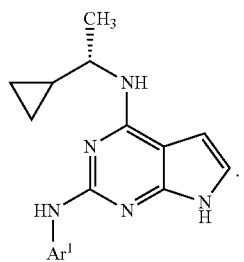
In a further aspect, the compound has a structure selected from:
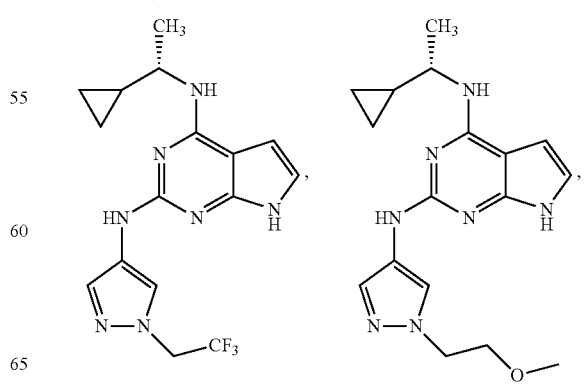

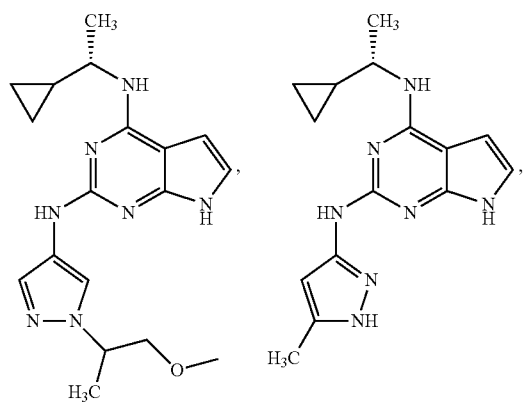
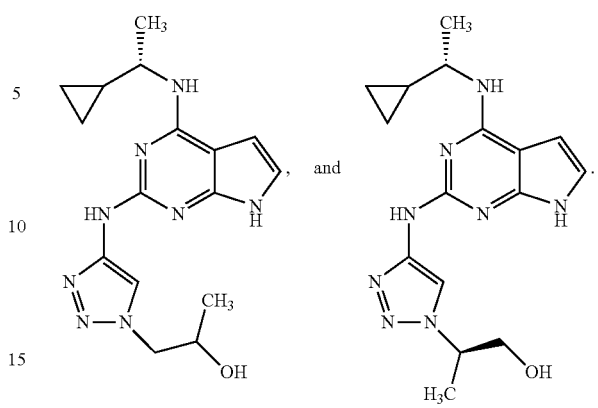
In a further aspect, the compound has a structure represented by a formula:
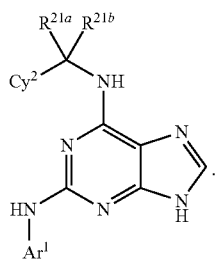
In a further aspect, the compound has a structure represented by a formula:
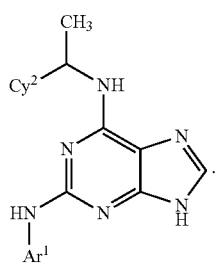
In a further aspect, the compound has a structure represented by a formula:
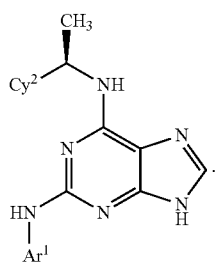
In a further aspect, the compound has a structure represented by a formula:

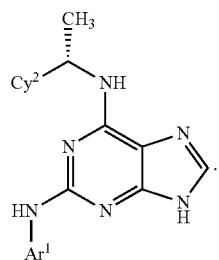

In a further aspect, the compound has a structure represented by a formula:

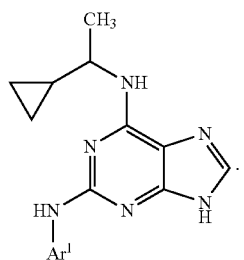

In a further aspect, the compound has a structure represented by a formula:

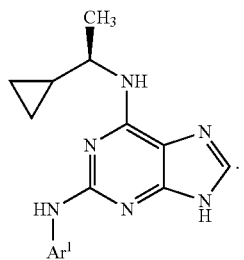

In a further aspect, the compound has a structure selected from:

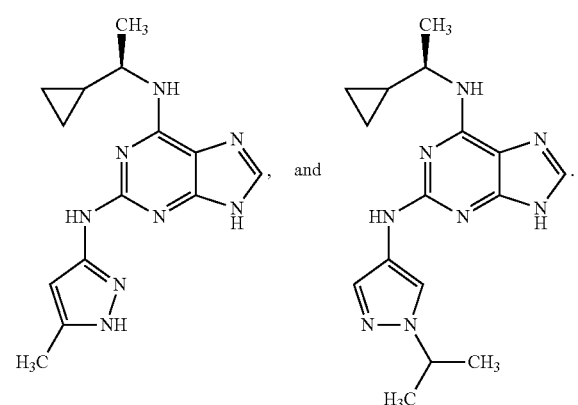

In a further aspect, the compound has a structure represented by a formula:

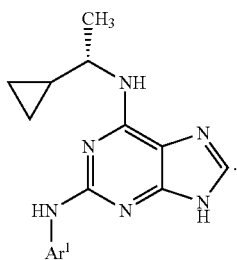

In a further aspect, the compound has a structure selected from:

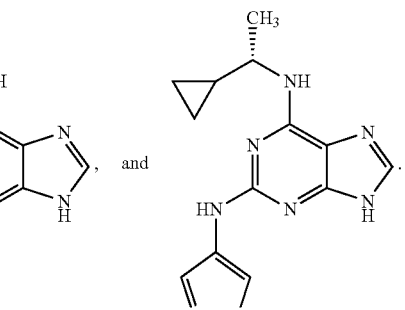

In a further aspect, the compound has a structure represented by a formula:

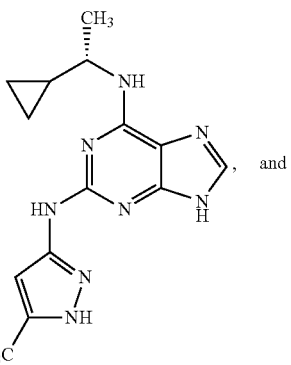

In a further aspect, the compound has a structure represented by a formula:

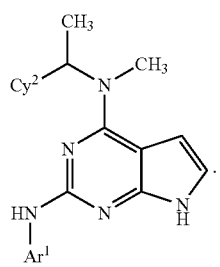

In a further aspect, the compound has a structure represented by a formula:

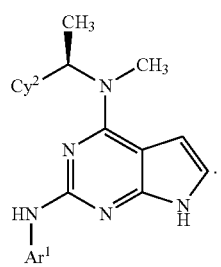

In a further aspect, the compound has a structure represented by a formula:

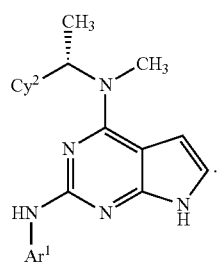

In a further aspect, the compound has a structure represented by a formula:

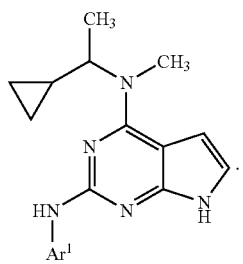

In a further aspect, the compound has a structure represented by a formula:

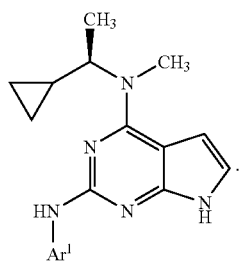

In a further aspect, the compound has a structure selected from:

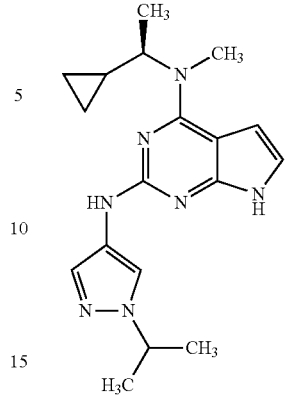 and 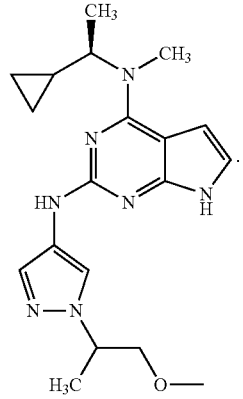

In a further aspect, the compound has a structure represented by a formula:

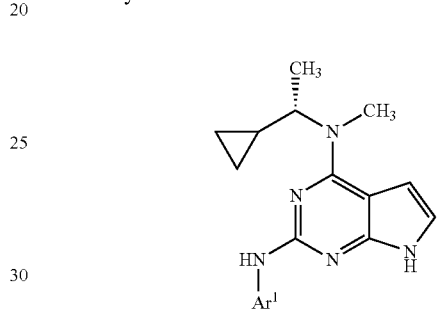

In a further aspect, the compound has a structure selected from:

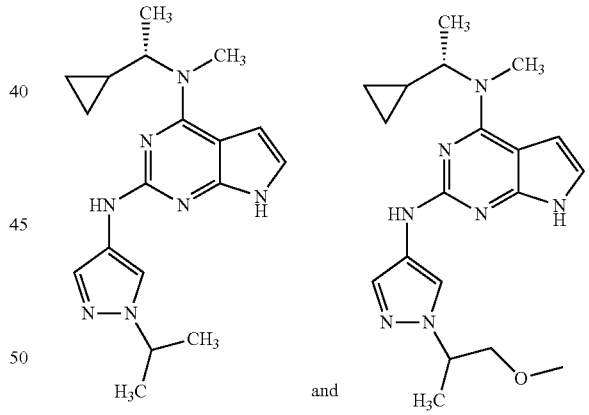

In a further aspect, the compound has a structure represented by a formula:

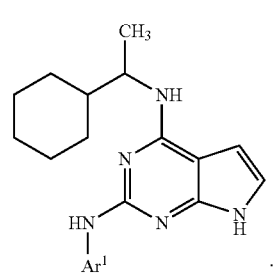

In a further aspect, the compound has a structure represented by a formula:

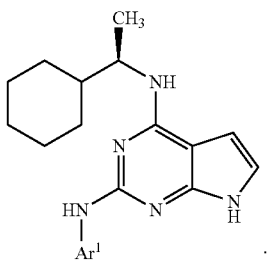

In a further aspect, the compound has a structure:

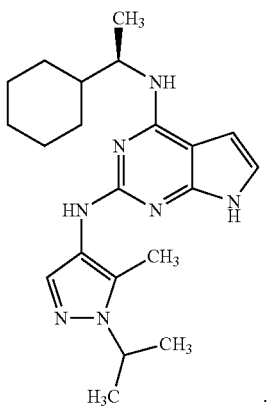 [SMILES: Cc1c(Nc2nc(N[C@H](C)C3CCCCC3)c3cc[nH]c3n2)cnn1C(C)C]

In a further aspect, the compound has a structure represented by a formula:

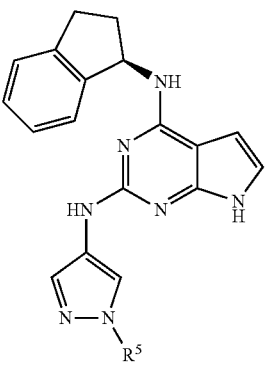

In a further aspect, the compound has a structure represented by a formula:

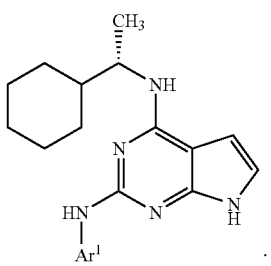

In a further aspect, the compound has a structure:

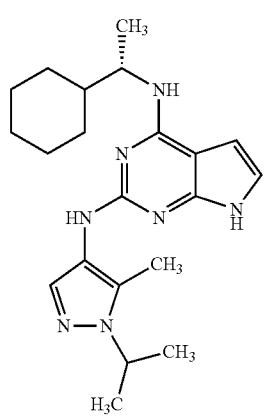

In a further aspect, the compound has a structure represented by a formula:

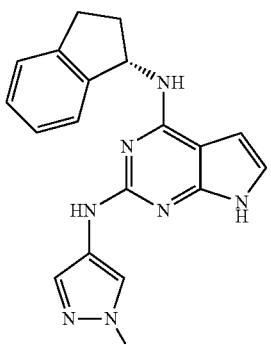

In a further aspect, the compound has a structure represented by a formula:

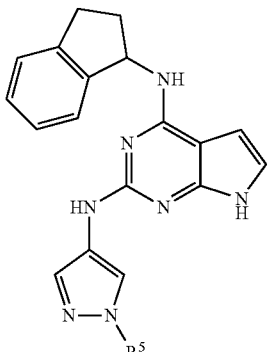

wherein $R^5$ is C1-C4 alkyl.

In a further aspect, the compound has a structure represented by a formula:

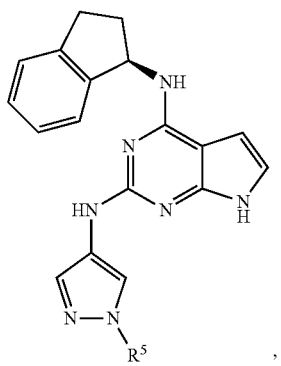

wherein R⁵ is C1-C4 alkyl.

In a further aspect, the compound has a structure selected from:

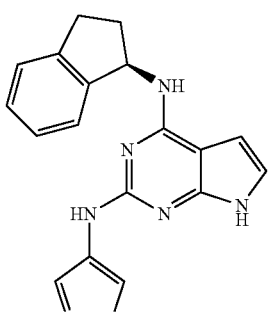

and

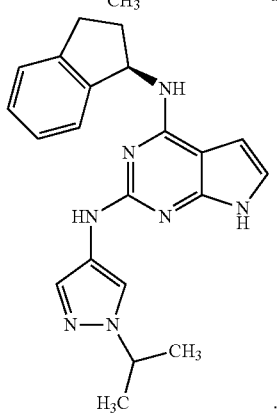

In a further aspect, the compound has a structure:

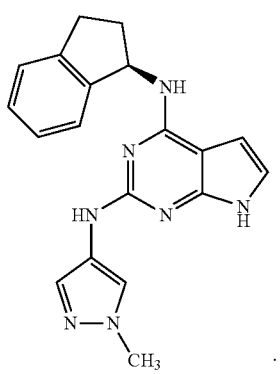 [SMILES: Cn1cc(Nc2nc(N[C@@H]3CCc4ccccc43)c3cc[nH]c3n2)cn1]

In a further aspect, the compound has a structure represented by a formula:

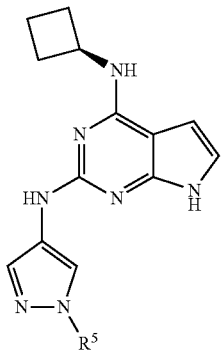

In a further aspect, the compound has a structure represented by a formula:

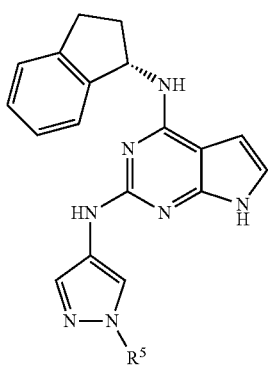

wherein R⁵ is C1-C4 alkyl.

In a further aspect, the compound has a structure selected from:

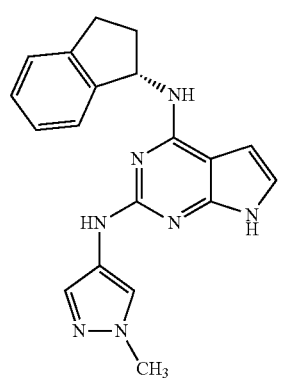

and

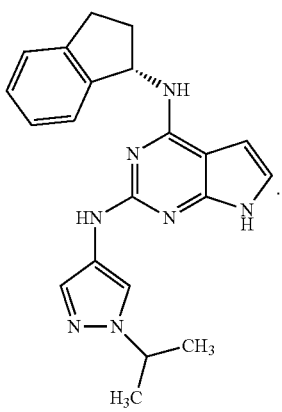

In a further aspect, the compound has a structure:

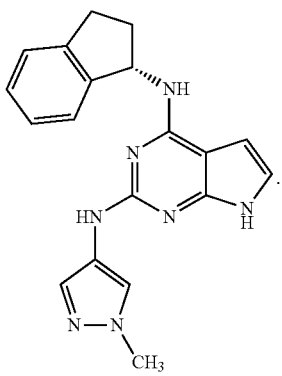 [SMILES: Cn1cc(Nc2nc(N[C@H]3CCc4ccccc43)c3cc[nH]c3n2)cn1]

In a further aspect, the compound has a structure represented by a formula:

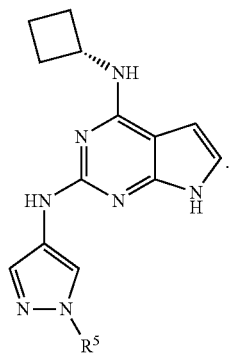

In a further aspect, the compound has a structure represented by a formula:

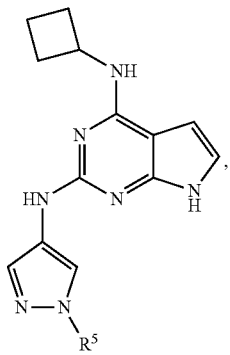

wherein $R^5$ is C1-C4 alkyl.

In a further aspect, the compound has a structure represented by a formula:

[structure]

wherein $R^5$ is C1-C4 alkyl.

In a further aspect, the compound has a structure selected from:

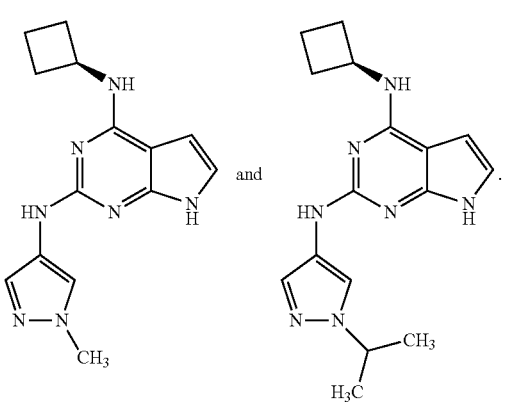

In a further aspect, the compound has a structure represented by a formula:

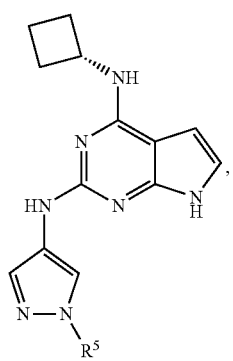

wherein $R^5$ is C1-C4 alkyl.

In a further aspect, the compound has a structure selected from:

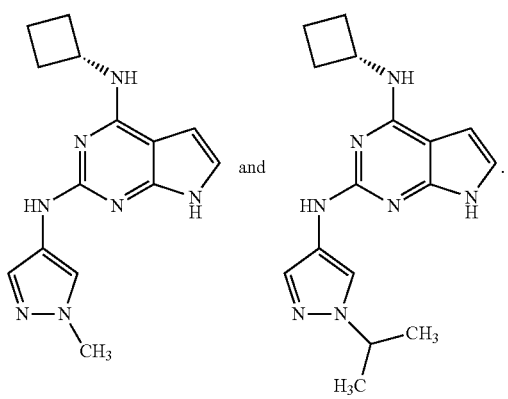

It is understood that the compounds of the present disclosure contain a stereocenter, as indicated with an asterisk below:

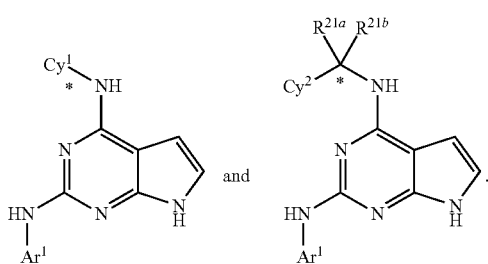

Thus, in various aspects, the disclosed compounds can be present as a racemic mixture. In a further aspect, the disclosed compounds can be enantiomerically enriched. For example, in a still further aspect, the compound can be at least about 50.1% enantiomerically enriched (e.e.). In yet a further aspect, the compound can be at least about 50.5% e.e. In an even further aspect, the compound can be at least about 60% e.e. In a still further aspect, a compound can be at least about 70% e.e. In yet a further aspect, the compound can be at least about 80% e.e. In an even further aspect, the compound can be at least about 90% e.e. In a still further aspect, the compound can be at least about 95% e.e. In yet a further aspect, the compound can be at least about 99% e.e.

a. A Groups

In one aspect, A is selected from $NR^{22}$ and $CR^{23a}R^{23b}$. In a further aspect, A is $NR^{22}$. In a still further aspect, A is $CR^{23a}R^{23b}$.

In a further aspect, two or three of A, $Q^1$, $Q^2$, and $Q^3$ are N. In a still further aspect, two of A, $Q^1$, $Q^2$, and $Q^3$ are N. In yet a further aspect, three of A, $Q^1$, $Q^2$, and $Q^3$ are N. In an even further aspect, A and $Q^1$ are N. In a still further aspect, A and $Q^2$ are N. In yet a further aspect, A and $Q^3$ are N. In an even further aspect, A, $Q^1$, and $Q^2$ are N. In a still further aspect, A, $Q^2$, and $Q^3$ are N. In yet a further aspect, A, $Q^1$, and $Q^3$ are N.

b. $Q^1$, $Q^2$, and $Q^3$ Groups

In one aspect, each of $Q^1$, $Q^2$, and $Q^3$ is independently selected from N and $CR^{24}$. In a further aspect, each of $Q^1$, $Q^2$, and $Q^3$ is independently selected from N and $CR^{24}$, provided that at least one of $Q^1$, $Q^2$, and $Q^3$ is N. In a still further aspect, each of $Q^1$, $Q^2$, and $Q^3$ is independently selected from N and $CR^{24}$, provided that at least two of $Q^1$, $Q^2$, and $Q^3$ is N. In yet a further aspect, each of $Q^1$, $Q^2$, and $Q^3$ is independently selected from N and $CR^{24}$, provided that all of $Q^1$, $Q^2$, and $Q^3$ are N.

In a further aspect, $Q^1$ and $Q^2$ are N. In a still further aspect, $Q^1$ and $Q^3$ are N. In yet a further aspect, $Q^2$ and $Q^3$ are N.

c. Z Groups

In one aspect, Z is selected from N and $CR^{20}$. In a further aspect, Z is N. In a still further aspect, Z is $CR^{20}$. In yet a further aspect, Z is CCN. In an even further aspect, Z is $CCH_3$. In a still further aspect, Z is CH.

d. $R^1$ Groups

In one aspect, $R^1$ is selected from $Cy^1$, $Ar^2$, —$CR^{21a}R^{21b}Cy^2$, and —$CR^{21a}R^{21b}Ar^2$. In a further aspect, $R^1$ is selected from $Ar^2$, —$CR^{21a}R^{21b}Cy^2$, and —$CR^{21a}R^{21b}Ar^2$. In a still further aspect, $R^1$ is selected from —$CR^{21a}R^{21b}Cy^2$ and —$CR^{21a}R^{21b}Ar^2$.

In a further aspect, $R^1$ is selected from $Ar^2$ and —$CR^{21a}R^{21b}Ar^2$. In a still further aspect, $R^1$ is selected from $Ar^2$ and —$CH(CH_3)Ar^2$. In yet a further aspect, $R^1$ is $Ar^2$. In an even further aspect, $R^1$ is —$CR^{21a}R^{21b}Ar^2$. In a still further aspect, $R^1$ is —$CH(CH_3)Ar^2$.

In a further aspect, $R^1$ is selected from $Cy^1$ and —$CR^{21a}R^{21b}Cy^2$. In a still further aspect, $R^1$ is selected from $Cy^1$ and —$CH(CH_3)Cy^2$. In yet a further aspect, $R^1$ is $Cy^1$. In an even further aspect, $R^1$ is —$CR^{21a}R^{21b}Cy^2$. In an even further aspect, $R^1$ is —$CH(CH_3)Cy^2$.

e. $R^2$, $R^3$, and $R^4$ Groups

In one aspect, each of $R^2$, $R^3$, and $R^4$ is independently selected from hydrogen and C1-C4 alkyl. In a further aspect, each of $R^2$, $R^3$, and $R^4$ is hydrogen.

In a further aspect, each of $R^2$, $R^3$, and $R^4$ is independently selected from hydrogen, methyl, ethyl, n-propyl, i-propyl, n-butyl, i-butyl, s-butyl, and t-butyl. In a still further aspect, each of $R^2$, $R^3$, and $R^4$ is independently selected from hydrogen, methyl, ethyl, n-propyl, and i-propyl. In yet a further aspect, each of $R^2$, $R^3$, and $R^4$ is independently selected from hydrogen, methyl, and ethyl. In an even further aspect, each of $R^2$, $R^3$, and $R^4$ is independently selected from hydrogen and ethyl. In a still further aspect, each of $R^2$, $R^3$, and $R^4$ is independently selected from hydrogen and methyl.

In a further aspect, each of $R^2$, $R^3$, and $R^4$ is C1-C4 alkyl. In a still further aspect, each of $R^2$, $R^3$, and $R^4$ is independently selected from methyl, ethyl, n-propyl, and i-propyl. In yet a further aspect, each of $R^2$, $R^3$, and $R^4$ is independently selected from methyl and ethyl. In an even further aspect, each of $R^2$, $R^3$, and $R^4$ is ethyl. In a still further aspect, each of $R^2$, $R^3$, and $R^4$ is methyl.

f. $R^5$ Groups

In one aspect, $R^5$ is C1-C8 alkyl. In a further aspect, $R^5$ is C1-C4 alkyl. In a still further aspect, $R^5$ is selected from methyl, ethyl, n-propyl, and i-propyl. In yet a further aspect, $R^5$ is selected from methyl and ethyl. In an even further aspect, $R^5$ is i-propyl. In a still further aspect, $R^5$ is n-propyl. In yet a further aspect, $R^5$ is ethyl. In an even further aspect, $R^5$ is methyl.

g. $R^{20}$ Groups

In one aspect, each occurrence of $R^{20}$, when present, is independently selected from hydrogen, —CN, and C1-C4 alkyl. In a further aspect, each occurrence of $R^{20}$, when present, is independently selected from hydrogen, —CN, —F, —Cl, —CF$_3$, and C1-C4 alkyl. In a further aspect, each occurrence of $R^{20}$, when present, is hydrogen.

In a further aspect, each occurrence of $R^{20}$, when present, is selected from hydrogen and C1-C4 alkyl. In a still further aspect, each occurrence of $R^{20}$, when present, is selected from hydrogen, methyl, ethyl, n-propyl, and i-propyl. In yet a further aspect, each occurrence of $R^{20}$, when present, is selected from hydrogen, methyl, and ethyl. In an even further aspect, each occurrence of $R^{20}$, when present, is selected from hydrogen and ethyl. In a still further aspect, each occurrence of $R^{20}$, when present, is selected from hydrogen and methyl.

In a further aspect, each occurrence of $R^{20}$, when present, is selected from hydrogen and —CN. In a still further aspect, each occurrence of $R^{20}$, when present, is —CN.

In a further aspect, each occurrence of $R^{20}$, when present, is C1-C4 alkyl. In a still further aspect, each occurrence of $R^{20}$, when present, is selected from methyl, ethyl, n-propyl, and i-propyl. In yet a further aspect, each occurrence of $R^{20}$, when present, is selected from methyl and ethyl. In an even further aspect, each occurrence of $R^{20}$, when present, is ethyl. In a still further aspect, each occurrence of $R^{20}$, when present, is methyl.

h. $R^{21A}$ and $R^{21B}$ Groups

In one aspect, each of $R^{21a}$ and $R^{21b}$, when present, is independently selected from hydrogen and C1-C4 alkyl. In a further aspect, each of $R^{21a}$ and $R^{21b}$, when present, is hydrogen.

In a further aspect, each of $R^{21a}$ and $R^{21b}$, when present, is independently selected from hydrogen, methyl, ethyl, n-propyl, i-propyl, n-butyl, i-butyl, s-butyl, and t-butyl. In a still further aspect, each of $R^{21a}$ and $R^{21b}$, when present, is independently selected from hydrogen, methyl, ethyl, n-propyl, and i-propyl. In yet a further aspect, each of $R^{21a}$ and $R^{21b}$, when present, is independently selected from hydrogen, methyl, and ethyl. In an even further aspect, each of $R^{21a}$ and $R^{21b}$, when present, is independently selected from hydrogen and ethyl. In yet a further aspect, each of $R^{21a}$ and $R^{21b}$, when present, is independently selected from hydrogen and methyl.

In a further aspect, each of $R^{21a}$ and $R^{21b}$, when present, is C1-C4 alkyl. In a still further aspect, each of $R^{21a}$ and $R^{21b}$, when present, is independently selected from methyl, ethyl, n-propyl, i-propyl, n-butyl, i-butyl, s-butyl, and t-butyl. In yet a further aspect, each of $R^{21a}$ and $R^{21b}$, when present, is independently selected from methyl, ethyl, n-propyl, and i-propyl. In an even further aspect, each of $R^{21a}$ and $R^{21b}$, when present, is independently selected from methyl and ethyl. In a still further aspect, each of $R^{21a}$ and $R^{21b}$, when present, is ethyl. In yet a further aspect, each of $R^{21a}$ and $R^{21b}$, when present, is methyl.

In a further aspect, $R^{21a}$, when present, is hydrogen and $R^{21b}$, when present, is C1-C4 alkyl. In a still further aspect, $R^{21a}$, when present, is hydrogen and $R^{21b}$, when present, is selected from methyl, ethyl, n-propyl, and i-propyl. In yet a further aspect, $R^{21a}$, when present, is hydrogen and $R^{21b}$, when present, is selected from methyl and ethyl. In an even further aspect, $R^{21a}$, when present, is hydrogen and $R^{21b}$, when present, is ethyl. In a still further aspect, $R^{21a}$, when present, is hydrogen and $R^{21b}$, when present, is methyl.

i. $R^{22}$ Groups

In one aspect, $R^{22}$, when present, is selected from hydrogen, halogen, C1-C8 alkyl, C1-C8 monohaloalkyl, C1-C8 polyhaloalkyl, C1-C8 hydroxyalkyl, C1-C8 alkoxyalkyl, —(C1-C8 alkyl)NH$_2$, —(C1-C8 alkyl)NH(C1-C8alkyl), —(C1-C8 alkyl)N(C1-C8 alkyl)(C1-C8 alkyl), C1-C8 alkylacid, —(C1-C4 alkyl)CONH$_2$, —(C1-C4 alkyl)CONH(C1-C4 alkyl), —(C1-C4 alkyl)CON(C1-C4 alkyl)(C1-C4 alkyl), —(C1-C4 alkyl)(C=O)Cy$^3$, and Cy$^3$. In a further aspect, $R^{22}$, when present, is selected from hydrogen, halogen, C1-C4 alkyl, C1-C4 monohaloalkyl, C1-C4 polyhaloalkyl, C1-C4 hydroxyalkyl, C1-C4 alkoxyalkyl, —(C1-C4 alkyl)NH$_2$, —(C1-C4 alkyl)NH(C1-C4 alkyl), —(C1-C4 alkyl)N(C1-C4 alkyl)(C1-C4 alkyl), C1-C4 alkylacid, —(C1-C4 alkyl)CONH$_2$, —(C1-C4 alkyl)CONH(C1-C4 alkyl), —(C1-C4 alkyl)CON(C1-C4 alkyl)(C1-C4 alkyl), —(C1-C4 alkyl)(C=O)Cy$^3$, and Cy$^3$.

In a further aspect, $R^{22}$, when present, is selected from hydrogen, C1-C8 alkyl, C1-C8 monohaloalkyl, C1-C8 polyhaloalkyl, C1-C8 hydroxyalkyl, C1-C8 alkoxyalkyl, —(C1-C8 alkyl)N(C1-C8 alkyl)(C1-C8 alkyl), C1-C8 alkylacid, —(C1-C4 alkyl)CONH(C1-C4 alkyl), —(C1-C4 alkyl)(C=O)Cy$^3$, and Cy$^3$. In a still further aspect, $R^{22}$, when present, is selected from hydrogen, C1-C4 alkyl, C1-C4 monohaloalkyl, C1-C4 polyhaloalkyl, C1-C4 hydroxyalkyl, C1-C4 alkoxyalkyl, —(C1-C4 alkyl)N(C1-C4 alkyl)(C1-C4 alkyl), C1-C4 alkylacid, —(C1-C4 alkyl)CONH(C1-C4 alkyl), —(C1-C4 alkyl)(C=O)Cy$^3$, and Cy$^3$.

In a further aspect, $R^{22}$, when present, is selected from hydrogen and C1-C8 alkylacid. In a still further aspect, $R^{22}$, when present, is selected from hydrogen and C1-C4 alkylacid. In yet a further aspect, $R^{22}$, when present, is selected from hydrogen, —CH$_2$CO$_2$H, —(CH$_2$)$_2$CO$_2$H, and —(CH$_2$)$_3$CO$_2$H. In an even further aspect, $R^{22}$, when present, is selected from hydrogen, —CH$_2$CO$_2$H, and —(CH$_2$)$_2$CO$_2$H. In a still further aspect, $R^{22}$, when present, is selected from hydrogen and —CH$_2$CO$_2$H.

In a further aspect, $R^{22}$, when present, is selected from hydrogen, —(C1-C8 alkyl)NH$_2$, —(C1-C8 alkyl)NH(C1-C8alkyl), —(C1-C8 alkyl)N(C1-C8 alkyl)(C1-C8 alkyl), —(C1-C4 alkyl)CONH$_2$, —(C1-C4 alkyl)CONH(C1-C4 alkyl), and —(C1-C4 alkyl)CON(C1-C4 alkyl)(C1-C4 alkyl). In a still further aspect, $R^{22}$, when present, is selected from hydrogen, —(C1-C4 alkyl)NH$_2$, —(C1-C4 alkyl)NH(C1-C4 alkyl), —(C1-C4 alkyl)N(C1-C4 alkyl)(C1-C4 alkyl), —(C1-C4 alkyl)CONH$_2$, —(C1-C4 alkyl)CONH (C1-C4 alkyl), and —(C1-C4 alkyl)CON(C1-C4 alkyl)(C1-C4 alkyl). In yet a further aspect, $R^{22}$, when present, is selected from hydrogen, —CH$_2$NH$_2$, —(CH$_2$)$_2$NH$_2$, —(CH$_2$)$_3$NH$_2$, —CH$_2$NHCH$_3$, —(CH$_2$)$_2$NHCH$_3$, —CH$_2$NHCH$_2$CH$_3$, —(CH$_2$)$_2$NHCH$_2$CH$_3$, —CH$_2$N(CH$_3$)$_2$, —(CH$_2$)$_2$N(CH$_3$)$_2$, —CH$_2$N(CH$_2$CH$_3$)$_2$, —CH$_2$CONH$_2$, —(CH$_2$)$_2$CONH$_2$, —(CH$_2$)$_3$CONH$_2$, —CH$_2$CONHCH$_3$, —(CH$_2$)$_2$CONHCH$_3$, —CH$_2$CONHCH$_2$CH$_3$, —(CH$_2$)$_2$CONHCH$_2$CH$_3$, —CH$_2$CON(CH$_3$)$_2$, —(CH$_2$)$_2$CON(CH$_3$)$_2$, and —CH$_2$CON(CH$_2$CH$_3$)$_2$. In an even further aspect, $R^{22}$, when present, is selected from hydrogen, —CH$_2$NH$_2$, —(CH$_2$)$_2$NH$_2$, —CH$_2$NHCH$_3$, —(CH$_2$)$_2$NHCH$_3$, —CH$_2$NHCH$_2$CH$_3$, —(CH$_2$)$_2$NHCH$_2$CH$_3$, —CH$_2$N(CH$_3$)$_2$, —(CH$_2$)$_2$N(CH$_3$)$_2$, —CH$_2$N(CH$_2$CH$_3$)$_2$, —CH$_2$CONH$_2$, —(CH$_2$)$_2$CONH$_2$, —CH$_2$CONHCH$_3$, —(CH$_2$)$_2$CONHCH$_3$, —CH$_2$CONHCH$_2$CH$_3$, —(CH$_2$)$_2$CONHCH$_2$CH$_3$, —CH$_2$CON(CH$_3$)$_2$, —(CH$_2$)$_2$CON(CH$_3$)$_2$, and —CH$_2$CON(CH$_2$CH$_3$)$_2$.

In a still further aspect, $R^{22}$, when present, is selected from hydrogen, —$CH_2NH_2$, —$CH_2NHCH_3$, —$(CH_2)_2NHCH_3$, —$CH_2N(CH_3)_2$, —$(CH_2)_2N(CH_3)_2$, —$CH_2CONH_2$, —$CH_2CONHCH_3$, —$(CH_2)_2CONHCH_3$, —$CH_2CON(CH_3)_2$, and —$(CH_2)_2CON(CH_3)_2$. In yet a further aspect, $R^{22}$, when present, is selected from hydrogen, —$CH_2NH_2$, —$CH_2NHCH_3$, —$CH_2N(CH_3)_2$, —$CH_2CONH_2$, —$CH_2CONHCH_3$, and —$CH_2CON(CH_3)_2$.

In a further aspect, $R^{22}$, when present, is selected from hydrogen, —(C1-C4 alkyl)(C=O)$Cy^3$, and $Cy^3$. In a still further aspect, $R^{22}$, when present, is selected from hydrogen, —$CH_2$(C=O)$Cy^3$, —$(CH_2)_2$(C=O)$Cy^3$, —$(CH_2)_3$(C=O)$Cy^3$, and $Cy^3$. In yet a further aspect, $R^{22}$, when present, is selected from hydrogen, —$CH_2$(C=O)$Cy^3$, —$(CH_2)_2$(C=O)$Cy^3$, and $Cy^3$. In an even further aspect, $R^{22}$, when present, is selected from hydrogen, —$CH_2$(C=O)$Cy^3$, and $Cy^3$. In a still further aspect, $R^{22}$, when present, is selected from hydrogen and —$CH_2$(C=O)$Cy^3$. In yet a further aspect, $R^{22}$, when present, is selected from hydrogen and $Cy^3$.

In a further aspect, $R^{22}$, when present, is selected from hydrogen, C1-C8 alkyl, C1-C8 monohaloalkyl, C1-C8 polyhaloalkyl, C1-C8 hydroxyalkyl, and C1-C8 alkoxyalkyl. In a still further aspect, $R^{22}$, when present, is selected from hydrogen, C1-C4 alkyl, C1-C4 monohaloalkyl, C1-C4 polyhaloalkyl, C1-C4 hydroxyalkyl, and C1-C4 alkoxyalkyl. In yet a further aspect, $R^{22}$, when present, is selected from hydrogen, methyl, ethyl, n-propyl, i-propyl, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$CH_2OH$, —$CH_2CH_2OH$, —$(CH_2)_2CH_2OH$, —$OCH_3$, —$OCH_2CH_3$, and —$O(CH_2)_2CH_3$. In an even further aspect, $R^{22}$, when present, is selected from hydrogen, methyl, ethyl, —$CH_2F$, —$CH_2Cl$, —$CH_2Br$, —$CH_2CH_2F$, —$CH_2CH_2Cl$, —$CH_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$CH_2OH$, —$CH_2CH_2OH$, —$OCH_3$, and —$OCH_2CH_3$. In a still further aspect, $R^{22}$, when present, is selected from hydrogen, methyl, —$CH_2F$, —$CH_2Cl$, —$CH_2Br$, —$CHF_2$, —$CF_3$, —$CHCl_2$, —$CCl_3$, —$CHBr_2$, —$CBr_3$, —$CH_2OH$, and —$OCH_3$.

In a further aspect, $R^{22}$, when present, is selected from hydrogen, C1-C8 hydroxyalkyl, and C1-C8 alkoxyalkyl. In a still further aspect, $R^{22}$, when present, is selected from hydrogen, C1-C4 hydroxyalkyl, and C1-C4 alkoxyalkyl. In yet a further aspect, $R^{22}$, when present, is selected from hydrogen, —$CH_2OH$, —$CH_2CH_2OH$, —$(CH_2)_2CH_2OH$, —$OCH_3$, —$OCH_2CH_3$, and —$O(CH_2)_2CH_3$. In an even further aspect, $R^{22}$, when present, is selected from hydrogen, —$CH_2OH$, —$CH_2CH_2OH$, —$OCH_3$, and —$OCH_2CH_3$. In a still further aspect, $R^{22}$, when present, is selected from hydrogen, —$CH_2OH$, and —$OCH_3$.

In a further aspect, $R^{22}$, when present, is selected from hydrogen, C1-C8 monohaloalkyl, and C1-C8 polyhaloalkyl. In a still further aspect, $R^{22}$, when present, is selected from hydrogen, C1-C4 monohaloalkyl, and C1-C4 polyhaloalkyl. In yet a further aspect, $R^{22}$, when present, is selected from hydrogen, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, and —$(CH_2)_2CBr_3$. In an even further aspect, $R^{22}$, when present, is selected from hydrogen, —$CH_2F$, —$CH_2Cl$, —$CH_2Br$, —$CH_2CH_2F$, —$CH_2CH_2Cl$, —$CH_2CH_2Br$, —$CHF_2$, —$CF_3$, —$CHCl_2$, —$CCl_3$, —$CHBr_2$, —$CBr_3$, —$CH_2CHF_2$, —$CH_2CF_3$, —$CH_2CHCl_2$, —$CH_2CCl_3$, —$CH_2CHBr_2$, and —$CH_2CBr_3$. In a still further aspect, $R^{22}$, when present, is selected from hydrogen, —$CH_2F$, —$CH_2Cl$, —$CH_2Br$, —$CHF_2$, —$CF_3$, —$CHCl_2$, —$CCl_3$, —$CHBr_2$, —$CBr_3$.

In a further aspect, $R^{22}$, when present, is selected from hydrogen and C1-C8 alkyl. In a still further aspect, $R^{22}$, when present, is selected from hydrogen and C1-C4 alkyl. In yet a further aspect, $R^{22}$, when present, is selected from hydrogen, methyl, ethyl, n-propyl, and i-propyl. In an even further aspect, $R^{22}$, when present, is selected from hydrogen, methyl, and ethyl. In a still further aspect, $R^{22}$, when present, is selected from hydrogen and ethyl. In yet a further aspect, $R^{22}$, when present, is selected from hydrogen and methyl.

In a further aspect, $R^{22}$, when present, is C1-C8 alkyl. In a still further aspect, $R^{22}$, when present, is C1-C4 alkyl. In yet a further aspect, $R^{22}$, when present, is selected from methyl, ethyl, n-propyl, and i-propyl. In an even further aspect, $R^{22}$, when present, is selected from methyl and ethyl. In a still further aspect, $R^{22}$, when present, is ethyl. In yet a further aspect, $R^{22}$, when present, is methyl.

j. $R^{23A}$ and $R^{23B}$ Groups

In one aspect, each of $R^{23a}$ and $R^{23b}$, when present, is independently selected from hydrogen, halogen, C1-C8 alkyl, C1-C8 monohaloalkyl, C1-C8 polyhaloalkyl, C1-C8 hydroxyalkyl, C1-C8 alkoxyalkyl, C1-C8 alkylacid, —(C1-C4 alkyl)(C=O)$Cy^1$, —(C1-C4 alkyl)$CONH_2$, —(C1-C4 alkyl)CONH(C1-C4 alkyl), —(C1-C4 alkyl)CON(C1-C4 alkyl)(C1-C4 alkyl), and $Cy^3$. In a further aspect, each of $R^{23a}$ and $R^{23b}$, when present, is independently selected from hydrogen, halogen, C1-C4 alkyl, C1-C4 monohaloalkyl, C1-C4 polyhaloalkyl, C1-C4 hydroxyalkyl, C1-C4 alkoxyalkyl, C1-C4 alkylacid, —(C1-C4 alkyl)(C=O)$Cy^1$, —(C1-C4 alkyl)$CONH_2$, —(C1-C4 alkyl)CONH(C1-C4 alkyl), —(C1-C4 alkyl)CON(C1-C4 alkyl)(C1-C4 alkyl), and $Cy^3$.

In a further aspect, each of $R^{23a}$ and $R^{23b}$, when present, is independently selected from hydrogen and C1-C8 alkylacid. In a still further aspect, each of $R^{23a}$ and $R^{23b}$, when present, is independently selected from hydrogen and C1-C4 alkylacid. In yet a further aspect, each of $R^{23a}$ and $R^{23b}$, when present, is independently selected from hydrogen, —$CH_2CO_2H$, —$(CH_2)_2CO_2H$, and —$(CH_2)_3CO_2H$. In an even further aspect, each of $R^{23a}$ and $R^{23b}$, when present, is independently selected from hydrogen, —$CH_2CO_2H$, and —$(CH_2)_2CO_2H$. In a still further aspect, each of $R^{23a}$ and $R^{23b}$, when present, is independently selected from hydrogen and —$CH_2CO_2H$.

In a further aspect, each of $R^{23a}$ and $R^{23b}$, when present, is independently selected from hydrogen, —(C1-C4 alkyl)$CONH_2$, —(C1-C4 alkyl)CONH(C1-C4 alkyl), and —(C1-C4 alkyl)CON(C1-C4 alkyl)(C1-C4 alkyl). In a still further aspect, each of $R^{23a}$ and $R^{23b}$, when present, is independently selected from hydrogen, —(C1-C4 alkyl)$CONH_2$, —(C1-C4 alkyl)CONH(C1-C4 alkyl), and —(C1-C4 alkyl)CON(C1-C4 alkyl)(C1-C4 alkyl). In yet a further aspect, each of $R^{23a}$ and $R^{23b}$, when present, is independently selected from hydrogen, —$CH_2CONH_2$, —$(CH_2)_2CONH_2$, —$(CH_2)_3CONH_2$, —$CH_2CONHCH_3$, —$(CH_2)_2CONHCH_3$, —$CH_2CONHCH_2CH_3$, —$(CH_2)_2CONHCH_2CH_3$, —$CH_2CON(CH_3)_2$, —$(CH_2)_2CON(CH_3)_2$, and —$CH_2CON(CH_2CH_3)_2$. In an even further aspect, each of $R^{23a}$ and $R^{23b}$, when present, is independently selected from hydrogen, —CH$_2$CONH$_2$, —(CH$_2$)$_2$CONH$_2$, —CH$_2$CONHCH$_3$, —(CH$_2$)$_2$CONHCH$_3$, —CH$_2$CONHCH$_2$CH$_3$, —(CH$_2$)$_2$CONHCH$_2$CH$_3$, —CH$_2$CON(CH$_3$)$_2$, —(CH$_2$)$_2$CON(CH$_3$)$_2$, and —CH$_2$CON(CH$_2$CH$_3$)$_2$. In a still further aspect, each of R$^{23a}$ and R$^{23b}$, when present, is independently selected from hydrogen, —CH$_2$CONH$_2$, —CH$_2$CONHCH$_3$, —(CH$_2$)$_2$CONHCH$_3$, —CH$_2$CON(CH$_3$)$_2$, and —(CH$_2$)$_2$CON(CH$_3$)$_2$. In yet a further aspect, each of R$^{23a}$ and R$^{23b}$, when present, is independently selected from hydrogen, —CH$_2$CONH$_2$, —CH$_2$CONHCH$_3$, and —CH$_2$CON(CH$_3$)$_2$.

In a further aspect, each of R$^{23a}$ and R$^{23b}$, when present, is independently selected from hydrogen, —(C1-C4 alkyl)(C═O)Cy$^1$, and Cy$^3$. In a still further aspect, each of R$^{23a}$ and R$^{23b}$, when present, is independently selected from hydrogen, —CH$_2$(C═O)Cy$^1$, —(CH$_2$)$_2$(C═O)Cy$^1$, —(CH$_2$)$_3$(C═O)Cy$^1$, and Cy$^3$. In yet a further aspect, each of R$^{23a}$ and R$^{23b}$, when present, is independently selected from hydrogen, —CH$_2$(C═O)Cy$^1$, —(CH$_2$)$_2$(C═O)Cy$^1$, and Cy$^3$. In an even further aspect, each of R$^{23a}$ and R$^{23b}$, when present, is independently selected from hydrogen, —CH$_2$(C═O)Cy$^1$, and Cy$^3$. In a still further aspect, each of R$^{23a}$ and R$^{23b}$, when present, is independently selected from hydrogen and —CH$_2$(C═O)Cy$^1$. In yet a further aspect, each of R$^{23a}$ and R$^{23b}$, when present, is independently selected from hydrogen and Cy$^3$.

In a further aspect, each of R$^{23a}$ and R$^{23b}$, when present, is independently selected from hydrogen, C1-C8 alkyl, C1-C8 monohaloalkyl, C1-C8 polyhaloalkyl, C1-C8 hydroxyalkyl, and C1-C8 alkoxyalkyl. In a still further aspect, each of R$^{23a}$ and R$^{23b}$, when present, is independently selected from hydrogen, C1-C4 alkyl, C1-C4 monohaloalkyl, C1-C4 polyhaloalkyl, C1-C4 hydroxyalkyl, and C1-C4 alkoxyalkyl. In yet a further aspect, each of R$^{23a}$ and R$^{23b}$, when present, is independently selected from hydrogen, methyl, ethyl, n-propyl, i-propyl, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —CH$_2$OH, —CH$_2$CH$_2$OH, —(CH$_2$)$_2$CH$_2$OH, —OCH$_3$, —OCH$_2$CH$_3$, and —O(CH$_2$)$_2$CH$_3$. In an even further aspect, each of R$^{23a}$ and R$^{23b}$, when present, is independently selected from hydrogen, methyl, ethyl, —CHF, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$OH, —CH$_2$CH$_2$OH, —OCH$_3$, and —OCH$_2$CH$_3$. In a still further aspect, each of R$^{23a}$ and R$^{23b}$, when present, is independently selected from hydrogen, methyl, —CHF, —CH$_2$Cl, —CH$_2$Br, —CF$_3$, —CHCl$_2$, —CCl$_3$, —CHBr$_2$, —CH$_2$OH, and —OCH$_3$.

In a further aspect, each of R$^{23a}$ and R$^{23b}$, when present, is independently selected from hydrogen, C1-C8 hydroxyalkyl, and C1-C8 alkoxyalkyl. In a still further aspect, each of R$^{23a}$ and R$^{23b}$, when present, is independently selected from hydrogen, C1-C4 hydroxyalkyl, and C1-C4 alkoxyalkyl. In yet a further aspect, each of R$^{23a}$ and R$^{23b}$, when present, is independently selected from hydrogen, —CH$_2$OH, —CH$_2$CH$_2$OH, —(CH$_2$)$_2$CH$_2$OH, —OCH$_3$, —OCH$_2$CH$_3$, and —O(CH$_2$)$_2$CH$_3$. In an even further aspect, each of R$^{23a}$ and R$^{23b}$, when present, is independently selected from hydrogen, —CH$_2$OH, —CH$_2$CH$_2$OH, —OCH$_3$, and —OCH$_2$CH$_3$. In a still further aspect, each of R$^{23a}$ and R$^{23b}$, when present, is independently selected from hydrogen, —CH$_2$OH, and —OCH$_3$.

In a further aspect, each of R$^{23a}$ and R$^{23b}$, when present, is independently selected from hydrogen, C1-C8 monohaloalkyl, and C1-C8 polyhaloalkyl. In a still further aspect, each of R$^{23a}$ and R$^{23b}$, when present, is independently selected from hydrogen, C1-C4 monohaloalkyl, and C1-C4 polyhaloalkyl. In yet a further aspect, each of R$^{23a}$ and R$^{23b}$, when present, is independently selected from hydrogen, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, and —(CH$_2$)$_2$CBr$_3$.

In an even further aspect, each of R$^{23a}$ and R$^{23b}$, when present, is independently selected from hydrogen, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, and —CH$_2$CBr$_3$. In a still further aspect, each of R$^{23a}$ and R$^{23b}$, when present, is independently selected from hydrogen, —CH$_2$F, —CH$_2$Cl, —CH$_2$Br, —CHF$_2$, —CF$_3$, —CHCl$_2$, —CCl$_3$, —CHBr$_2$, —CBr$_3$.

In a further aspect, each of R$^{23a}$ and R$^{23b}$, when present, is independently selected from hydrogen and C1-C8 alkyl. In a still further aspect, each of R$^{23a}$ and R$^{23b}$, when present, is independently selected from hydrogen and C1-C4 alkyl. In yet a further aspect, each of R$^{23a}$ and R$^{23b}$, when present, is independently selected from hydrogen, methyl, ethyl, n-propyl, and i-propyl. In an even further aspect, each of R$^{23a}$ and R$^{23b}$, when present, is independently selected from hydrogen, methyl, and ethyl. In a still further aspect, each of R$^{23a}$ and R$^{23b}$, when present, is independently selected from hydrogen and ethyl. In yet a further aspect, each of R$^{23a}$ and R$^{23b}$, when present, is independently selected from hydrogen and methyl.

In a further aspect, each of R$^{23a}$ and R$^{23b}$, when present, is C1-C8 alkyl. In a still further aspect, each of R$^{23a}$ and R$^{23b}$, when present, is C1-C4 alkyl. In yet a further aspect, each of R$^{23a}$ and R$^{23b}$, when present, is independently selected from methyl, ethyl, n-propyl, and i-propyl. In an even further aspect, each of R$^{23a}$ and R$^{23b}$, when present, is independently selected from methyl and ethyl. In a still further aspect, each of R$^{23a}$ and R$^{23b}$, when present, is ethyl. In yet a further aspect, each of R$^{23a}$ and R$^{23b}$, when present, is methyl.

k. R$^{24}$ Groups

In one aspect, each occurrence of R$^{24}$, when present, is independently selected from hydrogen, halogen, C1-C8 alkyl, C1-C8 monohaloalkyl, C1-C8 polyhaloalkyl, C1-C8 alkoxyalkyl, —(C1-C4 alkyl)CONH$_2$, —(C1-C4 alkyl)CONH(C1-C4 alkyl), —(C1-C4 alkyl)CON(C1-C4 alkyl)(C1-C4 alkyl). In a further aspect, each occurrence of R$^{24}$, when present, is independently selected from hydrogen, halogen, C1-C4 alkyl, C1-C4 monohaloalkyl, C1-C4 polyhaloalkyl, C1-C4 alkoxyalkyl, —(C1-C4 alkyl)CONH$_2$, —(C1-C4 alkyl)CONH(C1-C4 alkyl), —(C1-C4 alkyl)CON(C1-C4 alkyl)(C1-C4 alkyl).

In a further aspect, R$^{24}$, when present, is selected from hydrogen, —(C1-C4 alkyl)CONH$_2$, —(C1-C4 alkyl)CONH(C1-C4 alkyl), and —(C1-C4 alkyl)CON(C1-C4 alkyl)(C1-C4 alkyl). In a still further aspect, R$^{24}$, when present, is selected from hydrogen, —CH$_2$CONH$_2$, —(CH$_2$)$_2$CONH$_2$, —(CH$_2$)$_3$CONH$_2$, —CH$_2$CONHCH$_3$, —(CH$_2$)$_2$CON- HCH$_3$, —CH$_2$CONHCH$_2$CH$_3$, —(CH$_2$)$_2$CONHCH$_2$CH$_3$, —CH$_2$CON(CH$_3$)$_2$, —(CH$_2$)$_2$CON(CH$_3$)$_2$, and —CH$_2$CON(CH$_2$CH$_3$)$_2$. In an even further aspect, R$^{24}$, when present, is selected from hydrogen, —CH$_2$CONH$_2$, —(CH$_2$)$_2$CONH$_2$, —CH$_2$CONHCH$_3$, —(CH$_2$)$_2$CONHCH$_3$, —CH$_2$CONHCH$_2$CH$_3$, —(CH$_2$)$_2$CONHCH$_2$CH$_3$, —CH$_2$CON(CH$_3$)$_2$, —(CH$_2$)$_2$CON(CH$_3$)$_2$, and —CH$_2$CON(CH$_2$CH$_3$)$_2$. In a still further aspect, R$^{24}$, when present, is selected from hydrogen, —CH$_2$CONH$_2$, —CH$_2$CONHCH$_3$, —(CH$_2$)$_2$CONHCH$_3$, —CH$_2$CON(CH$_3$)$_2$, and —(CH$_2$)$_2$CON(CH$_3$)$_2$. In yet a further aspect, R$^{24}$, when present, is selected from hydrogen, —CH$_2$CONH$_2$, —CH$_2$CONHCH$_3$, and —CH$_2$CON(CH$_3$)$_2$.

In a further aspect, R$^{24}$, when present, is selected from hydrogen, C1-C8 alkyl, C1-C8 monohaloalkyl, C1-C8 polyhaloalkyl, and C1-C8 alkoxyalkyl. In a still further aspect, R$^{24}$, when present, is selected from hydrogen, C1-C4 alkyl, C1-C4 monohaloalkyl, C1-C4 polyhaloalkyl, and C1-C4 alkoxyalkyl. In yet a further aspect, R$^{24}$, when present, is selected from hydrogen, methyl, ethyl, n-propyl, i-propyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —OCH$_3$, —OCH$_2$CH$_3$, and —O(CH$_2$)$_2$CH$_3$. In an even further aspect, R$^{24}$, when present, is selected from hydrogen, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —OCH$_3$, and —OCH$_2$CH$_3$. In a still further aspect, R$^{24}$, when present, is selected from hydrogen, methyl, —CH$_2$F, —CH$_2$Cl, —CH$_2$Br, —CHF$_2$, —CF$_3$, —CHCl$_2$, —CCl$_3$, —CHBr$_2$, —CBr$_3$, and —OCH$_3$.

In a further aspect, R$^{24}$, when present, is selected from hydrogen and C1-C8 alkoxyalkyl. In a still further aspect, R$^{24}$, when present, is selected from hydrogen and C1-C4 alkoxyalkyl. In yet a further aspect, R$^{24}$, when present, is selected from hydrogen, —OCH$_3$, —OCH$_2$CH$_3$, and —O(CH$_2$)$_2$CH$_3$. In an even further aspect, R$^{24}$, when present, is selected from hydrogen, —OCH$_3$, and —OCH$_2$CH$_3$. In a still further aspect, R$^{24}$, when present, is selected from hydrogen and —OCH$_3$.

In a further aspect, R$^{24}$, when present, is selected from hydrogen, C1-C8 monohaloalkyl, and C1-C8 polyhaloalkyl. In a still further aspect, R$^{24}$, when present, is selected from hydrogen, C1-C4 monohaloalkyl, and C1-C4 polyhaloalkyl. In yet a further aspect, R$^{24}$, when present, is selected from hydrogen, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, and —(CH$_2$)$_2$CBr$_3$.

In an even further aspect, R$^{24}$, when present, is selected from hydrogen, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, and —CH$_2$CBr$_3$. In a still further aspect, R$^{24}$, when present, is selected from hydrogen, —CH$_2$F, —CH$_2$Cl, —CH$_2$Br, —CHF$_2$, —CF$_3$, —CHCl$_2$, —CCl$_3$, —CHBr$_2$, —CBr$_3$.

In a further aspect, R$^{24}$, when present, is selected from hydrogen and C1-C8 alkyl. In a still further aspect, R$^{24}$, when present, is selected from hydrogen and C1-C4 alkyl. In yet a further aspect, R$^{24}$, when present, is selected from hydrogen, methyl, ethyl, n-propyl, and i-propyl. In an even further aspect, R$^{24}$, when present, is selected from hydrogen, methyl, and ethyl. In a still further aspect, R$^{24}$, when present, is selected from hydrogen and ethyl. In yet a further aspect, R$^{24}$, when present, is selected from hydrogen and methyl.

In a further aspect, R$^{24}$, when present, is C1-C8 alkyl. In a still further aspect, R$^{24}$, when present, is C1-C4 alkyl. In yet a further aspect, R$^{24}$, when present, is selected from methyl, ethyl, n-propyl, and i-propyl. In an even further aspect, R$^{24}$, when present, is selected from methyl and ethyl. In a still further aspect, R$^{24}$, when present, is ethyl. In yet a further aspect, R$^{24}$, when present, is methyl.

1. Ar$^1$ Groups

In one aspect, Ar$^1$ is a structure selected from:

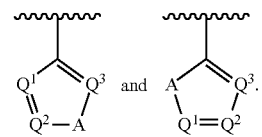

In a further aspect, Ar$^1$ is a structure having a formula:

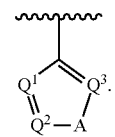

In a further aspect, Ar$^1$ is a structure having a formula selected from:

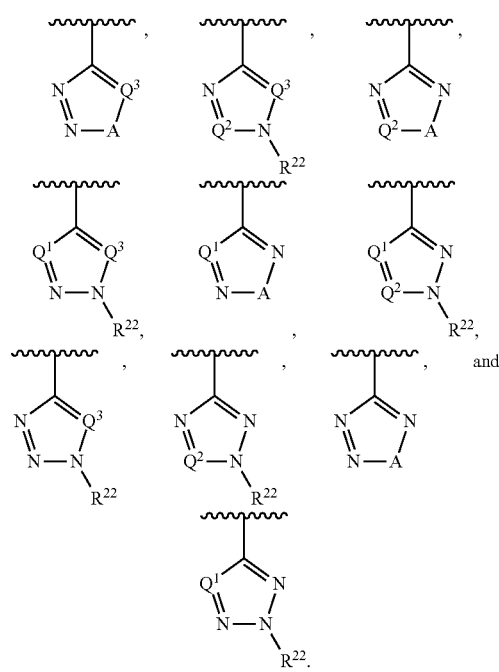

In a further aspect, $Ar^1$ is a structure having a formula selected from:

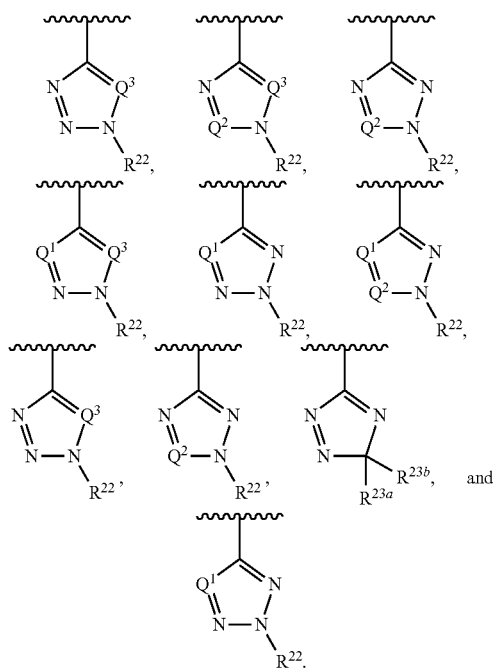

In a further aspect, $Ar^1$ is a structure having a formula selected from:

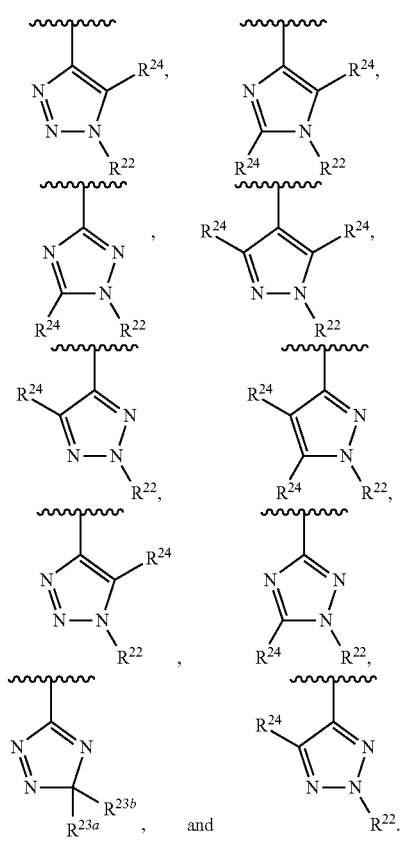

In a further aspect, $Ar^1$ is a structure having a formula selected from:

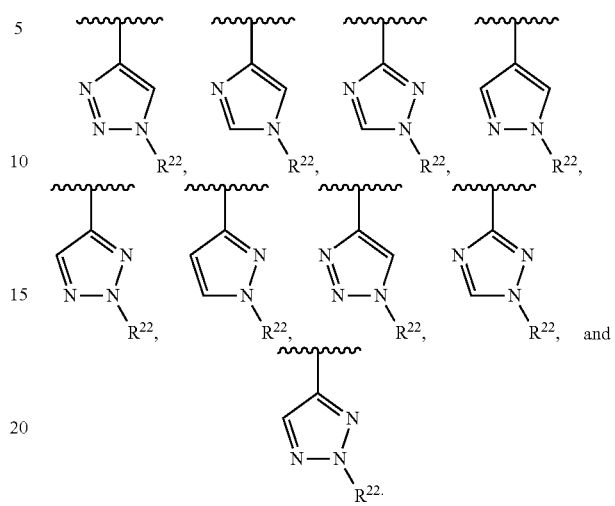

In a further aspect, $Ar^1$ is a structure having a formula selected from:

(structures shown above)

In a further aspect, $Ar^1$ is a structure having a formula:

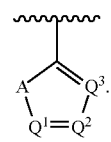

In a further aspect, $Ar^1$ is a structure having a formula selected from:

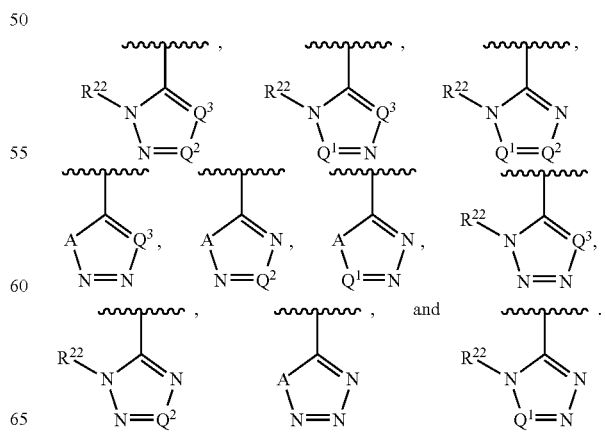

In a further aspect, Ar¹ is a structure having a formula selected from:

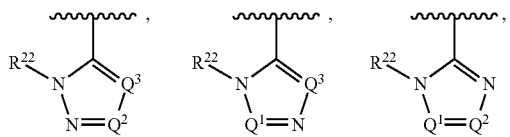

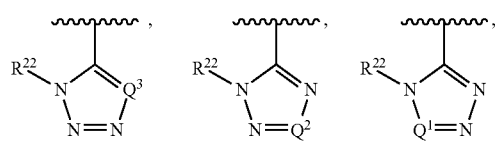

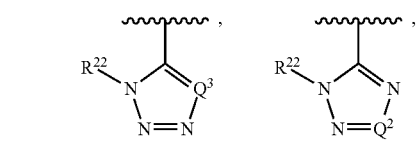

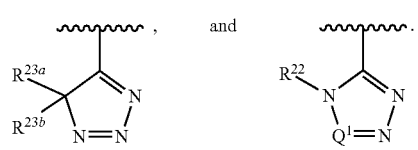

In a further aspect, Ar¹ is a structure having a formula selected from:

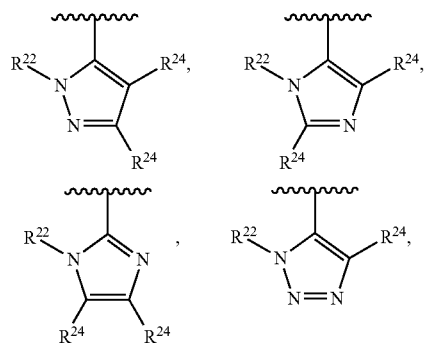

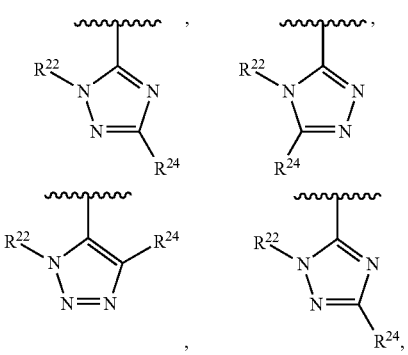

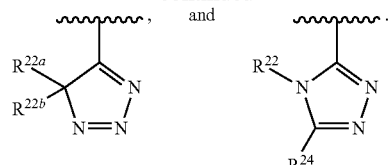

In a further aspect, Ar¹ is a structure having a formula:

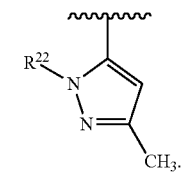

In a further aspect, Ar¹ is a structure having a formula:

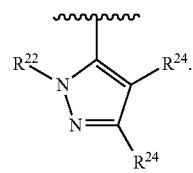

In a further aspect, Ar¹ is a structure having a formula selected from:

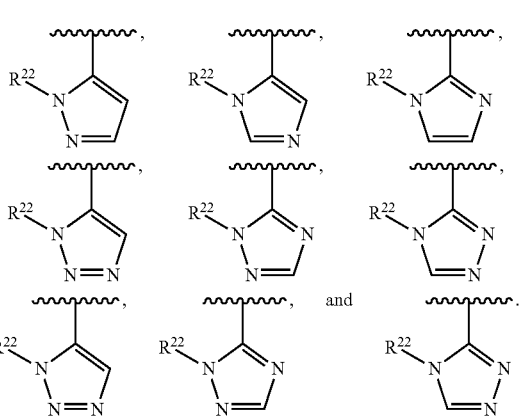

m. Ar² Groups

In one aspect, Ar², when present, is selected from C5-C6 aryl and C4-C5 heteroaryl and is substituted with 0, 1, or 2 groups independently selected from halogen, C1-C4 alkyl, C1-C4 monohaloalkyl, and C1-C4 polyhaloalkyl.

In a further aspect, Ar², when present, is C5-C6 aryl substituted with 0, 1, or 2 groups independently selected from halogen, C1-C4 alkyl, C1-C4 monohaloalkyl, and C1-C4 polyhaloalkyl. In a still further aspect, Ar², when present, is C5-C6 aryl substituted with 0 or 1 group selected from halogen, C1-C4 alkyl, C1-C4 monohaloalkyl, and C1-C4 polyhaloalkyl. In yet a further aspect, Ar², when present, is C5-C6 aryl monosubstituted with a group selected from halogen, C1-C4 alkyl, C1-C4 monohaloalkyl, and C1-C4 polyhaloalkyl. In an even further aspect, Ar², when present, is unsubstituted C5-C6 aryl.

In a further aspect, $Ar^2$, when present, is phenyl substituted with 0, 1, or 2 groups independently selected from halogen, C1-C4 alkyl, C1-C4 monohaloalkyl, and C1-C4 polyhaloalkyl. In a still further aspect, $Ar^2$, when present, is phenyl substituted with 0 or 1 group selected from halogen, C1-C4 alkyl, C1-C4 monohaloalkyl, and C1-C4 polyhaloalkyl. In yet a further aspect, $Ar^2$, when present, is phenyl monosubstituted with a group selected from halogen, C1-C4 alkyl, C1-C4 monohaloalkyl, and C1-C4 polyhaloalkyl. In an even further aspect, $Ar^2$, when present, is unsubstituted phenyl.

In a further aspect, $Ar^2$, when present, is C4-C5 heteroaryl substituted with 0, 1, or 2 groups independently selected from halogen, C1-C4 alkyl, C1-C4 monohaloalkyl, and C1-C4 polyhaloalkyl. In a still further aspect, $Ar^2$, when present, is C4-C5 heteroaryl substituted with 0 or 1 group selected from halogen, C1-C4 alkyl, C1-C4 monohaloalkyl, and C1-C4 polyhaloalkyl. In yet a further aspect, $Ar^2$, when present, is C4-C5 heteroaryl monosubstituted with a group selected from halogen, C1-C4 alkyl, C1-C4 monohaloalkyl, and C1-C4 polyhaloalkyl. In an even further aspect, $Ar^2$, when present, is unsubstituted C4-C5 heteroaryl.

In a further aspect, $Ar^2$, when present, is pyridinyl substituted with 0, 1, or 2 groups independently selected from halogen, C1-C4 alkyl, C1-C4 monohaloalkyl, and C1-C4 polyhaloalkyl. In a still further aspect, $Ar^2$, when present, is pyridinyl substituted with 0 or 1 group selected from halogen, C1-C4 alkyl, C1-C4 monohaloalkyl, and C1-C4 polyhaloalkyl. In yet a further aspect, $Ar^2$, when present, is pyridinyl monosubstituted with a group selected from halogen, C1-C4 alkyl, C1-C4 monohaloalkyl, and C1-C4 polyhaloalkyl. In an even further aspect, $Ar^2$, when present, is unsubstituted pyridinyl.

n. $Cy^1$ groups

In one aspect, $Cy^1$, when present, is selected from C3-C5 cycloalkyl and 2,3-dihydroindene and is substituted with 0, 1, or 2 groups independently selected from halogen, C1-C4 alkyl, C1-C4 monohaloalkyl, and C1-C4 polyhaloalkyl.

In a further aspect, $Cy^1$, when present, is C3-C5 cycloalkyl substituted with 0, 1, or 2 groups independently selected from halogen, C1-C4 alkyl, C1-C4 monohaloalkyl, and C1-C4 polyhaloalkyl. In a still further aspect, $Cy^1$, when present, is C3-C5 cycloalkyl substituted with 0 or 1 group selected from halogen, C1-C4 alkyl, C1-C4 monohaloalkyl, and C1-C4 polyhaloalkyl. In yet a further aspect, $Cy^1$, when present, is C3-C5 cycloalkyl monosubstituted with a group selected from halogen, C1-C4 alkyl, C1-C4 monohaloalkyl, and C1-C4 polyhaloalkyl. In an even further aspect, $Cy^1$, when present, is unsubstituted C3-C5 cycloalkyl.

In a further aspect, $Cy^1$, when present, is cyclopropyl substituted with 0, 1, or 2 groups independently selected from halogen, C1-C4 alkyl, C1-C4 monohaloalkyl, and C1-C4 polyhaloalkyl. In a still further aspect, $Cy^1$, when present, is cyclopropyl substituted with 0 or 1 group selected from halogen, C1-C4 alkyl, C1-C4 monohaloalkyl, and C1-C4 polyhaloalkyl. In yet a further aspect, $Cy^1$, when present, is cyclopropyl monosubstituted with a group selected from halogen, C1-C4 alkyl, C1-C4 monohaloalkyl, and C1-C4 polyhaloalkyl. In an even further aspect, $Cy^1$, when present, is unsubstituted cyclopropyl.

In a further aspect, $Cy^1$, when present, is cyclobutyl substituted with 0, 1, or 2 groups independently selected from halogen, C1-C4 alkyl, C1-C4 monohaloalkyl, and C1-C4 polyhaloalkyl. In a still further aspect, $Cy^1$, when present, is cyclobutyl substituted with 0 or 1 group selected from halogen, C1-C4 alkyl, C1-C4 monohaloalkyl, and C1-C4 polyhaloalkyl. In yet a further aspect, $Cy^1$, when present, is cyclobutyl monosubstituted with a group selected from halogen, C1-C4 alkyl, C1-C4 monohaloalkyl, and C1-C4 polyhaloalkyl. In an even further aspect, $Cy^1$, when present, is unsubstituted cyclobutyl.

In a further aspect, $Cy^1$, when present, is cyclopentyl substituted with 0, 1, or 2 groups independently selected from halogen, C1-C4 alkyl, C1-C4 monohaloalkyl, and C1-C4 polyhaloalkyl. In a still further aspect, $Cy^1$, when present, is cyclopentyl substituted with 0 or 1 group selected from halogen, C1-C4 alkyl, C1-C4 monohaloalkyl, and C1-C4 polyhaloalkyl. In yet a further aspect, $Cy^1$, when present, is cyclopentyl monosubstituted with a group selected from halogen, C1-C4 alkyl, C1-C4 monohaloalkyl, and C1-C4 polyhaloalkyl. In an even further aspect, $Cy^1$, when present, is unsubstituted cyclopentyl.

In a further aspect, $Cy^1$, when present, is 2,3-dihydroindene substituted with 0, 1, or 2 groups independently selected from halogen, C1-C4 alkyl, C1-C4 monohaloalkyl, and C1-C4 polyhaloalkyl. In a still further aspect, $Cy^1$, when present, is 2,3-dihydroindene substituted with 0 or 1 group selected from halogen, C1-C4 alkyl, C1-C4 monohaloalkyl, and C1-C4 polyhaloalkyl. In yet a further aspect, $Cy^1$, when present, is 2,3-dihydroindene monosubstituted with a group selected from halogen, C1-C4 alkyl, C1-C4 monohaloalkyl, and C1-C4 polyhaloalkyl. In an even further aspect, $Cy^1$, when present, is unsubstituted 2,3-dihydroindene.

o. $Cy^2$ Groups

In one aspect, $Cy^2$, when present, is selected from C3-C6 cycloalkyl, C2-C5 heterocycloalkyl, and 2,3-dihydroindene and is substituted with 0, 1, or 2 groups independently selected from halogen, C1-C4 alkyl, C1-C4 monohaloalkyl, and C1-C4 polyhaloalkyl.

In a further aspect, $Cy^2$, when present, is selected from C3-C6 cycloalkyl and 2,3-dihydroindene and is substituted with 0, 1, or 2 groups independently selected from halogen, C1-C4 alkyl, C1-C4 monohaloalkyl, and C1-C4 polyhaloalkyl. In a still further aspect, $Cy^2$, when present, is selected from C3-C6 cycloalkyl and 2,3-dihydroindene and is substituted with 0 or 1 group selected from halogen, C1-C4 alkyl, C1-C4 monohaloalkyl, and C1-C4 polyhaloalkyl. In yet a further aspect, $Cy^2$, when present, is selected from C3-C6 cycloalkyl and 2,3-dihydroindene and is monosubstituted with a group selected from halogen, C1-C4 alkyl, C1-C4 monohaloalkyl, and C1-C4 polyhaloalkyl. In an even further aspect, $Cy^2$, when present, is selected from C3-C6 cycloalkyl and 2,3-dihydroindene and is unsubstituted.

In a further aspect, $Cy^2$, when present, is selected from C2-C5 heterocycloalkyl and 2,3-dihydroindene and is substituted with 0, 1, or 2 groups independently selected from halogen, C1-C4 alkyl, C1-C4 monohaloalkyl, and C1-C4 polyhaloalkyl. In a still further aspect, $Cy^2$, when present, is selected from C2-C5 heterocycloalkyl and 2,3-dihydroindene and is substituted with 0 or 1 group selected from halogen, C1-C4 alkyl, C1-C4 monohaloalkyl, and C1-C4 polyhaloalkyl. In yet a further aspect, $Cy^2$, when present, is selected from C2-C5 heterocycloalkyl and 2,3-dihydroindene and is monosubstituted with a group selected from halogen, C1-C4 alkyl, C1-C4 monohaloalkyl, and C1-C4 polyhaloalkyl. In an even further aspect, $Cy^2$, when present, is selected from C2-C5 heterocycloalkyl and 2,3-dihydroindene and is unsubstituted.

In a further aspect, $Cy^2$, when present, is C3-C6 cycloalkyl substituted with 0, 1, or 2 groups independently selected from halogen, C1-C4 alkyl, C1-C4 monohaloalkyl, and C1-C4 polyhaloalkyl. In a still further aspect, $Cy^2$, when present, is C3-C6 cycloalkyl substituted with 0 or 1 group selected from halogen, C1-C4 alkyl, C1-C4 monohaloalkyl, and C1-C4 polyhaloalkyl. In yet a further aspect, $Cy^2$, when present, is C3-C6 cycloalkyl monosubstituted with a group selected from halogen, C1-C4 alkyl, C1-C4 monohaloalkyl, and C1-C4 polyhaloalkyl. In an even further aspect, $Cy^2$, when present, is unsubstituted C3-C6 cycloalkyl.

In a further aspect, $Cy^2$, when present, is cyclopropyl substituted with 0, 1, or 2 groups independently selected from halogen, C1-C4 alkyl, C1-C4 monohaloalkyl, and C1-C4 polyhaloalkyl. In a still further aspect, $Cy^2$, when present, is cyclopropyl substituted with 0 or 1 group selected from halogen, C1-C4 alkyl, C1-C4 monohaloalkyl, and C1-C4 polyhaloalkyl. In yet a further aspect, $Cy^2$, when present, is cyclopropyl monosubstituted with a group selected from halogen, C1-C4 alkyl, C1-C4 monohaloalkyl, and C1-C4 polyhaloalkyl. In an even further aspect, $Cy^2$, when present, is unsubstituted cyclopropyl.

In a further aspect, $Cy^2$, when present, is cyclobutyl substituted with 0, 1, or 2 groups independently selected from halogen, C1-C4 alkyl, C1-C4 monohaloalkyl, and C1-C4 polyhaloalkyl. In a still further aspect, $Cy^2$, when present, is cyclobutyl substituted with 0 or 1 group selected from halogen, C1-C4 alkyl, C1-C4 monohaloalkyl, and C1-C4 polyhaloalkyl. In yet a further aspect, $Cy^2$, when present, is cyclobutyl monosubstituted with a group selected from halogen, C1-C4 alkyl, C1-C4 monohaloalkyl, and C1-C4 polyhaloalkyl. In an even further aspect, $Cy^2$, when present, is unsubstituted cyclobutyl.

In a further aspect, $Cy^2$, when present, is cyclopentyl substituted with 0, 1, or 2 groups independently selected from halogen, C1-C4 alkyl, C1-C4 monohaloalkyl, and C1-C4 polyhaloalkyl. In a still further aspect, $Cy^2$, when present, is cyclopentyl substituted with 0 or 1 group selected from halogen, C1-C4 alkyl, C1-C4 monohaloalkyl, and C1-C4 polyhaloalkyl. In yet a further aspect, $Cy^2$, when present, is cyclopentyl monosubstituted with a group selected from halogen, C1-C4 alkyl, C1-C4 monohaloalkyl, and C1-C4 polyhaloalkyl. In an even further aspect, $Cy^2$, when present, is unsubstituted cyclopentyl.

In a further aspect, $Cy^2$, when present, is cyclohexyl substituted with 0, 1, or 2 groups independently selected from halogen, C1-C4 alkyl, C1-C4 monohaloalkyl, and C1-C4 polyhaloalkyl. In a still further aspect, $Cy^2$, when present, is cyclohexyl substituted with 0 or 1 group selected from halogen, C1-C4 alkyl, C1-C4 monohaloalkyl, and C1-C4 polyhaloalkyl. In yet a further aspect, $Cy^2$, when present, is cyclohexyl monosubstituted with a group selected from halogen, C1-C4 alkyl, C1-C4 monohaloalkyl, and C1-C4 polyhaloalkyl. In an even further aspect, $Cy^2$, when present, is unsubstituted cyclohexyl.

In a further aspect, $Cy^2$, when present, is C2-C5 heterocycloalkyl substituted with 0, 1, or 2 groups independently selected from halogen, C1-C4 alkyl, C1-C4 monohaloalkyl, and C1-C4 polyhaloalkyl. In a still further aspect, $Cy^2$, when present, is C2-C5 heterocycloalkyl substituted with 0 or 1 group selected from halogen, C1-C4 alkyl, C1-C4 monohaloalkyl, and C1-C4 polyhaloalkyl. In yet a further aspect, $Cy^2$, when present, is C2-C5 heterocycloalkyl monosubstituted with a group selected from halogen, C1-C4 alkyl, C1-C4 monohaloalkyl, and C1-C4 polyhaloalkyl. In an even further aspect, $Cy^2$, when present, is unsubstituted C2-C5 heterocycloalkyl.

In a further aspect, $Cy^2$, when present, is selected from oxirane, oxetane, azetidine, aziridine, piperidine, pyrrolidine, tetrahydro-2H-pyran, tetrahydro-2H-thiopyran, tetrahydrofuran, tetrahydrothiophene, thietane, thiirane, and morpholine and is substituted with 0, 1, or 2 groups independently selected from halogen, C1-C4 alkyl, C1-C4 monohaloalkyl, and C1-C4 polyhaloalkyl. In a still further aspect, $Cy^2$, when present, is selected from oxirane, oxetane, azetidine, aziridine, piperidine, pyrrolidine, tetrahydro-2H-pyran, tetrahydro-2H-thiopyran, tetrahydrofuran, tetrahydrothiophene, thietane, thiirane, and morpholine and is substituted with 0 or 1 group selected from halogen, C1-C4 alkyl, C1-C4 monohaloalkyl, and C1-C4 polyhaloalkyl. In yet a further aspect, $Cy^2$, when present, is selected from oxirane, oxetane, azetidine, aziridine, piperidine, pyrrolidine, tetrahydro-2H-pyran, tetrahydro-2H-thiopyran, tetrahydrofuran, tetrahydrothiophene, thietane, thiirane, and morpholine and is monosubstituted with a group selected from halogen, C1-C4 alkyl, C1-C4 monohaloalkyl, and C1-C4 polyhaloalkyl. In an even further aspect, $Cy^2$, when present, is selected from oxirane, oxetane, azetidine, aziridine, piperidine, pyrrolidine, tetrahydro-2H-pyran, tetrahydro-2H-thiopyran, tetrahydrofuran, tetrahydrothiophene, thietane, thiirane, and morpholine and is unsubstituted.

In a further aspect, $Cy^2$, when present, is 2,3-dihydroindene substituted with 0, 1, or 2 groups independently selected from halogen, C1-C4 alkyl, C1-C4 monohaloalkyl, and C1-C4 polyhaloalkyl. In a still further aspect, $Cy^2$, when present, is 2,3-dihydroindene substituted with 0 or 1 group selected from halogen, C1-C4 alkyl, C1-C4 monohaloalkyl, and C1-C4 polyhaloalkyl. In yet a further aspect, $Cy^2$, when present, is 2,3-dihydroindene monosubstituted with a group selected from halogen, C1-C4 alkyl, C1-C4 monohaloalkyl, and C1-C4 polyhaloalkyl. In an even further aspect, $Cy^2$, when present, is unsubstituted 2,3-dihydroindene.

p. $Cy^3$ Groups

In one aspect, each occurrence of $Cy^3$, when present, is independently selected from C3-C6 cycloalkyl and C2-C5 heterocycloalkyl and substituted with 0, 1, or 2 groups independently selected from halogen, C1-C4 alkyl, C1-C4 monohaloalkyl, and C1-C4 polyhaloalkyl.

In a further aspect, $Cy^3$, when present, is C3-C6 cycloalkyl substituted with 0, 1, or 2 groups independently selected from halogen, C1-C4 alkyl, C1-C4 monohaloalkyl, and C1-C4 polyhaloalkyl. In a still further aspect, $Cy^3$, when present, is C3-C6 cycloalkyl substituted with 0 or 1 group selected from halogen, C1-C4 alkyl, C1-C4 monohaloalkyl, and C1-C4 polyhaloalkyl. In yet a further aspect, $Cy^3$, when present, is C3-C6 cycloalkyl monosubstituted with a group selected from halogen, C1-C4 alkyl, C1-C4 monohaloalkyl, and C1-C4 polyhaloalkyl. In an even further aspect, $Cy^3$, when present, is unsubstituted C3-C6 cycloalkyl.

In a further aspect, $Cy^3$, when present, is cyclopropyl substituted with 0, 1, or 2 groups independently selected from halogen, C1-C4 alkyl, C1-C4 monohaloalkyl, and C1-C4 polyhaloalkyl. In a still further aspect, $Cy^3$, when present, is cyclopropyl substituted with 0 or 1 group selected from halogen, C1-C4 alkyl, C1-C4 monohaloalkyl, and C1-C4 polyhaloalkyl. In yet a further aspect, $Cy^3$, when present, is cyclopropyl monosubstituted with a group selected from halogen, C1-C4 alkyl, C1-C4 monohaloalkyl, and C1-C4 polyhaloalkyl. In an even further aspect, $Cy^3$, when present, is unsubstituted cyclopropyl.

In a further aspect, Cy³, when present, is cyclobutyl substituted with 0, 1, or 2 groups independently selected from halogen, C1-C4 alkyl, C1-C4 monohaloalkyl, and C1-C4 polyhaloalkyl. In a still further aspect, Cy³, when present, is cyclobutyl substituted with 0 or 1 group selected from halogen, C1-C4 alkyl, C1-C4 monohaloalkyl, and C1-C4 polyhaloalkyl. In yet a further aspect, Cy³, when present, is cyclobutyl monosubstituted with a group selected from halogen, C1-C4 alkyl, C1-C4 monohaloalkyl, and C1-C4 polyhaloalkyl. In an even further aspect, Cy³, when present, is unsubstituted cyclobutyl.

In a further aspect, Cy³, when present, is cyclopentyl substituted with 0, 1, or 2 groups independently selected from halogen, C1-C4 alkyl, C1-C4 monohaloalkyl, and C1-C4 polyhaloalkyl. In a still further aspect, Cy³, when present, is cyclopentyl substituted with 0 or 1 group selected from halogen, C1-C4 alkyl, C1-C4 monohaloalkyl, and C1-C4 polyhaloalkyl. In yet a further aspect, Cy³, when present, is cyclopentyl monosubstituted with a group selected from halogen, C1-C4 alkyl, C1-C4 monohaloalkyl, and C1-C4 polyhaloalkyl. In an even further aspect, Cy³, when present, is unsubstituted cyclopentyl.

In a further aspect, Cy³, when present, is cyclohexyl substituted with 0, 1, or 2 groups independently selected from halogen, C1-C4 alkyl, C1-C4 monohaloalkyl, and C1-C4 polyhaloalkyl. In a still further aspect, Cy³, when present, is cyclohexyl substituted with 0 or 1 group selected from halogen, C1-C4 alkyl, C1-C4 monohaloalkyl, and C1-C4 polyhaloalkyl. In yet a further aspect, Cy³, when present, is cyclohexyl monosubstituted with a group selected from halogen, C1-C4 alkyl, C1-C4 monohaloalkyl, and C1-C4 polyhaloalkyl. In an even further aspect, Cy³, when present, is unsubstituted cyclohexyl.

In a further aspect, Cy³, when present, is C2-C5 heterocycloalkyl substituted with 0, 1, or 2 groups independently selected from halogen, C1-C4 alkyl, C1-C4 monohaloalkyl, and C1-C4 polyhaloalkyl. In a still further aspect, Cy³, when present, is C2-C5 heterocycloalkyl substituted with 0 or 1 group selected from halogen, C1-C4 alkyl, C1-C4 monohaloalkyl, and C1-C4 polyhaloalkyl. In yet a further aspect, Cy³, when present, is C2-C5 heterocycloalkyl monosubstituted with a group selected from halogen, C1-C4 alkyl, C1-C4 monohaloalkyl, and C1-C4 polyhaloalkyl. In an even further aspect, Cy³, when present, is unsubstituted C2-C5 heterocycloalkyl.

In a further aspect, Cy³, when present, is selected from oxirane, oxetane, azetidine, aziridine, piperidine, pyrrolidine, tetrahydro-2H-pyran, tetrahydro-2H-thiopyran, tetrahydrofuran, tetrahydrothiophene, thietane, thiirane, and morpholine and is substituted with 0, 1, or 2 groups independently selected from halogen, C1-C4 alkyl, C1-C4 monohaloalkyl, and C1-C4 polyhaloalkyl. In a still further aspect, Cy³, when present, is selected from oxirane, oxetane, azetidine, aziridine, piperidine, pyrrolidine, tetrahydro-2H-pyran, tetrahydro-2H-thiopyran, tetrahydrofuran, tetrahydrothiophene, thietane, thiirane, and morpholine and is substituted with 0 or 1 group selected from halogen, C1-C4 alkyl, C1-C4 monohaloalkyl, and C1-C4 polyhaloalkyl. In yet a further aspect, Cy³, when present, is selected from oxirane, oxetane, azetidine, aziridine, piperidine, pyrrolidine, tetrahydro-2H-pyran, tetrahydro-2H-thiopyran, tetrahydrofuran, tetrahydrothiophene, thietane, thiirane, and morpholine and is monosubstituted with a group selected from halogen, C1-C4 alkyl, C1-C4 monohaloalkyl, and C1-C4 polyhaloalkyl. In an even further aspect, Cy³, when present, is selected from oxirane, oxetane, azetidine, aziridine, piperidine, pyrrolidine, tetrahydro-2H-pyran, tetrahydro-2H-thiopyran, tetrahydrofuran, tetrahydrothiophene, thietane, thiirane, and morpholine and is unsubstituted.

2. Example Compounds

In one aspect, a compound can be present as one or more of the following structures:

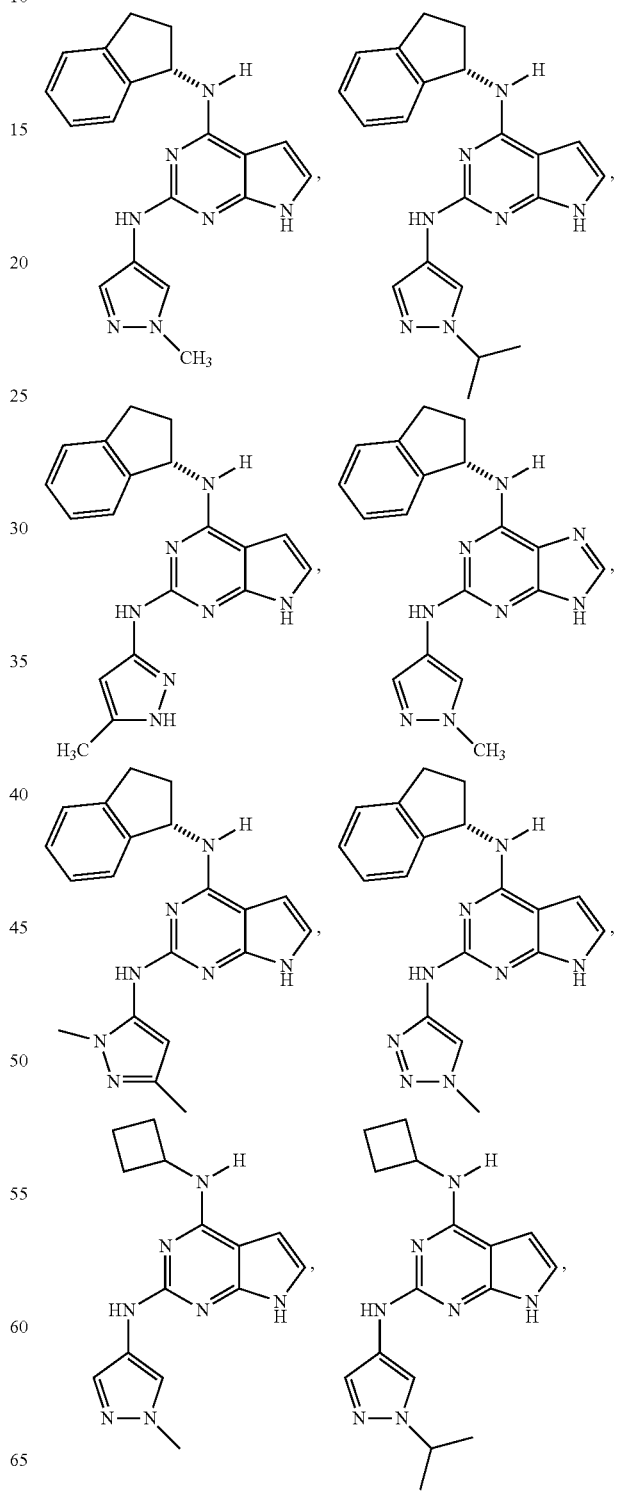

71
-continued
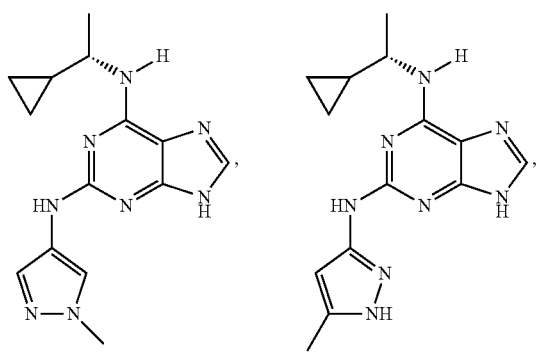
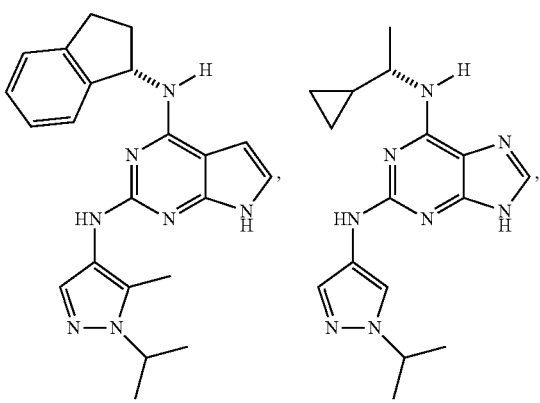
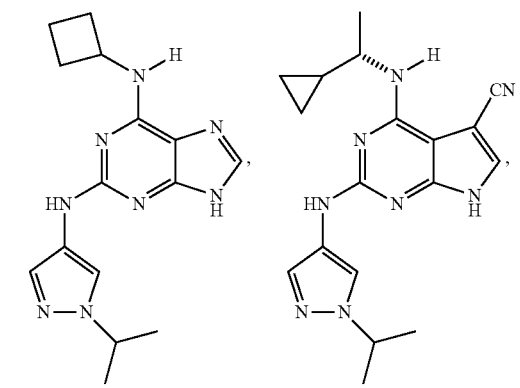
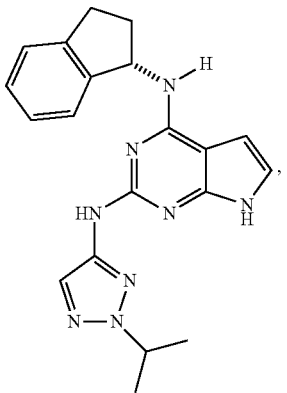
72
-continued
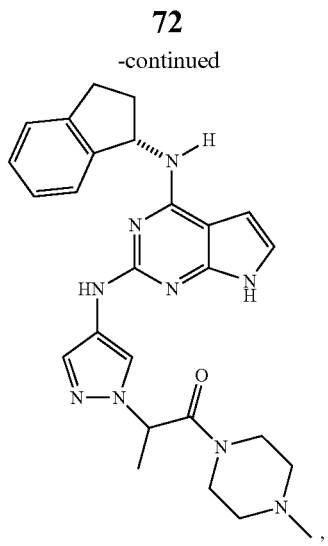
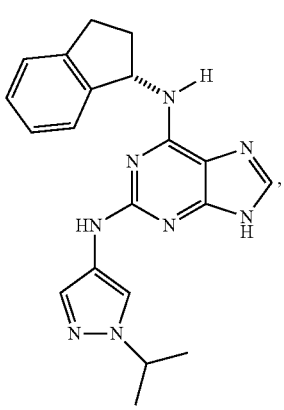
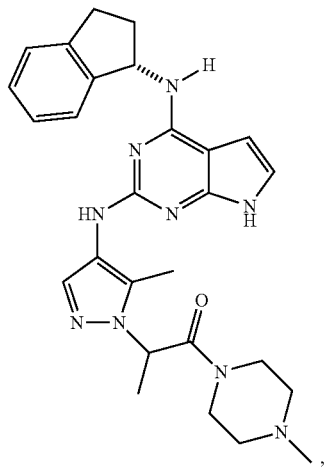

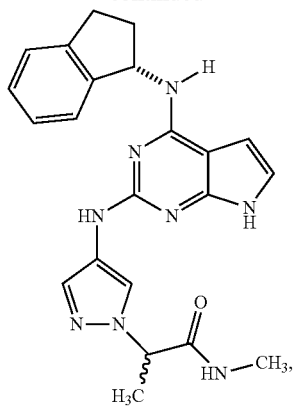
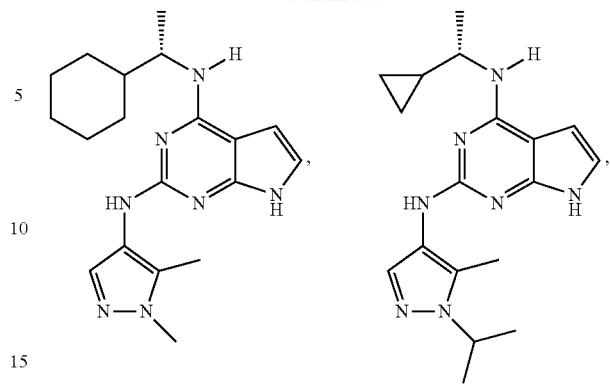
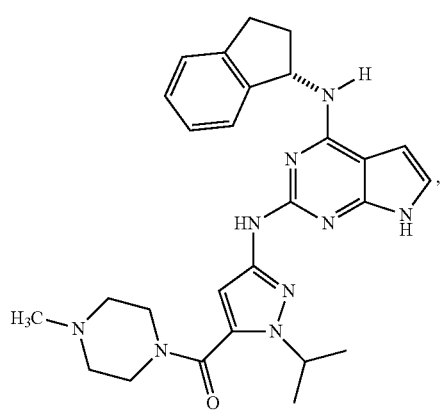
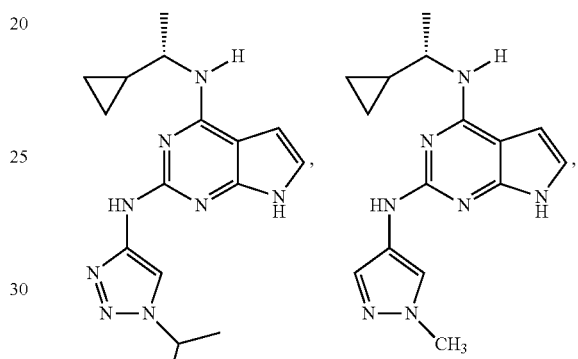
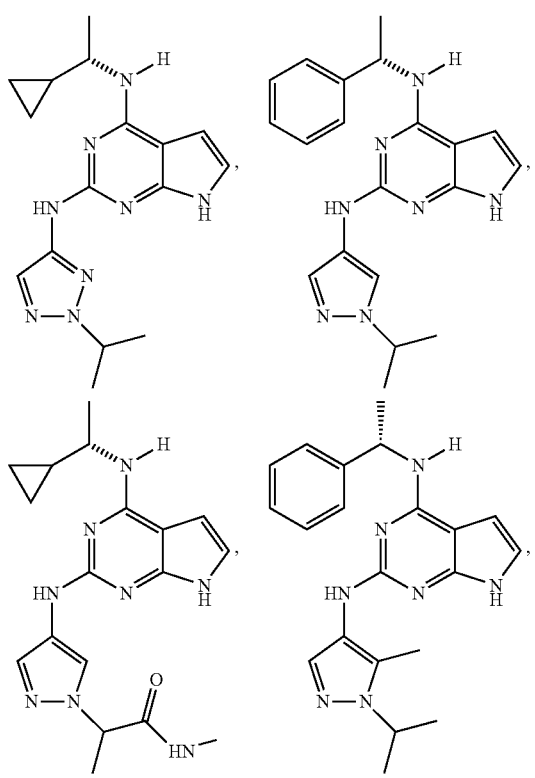
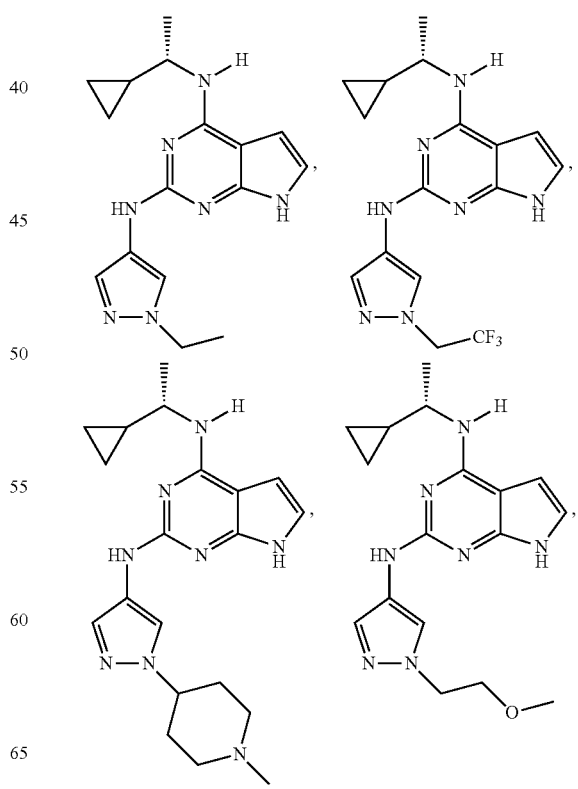

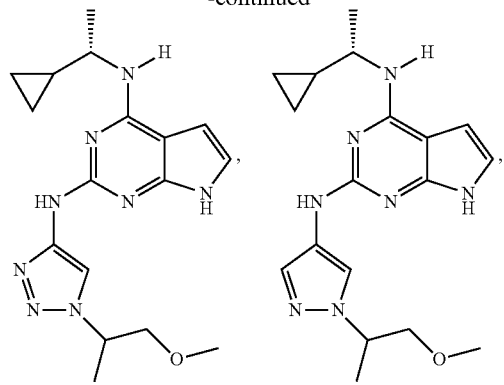
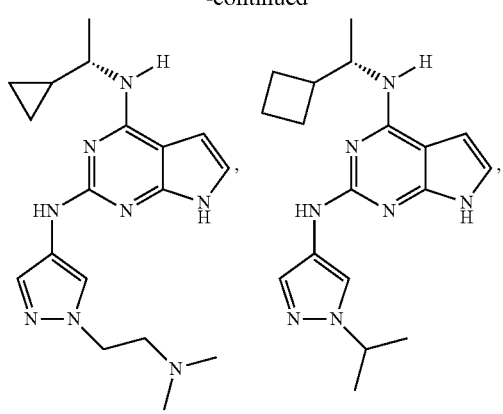
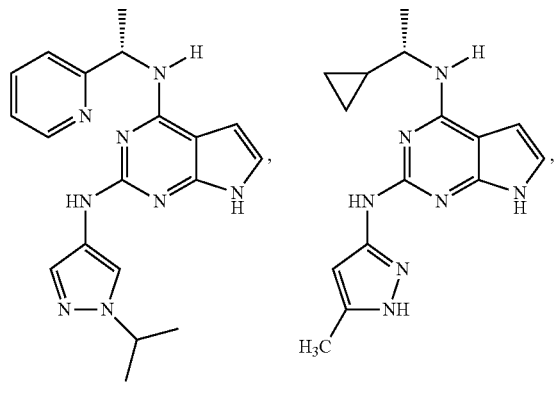
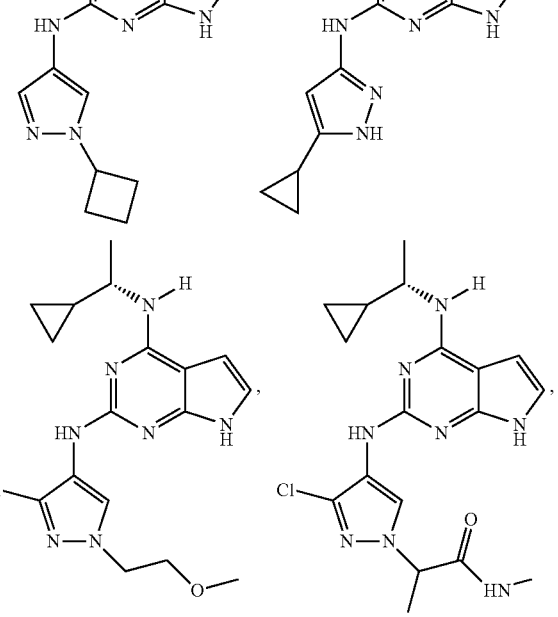
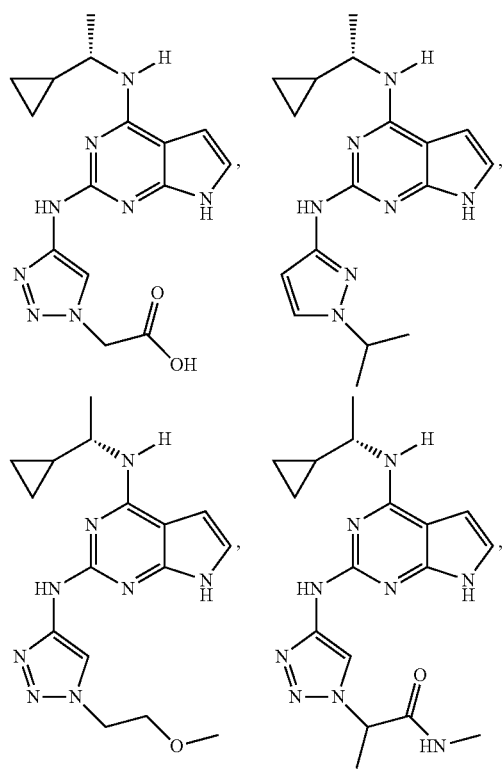
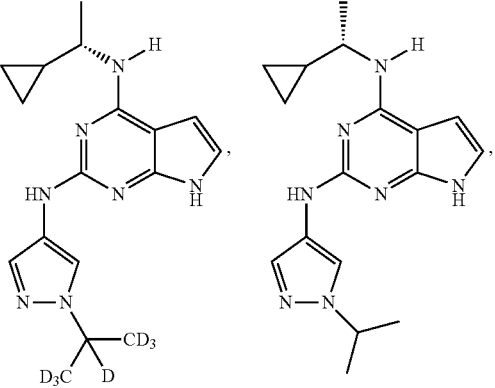

77
-continued
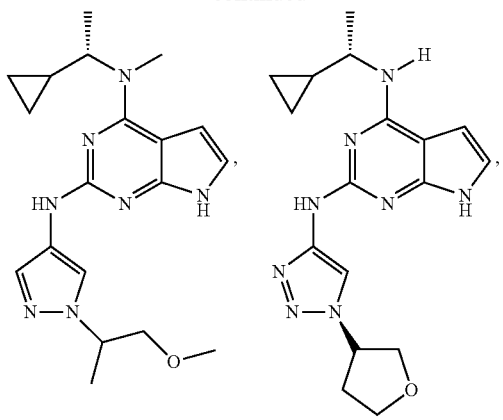
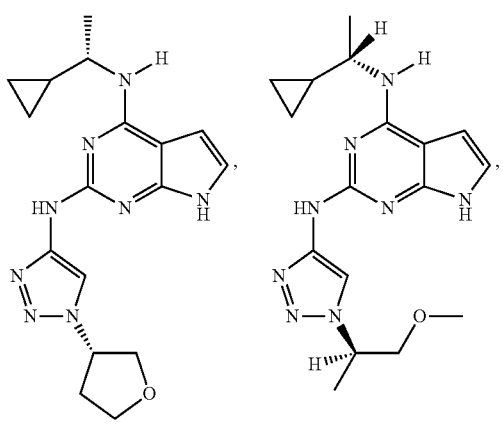
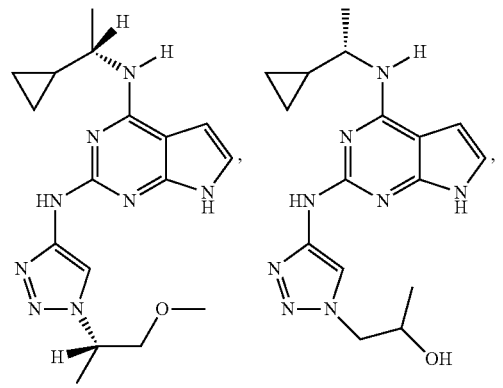
78
-continued
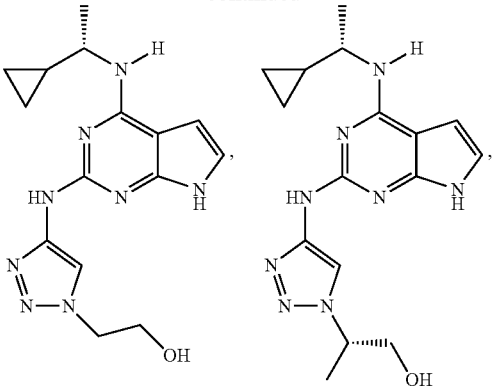
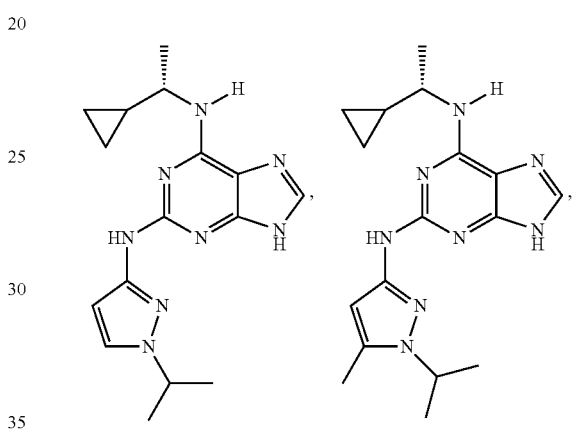
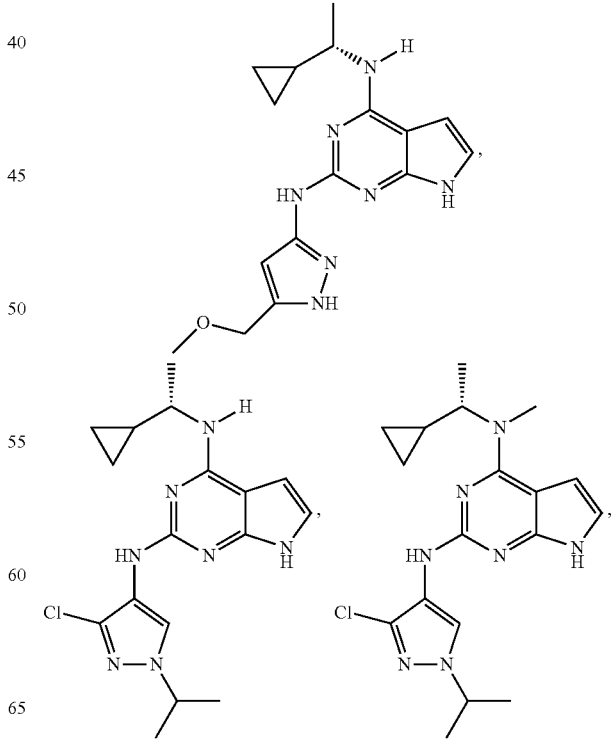

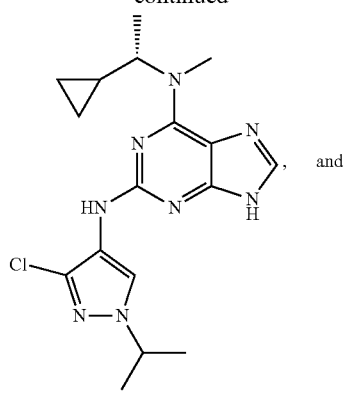

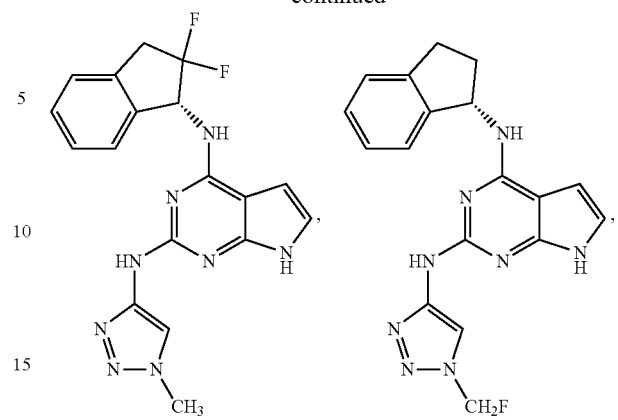

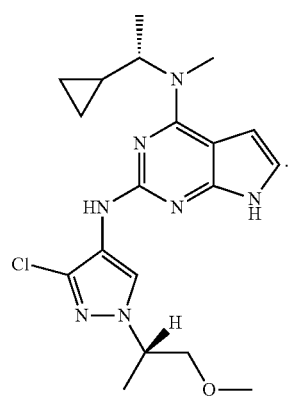 [SMILES: COC[C@H](C)n1cc(Nc2nc(N(C)[C@@H](C)C3CC3)c3cc[nH]c3n2)c(Cl)n1]

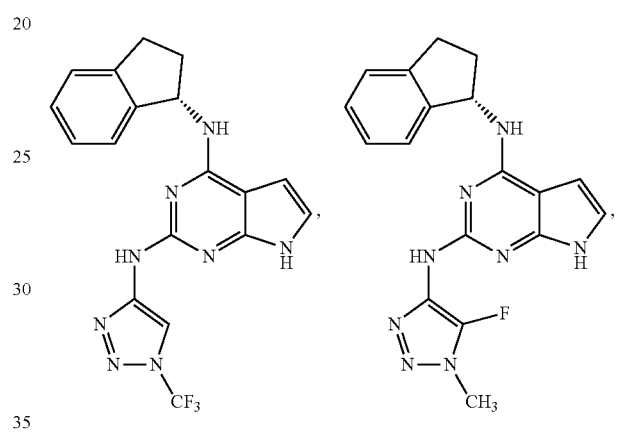

3. Prophetic Compound Examples

The following compound examples are prophetic, and can be prepared using the synthesis methods described herein above and other general methods as needed as would be known to one skilled in the art. It is anticipated that the prophetic compounds would be active as LRRK2 antagonists, and such activity can be determined using the assay methods described herein.

In one aspect, a compound can be selected from:

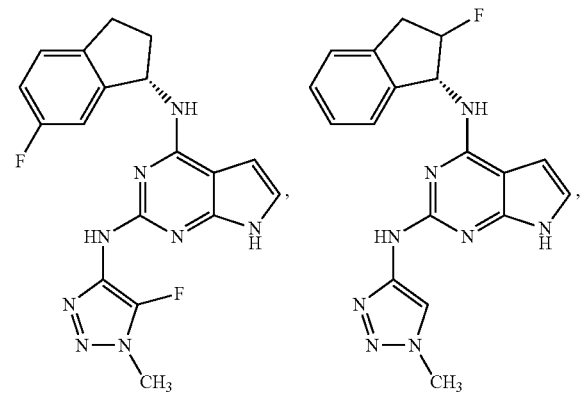

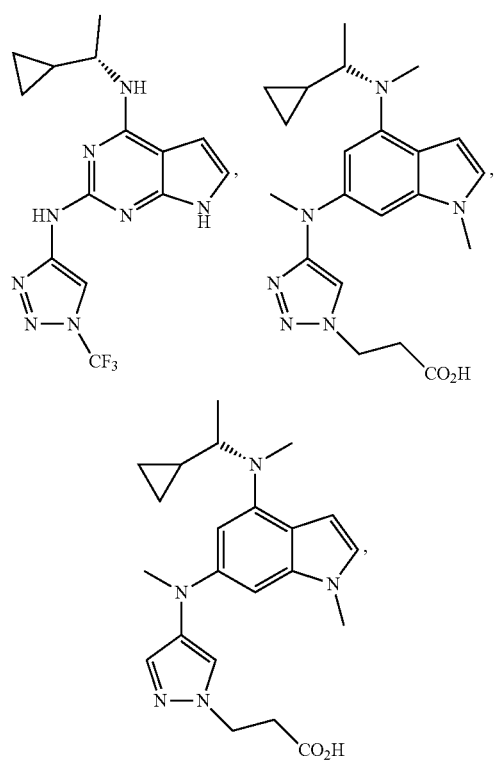

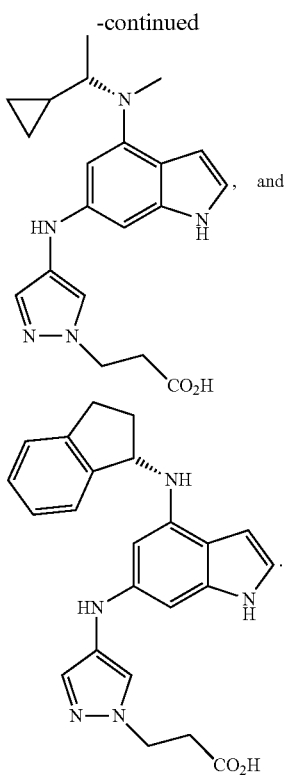

C. PHARMACEUTICAL COMPOSITIONS

In one aspect, the invention relates to pharmaceutical compositions comprising at least one disclosed compound and a pharmaceutically acceptable carrier. In a further aspect, a pharmaceutical composition can be provided comprising a therapeutically effective amount of at least one disclosed compound. In a still further aspect, a pharmaceutical composition can be provided comprising a prophylactically effective amount of at least one disclosed compound. In yet a further aspect, the invention relates to pharmaceutical compositions comprising a pharmaceutically acceptable carrier and a compound, wherein the compound is present in an effective amount.

The compounds are active against LRRK2, and generally have $IC_{50}$ values against LRRK2 ranging from 0.001 µM to 0.1 µM. $IC_{50}$ refers to the concentration of the compound that is required for 50% antagonism or inhibition of LRRK2. $IC_{50}$ also refers to the concentration of a substance that is required for 50% antagonism or inhibition of LRRK2 in vivo. The activity of the compounds, including $IC_{50}$, is determined according to the procedures discussed below in the Examples section.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of a disorder associated with LRRK2 kinase dysfunction. In a still further aspect, the mammal has been diagnosed with a need for treatment of a disorder associated with LRRK2 dysfunction prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The pyrrolopyrimidine compounds of the present disclosure alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1, 3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

In a further aspect, the composition further comprises at least one agent known to treat a disorder associated with LRRK2 kinase dysfunction. In a still further aspect, at least one agent known to treat a disorder associated with LRRK2 kinase dysfunction is selected from neurodegenerative disorders, such as Parkinson's disease, cancer, autoimmune disorders, and leprosy.

In a further aspect, the composition further comprises at least one agent known to have a side effect of increasing the risk of a disorder associated with LRRK2 kinase dysfunction.

It is understood that the disclosed compositions can be prepared from the disclosed compounds. It is also understood that the disclosed compositions can be employed in the disclosed methods of using.

D. METHODS OF MAKING THE COMPOUNDS

In various aspects, the inventions relates to methods of making compounds useful to treat disorders associated with LRRK2 dysfunction. Thus, in one aspect, disclosed are methods of making compounds having a structure represented by a formula:

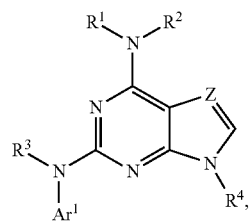

wherein Z is selected from N and CR$^{20}$; wherein each occurrence of R$^{20}$, when present, is independently selected from hydrogen, —CN, and C1-C4 alkyl; wherein R$^1$ is selected from $Cy^1$, $Ar^2$, $-CR^{21a}R^{21b}Cy^2$, and $-CR^{21a}R^{21b}Ar^2$; wherein each of $R^{21a}$ and $R^{21b}$, when present, are independently selected from hydrogen and C1-C4 alkyl; wherein $Cy^1$, when present, is selected from C3-C5 cycloalkyl and 2,3-dihydroindene and substituted with 0, 1, or 2 groups independently selected from halogen, C1-C4 alkyl, C1-C4 monohaloalkyl, and C1-C4 polyhaloalkyl; wherein $Cy^2$, when present, is selected from C3-C6 cycloalkyl, C2-C5 heterocycloalkyl, and 2,3-dihydroindene and substituted with 0, 1, or 2 groups independently selected from halogen, C1-C4 alkyl, C1-C4 monohaloalkyl, and C1-C4 polyhaloalkyl; wherein $Ar^2$, when present, is selected from C5-C6 aryl and C4-C5 heteroaryl and substituted with 0, 1, or 2 groups independently selected from halogen, C1-C4 alkyl, C1-C4 monohaloalkyl, and C1-C4 polyhaloalkyl; and wherein each of $R^2$, $R^3$, and $R^4$ are independently selected from hydrogen and C1-C4 alkyl; wherein $Ar^1$ is a structure selected from:

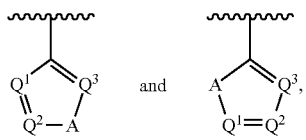

wherein A is selected from $NR^{22}$ and $CR^{23a}R^{23b}$; wherein $R^{22}$, when present, is selected from hydrogen, halogen, C1-C8 alkyl, C1-C8 monohaloalkyl, C1-C8 polyhaloalkyl, C1-C8 hydroxyalkyl, C1-C8 alkoxyalkyl, $-$(C1-C8 alkyl)$NH_2$, $-$(C1-C8 alkyl)NH(C1-C8alkyl), $-$(C1-C8 alkyl)N(C1-C8 alkyl)(C1-C8 alkyl), C1-C8 alkylacid, $-$(C1-C4 alkyl)$CONH_2$, $-$(C1-C4 alkyl)CONH(C1-C4 alkyl), $-$(C1-C4 alkyl)CON(C1-C4 alkyl)(C1-C4 alkyl), $-$(C1-C4 alkyl)(C=O)$Cy^3$, and $Cy^3$; wherein each occurrence of $Cy^3$, when present, is independently selected from C3-C6 cycloalkyl and C2-C5 heterocycloalkyl and substituted with 0, 1, or 2 groups independently selected from halogen, C1-C4 alkyl, C1-C4 monohaloalkyl, and C1-C4 polyhaloalkyl; wherein each of $R^{23a}$ and $R^{23b}$, when present, is independently selected from hydrogen, halogen, C1-C8 alkyl, C1-C8 monohaloalkyl, C1-C8 polyhaloalkyl, C1-C8 hydroxyalkyl, C1-C8 alkoxyalkyl, C1-C8 alkylacid, $-$(C1-C4 alkyl)(C=O)$Cy^1$, $-$(C1-C4 alkyl)$CONH_2$, $-$(C1-C4 alkyl)CONH(C1-C4 alkyl), $-$(C1-C4 alkyl)CON(C1-C4 alkyl)(C1-C4 alkyl), and $Cy^3$; wherein each of $Q^1$, $Q^2$, and $Q^3$ is independently selected from N and $CR^{24}$; and wherein each occurrence of $R^{24}$, when present, is independently selected from hydrogen, halogen, C1-C8 alkyl, C1-C8 monohaloalkyl, C1-C8 polyhaloalkyl, C1-C8 alkoxyalkyl, $-$(C1-C4 alkyl)$CONH_2$, $-$(C1-C4 alkyl)CONH(C1-C4 alkyl), $-$(C1-C4 alkyl)CON(C1-C4 alkyl)(C1-C4 alkyl), provided that two or three of A, $Q^1$, $Q^2$, and $Q^3$ are N, and provided that if $Ar^1$ is a structure represented by a formula:

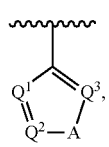

wherein each of Z, $Q^1$, and $Q^3$ are CH, $Q^2$ is N, A is $NR^{22}$, $R^{22}$ is C1-C8 alkyl, and each of $R^2$, $R^3$, and $R^4$ are hydrogen, then $R^1$ is selected from $Ar^2$, $-CR^{21a}R^{21b}Cy^2$, and $-CR^{21a}R^{21b}Ar^2$; or a pharmaceutically acceptable salt thereof.

In one aspect, disclosed are methods of making compounds having a structure represented by a formula:

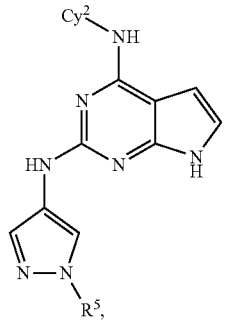

wherein $Cy^2$, when present, is selected from C3-C5 cycloalkyl and 2,3-dihydroindene and substituted with 0, 1, or 2 groups independently selected from halogen, C1-C4 alkyl, C1-C4 monohaloalkyl, and C1-C4 polyhaloalkyl; and wherein $R^5$ is C1-C8 alkyl, or a pharmaceutically acceptable salt thereof.

Compounds according to the present disclosure can, for example, be prepared by the several methods outlined below, in addition to other standard manipulations that are known in the literature, exemplified in the experimental sections or clear to one skilled in the art. For clarity, examples having a single substituent are shown where multiple substituents are allowed under the definitions disclosed herein. A practitioner skilled in the art will understand the appropriate use of protecting groups [see: Greene and Wuts, *Protective Groups in Organic Synthesis*] and the preparation of known compounds found in the literature using the standard methods of organic synthesis. There may come from time to time the need to rearrange the order of the recommended synthetic steps, however this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, substituted 1H-1,2,3-triazol-4-amines can be prepared as shown below.

SCHEME 1A.

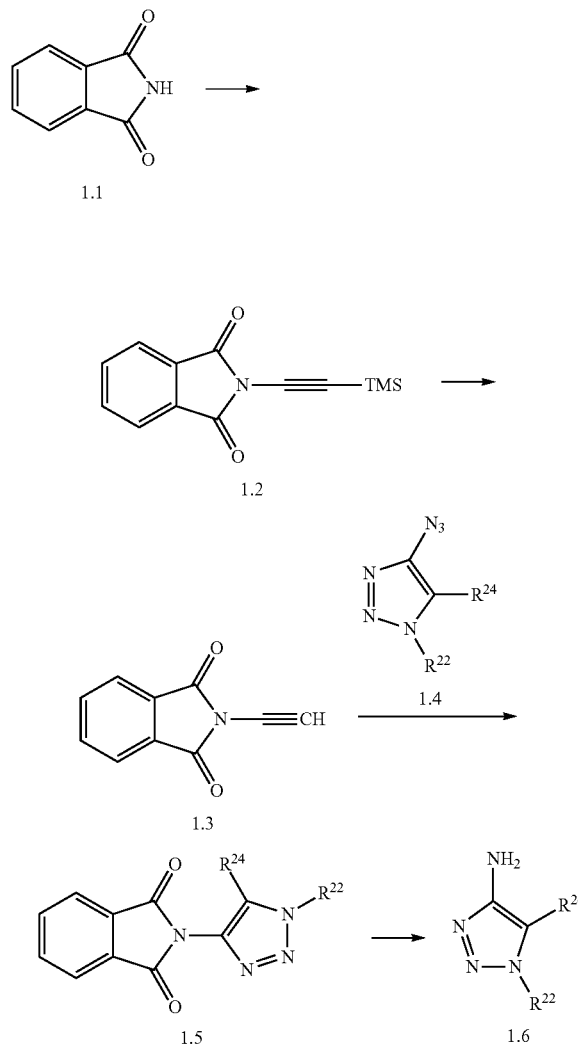

Compounds are represented in generic form, with substituents as noted in compound descriptions elsewhere herein. A more specific example is set forth below.

SCHEME 1B.

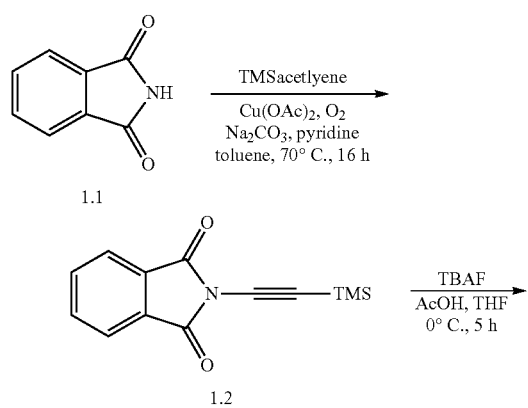

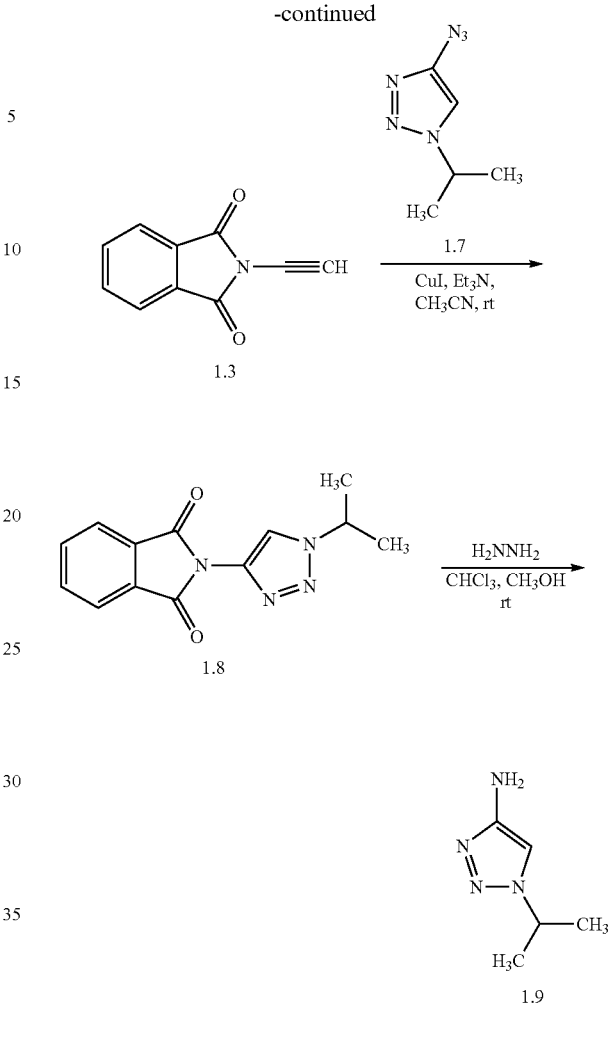

In one aspect, compounds of type 1.6, and similar compounds, can be prepared according to reaction Scheme 1B above. Thus, compounds of type 1.2 can be prepared by an alkylation reaction of an appropriate isoindoline-1,3-dione, e.g., 1.1 as shown above, and an appropriate alkyne, e.g., trimethylsilyl acetylene. Appropriate isoindoline-1,3-diones are commercially available or prepared by methods known to one skilled in the art. The alkylation reaction is carried out in the presence of an appropriate catalyst, e.g., copper (II) acetate, with an appropriate base, e.g., sodium carbonate, with an appropriate solvent, e.g., toluene, at an appropriate temperature, e.g., 70° C., for an appropriate period of time, e.g., 16 hours. Compounds of type 1.3 can be prepared by deprotection of an appropriate alkyne, e.g., 1.2 as shown above. The deprotection is carried out in the presence of an appropriate deprotecting agent, e.g., tetrabutylammonium fluoride, and an appropriate acid, e.g., acetic acid, in an appropriate solvent, e.g., tetrahydrofuran, at an appropriate temperature, e.g., 0° C., for an appropriate period of time, e.g., 5 hours. Compounds of type 1.8 can be prepared by a coupling reaction of an appropriate alkyne, e.g., 1.3 as shown above, and an appropriate azide, e.g., 1.7 as shown above. Appropriate azides are commercially available or prepared by methods known to one skilled in the art. The coupling reaction is carried out in the presence of an appropriate catalyst, e.g., copper iodide, and an appropriate base, e.g., triethylamine, in an appropriate solvent, e.g., acetonitrile. Compounds of type 1.9 can be prepared by deprotection of an appropriate phthalimide, e.g., 1.8 as shown above. The deprotection is carried out in the presence of an appropriate hydrazine, e.g., hydrazine, and an appropriate alkyl halide, e.g., trichloromethyl, in an appropriate protic solvent, e.g., methanol. As can be appreciated by one skilled in the art, the above reaction provides an example of a generalized approach wherein compounds similar in structure to the specific reactants above (compounds similar to compounds of type 1.1, 1.2, 1.3, 1.4, and 1.5), can be substituted in the reaction to provide substituted 1H-1,2,3-triazol-4-amines similar to Formula 1.6.

2. Route II

In one aspect, substituted 2-(4-amino-1H-pyrazol-1-yl) propan-1-ones can be prepared as shown below.

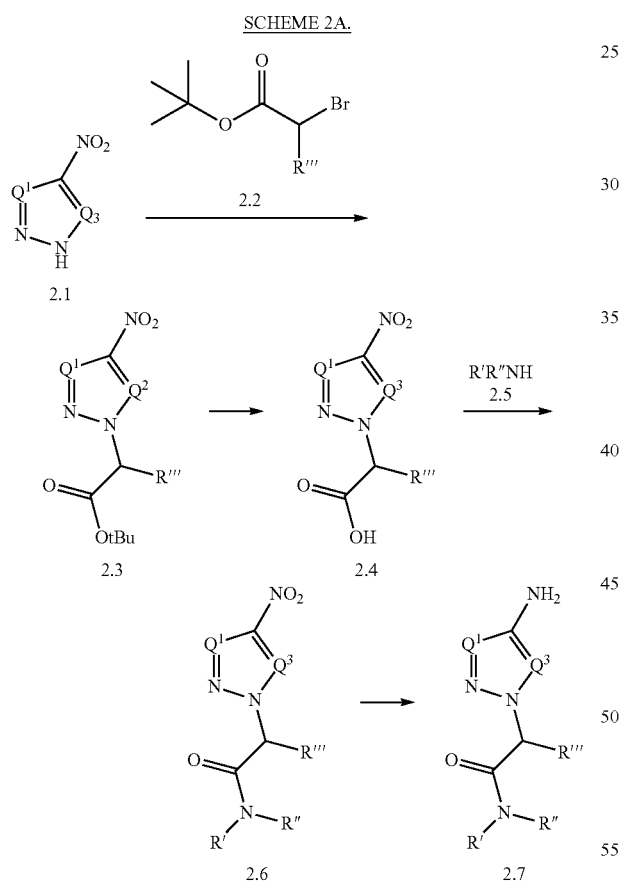

Compounds are represented in generic form, wherein each of R' and R" is independently selected from hydrogen and optionally substituted C1-C8 alkyl, or wherein each of R' and R", together with the intermediate atoms, comprise a 5- or 6-membered cycle or heterocycle, wherein R'" is selected from hydrogen and optionally substituted C1-C8 alkyl, and with additional substituents as noted in compound descriptions elsewhere herein. A more specific example is set forth below.

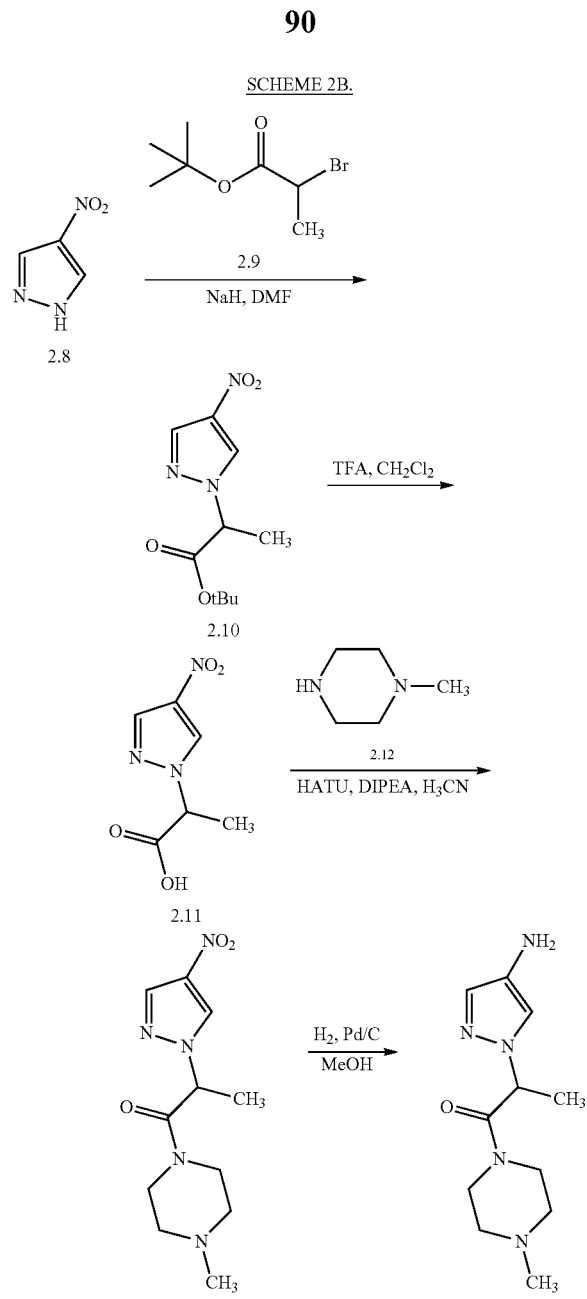

In one aspect, compounds of type 2.7, and similar compounds, can be prepared according to reaction Scheme 2B above. Thus, compounds of type 2.10 can be prepared by an alkylation reaction of an appropriate pyrazole, e.g., 2.8 as shown above, and an appropriate alkyl halide, e.g., 2.9 as shown above. Appropriate pyrazoles and appropriate alkyl halides are commercially available or prepared by methods known to one skilled in the art. The alkylation reaction is carried out in the presence of an appropriate base, e.g., sodium hydride, in an appropriate solvent, e.g., dimethylformamide. Compounds of type 2.11 can be prepared by reduction of an appropriate ester, e.g., 2.10 as shown above. The reduction is carried out in the presence of an appropriate acid, e.g., trifluoroacetic acid, in an appropriate solvent, e.g., dichloromethane. Compounds of type 2.13 can be prepared by a coupling reaction of an appropriate carboxylic acid, e.g., 2.11 as shown above, and an appropriate amine, e.g., 2.12 as shown above. Appropriate amines are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxide hexafluorophosphate (HATU), and an appropriate base, e.g., N,N-diisopropylethylamine (DIPEA), in an appropriate solvent, e.g., acetonitrile. Compounds of type 2.14 can be prepared by reduction of an appropriate nitro-pyrazole, e.g., 2.13 as shown above. The reduction is carried out in the presence of an appropriate hydride source, e.g., hydrogen gas, and an appropriate catalyst, e.g., Palladium on Carbon, in an appropriate protic solvent, e.g., methanol. As can be appreciated by one skilled in the art, the above reaction provides an example of a generalized approach wherein compounds similar in structure to the specific reactants above (compounds similar to compounds of type 2.1, 2.2, 2.3, 2.4, 2.5, and 2.6), can be substituted in the reaction to provide substituted 2-(4-amino-1H-pyrazol-1-yl)propan-1-ones similar to Formula 2.7.

3. Route III

In one aspect, substituted (3-amino-1H-pyrazol-5-yl)methanones can be prepared as shown below.

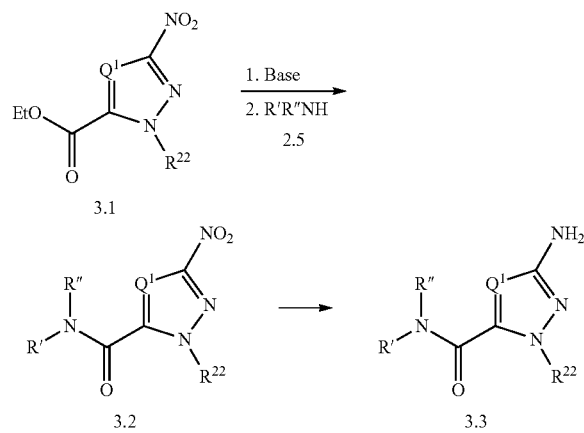

Compounds are represented in generic form, wherein each of R' and R" is independently selected from hydrogen and optionally substituted C1-C8 alkyl, or wherein each of R' and R", together with the intermediate atoms, comprise a 5- or 6-membered cycle or heterocycle, and with additional substituents as noted in compound descriptions elsewhere herein. A more specific example is set forth below.

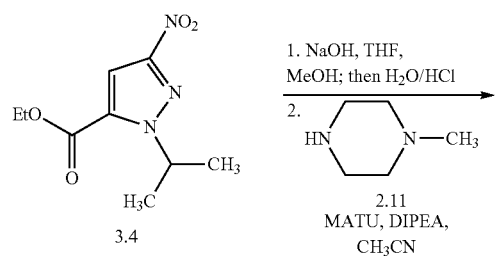

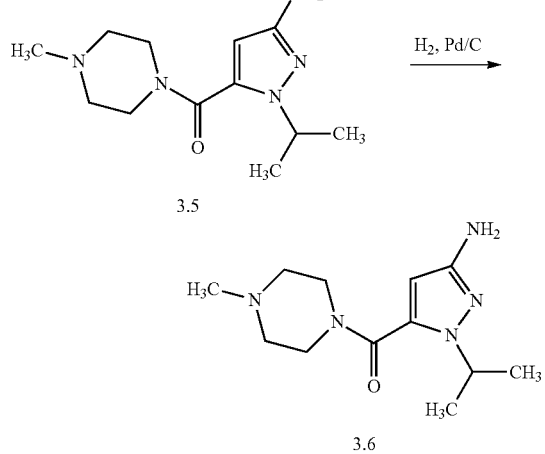

In one aspect, compounds of type 3.3, and similar compounds, can be prepared according to reaction Scheme 3B above. Thus, compounds of type 3.5 can be prepared by a reduction, followed by a coupling reaction, of an appropriate ester, e.g., 3.4 as shown above, and an appropriate amine, e.g., 2.11 as shown above. Appropriate esters and appropriate amines are commercially available or prepared by methods known to one skilled in the art. The reduction is carried out in the presence of an appropriate base, e.g., sodium hydroxide, in an appropriate protic solvent, e.g., methanol, followed by an acidic workup. The coupling reaction is carried out in the presence of an appropriate coupling agent, e.g., HATU, and an appropriate base, e.g., N,N-diisopropylethylamine (DIPEA), in an appropriate solvent, e.g., acetonitrile. Compounds of type 3.6 can be prepared by reduction of an appropriate nitro-pyrazole, e.g., 2.12 as shown above. The reduction is carried out in the presence of an appropriate hydride source, e.g., hydrogen gas, and an appropriate catalyst, e.g., Palladium on Carbon, in an appropriate protic solvent, e.g., methanol. As can be appreciated by one skilled in the art, the above reaction provides an example of a generalized approach wherein compounds similar in structure to the specific reactants above (compounds similar to compounds of type 2.5, 3.1, and 3.2), can be substituted in the reaction to provide substituted (3-amino-1H-pyrazol-5-yl)methanones similar to Formula 3.3.

4. Route IV

In one aspect, substituted 1H-pyrazol-4-amines can be prepared as shown below.

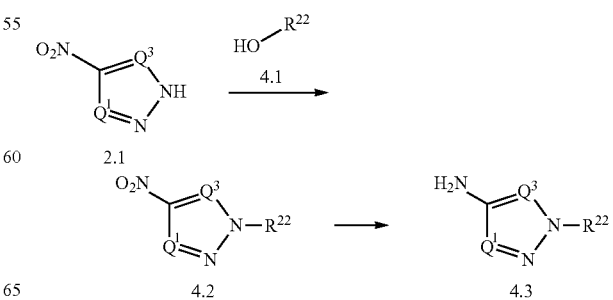

Compounds are represented in generic form, with additional substituents as noted in compound descriptions elsewhere herein. A more specific example is set forth below.

SCHEME 4B.

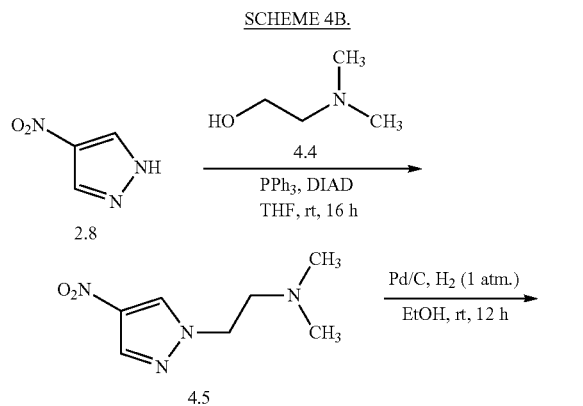

In one aspect, compounds of type 4.3, and similar compounds, can be prepared according to reaction Scheme 4B above. Thus, compounds of type 4.5 can be prepared by a coupling reaction of an appropriate pyrazole, e.g., 2.8 as shown above, and an appropriate alcohol, e.g., 4.4 as shown above. Appropriate pyrazoles and appropriate alcohols are commercially available or prepared by methods known to one skilled in the art. The coupling reaction is carried out in the presence of an appropriate coupling agent, e.g., triphenylphosphine and diisopropyl azodicarboxylate (DIAD), in an appropriate solvent, e.g., tetrahydrofuran. Compounds of type 4.6 can be prepared by reduction of an appropriate nitro-pyrazole, e.g., 4.5 as shown above. The reduction is carried out in the presence of an appropriate hydride source, e.g., hydrogen gas, and an appropriate catalyst, e.g., Palladium on Carbon, in an appropriate protic solvent, e.g., methanol. As can be appreciated by one skilled in the art, the above reaction provides an example of a generalized approach wherein compounds similar in structure to the specific reactants above (compounds similar to compounds of type 2.1, 4.1, and 4.2), can be substituted in the reaction to provide substituted 1H-pyrazol-4-amines similar to Formula 4.3.

5. Route V

In one aspect, 3-substituted 1H-pyrazol-4-amines can be prepared as shown below.

SCHEME 5A.

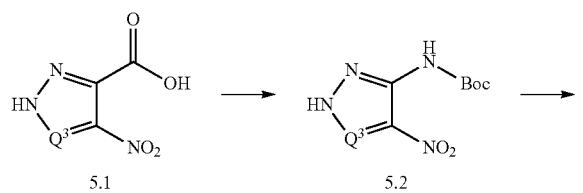

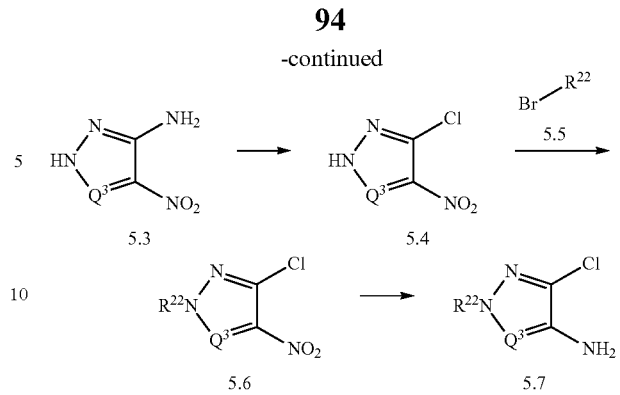

Compounds are represented in generic form, with additional substituents as noted in compound descriptions elsewhere herein. A more specific example is set forth below.

SCHEME 5B.

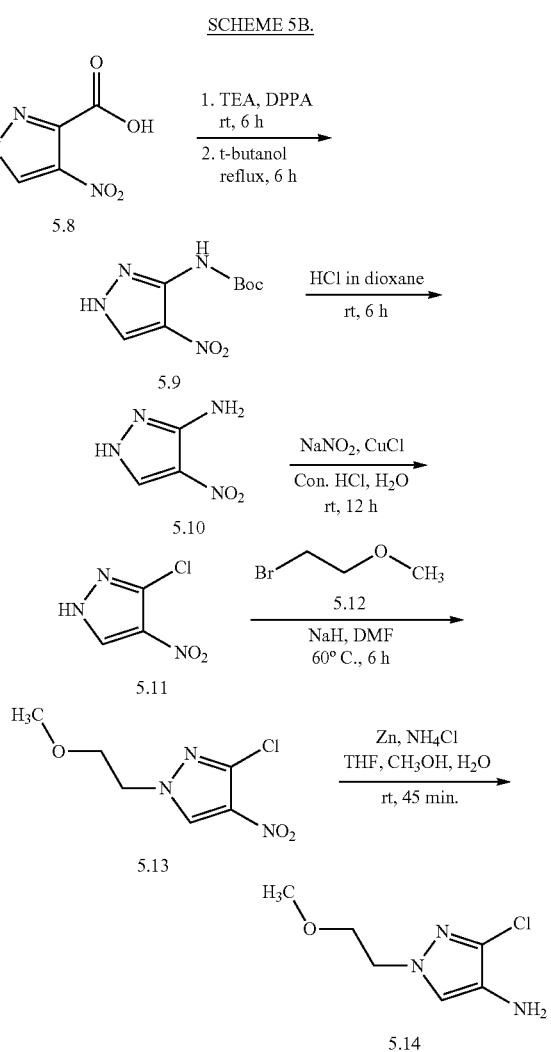

In one aspect, compounds of type 5.7, and similar compounds, can be prepared according to reaction Scheme 5B above. Thus, compounds of type 5.9 can be prepared by conversion of an appropriate carboxylic acid, e.g., 5.8 as shown above, to carbamate. Appropriate carboxylic acids are commercially available or prepared by methods known to one skilled in the art. The conversion reaction is carried out in the presence of an appropriate acyl azide, e.g., diphenylphosphoryl azide (DPPA), in an appropriate base, e.g., triethylamine, followed addition of an appropriate alcohol, e.g., t-butanol, at an appropriate temperature, e.g., reflux. Compounds of type 5.9 can be prepared by reduction of an appropriate carbamate, e.g., 5.9 as shown above. The reduction is carried out in the presence of an appropriate acid, e.g., hydrochloric acid, in an appropriate solvent, e.g., dioxane. Compounds of type 5.11 can be prepared by a substitution reaction of an appropriate amine, e.g., 5.10 as shown above. The coupling reaction is carried out in the presence of an appropriate halide salt, e.g., copper (II) chloride, and an appropriate salt, e.g., sodium nitrite, and an appropriate acid, e.g., concentrated hydrochloric acid. Compounds of type 5.13 can be prepared by alkylation of an appropriate pyrazole, e.g., 5.11 as shown above, with an appropriate alkyl halide, e.g., 512 as shown above. Appropriate alkyl halides are commercially available or prepared by methods known to one skilled in the art. The alkylation is carried out in the presence of an appropriate base, e.g., sodium hydride, in an appropriate solvent, e.g., dimethylformamide. Compounds of type 5.14 can be prepared by reduction of an appropriate nitro-pyrazole, e.g., 513 as shown above. The reduction is carried out in the presence of an appropriate metal, e.g., zinc dust, and an appropriate hydride source, e.g., ammonium chloride, and an appropriate protic solvent, e.g., methanol. As can be appreciated by one skilled in the art, the above reaction provides an example of a generalized approach wherein compounds similar in structure to the specific reactants above (compounds similar to compounds of type 5.1, 5.2, 5.3, 5.4, 5.5, and 5.6), can be substituted in the reaction to provide 3-substituted 1H-pyrazol-4-amines similar to Formula 5.7.

6. Route VI

In one aspect, substituted pyrrolopyrimidines can be prepared as shown below.

SCHEME 6A.

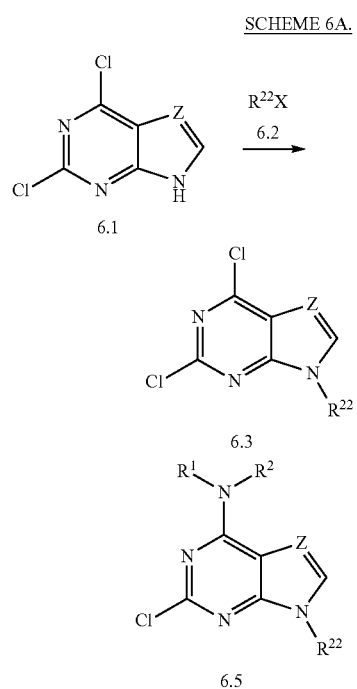

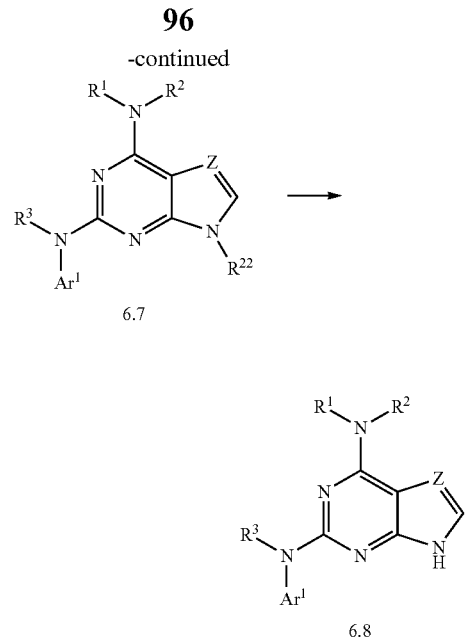

Compounds are represented in generic form, wherein X is halogen and with additional substituents as noted in compound descriptions elsewhere herein. A more specific example is set forth below.

SCHEME 6B.

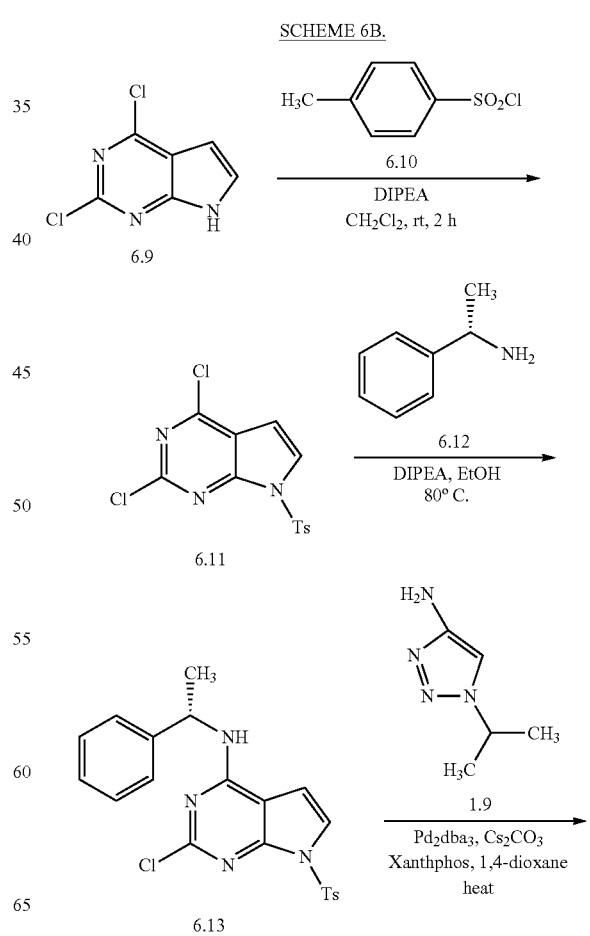

-continued

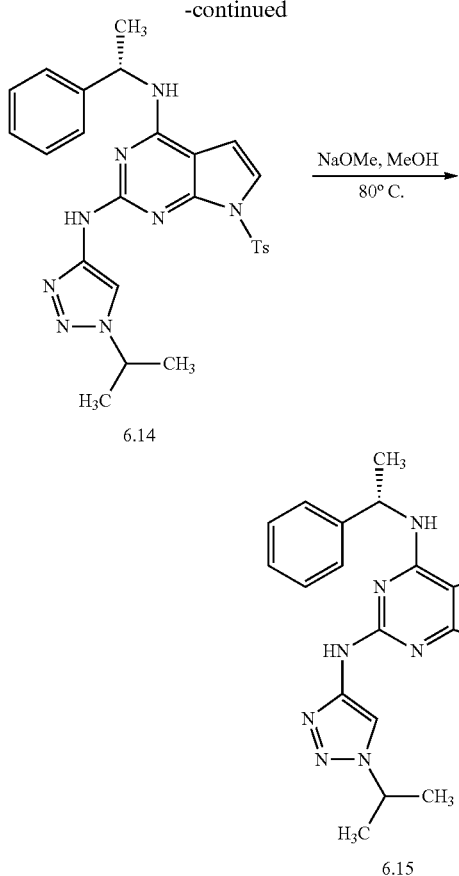

6.14

6.15

In one aspect, compounds of type 6.8, and similar compounds, can be prepared according to reaction Scheme 6B above. Thus, compounds of type 6.11 can be prepared by substitution of an appropriate pyrrolo[2,3-d]pyrimidine, e.g., 6.9 as shown above. Appropriate pyrrolo[2,3-d]pyrimidines are commercially available or prepared by methods known to one skilled in the art. The substitution is carried out in the presence of an appropriate halide, e.g., 6.10, in the presence of an appropriate base, e.g., DIPEA, in an appropriate solvent, e.g., dichloromethane. Compounds of type 6.13 can be prepared by a substitution reaction of an appropriate pyrrolo[2,3-d]pyrimidine, e.g., 6.11 as shown above, and an appropriate amine, e.g., 6.12 as shown above. Appropriate amines are commercially available or prepared by methods known to one skilled in the art. The substitution reaction is carried out in the presence of an appropriate base, e.g., DIPEA, in an appropriate protic solvent, e.g., ethanol. Compounds of type 6.14 can be prepared by a substitution reaction of an appropriate pyrrolo[2,3-d]pyrimidine, e.g., 6.13 as shown above, and an appropriate amine, e.g., 1.9 as shown above. Appropriate amines are commercially available or prepared by methods known to one skilled in the art. The substitution reaction is carried out in the presence of an appropriate catalyst, e.g., tris(dibenzylideneacetone)dipalladium (0), an appropriate ligand, e.g., xantphos, and an appropriate base, e.g., cesium carbonate, in an appropriate solvent, e.g., 1,4-dioxane, at an appropriate temperature, e.g., with heat. Compounds of type 6.15 can be prepared by deprotection of an appropriate pyrrolo[2,3-d]pyrimidine, e.g., 6.14 as shown above. The deprotection is carried out in the presence of an appropriate base, e.g., sodium methoxide, in an appropriate protic solvent, e.g., methanol, at an appropriate temperature, e.g., 80° C. As can be appreciated by one skilled in the art, the above reaction provides an example of a generalized approach wherein compounds similar in structure to the specific reactants above (compounds similar to compounds of type 6.1, 6.2, 6.3, 6.4, 6.5, 6.6, and 6.7), can be substituted in the reaction to provide substituted pyrrolopyrimidines similar to Formula 6.8.

7. Route VII

In one aspect, substituted pyrrolopyrimidines can be prepared as shown below.

SCHEME 7A.

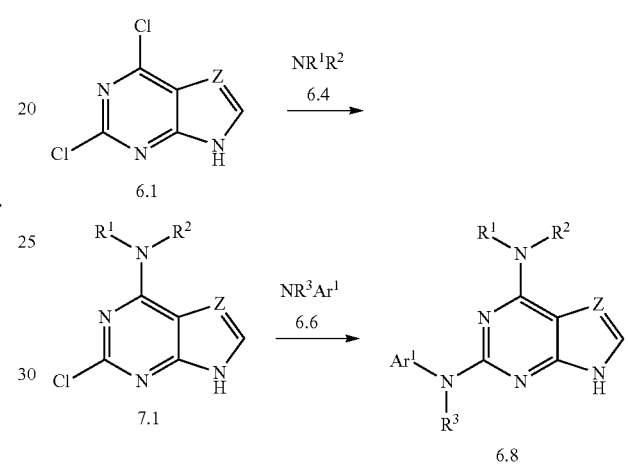

Compounds are represented in generic form, with additional substituents as noted in compound descriptions elsewhere herein. A more specific example is set forth below.

SCHEME 7B.

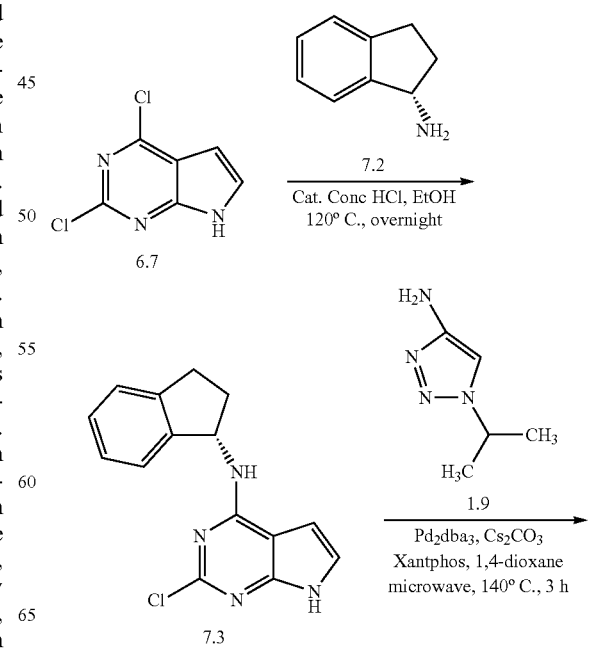

-continued

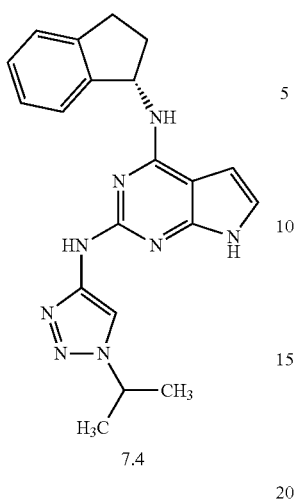

7.4

In one aspect, compounds of type 6.8, and similar compounds, can be prepared according to reaction Scheme 7B above. Thus, compounds of type 7.3 can be prepared by a substitution reaction of an appropriate pyrrolo[2,3-d]pyrimidine, e.g., 6.7 as shown above, and an appropriate amine, e.g., 7.2 as shown above. Appropriate pyrrolo[2,3-d]pyrimidines and amines are commercially available or prepared by methods known to one skilled in the art. The substitution reaction is carried out in the presence of an appropriate acid, e.g., concentrated hydrochloric acid, in an appropriate protic solvent, e.g., ethanol, at an appropriate temperature, e.g., 120° C. Compounds of type 7.4 can be prepared by a substitution reaction of an appropriate pyrrolo[2,3-d]pyrimidine, e.g., 7.3 as shown above, and an appropriate amine, e.g., 1.9 as shown above. Appropriate amines are commercially available or prepared by methods known to one skilled in the art. The substitution reaction is carried out in the presence of an appropriate catalyst, e.g., tris(dibenzylideneacetone)dipalladium (0), an appropriate ligand, e.g., xantphos, and an appropriate base, e.g., cesium carbonate, in an appropriate solvent, e.g., 1,4-dioxane, at an appropriate temperature, e.g., 140° C. As can be appreciated by one skilled in the art, the above reaction provides an example of a generalized approach wherein compounds similar in structure to the specific reactants above (compounds similar to compounds of type 6.1, 6.4, 6.6, and 7.1), can be substituted in the reaction to provide substituted pyrrolopyrimidines similar to Formula 6.8.

8. Route VIII

In one aspect, substituted pyrrolopyrimidines can be prepared as shown below.

SCHEME 8A.

Compounds are represented in generic form, with additional substituents as noted in compound descriptions elsewhere herein. A more specific example is set forth below.

SCHEME 8B.

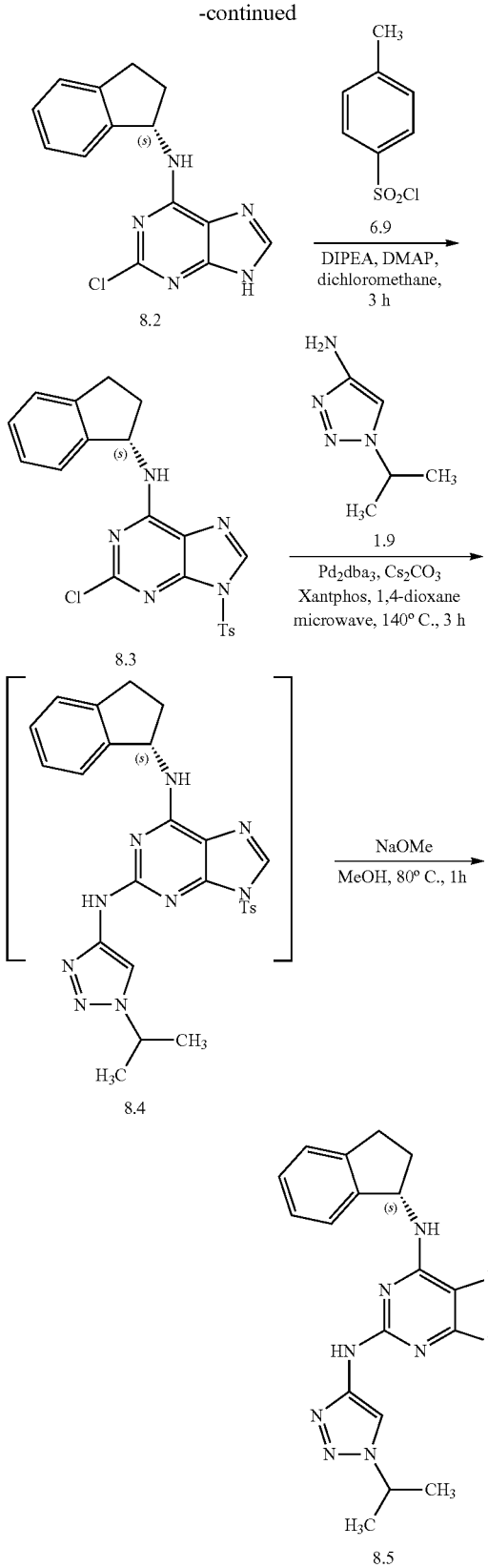

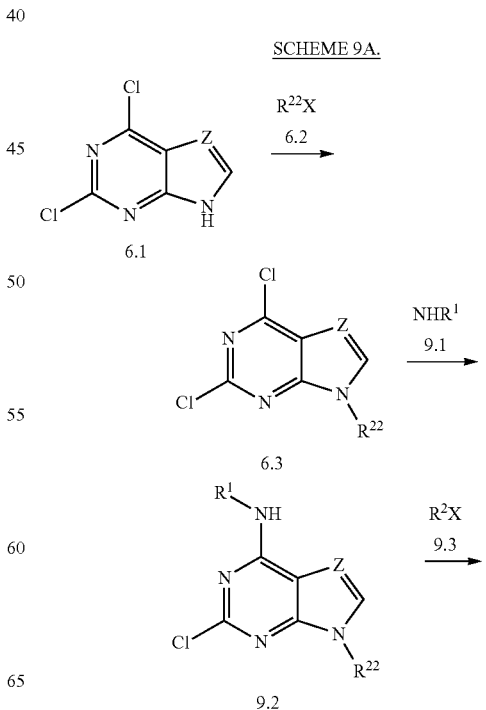

substitution reaction of an appropriate purine, e.g., 8.1 as shown above, and an appropriate amine, e.g., 7.3 as shown above. Appropriate purines and appropriate amines are commercially available or prepared by methods known to one skilled in the art. The substitution reaction is carried out in the presence of an appropriate base, e.g., DIPEA, in an appropriate protic solvent, e.g., ethanol, at an appropriate temperature, e.g., 120° C. Compounds of type 8.3 can be prepared by substitution of an appropriate purine, e.g., 8.2 as shown above. The substitution is carried out in the presence of an appropriate halide, e.g., 6.9, in the presence of an appropriate base, e.g., DIPEA, and an appropriate catalyst, e.g., 4-dimethylaminopyridine (DMAP), in an appropriate solvent, e.g., dichloromethane. Compounds of type 8.5 can be prepared by a substitution reaction of an appropriate purine, e.g., 8.3 as shown above, and an appropriate amine, e.g., 1.9 as shown above, followed by deprotection. Appropriate amines are commercially available or prepared by methods known to one skilled in the art. The substitution reaction is carried out in the presence of an appropriate catalyst, e.g., tris(dibenzylideneacetone)dipalladium (0), an appropriate ligand, e.g., xantphos, and an appropriate base, e.g., cesium carbonate, in an appropriate solvent, e.g., 1,4-dioxane, at an appropriate temperature, e.g., 140° C. The deprotection is carried out in the presence of an appropriate base, e.g., sodium methoxide, in an appropriate protic solvent, e.g., methanol, at an appropriate temperature, e.g., 80° C. As can be appreciated by one skilled in the art, the above reaction provides an example of a generalized approach wherein compounds similar in structure to the specific reactants above (compounds similar to compounds of type 6.1, 6.2, 6.4, 6.5, 6.6, 6.7, and 7.1), can be substituted in the reaction to provide substituted pyrrolopyrimidines similar to Formula 6.8.

9. Route IX

In one aspect, substituted pyrrolopyrimidines can be prepared as shown below.

SCHEME 9A.

In one aspect, compounds of type 6.8, and similar compounds, can be prepared according to reaction Scheme 8B above. Thus, compounds of type 8.2 can be prepared by a

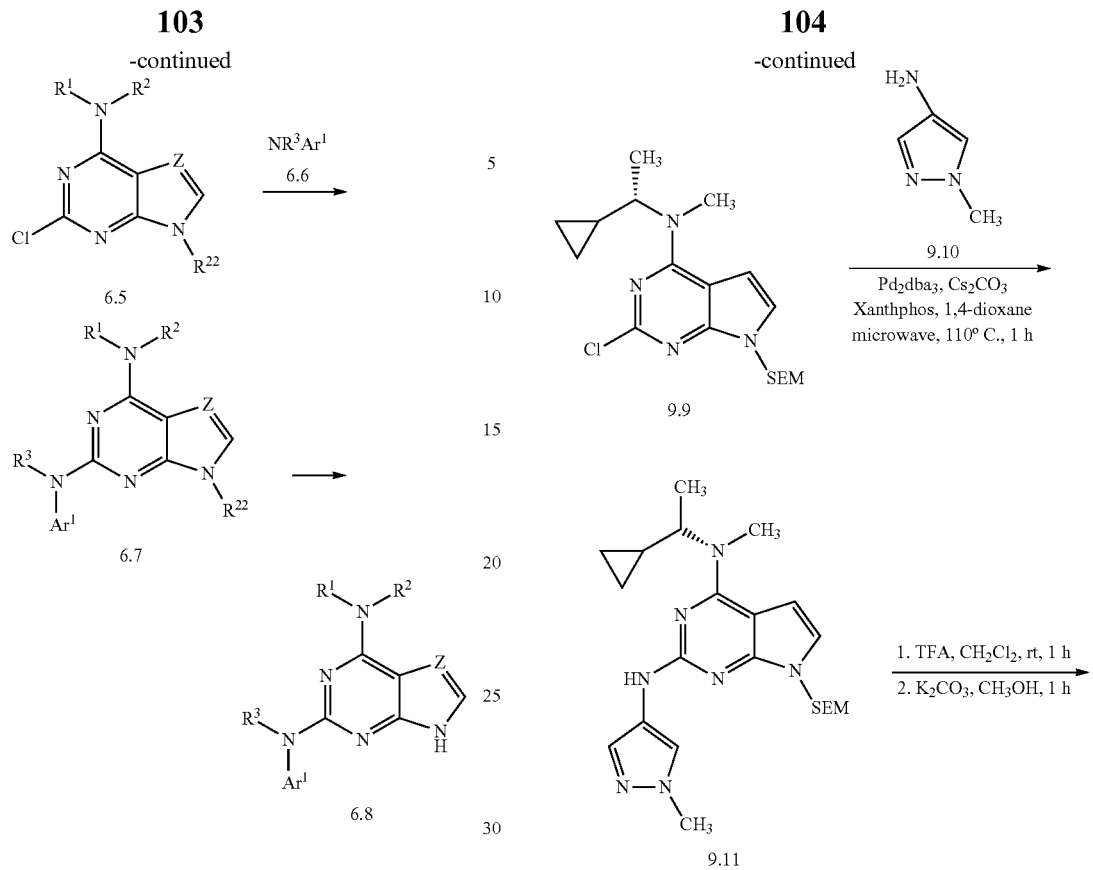

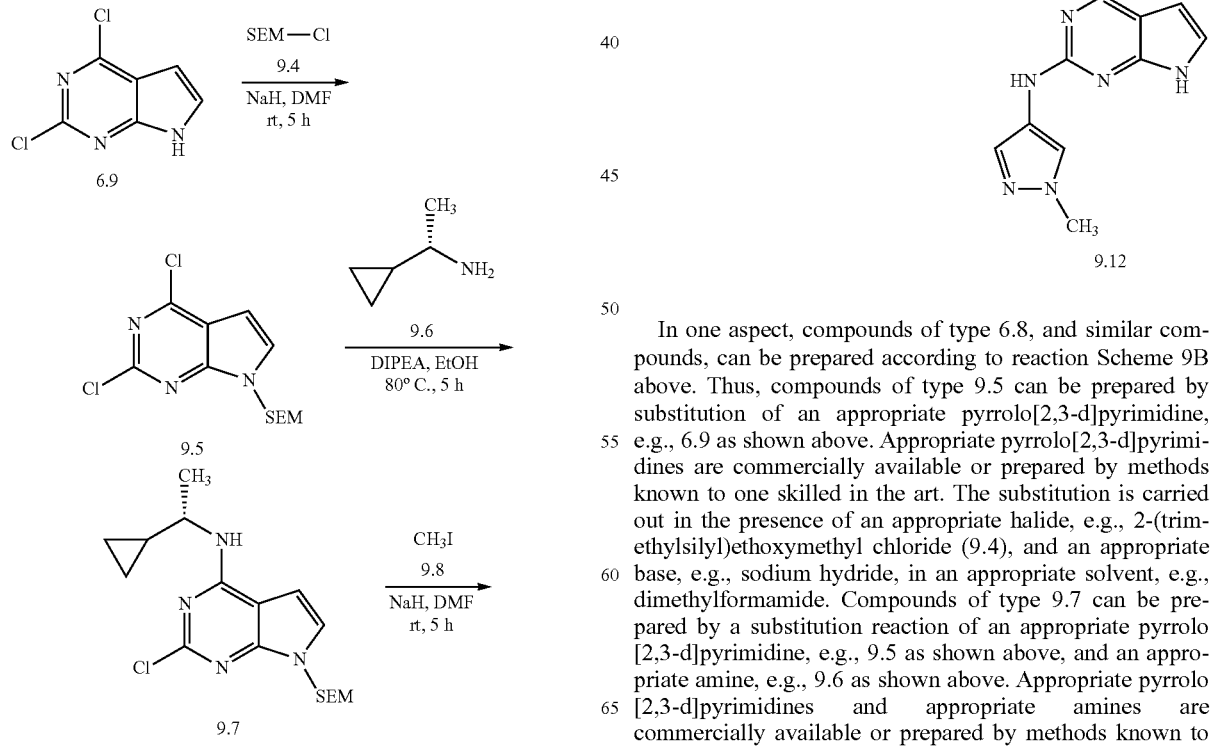

Compounds are represented in generic form, with additional substituents as noted in compound descriptions elsewhere herein. A more specific example is set forth below.

In one aspect, compounds of type 6.8, and similar compounds, can be prepared according to reaction Scheme 9B above. Thus, compounds of type 9.5 can be prepared by substitution of an appropriate pyrrolo[2,3-d]pyrimidine, e.g., 6.9 as shown above. Appropriate pyrrolo[2,3-d]pyrimidines are commercially available or prepared by methods known to one skilled in the art. The substitution is carried out in the presence of an appropriate halide, e.g., 2-(trimethylsilyl)ethoxymethyl chloride (9.4), and an appropriate base, e.g., sodium hydride, in an appropriate solvent, e.g., dimethylformamide. Compounds of type 9.7 can be prepared by a substitution reaction of an appropriate pyrrolo[2,3-d]pyrimidine, e.g., 9.5 as shown above, and an appropriate amine, e.g., 9.6 as shown above. Appropriate pyrrolo[2,3-d]pyrimidines and appropriate amines are commercially available or prepared by methods known to one skilled in the art. The substitution reaction is carried out in the presence of an appropriate base, e.g., DIPEA, in an appropriate protic solvent, e.g., ethanol, at an appropriate temperature, e.g., 80° C. Compounds of type 9.9 can be prepared by alkylation of an appropriate amine, e.g., 9.7 as shown above. The alkylation is carried out in the presence of an appropriate alkyl halide, e.g., 9.8 as shown above, and an appropriate base, e.g., sodium hydride, in an appropriate solvent, e.g., dimethylformamide. Appropriate alkyl halides are commercially available or prepared by methods known to one skilled in the art. Compounds of type 9.11 can be prepared by a substitution reaction of an appropriate pyrrolo[2,3-d]pyrimidine, e.g., 9.9 as shown above, and an appropriate amine, e.g., 9.10 as shown above. Appropriate amines are commercially available or prepared by methods known to one skilled in the art. The substitution reaction is carried out in the presence of an appropriate catalyst, e.g., tris(dibenzylideneacetone)dipalladium (0), an appropriate ligand, e.g., xantphos, and an appropriate base, e.g., cesium carbonate, in an appropriate solvent, e.g., 1,4-dioxane, at an appropriate temperature, e.g., 110° C. Compounds of type 9.12 can be prepared by deprotection of an appropriate pyrrolo[2,3-d]pyrimidine, e.g., 9.11 as shown above. The deprotection is carried out in the presence of an appropriate acid, e.g., trifluoroacetic acid, in an appropriate solvent, e.g., dichloromethane, followed by addition of an appropriate base, e.g., potassium carbonate, and an appropriate protic solvent, e.g., methanol. As can be appreciated by one skilled in the art, the above reaction provides an example of a generalized approach wherein compounds similar in structure to the specific reactants above (compounds similar to compounds of type 6.1, 6.2, 6.3, 6.5, 6.6, 6.7, 9.1, 9.2, and 9.3), can be substituted in the reaction to provide substituted pyrrolopyrimidines similar to Formula 6.8.

10. Route X

In one aspect, substituted pyrrolopyrimidines can be prepared as shown below.

Compounds are represented in generic form, with additional substituents as noted in compound descriptions elsewhere herein. A more specific example is set forth below.

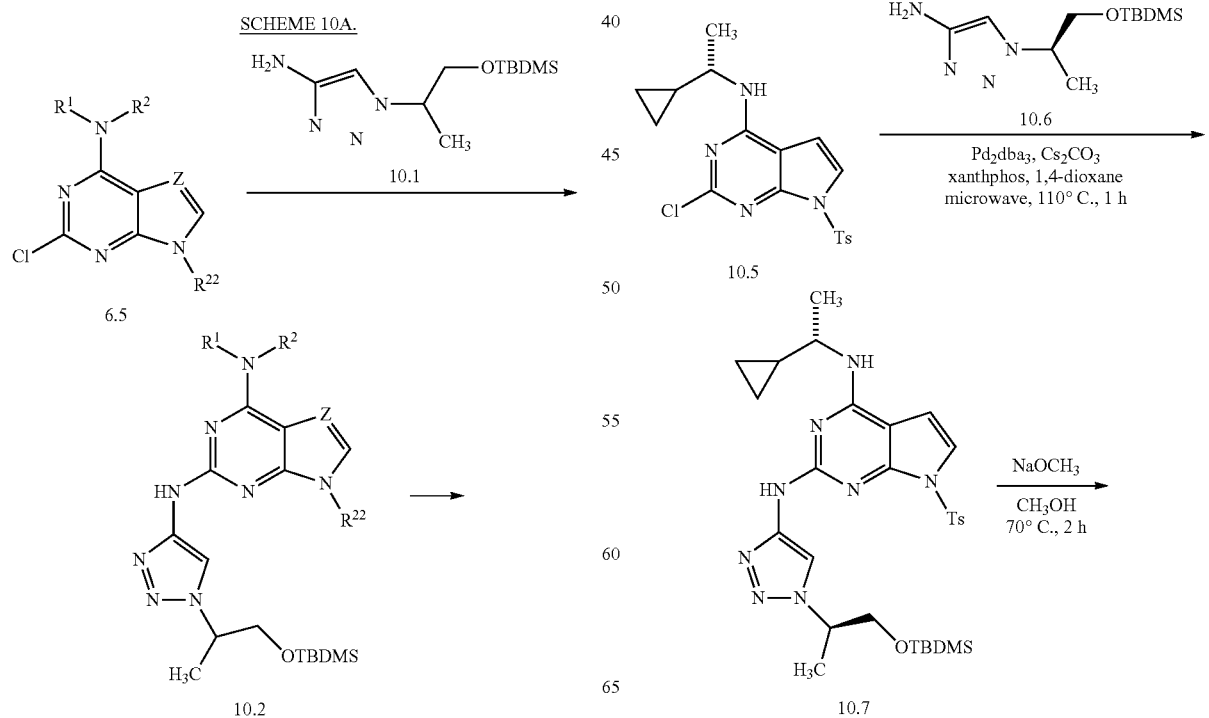

-continued

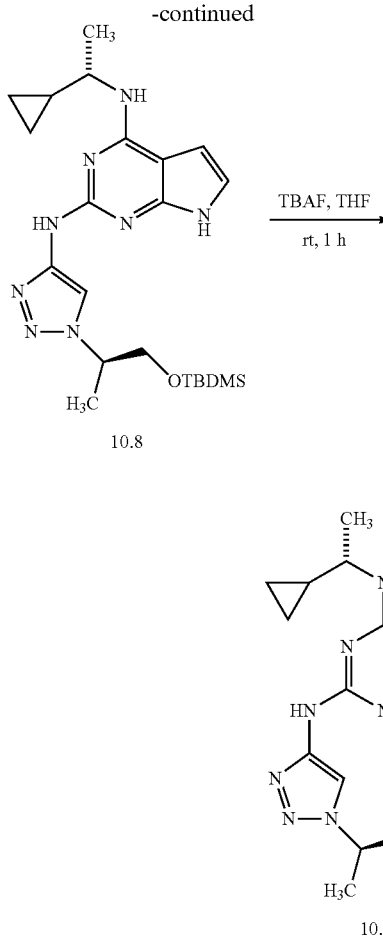

In one aspect, compounds of type 10.4, and similar compounds, can be prepared according to reaction Scheme 10B above. Thus, compounds of type 10.7 can be prepared by a substitution reaction of an appropriate pyrrolo[2,3-d]pyrimidine, e.g., 10.5 as shown above, and an appropriate amine, e.g., 10.6 as shown above. Appropriate pyrrolo[2,3-d]pyrimidines and appropriate amines are commercially available or prepared by methods known to one skilled in the art. The substitution reaction is carried out in the presence of an appropriate catalyst, e.g., tris(dibenzylideneacetone)dipalladium (0), an appropriate ligand, e.g., xantphos, and an appropriate base, e.g., cesium carbonate, in an appropriate solvent, e.g., 1,4-dioxane, at an appropriate temperature, e.g., 110° C. Compounds of type 10.8 can be prepared by deprotection of an appropriate pyrrolo[2,3-d]pyrimidine, e.g., 10.7 as shown above. The deprotection is carried out in the presence of an appropriate base, e.g., sodium methoxide, in an appropriate protic solvent, e.g., methanol, at an appropriate temperature, e.g., 70° C. Compounds of type 10.9 can be prepared by deprotection of an appropriate silyl ether, e.g., 10.8 as shown above. The deprotection is carried out in the presence of an appropriate deprotecting agent, e.g., tetrabutylammonium fluoride, in an appropriate solvent, e.g., tetrahydrofuran. As can be appreciated by one skilled in the art, the above reaction provides an example of a generalized approach wherein compounds similar in structure to the specific reactants above (compounds similar to compounds of type 6.5, 10.1, 10.2, and 10.3), can be substituted in the reaction to provide substituted pyrrolopyrimidines similar to Formula 10.3.

11. Route XI

In one aspect, substituted pyrrolopyrimidines can be prepared as shown below.

SCHEME 11A.

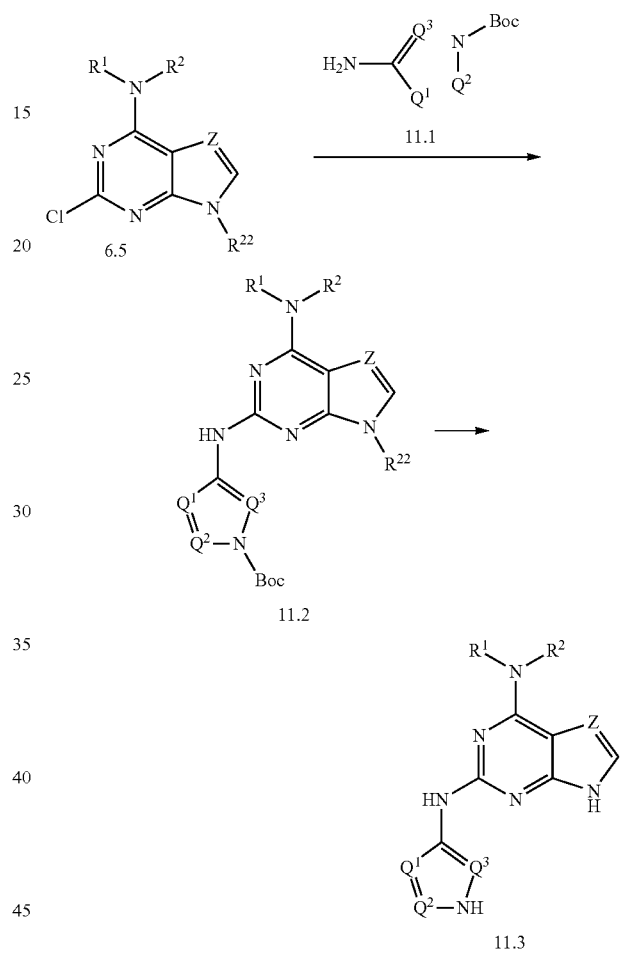

Compounds are represented in generic form, with additional substituents as noted in compound descriptions elsewhere herein. A more specific example is set forth below.

SCHEME 11B.

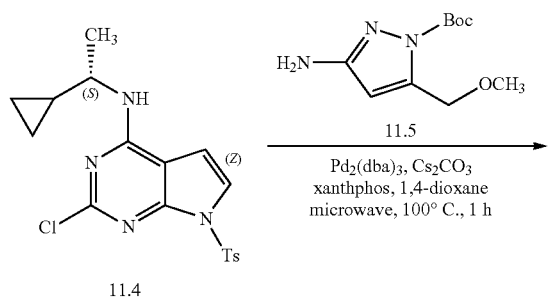

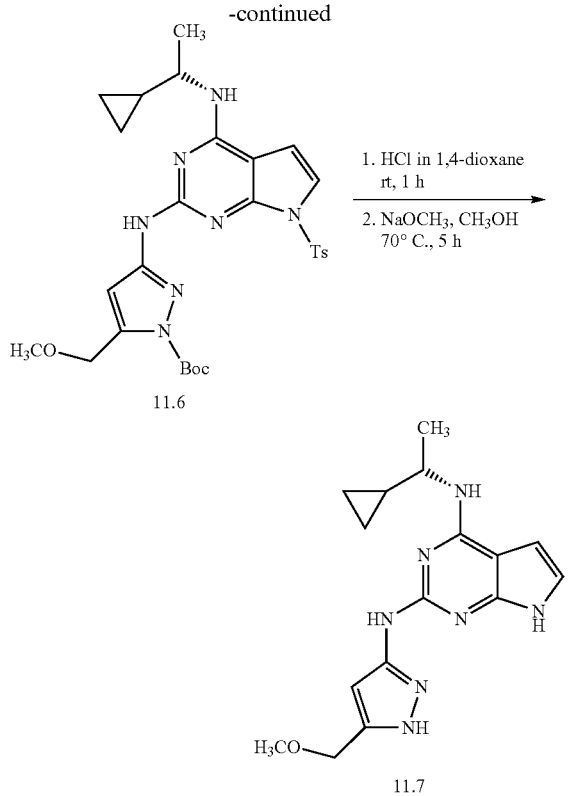

In one aspect, compounds of type 11.3, and similar compounds, can be prepared according to reaction Scheme 11B above. Thus, compounds of type 11.6 can be prepared by a substitution reaction of an appropriate pyrrolo[2,3-d]pyrimidine, e.g., 11.4 as shown above, and an appropriate amine, e.g., 11.5 as shown above. Appropriate pyrrolo[2,3-d]pyrimidines and appropriate amines are commercially available or prepared by methods known to one skilled in the art. The substitution reaction is carried out in the presence of an appropriate catalyst, e.g., tris(dibenzylideneacetone)dipalladium (0), an appropriate ligand, e.g., xantphos, and an appropriate base, e.g., sodium t-butoxide, in an appropriate solvent, e.g., 1,4-dioxane, at an appropriate temperature, e.g., 100° C. Compounds of type 11.7 can be prepared by deprotection of an appropriate pyrrolo[2,3-d]pyrimidine, e.g., 11.6 as shown above. The deprotection is carried out in the presence of an appropriate acid, e.g., hydrochloric acid, in an appropriate solvent, e.g., 1,4-dioxane, followed by addition of an appropriate base, e.g., sodium methoxide, in an appropriate protic solvent, e.g., methanol, at an appropriate temperature, e.g., 70° C. As can be appreciated by one skilled in the art, the above reaction provides an example of a generalized approach wherein compounds similar in structure to the specific reactants above (compounds similar to compounds of type 6.5, 11.1, and 11.2), can be substituted in the reaction to provide substituted pyrrolopyrimidines similar to Formula 11.3.

E. METHODS OF USING THE COMPOUNDS

The compounds and pharmaceutical compositions of the invention are useful in treating or controlling disorders associated with LRRK2 kinase dysfunction, in particular neurodegenerative disorders, such as Parkinson's disease, cancer, such as renal cancer and thyroid cancer, autoimmune disorders, such as Crohn's disease, rheumatoid arthritis, and psoriasis, and leprosy.

Examples of neurodegenerative disorders for which the compounds and compositions can be useful in treating, include, but are not limited to, Alzheimer's disease, Parkinson's disease, Huntington's disease, Amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia and Lewy body disease. In a further aspect, the neurodegenerative disorder is Parkinson's disease.

Examples of cancers for which the compounds and compositions can be useful in treating, include, but are not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma, osteosarcoma, colorectal, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. In a further aspect, the cancer is selected from renal cancer and thyroid cancer.

Examples of autoimmune disorders for which the compounds and compositions can be useful in treating, include, but are not limited to, demyelinating inflammatory disorders, rheumatoid arthritis, systemic lupus erythematosus, Sjogren's syndrome; and cryptogenic causes, including, but not limited to, idiopathic distal small-fiber neuropathy. In a further aspect, the autoimmune disorder is selected from type 1 insulin-dependent diabetes mellitus, inflammatory bowel disease, psoriasis, Crohn's disease, ulcerative colitis, dermatitis, meningitis, thrombotic thrombocytopenic purpura, Sjögren's syndrome, encephalitis, uveitis, leukocyte adhesion deficiency, rheumatoid and other forms of immune arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune hemolytic anemia, Hashimoto's thyroiditis, Graves disease, habitual spontaneous abortions, Renard's syndrome, glomerulonephritis, dermatomyositis, chronic active hepatitis, celiac disease, autoimmune complications of AIDS, atrophic gastritis, ankylosing spondylitis and Addison's disease. In a still further aspect, the autoimmune disorder is selected from Crohn's disease, psoriasis, and rheumatoid arthritis.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a cell proliferative disorder, such as cancer.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or condition, such as cancer.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with LRRK2 kinase dysfunction, in particular neurodegenerative disorders, such as Parkinson's disease, cancer, such as renal cancer and thyroid cancer, autoimmune disorders, such as Crohn's disease, rheumatoid arthritis, and psoriasis, and leprosy. Thus, provided is a method comprising administering a therapeutically effective amount of a composition comprising a disclosed compound to a subject. In a further aspect, the method can be a method for treating a disorder associated with LRRK2 kinase dysfunction.

A. Treating a Disorder Associated with LRRK2 Kinase Dysfunction

In one aspect, disclosed are methods of treating a disorder associated with LRRK2 kinase dysfunction in a mammal, the method comprising the step of administering to the mammal an effective amount of at least one disclosed compound, or a pharmaceutically acceptable salt thereof.

In one aspect, disclosed are method for the treatment of a disorder associated with LRRK2 kinase dysfunction in a mammal, the method comprising the step of administering to the mammal an effective amount of at least one compound having a structure represented by a formula:

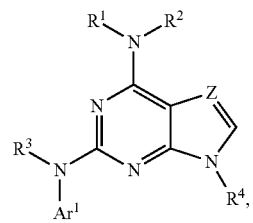

wherein Z is selected from N and $CR^{20}$; wherein each occurrence of $R^{20}$, when present, is independently selected from hydrogen, —CN, and C1-C4 alkyl; wherein $R^1$ is selected from $Cy^1$, $Ar^2$, —$CR^{21a}R^{21b}Cy^2$, and —$CR^{21a}R^{21b}Ar^2$; wherein each of $R^{21a}$ and $R^{21b}$, when present, are independently selected from hydrogen and C1-C4 alkyl; wherein $Cy^1$, when present, is selected from C3-C5 cycloalkyl and 2,3-dihydroindene and substituted with 0, 1, or 2 groups independently selected from halogen, C1-C4 alkyl, C1-C4 monohaloalkyl, and C1-C4 polyhaloalkyl; wherein $Cy^2$, when present, is selected from C3-C6 cycloalkyl, C2-C5 heterocycloalkyl, and 2,3-dihydroindene and substituted with 0, 1, or 2 groups independently selected from halogen, C1-C4 alkyl, C1-C4 monohaloalkyl, and C1-C4 polyhaloalkyl; wherein $Ar^2$, when present, is selected from C5-C6 aryl and C4-C5 heteroaryl and substituted with 0, 1, or 2 groups independently selected from halogen, C1-C4 alkyl, C1-C4 monohaloalkyl, and C1-C4 polyhaloalkyl; and wherein each of $R^2$, $R^3$, and $R^4$ are independently selected from hydrogen and C1-C4 alkyl; wherein $Ar^1$ is a structure selected from:

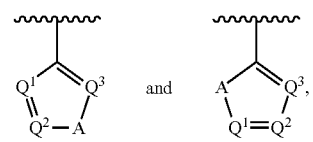

wherein A is selected from $NR^{22}$ and $CR^{23a}R^{23b}$; wherein $R^{22}$, when present, is selected from hydrogen, halogen, C1-C8 alkyl, C1-C8 monohaloalkyl, C1-C8 polyhaloalkyl, C1-C8 hydroxyalkyl, C1-C8 alkoxyalkyl, —(C1-C8 alkyl)$NH_2$, —(C1-C8 alkyl)NH(C1-C8alkyl), —(C1-C8 alkyl)N(C1-C8 alkyl)(C1-C8 alkyl), C1-C8 alkylacid, —(C1-C4 alkyl)$CONH_2$, —(C1-C4 alkyl)CONH(C1-C4 alkyl), —(C1-C4 alkyl)CON(C1-C4 alkyl)(C1-C4 alkyl), —(C1-C4 alkyl)(C=O)$Cy^3$, and $Cy^3$; wherein each occurrence of $Cy^3$, when present, is independently selected from C3-C6 cycloalkyl and C2-C5 heterocycloalkyl and substituted with 0, 1, or 2 groups independently selected from halogen, C1-C4 alkyl, C1-C4 monohaloalkyl, and C1-C4 polyhaloalkyl; wherein each of $R^{23a}$ and $R^{23b}$, when present, is independently selected from hydrogen, halogen, C1-C8 alkyl, C1-C8 monohaloalkyl, C1-C8 polyhaloalkyl, C1-C8 hydroxyalkyl, C1-C8 alkoxyalkyl, C1-C8 alkylacid, —(C1-C4 alkyl)(C=O)$Cy^1$, —(C1-C4 alkyl)$CONH_2$, —(C1-C4 alkyl)CONH(C1-C4 alkyl), —(C1-C4 alkyl)CON(C1-C4 alkyl)(C1-C4 alkyl), and $Cy^3$; wherein each of $Q^1$, $Q^2$, and $Q^3$ is independently selected from N and $CR^{24}$; and wherein each occurrence of $R^{24}$, when present, is independently selected from hydrogen, halogen, C1-C8 alkyl, C1-C8 monohaloalkyl, C1-C8 polyhaloalkyl, C1-C8 alkoxyalkyl, —(C1-C4 alkyl)$CONH_2$, —(C1-C4 alkyl)CONH(C1-C4 alkyl), —(C1-C4 alkyl)CON(C1-C4 alkyl)(C1-C4 alkyl), provided that two or three of A, $Q^1$, $Q^2$, and $Q^3$ are N, or a pharmaceutically acceptable salt thereof, wherein the disorder is selected from a neurodegenerative disorder and leprosy. In a further aspect, the neurodegenerative disorder is Parkinson's disease.

Examples of disorders associated with LRRK2 kinase dysfunction include, but are not limited to, neurodegenerative disorders, such as Parkinson's disease, cancer, autoimmune disorders, and leprosy.

In a further aspect, the subject has been diagnosed with a need for treatment of the disorder prior to the administering step.

In a further aspect, the subject is a mammal. In a still further aspect, the mammal is a human.

In a further aspect, the method further comprises the step of identifying a subject in need of treatment of the disorder.

In a further aspect, the disorder is associated with LRRK2 overexpression.

In a further aspect, the disorder is a neurodegenerative disorder. In a still further aspect, the neurodegenerative disorder is selected from Alzheimer's disease, Parkinson's disease, Huntington's disease, Amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia and Lewy body disease. In a further aspect, the neurodegenerative disorder is Parkinson's disease.

In a further aspect, the method further comprises the step of administering a therapeutically effective amount of at least one agent known to treat a neurodegenerative disorder. In a still further aspect, the at least one agent is selected from an anti-Alzheimer's agent, beta-secretase inhibitor, gamma-secretase inhibitor, muscarinic agonist, muscarinic potentiator, HMG-CoA reductase inhibitor, NSAID, anti-amyloid antibodies, carbidopa, levodopa, pramipexole, ropinirole, rotigotine, apomorphine, selegiline, rasagiline, monoamine oxidase B, entacapone, tolcapone, benztropine, trihexyphenidyl, amantadine, In a further aspect, the disorder is a cancer. In a still further aspect, the cancer is selected from leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma, osteosarcoma, colorectal, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. In yet a further aspect, the cancer is selected from renal cancer and thyroid cancer.

In a further aspect, the method further comprises the step of administering a therapeutically effective amount of at least one agent known to treat a cancer. In a still further aspect, the at least one agent is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin (Eloxatin®), iressa (gefinitib, Zd1839), XELODA® (capecitabine), Tarceva® (erlotinib), azacitidine (5-Azacytidine; 5-AzaC), temozolomide (Temodar®), gemcitabine (e.g., GEMZAR® (gemcitabine HCl)), and vasostatin.

In a further aspect, the disorder is an autoimmune disorder. In a still further aspect, the autoimmune disorder is selected from type 1 insulin-dependent diabetes mellitus, inflammatory bowel disease, psoriasis, Crohn's disease, ulcerative colitis, dermatitis, meningitis, thrombotic thrombocytopenic purpura, Sjögren's syndrome, encephalitis, uveitis, leukocyte adhesion deficiency, rheumatoid and other forms of immune arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune hemolytic anemia, Hashimoto's thyroiditis, Graves disease, habitual spontaneous abortions, Renard's syndrome, glomerulonephritis, dermatomyositis, chronic active hepatitis, celiac disease, autoimmune complications of AIDS, atrophic gastritis, ankylosing spondylitis and Addison's disease. In a still further aspect, the autoimmune disorder is selected from Crohn's disease, psoriasis, and rheumatoid arthritis.

In a further aspect, the method further comprises the step of administering a therapeutically effective amount of at least one agent known to treat an autoimmune disorder. In a still further aspect, the at least one agent is selected from sulfasalazine, mesalamine, prednisone, budesonide, azathioprine, mercaptopurine, infliximab, adalimumab, certolizumab pegol, methotrexate, cyclosporine, tacrolimus, natalizumab, vedolizumab, ustekinumab, metronidazole, ciprofloxacin, methylcellulose, psllyium powder, acetaminophen, a corticosteroid, vitamin D, tazarotene, tacrolimus, pimecrolimus, salicyclic acid, coal tar, a retinoid, etanercept, ustekinumab, thioguanine, hydroxyurea, meloxicam, naproxen, diclofenac, methylprednisone, indomethacin, ibuprofen, etodolac, nabumetone, minocycline, hydroxychloroquine, piroxicam, leflunomide, azathioprine, naproxen, sulindac, salsalate, oxaprozin, aspirin, methotrexate sodium, hydrocortisone, diflunisal, triamcinolone acetonide, cortisone, cyclophosphamide, betamethasone acetate, etanercept, meclofenamate, and flurbiprofen.

In a further aspect, the disorder is leprosy.

In a further aspect, the method further comprises the step of administering a therapeutically effective amount of at least one agent known to treat leprosy. In a still further aspect, the at least one agent is selected from dapsone, rifampicin, minocycline, clofazimine, and ofloxacin.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods of Inhibiting LRRK2 Kinase Activity in a Mammal

In one aspect, disclosed are methods of inhibiting LRRK2 kinase activity in a mammal, the method comprising the step of administering to the mammal a therapeutically effective amount of at least one disclosed compound, or a pharmaceutically acceptable salt thereof.

In a further aspect, the compound exhibits inhibition of LRRK2 activity. In a still further aspect, the compound exhibits a decrease in LRRK2 kinase activity.

In a further aspect, the compound exhibits inhibition of LRRK2 kinase activity with an $IC_{50}$ of less than about 0.1 µM. In a still further aspect, the compound exhibits inhibition of LRRK2 kinase activity with an $IC_{50}$ of less than about 0.05 µM. In yet a further aspect, the compound exhibits inhibition of LRRK2 kinase activity with an $IC_{50}$ of less than about 0.01 µM. In an even further aspect, the compound exhibits inhibition of LRRK2 kinase activity with an $IC_{50}$ of less than about 0.005 µM.

In a further aspect, the subject is a mammal. In a still further aspect, the subject is a human.

In a further aspect, the subject has been diagnosed with a need for treatment of the disorder prior to the administering step. In a still further aspect, the method further comprises the step of identifying a subject in need of treatment of the disorder.

3. Methods of Inhibiting LRRK2 Kinase Activity in at Least One Cell

In one aspect, disclosed are methods for inhibiting LRRK2 kinase activity in at least one cell, the method comprising the step of contacting the at least one cell with an effective amount of at least one disclosed compound, or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal.

4. Use of Compounds

In one aspect, the invention relates to the use of a disclosed compound or a product of a disclosed method. In a further aspect, a use relates to the manufacture of a medicament for the treatment of a disorder associated with LRRK2 dysfunction in a mammal.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for LRRK2 antagonism. In one aspect, the use is characterized in that the mammal is a human. In one aspect, the use is characterized in that the disorder is a disorder associated with LRRK2 dysfunction. In one aspect, the disorder associated with LRRK2 dysfunction is treated by antagonism of LRRK2 activity in a mammal.

In a further aspect, the use relates to the manufacture of a medicament for the treatment of a disorder associated with LRRK2 dysfunction in a mammal.

In a further aspect, the use relates to antagonism of LRRK2 activity in a mammal. In a further aspect, the use relates to modulating LRRK2 activity in a mammal. In a still further aspect, the use relates to modulating LRRK2 activity in a cell. In yet a further aspect, the mammal is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder associated with LRRK2 dysfunction in a mammal. In a further aspect, the disorder is a neurodegenerative disorder, a cancer, an autoimmune disorder, or leprosy.

5. Manufacture of a Medicament

In one aspect, the invention relates to a method for the manufacture of a medicament for treating a disorder associated with LRRK2 dysfunction in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of kinase protein and especially LRRK2. The method also includes the administration of a therapeutically effect amount of the compound for the treatment of patient having a predisposition for being afflicted with Parkinson's disease. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the cancer.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, the invention relates to a kit comprising a therapeutically effective amount of at least one disclosed compound, or a pharmaceutically acceptable salt thereof, and one or more of: a) an effective amount of at least one agent known to treat a neurodegenerative disorder; b) at least one agent known to treat cancer; c) at least one agent known to treat an autoimmune disorder; d) at least one agent known to treat leprosy; e) instructions for treating a neurodegenerative disorder; f) instructions for treating cancer; g) instructions for treating an autoimmune disorder; or h) instructions for treating leprosy.

In a further aspect, the at least one compound and the at least one agent known to treat a neurodegenerative disorder are co-formulated. In a further aspect, the at least one compound and the at least one agent known to treat a neurodegenerative disorder are co-packaged.

In a further aspect, the at least one compound and the at least one agent known to treat cancer are co-formulated. In a further aspect, the at least one compound and the at least one agent known to treat cancer are co-packaged.

In a further aspect, the at least one compound and the at least one agent known to treat an autoimmune disorder are co-formulated. In a further aspect, the at least one compound and the at least one agent known to treat an autoimmune disorder are co-packaged.

In a further aspect, the at least one compound and the at least one agent known to treat leprosy are co-formulated. In a further aspect, the at least one compound and the at least one agent known to treat leprosy are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

Exemplary embodiments of the present disclosure include:

Embodiment A

A compound as disclosed herein.

Embodiment B

A compound according to A, wherein the isomers are enantiomers or diastereomers.

Embodiment C

A pharmaceutical composition comprising a compound or derivative according to any one of Embodiments A to B and a pharmaceutically acceptable carrier.

Embodiment D

A method of treating a patient with a disease caused by or associated with abnormal LRRK2 kinase activity, which comprises administering to the patient an effective treatment amount of at least one compound, derivative or composition according to any one of Embodiments A to C.

Embodiment E

A method for treating a patient having a neurodegenerative disease, which comprises administering to the patient an effective treatment amount of at least one compound, derivative or composition according to any Embodiments A to D.

Embodiment F

The method according to Embodiment E, wherein the neurodegenerative disease is Parkinson's disease.

Embodiment G

A method for treating a patient suffering from cancer, which comprises administering to the patient an effective treatment amount of at least one compound, derivative or composition according to any one of Embodiments A to C.

Embodiment H

The method according to Embodiment G, wherein said cancer is renal cancer or thyroid cancer.

Embodiment I

A method for treating a patient having an autoimmune disease, which comprises administering to the patient an effective treatment amount of at least one compound, derivative or composition according to any one of Embodiments A to C.

Embodiment J

The method according to Embodiment I, wherein the autoimmune disease is selected from the group consisting of Crohn's disease, rheumatoid arthritis and psoriasis.

Embodiment K

A method for treating a patient having leprosy, which comprises administering to the patient an effective treatment amount of at least one compound, derivative or composition according to any one of Embodiments A to C.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. EXAMPLES

The following preparations and examples are given to enable those skilled in the art to more clearly understand and to practice the present invention. They should not be considered as limiting the scope of the invention, but merely as being illustrative and representative.

1. General Experimental Methods

Reagents were purchased from commercial sources and were used as received. Proton nuclear magnetic resonance spectra were obtained on a Bruker AVANCE 400 spectrometer at 400 MHz with tetramethylsilane used as an internal reference. Carbon nuclear magnetic resonance spectra were obtained on a Bruker AVANCE 400 spectrometer at 100 MHz with the solvent peak used as the reference. UPLC were obtained with Waters instrument using the following condition for all the final compounds: 10 mM ammonium formate and acetonitrile, Acquity BEH-C18 column (2.1×50 mm, 1.7µ), flow rate 0.5 mL/min; Thin-layer chromatography (TLC) was performed using Whatman No. 4500-101 (Diamond No. MK6F silica-gel 60 Å) plates. Visualization of TLC plates was performed using UV and $KMnO_4$ stain. All the azides were prepared from corresponding halo derivatives under the conditions sodium azide in DMF at 90° C. and obtained azide by usual workup. The following intermediates used in these procedures are commercially available: S-1 (CAS #90213-66-4), S-3 (CAS #2627-86-3), S-5f (CAS #860176-01-8), S-5j; (CAS #956440-80-5), S-11 (CAS #195604-39-8), S-34 (CAS #66399-30-2), S-46; (CAS #68285-24-5), S-50 (CAS #13375-29-6), S-62 (CAS #222714-37-6), S-14a; (CAS #127107-23-7), S-14b (CAS #876343-24-7), S-14c (CAS #97421-16-4), S-14d (CAS #919278-39-0), S-14g (CAS #97421-16-4).

2. Chemistry Experimentals a. Synthesis of S-4

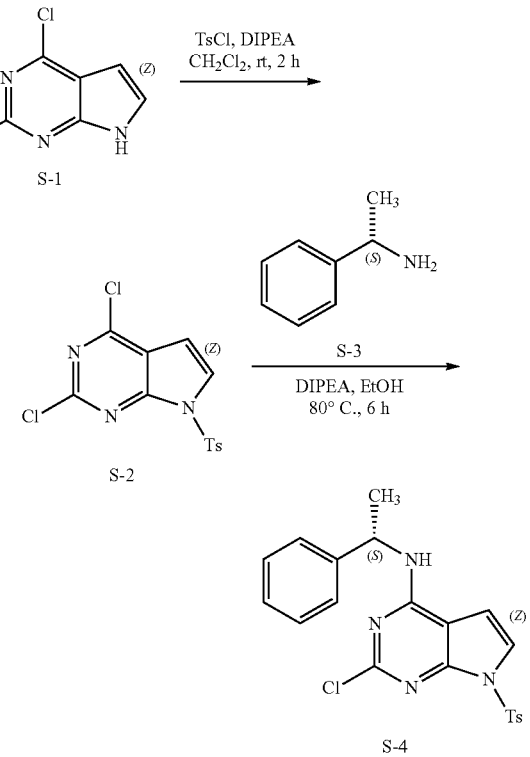

i. Preparation of S-2

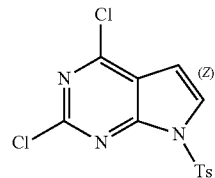 [SMILES: Cc1ccc(S(=O)(=O)n2ccc3c(Cl)nc(Cl)nc32)cc1]

A stirred solution of S-1 (2.00 g, 10.7 mmol) in $CH_2Cl_2$ (20 mL) taken in a round-bottom flask was charged with DIPEA (3.7 mL, 21.4 mmol), DMAP (0.039 g, 0.32 mmol) and p-toluene sulfonyl chloride (2.25 g, 11.7 mmol) successively at ambient temperature under nitrogen atmosphere. The reaction mixture was stirred for 2 h at same temperature. The reaction mixture was diluted with $CH_2Cl_2$ (100 mL) and was washed with water (40 mL) and HCl (1 N, 40 mL). The combined organic layer was washed with brine (1×50 mL), dried over anhydrous $Na_2SO_4$ and was concentrated under reduced pressure. The obtained residue was washed with hexanes (2×50 mL) and was dried under vacuum to afford S-2 (3.50 g, 95%, AMRI lot # IN-SKY-C-03) as an off-white solid. The compound was characterized by $^1H$ NMR analysis. $^1$H NMR (400 MHz, CDCl$_3$): δ 8.03 (d, J=8.4 Hz, 2H), 7.68 (d, J=4 Hz, 1H), 7.29 (d, J=8.12 Hz, 2H), 6.60 (d, J=4 Hz, 1H), 2.36 (s, 3H).

ii. Preparation of S-4

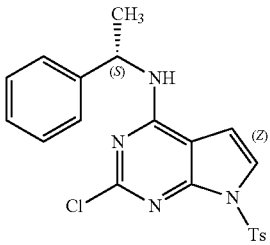

A stirred solution of S-2 (2.00 g, 5.8 mmol) in EtOH (20 mL) taken in a round-bottom flask was charged with DIPEA (2.01 mL, 8.2 mmol) and S-3 (0.99 g, 8.2 mmol) at room temperature. The reaction mixture was heated to 80° C. for 6 h under nitrogen atmosphere. The reaction mixture was concentrated under reduced pressure and the crude residue was purified by column chromatography on silica gel using 0-50% EtOAc in hexanes as eluent to afford S-4 (1.70 g, 68%, AMRI lot # IN-SKY-C-06) as an off-white solid. The compound was characterized by $^1$H NMR analysis. $^1$H NMR (400 MHz, DMSO-d$_6$): δ 8.61 (d, J=7.72 Hz, 1H), 7.93 (d, J=8.28 Hz, 2H), 7.56 (d, J=3.76 Hz, 1H), 7.44 (d, J=8.2 Hz, 2H), 7.36 (d, J=7.4 Hz, 2H), 7.32-7.29 (m, 2H), 7.23-7.19 (m, 1H), 7.00 (d, J=3.2 Hz, 1H), 5.36-5.32 (m, 1H), 2.35 (s, 3H), 1.50 (d, J=6.96 Hz, 3H).

b. General Synthesis of 2-Triazol-4-yl-isoindoline-1,3-diones (S-10)

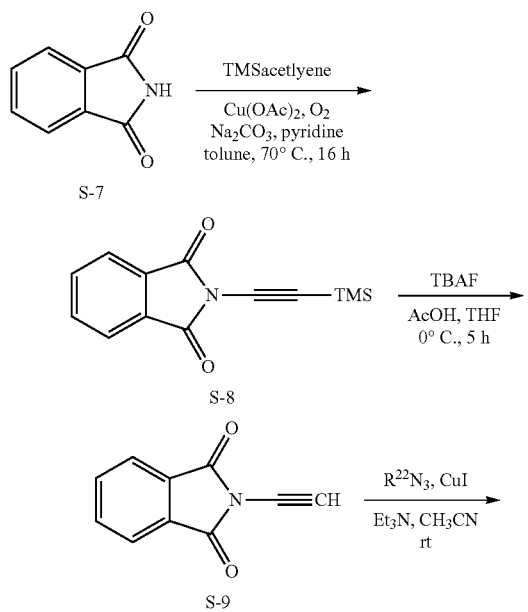

-continued

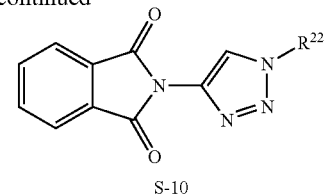

i. Preparation of S-8

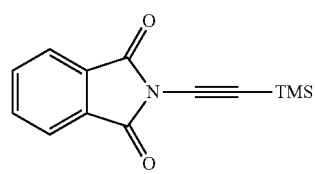 [SMILES: C[Si](C)(C)C#CN1C(=O)c2ccccc2C1=O]

A stirred suspension of phthalimide (S-7, 30.0 g, 0.20 mol) in toluene (280 mL) was charged with copper(I) acetate (1.47 g, 0.008 mol), Na$_2$CO$_3$ (8.65 g, 0.08 mol), pyridine (6.44 g, 0.08 mol), 4 Å molecular sieves (24.0 g) and the reaction mixture was purged with oxygen for 15 min. The reaction mixture was heated at 70° C. for 2 h. Trimethylsilyl acetylene (4.00 g, 0.04 mol) in toluene (20 mL) was added dropwise over 30 min and heated at same temperature for 16 h. When TLC showed complete consumption of the starting material, the reaction mixture was cooled to room temperature, diluted with the water (500 mL) and extracted with EtOAc (2×200 mL). The combined organic layer was washed with saturated NH$_4$Cl (200 mL). The organic layer was dried over anhydrous Na$_2$SO$_4$ and concentrated under reduced pressure followed by purification by column chromatography on silica gel using 0-15% EtOAc in hexanes as eluent to afford S-8 (6.00 g, 60%, AMRI lot # IN-AKK-I-4) as a white solid. The compound was characterized by $^1$H NMR analysis. $^1$H NMR (300 MHz, CDCl$_3$): δ 7.94-7.90 (m, 2H), 7.84-7.78 (m, 2H), 0.28 (s, 9H).

ii. Preparation of S-9

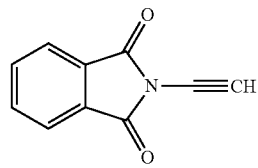

A solution of S-8 (300 mg, 1.23 mmol) in THF (20 mL) was charged with acetic acid (88.0 mg, 1.47 mmol) followed by tetrabutylammonium fluoride (1 M in THF, 1.85 mL, 1.85 mmol) at 0° C. The reaction mixture was stirred for 5 h at same temperature. When TLC showed complete consumption of the starting material, the reaction mixture was diluted with EtOAc (20 mL) and extracted with EtOAc (2×20 mL). The combined organic layer was washed with water (20 mL). The organic layer was dried over anhydrous Na$_2$SO$_4$ and concentrated under reduced pressure followed by purification by column chromatography on silica gel using 0-10% EtOAc in hexanes as eluent to afford S-9 (110 mg, 52%, AMRI lot # IN-AKK-I-2) as a white solid. The compound was characterized by ¹H NMR analysis. ¹H NMR (300 MHz, CDCl₃): δ 7.98-7.93 (m, 2H), 7.86-7.82 (m, 2H), 3.35 (s, 1H).

iii. Preparation of S-10a

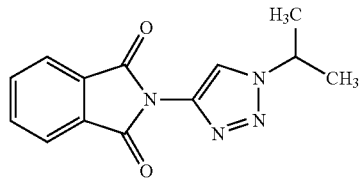 [SMILES: CC(C)n1cc(N2C(=O)c3ccccc3C2=O)nn1]

A solution of S-9 (1.00 g, 5.84 mmol) in acetonitrile (20 mL) was charged with copper(I)iodide (33.0 mg, 0.175 mmol) and triethylamine (17.6 mg, 0.17 mmol) at room temperature. Isopropyl azide (497 mg, 5.84 mmol) was added dropwise to the reaction mixture and stirred for 16 h at room temperature. When TLC showed complete consumption of the starting material, the reaction mixture was diluted with EtOAc (20 mL), filtered and washed with water (50 mL). The obtained was dried over anhydrous Na₂SO₄ and concentrated under reduced pressure followed by purification of the crude product by column chromatography on silica gel using 0-30% EtOAc in hexanes as eluent to afford S-10a (650 mg, 43%, AMRI lot # IN-AKK-I-12) as a white solid. The compound was characterized by ¹H NMR analysis. ¹H NMR (300 MHz, CDCl₃): δ 7.93-7.87 (m, 2H), 7.79-7.71 (m, 3H), 4.89-4.75 (m, 1H), 1.58 (d, J=6.9 Hz, 6H).

iv. Preparation of S-10i

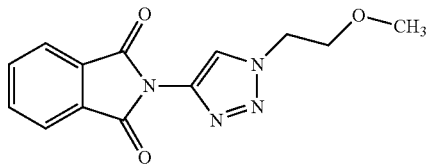 [SMILES: COCCn1cc(N2C(=O)c3ccccc3C2=O)nn1]

A solution of S-9 (1.00 g, 5.84 mmol) in acetonitrile (20 mL) was charged with copper(I)iodide (33.0 mg, 0.175 mmol) and triethylamine (17.6 mg, 0.17 mmol) at room temperature. 1-azido-2-methoxyethane (590 mg, 5.84 mmol) was added dropwise to the reaction mixture and was stirred for 16 h at room temperature. When TLC showed complete consumption of the starting material, the reaction mixture was diluted with EtOAc (20 mL), filtered, washed with water (50 mL) and was dried over anhydrous Na₂SO₄. The organic layer was concentrated under reduced pressure followed by purification of the crude product by column chromatography on silica gel using 5-20% MeOH in CH₂Cl₂ as eluent to afford S-10i (320 mg, 20%, AMRI lot # IN-AKK-I-102-1) as a white solid. The compound was characterized by ¹H NMR analysis. ¹H NMR (300 MHz, DMSO-d₆): δ 8.31 (s, 1H), 8.02-7.92 (m, 4H), 4.64 (t, J=5.1 Hz, 2H), 3.80 (t, J=5.4 Hz, 2H), 3.28 (s, 3H).

v. Preparation of S-10j

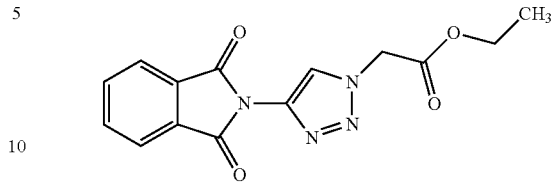

A solution of S-9 (1.00 g, 5.84 mmol) in acetonitrile (20 mL) was charged with copper(I)iodide (33.0 mg, 0.175 mmol) and triethylamine (17.6 mg, 0.17 mmol) at room temperature. 1-azido-2-methoxyethane (497 mg, 5.84 mmol) was added dropwise to the reaction mixture and stirred for 16 h at room temperature. When TLC showed complete consumption of the starting material, the reaction mixture was diluted with the EtOAc (20 mL), filtered and washed with water (50 mL) and was dried over anhydrous Na₂SO₄. The organic layer was concentrated under reduced pressure followed by purification by column chromatography on silica gel using 10-30% MeOH in CH₂Cl₂ as eluent to afford S-10j (650 mg, 37%, AMRI lot # IN-AKK-I-114-1) as a white solid. The compound was characterized by ¹H NMR analysis. ¹H NMR (400 MHz, DMSO-d₆): δ 8.37 (s, 1H), 8.02-7.92 (m, 4H), 5.51 (s, 2H), 4.25-4.18 (q, J=7.2 Hz, 2H), 1.25 (t, J=7.2 Hz, 3H).

vi. Preparation of S-10l

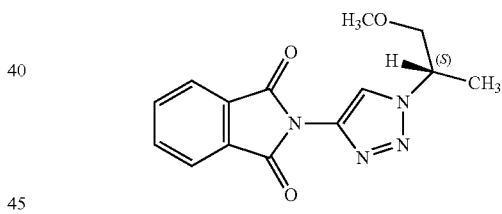

A solution of S-9 (1.00 g, 5.84 mmol) in acetonitrile (20 mL) was charged with copper(I)iodide (33.0 mg, 0.175 mmol) and triethylamine (17.6 mg, 0.17 mmol) at room temperature. (S)-2-Azido-1-methoxypropane (740 mg, 6.42 mmol) was added dropwise to the reaction mixture and was stirred for 16 h at room temperature. When TLC showed complete consumption of the starting material, the reaction mixture was diluted with the EtOAc (20 mL), filtered, washed with water (50 mL) and was dried over anhydrous Na₂SO₄. The organic layer was concentrated under reduced pressure followed by purification of the crude product by column chromatography on silica gel using 0-30% EtOAc in hexanes as eluent to afford S-10l (0.40 g, 34%, AMRI lot # IN-CKB-G-139) as a brown solid. The compound was characterized by ¹H NMR analysis. ¹H NMR (400 MHz, CDCl₃): δ 7.99-7.97 (m, 2H), 7.93 (s, 1H), 7.82-7.78 (m, 2H), 4.92-4.88 (m, 1H), 3.73 (q, J=5.60 Hz, 2H), 3.35 (s, 3H), 1.68 (d, J=6.80 Hz, 3H).

vii. Preparation of S-10m

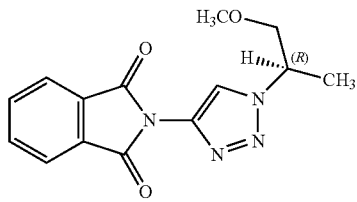

A solution of S-9 (1.00 g, 5.84 mmol) in acetonitrile (20 mL) was charged with copper(I)iodide (33.3 mg, 0.175 mmol) and triethylamine (17.6 mg, 0.17 mmol) at room temperature. (R)-2-Azido-1-methoxypropane (740 mg, 6.42 mmol) was added dropwise to the reaction mixture and was stirred for 16 h at room temperature. When TLC showed complete consumption of the starting material, the reaction mixture was diluted with EtOAc (20 mL), filtered, washed with water (50 mL) and was dried over anhydrous $Na_2SO_4$. The organic layer was concentrated under reduced pressure followed by purification of the crude product by column chromatography on silica gel using 0-30% EtOAc in hexanes as eluent to afford S-10m (0.40 g, 34%, AMRI lot # IN-CKB-G-130) as a brown solid. The compound was characterized by UPLC-MS analysis. MS-UPLC (MM) m/z 286.2 $[M+H]^+$.

viii. Preparation of S-10q

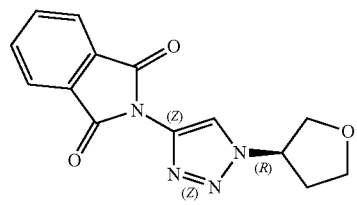

A solution of S-9 (1.00 g, 5.84 mmol) in acetonitrile (20 mL) was charged with copper(I)iodide (33.0 mg, 0.175 mmol) and triethylamine (17.6 mg, 0.17 mmol) at room temperature. (R)-3-Azidotetrahydrofuran (660 mg, 5.84 mmol) was added dropwise to the reaction mixture and stirred for 16 h at room temperature. When TLC showed complete consumption of the starting material, the reaction mixture was diluted with EtOAc (20 mL), filtered and washed with water (50 mL). The obtained was dried over anhydrous $Na_2SO_4$ and concentrated under reduced pressure followed by purification of the crude product by column chromatography on silica gel using 0-30% EtOAc in hexanes as eluent to afford S-10q (1.10 g, 66%, AMRI lot # IN-AKK-I-159) as a white solid. The compound was characterized by $^1H$ NMR analysis. $^1H$ NMR (400 MHz, $CDCl_3$): δ 7.99-7.97 (m, 2H), 7.91 (s, 1H), 7.83-7.80 (m, 2H), 5.41-5.32 (m, 1H), 4.28-3.95 (m, 4H), 2.68-2.38 (m, 2H).

ix. Preparation of S-10p

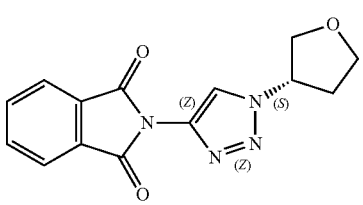

A solution of S-9 (1.50 g, 8.77 mmol) in acetonitrile (20 mL) was charged with copper(I)iodide (50.0 mg, 0.26 mmol) and triethylamine (26.0 mg, 0.26 mmol) at room temperature. (S)-3-Azidotetrahydrofuran (1.09 g, 9.64 mmol) was added dropwise to the reaction mixture and stirred for 16 h at room temperature. When TLC showed complete consumption of the starting material, the reaction mixture was diluted with EtOAc (20 mL), filtered and washed with water (50 mL). The obtained was dried over anhydrous $Na_2SO_4$ and concentrated under reduced pressure followed by purification of the crude product by column chromatography on silica gel using 0-20% EtOAc in hexanes as eluent to afford S-10p (500 mg, 20%, AMRI lot # IN-AKK-I-163) as a white solid. The compound was characterized by MS analysis. MS-UPLC (MM) m/z 284.9 $[M+H]^+$.

x. Preparation of S-10s

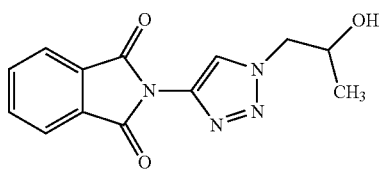 [SMILES: CC(O)Cn1cc(N2C(=O)c3ccccc3C2=O)nn1]

A solution of S-9 (1.00 g, 5.84 mmol) in acetonitrile (20 mL) was charged with copper(I)iodide (33.0 mg, 0.175 mmol) and triethylamine (17.6 mg, 0.17 mmol) at room temperature. 1-Azidopropan-2-ol (R1-s, 885.6 mg, 8.76 mmol) was added dropwise to the reaction mixture and was stirred for 16 h at room temperature. When TLC showed complete consumption of the starting material, the reaction mixture was diluted with the EtOAc (20 mL), filtered, washed with water (50 mL) and was dried over anhydrous $Na_2SO_4$. The organic layer was concentrated under reduced pressure followed by purification of the crude product by column chromatography on silica gel using 0-30% EtOAc in hexanes as eluent to afford S-10s (0.50 g, 31%, AMRI lot # IN-CKB-G-147) as a brown solid. The compound was characterized by UPLC-MS analysis. MS-UPLC (MM) m/z 273.1 $[M+H]^+$.

xi. Preparation of S-10t

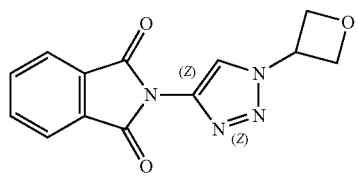 [SMILES: O=C1c2ccccc2C(=O)N1c1cn(C2COC2)nn1]

A solution of S-9 (1.00 g, 5.84 mmol) in acetonitrile (20 mL) was charged with copper(I)iodide (33.0 mg, 0.17 mmol) and triethylamine (17.0 mg, 0.17 mmol) at room temperature. 3-Azidooxetane (578 mg, 5.84 mmol) was added dropwise to the reaction mixture and stirred for 16 h at room temperature. When TLC showed complete consumption of the starting material, the reaction mixture was diluted with EtOAc (20 mL), filtered and washed with water (50 mL). The obtained was dried over anhydrous $Na_2SO_4$ and concentrated under reduced pressure followed by purification of the crude product by column chromatography on silica gel using 0-30% EtOAc in hexanes as eluent to afford S-10t (1.20 g, 76%, AMRI lot # IN-AKK-I-188) as a white solid. The compound was characterized by $^1H$ NMR analysis. $^1H$ NMR (400 MHz, DMSO-$d_6$): δ 8.56 (s, 1H), 8.03-8.00 (m, 2H), 7.97-7.94 (m, 2H), 5.98-5.91 (m, 1H), 5.05 (t, J=7.2 Hz, 2H), 4.98 (t, J=6.4 Hz, 2H).

xii. Preparation of S-10v

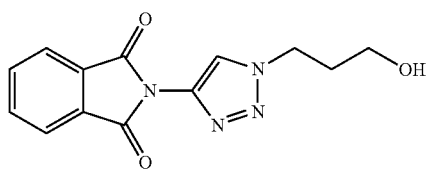 [SMILES: O=C1c2ccccc2C(=O)N1c1cn(CCCO)nn1]

A stirred solution of S-9 (1.00 g, 5.8 mmol) in acetonitrile (10 mL) taken in a round-bottom flask was charged with copper(I)iodide (0.033 g, 0.17 mmol) and $Et_3N$ (0.031 mL, 0.17 mmol) at room temperature. 3-Azidopropan-1-ol (0.79 g, 5.8 mmol) was added dropwise to the reaction mixture and was stirred for 5 h at room temperature. When TLC showed complete consumption of the starting material, the reaction mixture was diluted with EtOAc (50 mL), filtered, washed with water (50 mL) and was dried over anhydrous $Na_2SO_4$. The organic layer was concentrated under reduced pressure followed by purification of the crude product by column chromatography on silica gel using 0-70% EtOAc in hexanes as eluent to afford S-10v (0.45 g, 28%, AMRI lot # IN-SKY-C-169) as a brown gummy material. The compound was characterized by UPLC-MS analysis. MS-UPLC (MM) m/z 273.1 [M+H]$^+$.

xiii. Preparation of S-10w

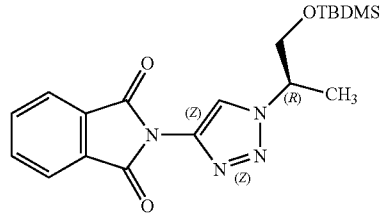

A solution of S-9 (2.20 g, 12.86 mmol) in acetonitrile (20 mL) was charged with copper(I)iodide (73.0 mg, 0.38 mmol) and triethylamine (38.0 mg, 0.38 mmol) at room temperature. (R)-(2-Azidopropoxy)(tert-butyl)dimethylsilane (3.04 g, 14.15 mmol) was added dropwise to the reaction mixture and stirred for 16 h at room temperature. When TLC showed complete consumption of the starting material, the reaction mixture was diluted with EtOAc (20 mL), filtered and washed with water (50 mL). The obtained was dried over anhydrous $Na_2SO_4$ and concentrated under reduced pressure followed by purification of the crude product by column chromatography on silica gel using 0-30% EtOAc in hexanes as eluent to afford S-10w (500 mg, 10%, AMRI lot # IN-AKK-I-192) as an oil. The compound was characterized by MS analysis. MS (MM) m/z 386.9 [M+H]$^+$;

xiv. Preparation of S-10x

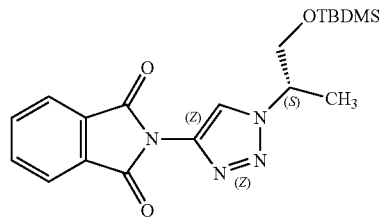

A solution of S-9 (2.20 g, 12.86 mmol) in acetonitrile (20 mL) was charged with copper(I)iodide (73.0 mg, 0.38 mmol) and triethylamine (38.0 mg, 0.38 mmol) at room temperature. (S)-(2-Azidopropoxy)(tert-butyl)dimethylsilane (3.04 g, 14.15 mmol) was added dropwise to the reaction mixture and stirred for 16 h at room temperature. When TLC showed complete consumption of the starting material, the reaction mixture was diluted with EtOAc (20 mL), filtered and washed with water (50 mL). The obtained was dried over anhydrous $Na_2SO_4$ and concentrated under reduced pressure followed by purification of the crude product by column chromatography on silica gel using 0-30% EtOAc in hexanes as eluent to afford S-10x (500 mg, 10%, AMRI lot # IN-AKK-I-198) as an oil. The compound was characterized by MS analysis. MS (MM) m/z 386.9 [M+H]$^+$;

c. General Synthesis of 1-Substituted 1H-1,2,3-Triazol-4-amines (S-5)

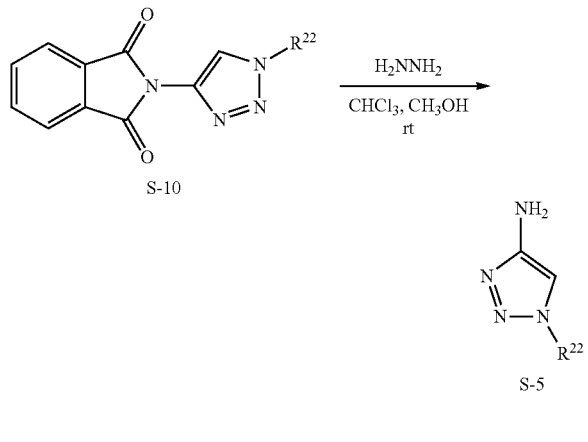

i. Preparation of S-5a

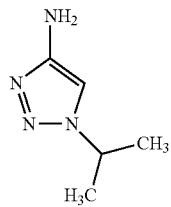

A solution of S-10a (650 mg, 2.54 mmol) in chloroform (16 mL) and MeOH (4.0 mL) was charged with 80% hydrazine hydrate (0.31 mL, 6.34 mmol) and stirred for 16 h at room temperature. When TLC showed complete consumption of the starting material, the reaction mixture was diluted with $CH_2Cl_2$ (20 mL) and filtered. The obtained was dried over anhydrous $Na_2SO_4$ and concentrated under reduced pressure followed by purification by column chromatography on silica gel using 0-2% MeOH in $CH_2Cl_2$ as eluent to afford S-5a (300 mg, 93%, AMRI lot # IN-AKK-I-17) as a white solid. The compound was characterized by $^1H$ NMR analysis. $^1H$ NMR (400 MHz, $CDCl_3$): δ 6.92 (s, 1H), 4.74-4.64 (m, 1H), 1.53 (d, J=6.8 Hz, 6H).

ii. Preparation of S-5i

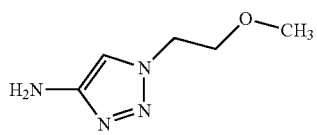

A solution of S-10i (320 mg, 1.17 mmol) in chloroform (16 mL) and MeOH (4 mL) was charged with 80% hydrazine hydrate (0.31 mL, 6.34 mmol) at room temperature. The reaction mixture was stirred for 16 h at room temperature. When TLC showed complete consumption of the starting material, the reaction mixture was diluted with the $CH_2Cl_2$ (20 mL), filtered and was dried over anhydrous $Na_2SO_4$. The organic layer was concentrated under reduced pressure followed by purification by column chromatography on silica gel using 1-3% MeOH in $CH_2Cl_2$ in as eluent to afford S-5i (140 mg, 87%, AMRI lot # IN-AKK-I-103-1) as a white solid. The compound was characterized by $^1H$ NMR analysis. $^1H$ NMR (300 MHz, DMSO-$d_6$): δ 7.06 (s, 1H), 4.66 (bs, 2H), 4.32 (t, J=5.1 Hz, 2H), 3.62 (t, J=5.4 Hz, 2H), 3.23 (s, 3H).

iii. Preparation of S-5j

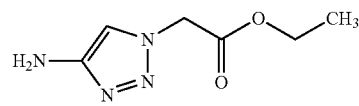

A solution of S-10j (400 mg, 1.13 mmol) in chloroform (16 mL) and MeOH (4 mL) was charged with 80% hydrazine hydrate (3.33 mL, 6.34 mmol) at room temperature. The reaction mixture was stirred for 16 h at room temperature. When TLC showed complete consumption of the starting material, the reaction mixture was diluted with the $CH_2Cl_2$ (20 mL), filtered and was dried over anhydrous $Na_2SO_4$. The organic layer was concentrated under reduced pressure followed by purification of the crude product by column chromatography on silica gel using 1-3% MeOH in $CH_2Cl_2$ as eluent to afford S-5j (150 mg, 68%, AMRI lot # IN-AKK-I-117-1) as a white solid. The compound was characterized by MS analysis. MS (MM) m/z 171.2 $[M+H]^+$.

iv. Preparation of S-5l

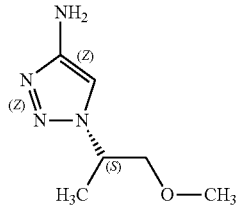

A solution of S-10l (400 mg, 1.39 mmol) in chloroform (8.0 mL) and MeOH (2.0 mL) was charged with 80% hydrazine hydrate (0.17 mL, 3.47 mmol) at room temperature. The reaction mixture was stirred for 16 h at room temperature. When TLC showed complete consumption of the starting material, the reaction mixture was diluted with $CH_2Cl_2$ (20 mL), filtered and was dried over anhydrous $Na_2SO_4$. The organic phase was concentrated under reduced pressure followed by purification of the crude product by column chromatography on silica gel using 0-3% MeOH in $CH_2Cl_2$ as eluent to afford S-5l (160 mg, 76%, AMRI lot # IN-CKB-G-141) as an off-white liquid. The compound was characterized by $^1H$ NMR analysis. $^1H$ NMR (400 MHz, $CDCl_3$): δ 7.03 (s, 1H), 4.72-4.66 (m, 1H), 3.66-3.63 (m, 2H), 3.33 (s, 3H), 1.55 (d, J=6.80 Hz, 3H).

v. Preparation of S-5m

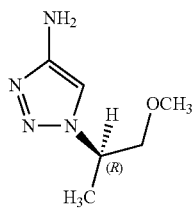

S-5-m

A solution of S-10m (400 mg, 0.64 mmol) in chloroform (8.0 mL) and MeOH (2.0 mL) was charged with 80% hydrazine hydrate (0.1 mL, 1.95 mmol) at room temperature. The reaction mixture was stirred for 16 h at room temperature. When TLC showed complete consumption of the starting material, the reaction mixture was diluted with CH$_2$Cl$_2$ (20 mL), filtered and was dried over anhydrous Na$_2$SO$_4$. The organic phase was concentrated under reduced pressure followed by purification of the crude product by column chromatography on silica gel using 0-3% MeOH in CH$_2$Cl$_2$ as eluent to afford S-5m (120 mg, 59%, AMRI lot #IN-CKB-G-138) as a white solid. The compound was characterized by $^1$H NMR analysis. $^1$H NMR (400 MHz, CDCl$_3$): δ 7.03 (s, 1H), 4.73-4.68 (m, 1H), 3.66-3.60 (m, 2H), 3.33 (s, 3H), 1.55 (d, J=6.80 Hz, 3H).

vi. Preparation of S-5q

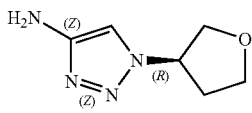

A solution of S-10q (1.10 g, 3.88 mmol) in chloroform (16 mL) and MeOH (4.0 mL) was charged with 80% hydrazine hydrate (0.60 mL, 9.7 mmol) at room temperature. The reaction mixture was stirred for 16 h at room temperature. When TLC showed complete consumption of the starting material, the reaction mixture was diluted with CH$_2$Cl$_2$ (20 mL) and filtered. The obtained was dried over anhydrous Na$_2$SO$_4$ and concentrated under reduced pressure followed by purification by column chromatography on silica gel using 0-2% MeOH in CH$_2$Cl$_2$ as eluent to afford S-5p (520 mg, 88%, AMRI lot # IN-AKK-I-164) as a white solid. The compound was characterized by $^1$H NMR analysis. $^1$H NMR (400 MHz, CDCl$_3$): δ 6.94 (s, 1H), 5.14-5.09 (m, 1H), 4.09-3.81 (m, 4H), 3.68 (s, 2H), 2.55-2.40 (m, 1H), 2.24-2.17 (m, 1H).

vii. Preparation of S-5p

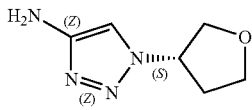

A solution of S-10p (500 mg, 3.88 mmol) in chloroform (10 mL) and MeOH (2.0 mL) was charged with 80% hydrazine hydrate (0.27 mL, 4.4 mmol) at room temperature. The reaction mixture was stirred for 16 h at room temperature. When TLC showed complete consumption of the starting material, the reaction mixture was diluted with CH$_2$Cl$_2$ (20 mL) and filtered. The obtained was dried over anhydrous Na$_2$SO$_4$ and concentrated under reduced pressure followed by purification by column chromatography on silica gel using 0-2% MeOH in CH$_2$Cl$_2$ as eluent to afford S-5p (200 mg, 74%, AMRI lot # IN-AKK-I-165) as a white solid. The compound was characterized by $^1$H NMR analysis. $^1$H NMR (400 MHz, CDCl$_3$): δ 7.01 (s, 1H), 5.22-5.17 (m, 1H), 4.16-3.85 (m, 4H), 3.69 (s, 2H), 2.62-2.45 (m, 1H), 2.31-2.23 (m, 1H).

viii. Preparation of S-5s

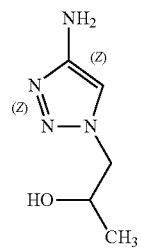

A solution of S-10s (500 mg, 1.83 mmol) in chloroform (8.0 mL) and MeOH (2.0 mL) was charged with 80% hydrazine hydrate (0.2 mL, 4.6 mmol) at room temperature. The reaction mixture was stirred for 16 h at room temperature. When TLC showed complete consumption of the starting material, the reaction mixture was diluted with CH$_2$Cl$_2$ (20 mL), filtered and was dried over anhydrous Na$_2$SO$_4$. The organic phase was concentrated under reduced pressure followed by purification of the crude product by column chromatography on silica gel using 0-3% MeOH in CH$_2$Cl$_2$ as eluent to afford S-5s (130 mg, 50%, AMRI lot #IN-CKB-G-149) as a colorless liquid. The compound was characterized by UPLC-MS analysis. MS-UPLC (MM) m/z 143.1 [M+H]$^+$.

ix. Preparation of S-5t

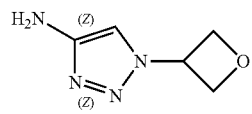

A solution of S-10t (1.20 g, 4.4 mmol) in chloroform (16 mL) and MeOH (4.0 mL) was charged with 80% hydrazine hydrate (0.68 mL, 11.1 mmol) and stirred for 16 h at room temperature. When TLC showed complete consumption of the starting material, the reaction mixture was diluted with CH$_2$Cl$_2$ (20 mL) and filtered. The obtained was dried over anhydrous Na$_2$SO$_4$ and concentrated under reduced pressure followed by purification by column chromatography on silica gel using 0-2% MeOH in CH$_2$Cl$_2$ as eluent to afford S-5t (440 mg, 72%, AMRI lot # IN-AKK-I-189) as a white solid. The compound was characterized by $^1$H NMR analysis. $^1$H NMR (400 MHz, DMSO-d$_6$): δ 7.32 (s, 1H), 5.67-5.60 (m, 1H), 4.94 (t, J=7.2 Hz, 2H), 4.84 (t, J=6.4 Hz, 2H), 4.80 (s, 2H).

x. Preparation of S-5v

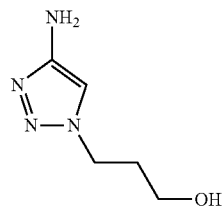

A stirred solution of S-10v (150 mg, 0.55 mmol) in chloroform (2.0 mL) and MeOH (0.5 mL) was charged with 80% hydrazine hydrate (0.035 mL, 1.10 mmol) at room temperature. The reaction mixture was stirred for 16 h at room temperature. When TLC showed complete consumption of the starting material, the reaction mixture was diluted with $CH_2Cl_2$ (20 mL) and filtered. The obtained was dried over anhydrous $Na_2SO_4$ and concentrated under reduced pressure to afford S-5v (50.0 mg, 64%, AMRI lot #IN-SKY-C-178) as a white solid. The compound was characterized by UPLC-MS analysis. MS-UPLC (MM) m/z 143.1 $[M+H]^+$.

xi. Preparation of S-5w

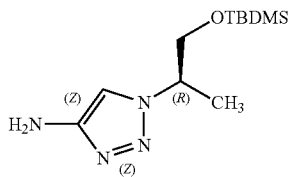

A solution of S-10w (500 mg, 1.29 mmol) in chloroform (10 mL) and MeOH (2.0 mL) was charged with 80% hydrazine hydrate (0.2 mL, 3.23 mmol) at room temperature. The reaction mixture was stirred for 16 h at room temperature. When TLC showed complete consumption of the starting material, the reaction mixture was diluted with $CH_2Cl_2$ (20 mL) and filtered. The obtained was dried over anhydrous $Na_2SO_4$ and concentrated under reduced pressure followed by purification by column chromatography on silica gel using 0-2% MeOH in $CH_2Cl_2$ as eluent to afford S-5w (270 mg, 81%, AMRI lot # IN-AKK-I-193-1) as a white solid. The compound was characterized by $^1$H NMR analysis. $^1$H NMR (400 MHz, DMSO-$d_6$): δ 7.13 (s, 1H), 4.69 (bs, 2H), 4.62-4.54 (m, 1H), 3.85 (d, J=4.8 Hz, 2H), 4.44 (d, J=7.2 Hz, 3H), 0.86 (s, 9H), 0.02 (s, 3H), 0.00 (s, 3H).

xii. Preparation of S-5x

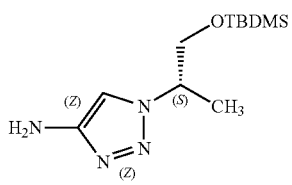

A solution of S-10x (500 mg, 1.29 mmol) in chloroform (10 mL) and MeOH (2.0 mL) was charged with 80% hydrazine hydrate (0.20 mL, 3.23 mmol) at room temperature. The reaction mixture was stirred for 16 h at room temperature. When TLC showed complete consumption of the starting material, the reaction mixture was diluted with $CH_2Cl_2$ (20 mL) and filtered. The obtained was dried over anhydrous $Na_2SO_4$ and concentrated under reduced pressure followed by purification by column chromatography on silica gel using 0-2% MeOH in $CH_2Cl_2$ as eluent to afford S-5x (270 mg, 81%, AMRI lot # IN-AKK-I-199) as a light green solid. The compound was characterized by MS analysis. MS (MM) m/z 256.9 $[M+H]^+$.

d. General Synthesis of Amine 7 and Amine 13

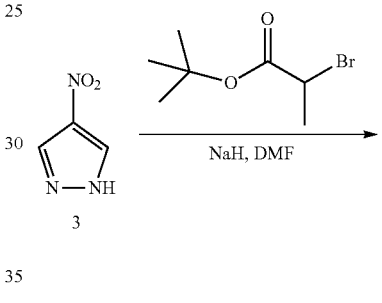

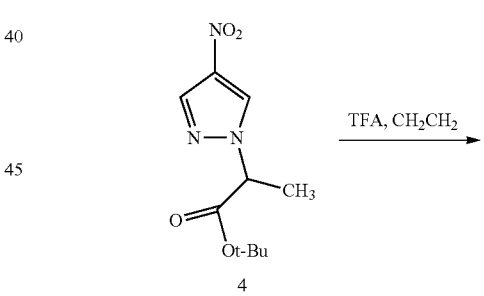

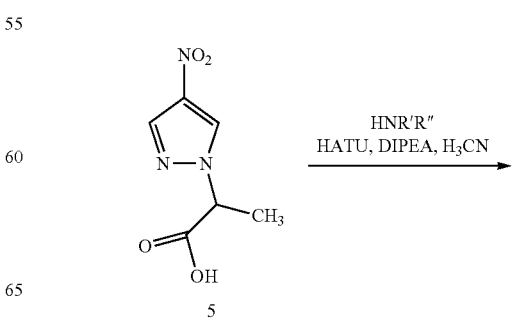

-continued

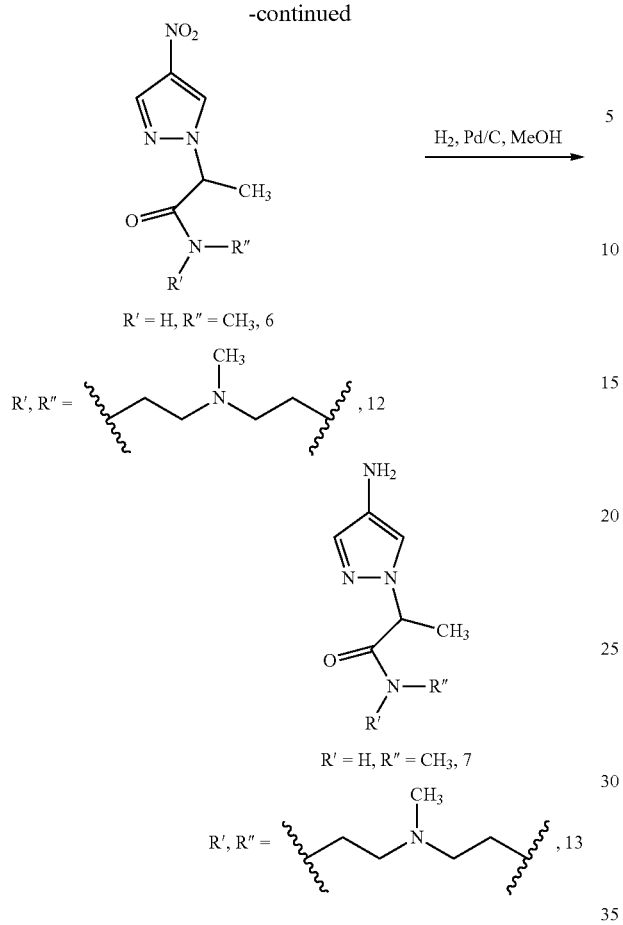

i. Preparation of Amine 7

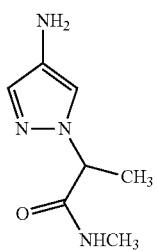

To a cold solution of nitro 3 (2.8 g, 24.77 mmol) and NaH (1.07 g, 60%) in DMF (50 mL) was added tert-butyl 2-bromopropanoate (5.34 mL, 32.02 mmol) through a septum for 15 minutes and then the mixture was stirred at room temperature for 16 hours under argon stream. The reaction mixture was diluted with EtOAc, washed with water twice and the organic phase was evaporated and chromatographed to give nitro 4 (1.55 g, 26%): FABMS (M+H) 242.1. This later was treated with TFA (10 mL) in cold $CH_2Cl_2$ (10 mL) and stirred for one hour. After evaporation to dryness the obtained carboxylic crude carboxylic acid 5 [FABMS (M+H) 186.04] was precipitated in EtOAc and used without purification. To a solution of carboxylic acid 5 (0.5 g, 2.7 mmol) in acetonitrile (10 mL) was added HATU (1.54 g, 4.05 mmol), methylamine (1 eq) and DIPEA (0.7 mL, 4.05 mmol). The mixture was stirred for three hours at room temperature then water was added and the solution was extracted with EtOAc, dried and evaporated to afford the crude methylamide 6 [0.32 g, 70%, FABMS (M+H) 199.1]. Reduction of methylamide 6 was done, using palladium on carbon (0.2 g, 10%) in methanol (10 mL) under hydrogen pressure for one hour, leading to amine 7 [0.23 g, 82%, FABMS (M+H) 169.1].

ii. Preparation of Amine 13

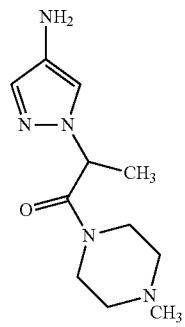

Amine 13 was prepared according to the same procedure described for the synthesis of amine 7 from methylamide 12 (0.33 g, 80%, FABMS (M+H) 238.2).

e. Synthesis of Amine 16

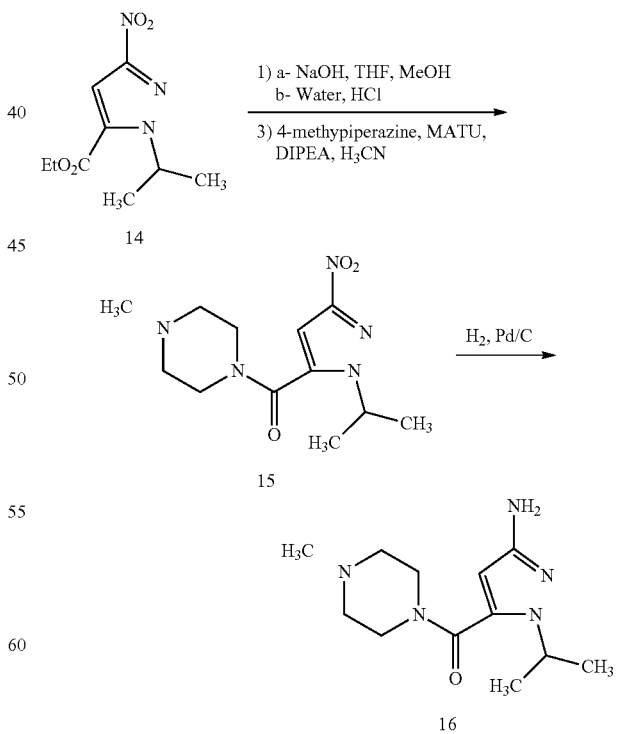

Amine 16 was prepared according to the same procedure reported for the preparation of amine 7.

f. Synthesis of Amine 22

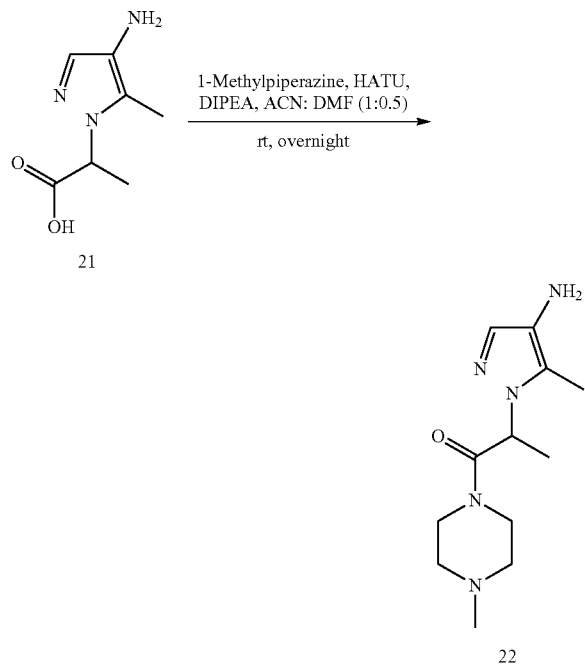

To a stirred solution of amine 21 (0.2 g, 1.18 mmol), 1-methylpiperazine (0.26 mL, 2.3 mmol) and DIPEA (0.82 mL, 0.611 mmol) in ACN:DMF (5 mL, 1:0.5) was added HATU (0.539, 1.41 mmol) at rt and the reaction mixture was stirred at rt overnight. Solvents removed in vacuo and ethyl acetate was added to this residue and organic layer was washed with Saturated sodium bicarbonate followed by brine and dries over sodium sulphate, solvent was removed in vacuo to afford amine 22 (0.8, 94%). MS-251 (M+H).

g. Synthesis of Amine S-14j

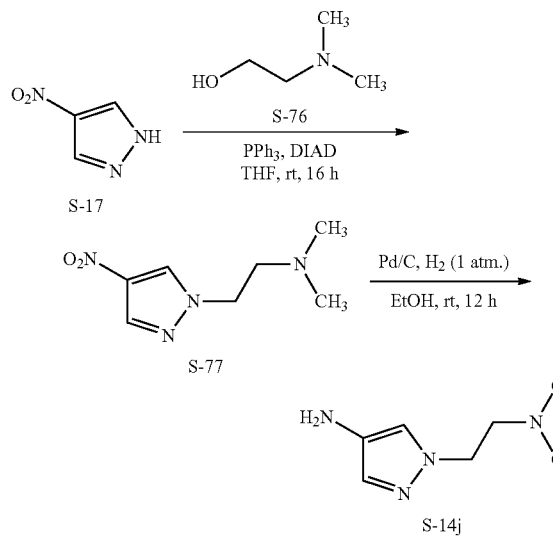

i. Preparation of S-77

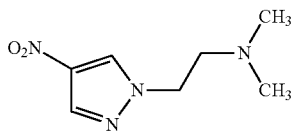

A cooled solution of S-17 (1.60 g, 14.14 mmol), S-76 (1.0 g, 11.31 mmol) and triphenylphosphine (4.60 g, 17.67 mmol) in THF (50 mL) was charged with DIAD (3.7 mL, 17.67 mmol) dropwise at 0° C. under nitrogen atmosphere. The reaction mixture was stirred for 5 min, cooled to room temperature and then stirred for 16 h. The reaction mixture was partitioned between $CH_2Cl_2$ (50 mL) and HCl (1 M, 20 mL). The organic phase was separated and was washed with HCl (1 M, 2×20 mL). The combined aqueous phase was basified by the addition of 40% NaOH solution and was extracted with $CH_2Cl_2$ (2×50 mL). The combined organic phase was washed with brine (2×20 mL). The organic layer was dried over anhydrous $Na_2SO_4$ and was concentrated under reduced pressure. The crude compound was purified by column chromatography on silica gel using 0-3% MeOH in $CH_2Cl_2$ as eluent to afford S-77 (1.20 g, 75%, AMRI lot # IN-CKB-G-81) as an off-white solid. The compound was characterized by $^1H$ NMR analysis. $^1H$ NMR (300 MHz, DMSO-$d_6$): δ 8.87 (s, 1H), 8.25 (s, 1H), 4.26 (t, J=6.30 Hz, 2H), 2.67 (t, J=6.30 Hz, 2H), 2.16 (s, 6H).

ii. Preparation of S-14j

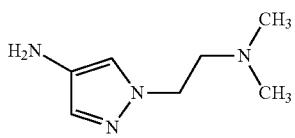

A stirred solution of S-77 (1.20 g, 6.52 mmol) in EtOH (30 mL) taken in a round-bottom flask was charged with 5% Palladium on carbon (0.20 g) at ambient temperature under nitrogen atmosphere. The reaction mixture was stirred for 12 h at room temperature under hydrogen balloon pressure. The reaction mixture was filtered, washed with EtOAc (50 mL) and the filtrate was concentrated under reduced pressure to afford S-14j (0.80 g, 80%, AMRI lot # IN-CKB-G-82) as a brown liquid. The compound was characterized by UPLC-MS analysis. MS-UPLC (MM) m/z 155.1 [M+H]$^+$.

h. Synthesis of Amine S-90

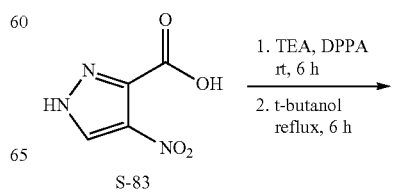

ii. Preparation of S-86

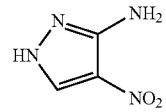

A stirred solution of S-91 (0.20 g) in 1,4 dioxane (2 mL) taken in a round-bottom flask was charged with HCl in dioxane (2 mL) and stirred for 6 h at room temperature under nitrogen atmosphere. When TLC showed complete consumption of starting material, the reaction mixture was concentrated under reduced pressure to afford S-86 (0.10 g, 89%, AMRI lot # IN-SKY-C-114) as an off-white solid. The compound was characterized by UPLC analysis. MS-UPLC (MM) m/z 129.2 [M+]$^+$.

iii. Preparation of S-87

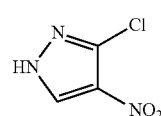

A stirred solution of S-86 (0.10 g, 0.78 mmol) in HCl (6 N, 2 mL) taken in a round-bottom flask was charged with NaNO$_2$ (0.10 g, 1.56 mmol) in water (1.0 mL), stirred for 1 h at room temperature. At this time, Cu(I)Cl (0.15 g, 1.56 mmol) was added to the reaction mixture and stirred for 12 h at room temperature. When TLC showed complete consumption of starting material, diluted with the water (10 mL) and extracted with EtOAc (2×10 mL). The combined organic layers were washed with water (10 mL). The organic layers were dried over anhydrous Na$_2$SO$_4$ and concentrated under reduced pressure to afford S-87 (0.05 g, 43%, AMRI lot # IN-SKY-C-115) as an off-white solid. The compound was characterized by UPLC analysis. MS-UPLC (MM) m/z 145.2 [M−]$^-$.

iv. Preparation of S-89

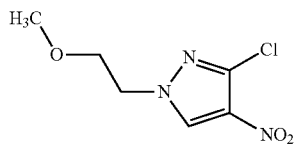

A stirred solution of S-87 (0.08 g, 0.54 mmol) in DMF (50 mL) taken in a round-bottom flask was charged with NaH (0.025 g, 0.54 mmol) and S-88 (0.11 g, 0.81 mmol) at 0° C. temperature under nitrogen atmosphere. The reaction mixture was stirred for 6 h at 60° C. When TLC showed complete consumption of starting material, the reaction mixture was diluted with ice water (5 mL) and extracted with EtOAc (2×10 mL). The combined organic layers were washed with water (10 mL). The organic layers were dried over anhydrous Na$_2$SO$_4$, and concentrated under reduced pressure to afford S-89 (0.08 g, 71%, AMRI lot # IN-SKY- -continued

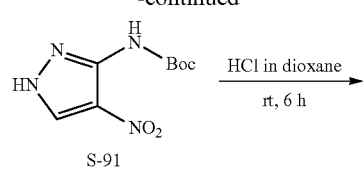

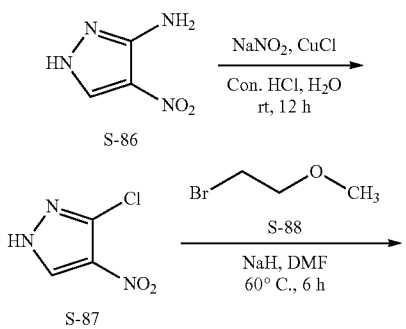

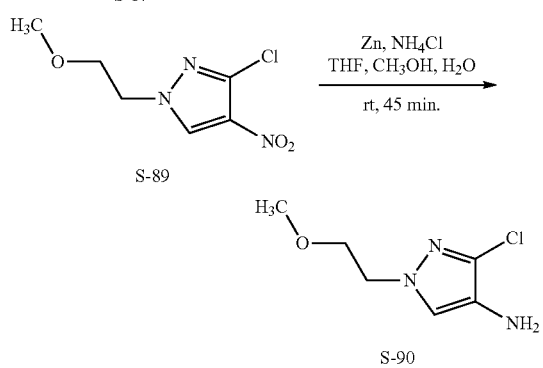

i. Preparation of S-91

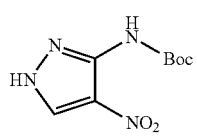

A stirred solution of S-83 (1.00 g, 6.36 mmol) in THF (10 mL) taken in a round-bottom flask was charged with Et$_3$N (1.3 mL, 9.55 mmol) and DPPA (2.62 g, 9.55 mmol) at room temperature. The reaction mixture was stirred for 6 h at room temperature under nitrogen atmosphere. At this time, t-butanol (10 mL) was added and refluxed for 6 h under nitrogen atmosphere. When TLC showed complete consumption of starting material, the reaction mixture was diluted with the water (10 mL) and extracted with EtOAc (2×10 mL). The combined organic layers were washed with water (10 mL). The organic layers were dried over anhydrous Na$_2$SO$_4$, and concentrated under reduced pressure. The crude product was purified by column chromatography on silica gel using 0-50% EtOAc in hexanes as eluent to afford S-91 (0.20 g, 14%, AMRI lot # IN-SKY-C-110) as an off-white solid. The compound was characterized by UPLC analysis. MS-UPLC (MM) m/z 127.2 [M−]$^-$.

C-122) as an off-white solid. The compound was characterized by UPLC analysis. MS-UPLC (MM) m/z 204.2 [M−]⁻ v. Preparation of S-90

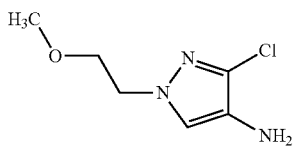

A stirred solution of S-89 (0.08 g, 0.39 mmol) in THF/MeOH/H$_2$O (3:2:1, 3 mL) was charged with ammonium chloride (0.26 g, 5.07 mmol) and zinc metal (0.20 g, 3.12 mmol) at ambient temperature under nitrogen atmosphere. The suspension was stirred for 45 min. When TLC showed complete consumption of starting material, the suspension was filtered over celite and washed with EtOAc (10 mL). The organic phase washed with water (2×5.0 mL). The aqueous phase is re-extracted with EtOAc (1×10 mL). The combined organic layer was washed with brine (1×5 mL). The organic layer was dried over anhydrous Na$_2$SO$_4$ and was concentrated under reduced pressure to afford S-90 (0.05 g, 73%, AMRI lot # IN-SKY-C-125) as a gummy. The compound was characterized by UPLC analysis. MS-UPLC (MM) m/z 176.2 [M+]⁺.

i. Synthesis of Amine S-104

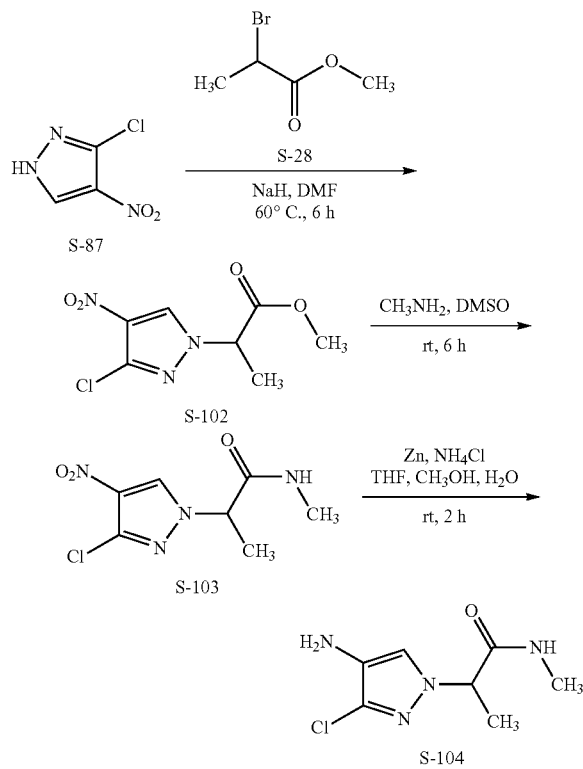

i. Preparation of S-102

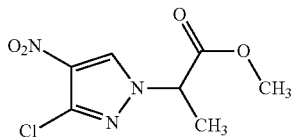

A stirred solution of S-87 (0.80 g, 5.4 mmol) in DMF (10 mL) taken in a round-bottom flask was charged with NaH (0.25 g, 8.16 mmol) and S-28 (1.34 g, 26.5 mmol) successively at 0° C. under nitrogen atmosphere. The reaction mixture was stirred for 6 h at 60° C. To the reaction mixture, ice cold water (30 mL) was added and extracted with EtOAc (50 mL). The organic layer was washed with brine (1×30 mL). The organic layer was dried over anhydrous Na$_2$SO$_4$ and was concentrated under reduced pressure. The crude compound was purified by column chromatography on silica gel using 5-40% EtOAc in hexanes as eluent to afford S-102 (0.70 g, 40%, AMRI lot # IN-SKY-C-134) as an off-white solid. The compound was characterized by ¹H NMR analysis. ¹H NMR (400 MHz, CDCl$_3$): δ 8.35 (s, 1H), 5.07-5.02 (m, 1H), 3.76 (s, 3H), 1.86-1.82 (d, 3H).

ii. Preparation of S-103

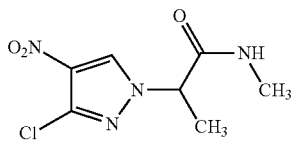

A stirred solution of S-102 (0.15 g, 0.64 mmol) in DMSO (0.5 mL) taken in a round-bottom flask was charged with methylamine in MeOH (0.5 mL) at ambient temperature under nitrogen atmosphere. The reaction mixture was stirred for 6 h at room temperature. To the reaction mixture, ice cold water (1.0 mL) was added and the precipitated solid was collected by filtration. The solid was washed with water (10 mL) and dried by vacuum to afford S-103 (0.10 g, 66%, AMRI lot # IN-SKY-C-138) as an off-white solid. The compound was characterized by ¹H NMR analysis. ¹H NMR (400 MHz, DMSO-d$_6$): δ 9.0 (s, 1H), 8.16 (d, J=3.6 Hz, 1H), 5.06-5.01 (m, 1H), 2.61 (d, J=4.4 Hz, 3H), 1.62 (d, J=7.2 Hz, 3H).

iii. Preparation of S-104

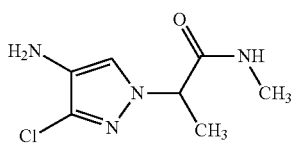

A stirred solution of S-103 (0.55 g, 2.37 mmol) in THF/MeOH/H$_2$O (3:2:1, 10 mL) was charged with ammonium chloride (1.63 g, 30.8 mmol) and zinc metal (1.23 g, 18.9 mmol) at ambient temperature under nitrogen atmosphere. The suspension was stirred for 2 h at same temperature. When TLC showed complete consumption of starting material, the suspension was filtered over celite and washed with EtOAc (30 mL). The organic phase was washed with water (2×10 mL). The aqueous phase was re-extracted with EtOAc (1×20 mL). The combined organic layer was washed with brine (1×5.0 mL). The organic layer was dried over anhydrous $Na_2SO_4$ and was concentrated under reduced pressure to afford S-104 (0.35 g, 73%, AMRI lot # IN-SKY-C-142) as a gummy material. The compound was characterized by UPLC analysis. MS-UPLC (MM) m/z 203.2 $[M+H]^+$.

j. Synthesis of Amine S-107

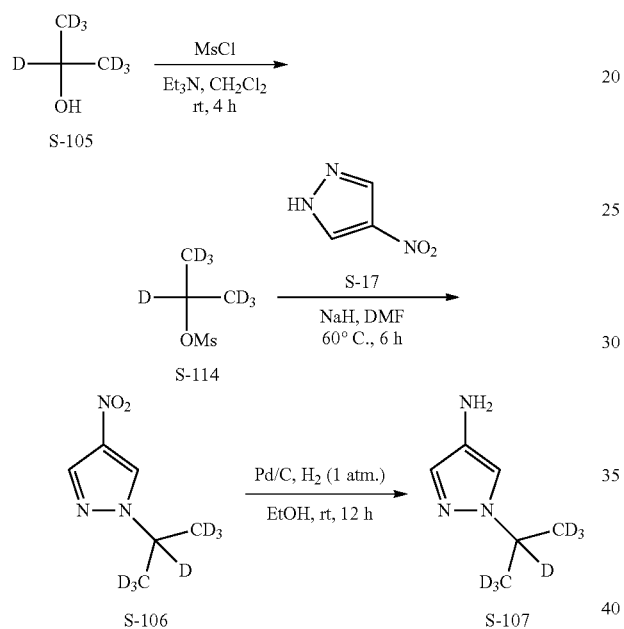

i. Preparation of S-114

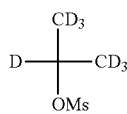

A stirred solution of S-105 (0.50 g, 7.46 mmol) in $CH_2Cl_2$ (10 mL) taken in a round-bottom flask was charged with $Et_3N$ (2.03 mL, 14.9 mmol) and methane sulfonyl chloride (0.57 mL, 7.46 mmol) successively at ambient temperature under nitrogen atmosphere. The reaction mixture was stirred for 4 h at same temperature. The reaction mixture was diluted with $CH_2Cl_2$ (50 mL), washed with water (20 mL) and HCl (1 N, 20 mL). The combined organic layer was washed with brine (1×50 mL). The organic layer was dried over anhydrous $Na_2SO_4$ and was concentrated under reduced pressure to afford S-114 (0.55 g, 50%, AMRI lot # IN-SKY-C-136) as a colorless liquid. The crude product was used as such for the next step.

ii. Preparation of S-106

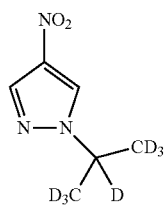

A stirred solution of S-114 (0.55 g, 3.79 mmol) in DMF (10 mL) taken in a round-bottom flask was charged with NaH (0.18 g, 3.79 mmol) and S-17 (0.64 g, 5.68 mmol) successively at 0° C. under nitrogen atmosphere. The reaction mixture was stirred for 6 h at 60° C. To the reaction mixture, ice cold water was added (30 mL) and extracted with EtOAc (50 mL). The organic layer was washed with brine (1×30 mL). The organic layer was dried over anhydrous $Na_2SO_4$ and was concentrated under reduced pressure. The crude compound was purified by column chromatography on silica gel using 5-40% EtOAc in hexanes as eluent to afford S-106 (0.22 g, 33%, AMRI lot # IN-SKY-C-141) as an off-white solid. The compound was characterized by $^1H$ NMR analysis. $^1H$ NMR (300 MHz, $CDCl_3$): δ 8.15 (s, 1H), 8.07 (s, 1H).

iii. Preparation of S-107

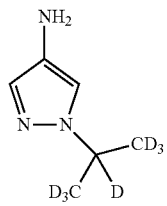 [SMILES: [2H]C([2H])([2H])C([2H])(n1cc(N)cn1)C([2H])([2H])[2H]]

A stirred solution of S-106 (0.22 g, 1.35 mmol) in EtOH (10 mL) taken in a round-bottom flask was charged with 5% palladium on carbon (0.04 g) at ambient temperature under nitrogen atmosphere. The reaction mixture was stirred for 12 h at room temperature under hydrogen balloon pressure. The reaction mixture was filtered, washed with EtOAc (50 mL) and the filtrate was concentrated under reduced pressure to afford S-107 (0.14 g, 78%, AMRI lot # IN-SKY-C-144) as a brown liquid. The compound was characterized by $^1H$ NMR analysis. $^1H$ NMR (400 MHz, DMSO-$d_6$): δ 7.02 (s, 1H), 6.87 (s, 1H), 3.76 (bs, 2H).

k. Synthesis of Amine S-159

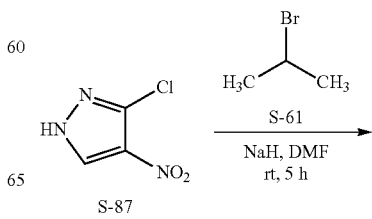

145

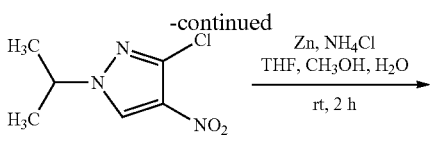

i. Preparation of S-158

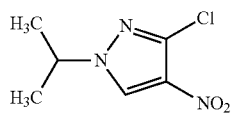

A stirred solution of S-87 (2500 mg, 17.1 mmol) in DMF (25 mL) taken in a round-bottom flask was charged with NaH (1020 mg, 25.6 mmol) and S-61 (2480 mg, 20.5 mmol) successively at 0° C. under nitrogen atmosphere. The reaction mixture was stirred for 5 h at ambient temperature under nitrogen atmosphere. To the reaction mixture, ice cold water was added (50 mL) and extracted with EtOAc (100 mL). The organic layer was washed with brine (1×50 mL). The organic layer was dried over anhydrous $Na_2SO_4$ and was concentrated under reduced pressure. The crude compound was purified by column chromatography on silica gel using 5-40% EtOAc in hexanes as eluent to afford S-158 (1200 mg, 37%, AMRI lot # IN-SKY-D-34) as an off-white solid. The compound was characterized by $^1H$ NMR analysis. $^1H$ NMR (400 MHz, DMSO-$d_6$): δ 9.05 (s, 1H), 4.60-4.50 (m, 1H), 1.43 (d, J=6.4 Hz, 6H).

ii. Preparation of S-159

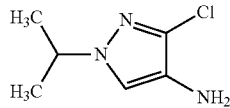

A stirred solution of S-158 (1200 mg, 6.3 mmol) in THF/MeOH/$H_2O$ (3:2:1, 12 mL) was charged with ammonium chloride (4300 mg, 82.5 mmol) and zinc metal (3200 mg, 50.4 mmol) at ambient temperature under nitrogen atmosphere. The suspension was stirred for 2 h at same temperature. Upon complete consumption of the starting material by TLC, the suspension was filtered over celite and washed with EtOAc (50 mL). The organic phase was washed with water (2×20 mL). The aqueous phase was re-extracted with EtOAc (1×40 mL). The combined organic layer was washed with brine (1×20 mL). The organic layer was dried over anhydrous $Na_2SO_4$ and was concentrated under reduced pressure to afford S-159 (800 mg, 80%, AMRI lot # IN-SKY-D-35) as a gummy solid. The compound was characterized by UPLC-MS analysis. MS-UPLC (MM) m/z 160.1 $[M+H]^+$.

146 l. General Synthesis of (S)—N4-(1-cyclopropyl-ethyl)-7-tosyl-N2-(1H-1,2,3-triazol-4-yl)-7H-pyrrolo[2,3-d]pyrimidine-2,4-diamines (S-13)

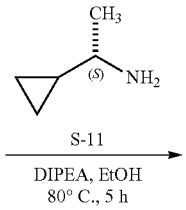

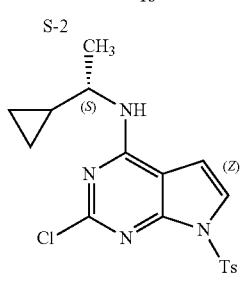

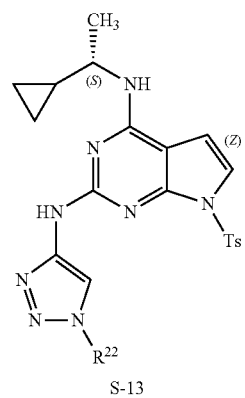

i. Preparation of S-12

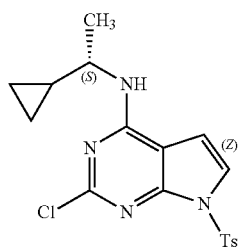

A stirred solution of S-2 (5.00 g, 14.6 mmol) in EtOH (50 mL) taken in a round-bottom flask was charged with DIPEA (5.0 mL, 29.2 mmol) and S-11 (1.74 g, 20.5 mmol) at room temperature. The reaction mixture was heated to 80° C. for 5 h under nitrogen atmosphere and was concentrated under reduced pressure. The crude residue was purified by column chromatography on silica gel using 0-50% EtOAc in hexanes as eluent to afford S-12 (3.80 g, 65%, AMRI lot # IN-SKY-C-11) as an off-white solid. The compound was characterized by 1H NMR analysis. $^1H$ NMR (400 MHz, CDCl$_3$): δ 8.08 (d, J=8.36 Hz, 2H), 7.39 (d, J=4 Hz, 1H), 7.30 (d, J=8.12 Hz, 2H), 6.43 (d, J=4 Hz, 1H), 5.25 (d, J=7.48 Hz, 1H), 3.7 (q, J=14.44 Hz, 1H), 2.39 (s, 3H), 1.28 (d, J=6.52 Hz, 3H), 0.91-0.87 (m, 1H), 0.56-0.41 (m, 2H), 0.39-0.24 (m, 2H).

ii. Preparation of S-13a

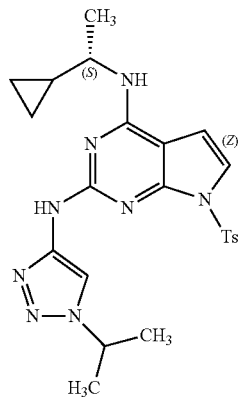

A solution of S-12 (0.2 g, 0.55 mmol), amine S-5a (0.084 g, 0.66 mmol), Cs$_2$CO$_3$ (0.358 g, 1.1 mmol) and 1,4-dioxane (3 mL) were charged into a microwave vial with stirrer bar. Argon gas was purged through septum and the reaction mixture was degassed for about 5 min. To this reaction mixture, Xantphos (0.021 g, 0.055 mmol) and Pd$_2$(dba)$_3$ (0.05 g, 0.055 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 0-3% MeOH in CH$_2$Cl$_2$ as eluent to afford S-13a (0.16 g, 66%, AMRI lot # IN-AKK-I-24) as a brown solid. The compound was characterized by $^1$H NMR analysis. $^1$H NMR (400 MHz, CDCl$_3$): δ 8.70 (bs, 1H), 7.93 (d, J=8.4 Hz, 2H), 7.57 (bs, 1H), 7.21-7.16 (m, 3H), 6.34 (d, J=4.4 Hz, 1H), 4.89-4.82 (m, 1H), 3.72-3.63 (m, 1H), 2.34 (s, 3H), 1.64 (d, J=6.8 Hz, 6H), 1.30 (d, J=6.4 Hz, 3H), 0.99-0.90 (m, 1H), 0.57-0.52 (m, 4H).

i. Preparation of S-13g

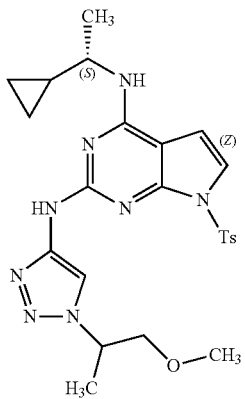

A solution of S-12 (0.20 g, 0.51 mmol), 1-(1-methoxy-propan-2-yl)-1H-1,2,3-triazol-4-amine S-5g (0.95 g, 0.61 mmol), Cs$_2$CO$_3$ (0.332 g, 1.02 mmol) and 1,4-dioxane (3 mL) was charged into a microwave vial with stirrer bar. Argon gas was purged through septum and the reaction mixture was degassed for about 5 min. To this reaction mixture, xantphos (0.029 g, 0.051 mmol) and Pd$_2$(dba)$_3$ (0.046 g, 0.051 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-5% MeOH in CH$_2$Cl$_2$ as eluent to afford S-13g (0.14 g, 53%, AMRI lot # IN-SKY-C-55) as an off-white solid. The product was used as such for the next step.

ii. Preparation of S-13h

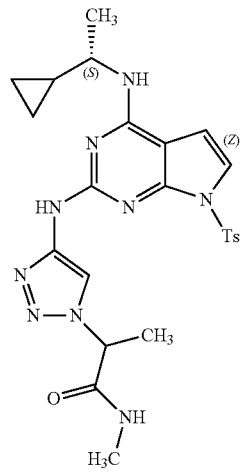

A solution of S-12 (0.30 g, 0.76 mmol), 2-(4-amino-1H-1,2,3-triazol-1-yl)-N-methylpropanamide S-5h (0.15 g, 0.92 mmol), Cs$_2$CO$_3$ (0.49 g, 1.52 mmol) and 1,4-dioxane (3 m) was charged into a microwave vial with stirrer bar. Argon gas was purged through septum and the reaction mixture was degassed for about 5 min. To this reaction mixture, xantphos (0.036 g, 0.076 mmol) and Pd$_2$(dba)$_3$ (0.070 g, 0.076 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 0-3% MeOH in CH$_2$Cl$_2$ as eluent to afford compound S-13h (0.14 g, 35%, AMRI lot # IN-AKK-I-108-1) as a brown solid. The compound was characterized by $^1$H NMR analysis. $^1$H NMR (400 MHz, DMSO-d$_6$): δ 9.62 (bs, 1H), 8.58 (bs, 1H), 8.33 (d, J=4.2 Hz, 1H), 7.97 (s, 2H), 7.51 (d, J=6.8 Hz, 1H), 7.35 (d, J=8.8 Hz, 2H), 7.21 (d, J=4 Hz, 1H), 6.80 (d, J=4 Hz, 1H), 5.33-5.28 (m, 1H), 3.76-3.75 (m, 1H), 2.64 (d, J=4.8 Hz, 3H), 2.32 (s, 3H), 1.71 (d, J=6.8 Hz, 3H), 1.23 (d, J=5.6 Hz, 3H), 0.96 (s, 1H), 0.45-0.19 (m, 4H).

iii. Preparation of S-13i

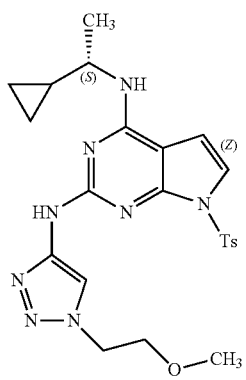

A solution of S-12 (0.20 g, 0.51 mmol), amine S-5i (0.087 g, 0.61 mmol), Cs$_2$CO$_3$ (0.33 g, 1.02 mmol) and 1,4-dioxane (3 mL) was charged into a microwave vial with stirrer bar. Argon gas was purged through septum and the reaction mixture was degassed for about 5 min. To this reaction mixture, xantphos (0.034 g, 0.051 mmol) and Pd$_2$(dba)$_3$ (0.046 g, 0.051 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 0-3% MeOH in CH$_2$Cl$_2$ as eluent to afford S-13i (0.11 g, 44%, AMRI lot # IN-AKK-I-107) as a brown solid. The compound was characterized by $^1$H NMR analysis. $^1$H NMR (400 MHz, DMSO): δ 9.56 (s, 1H), 8.35 (s, 1H), 7.94 (s, 2H), 7.50 (d, J=6.8 Hz, 1H), 7.36 (d, J=8 Hz, 2H), 7.21 (d, J=4 Hz, 1H), 6.80 (d, J=4 Hz, 1H), 4.53 (t, J=5.2 Hz, 2H), 3.77 (t, J=4.8 Hz, 2H), 3.26 (s, 3H), 2.32 (s, 3H), 1.22 (d, J=6.4 Hz, 3H), 0.99-0.95 (m, 1H), 0.46-0.17 (m, 4H).

iv. Preparation of S-13j

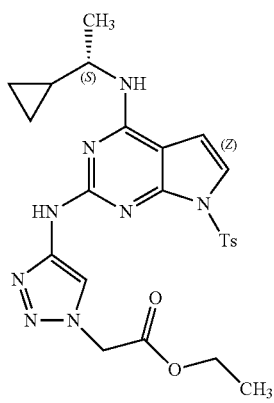

A solution of S-12 (0.3 g, 0.76 mmol), amine S-5j (0.15 g, 0.92 mmol), Cs$_2$CO$_3$ (0.49 g, 1.52 mmol) and 1,4-dioxane (3 mL) was charged into a microwave vial with stirrer bar. Argon gas was purged through septum and the reaction mixture was degassed for about 5 min. To this reaction mixture, xantphos (0.036 g, 0.076 mmol) and Pd$_2$(dba)$_3$ (0.070 g, 0.076 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product S-13j was used as such for the next step.

v. Preparation of S-13l

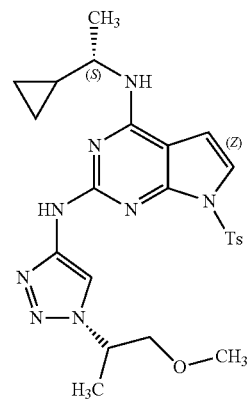

A solution of S-12 (0.30 g, 0.77 mmol), amine S-5l (0.146 g, 0.92 m mol), Cs$_2$CO$_3$ (0.50 g, 1.54 mmol) and 1,4-dioxane (4.0 mL) was charged into a microwave vial with stirrer bar. Argon gas was purged through septum and the reaction mixture was degassed for about 5 min. To this reaction mixture, xantphos (0.044 g, 0.077 mmol) and Pd$_2$(dba)$_3$ (0.07 g, 0.077 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 0-3% MeOH in CH$_2$Cl$_2$ as eluent to afford S-13l (0.15 g, 38%, AMRI lot # IN-CKB-G-142) as a yellow solid. The compound was characterized by UPLC-MS analysis. MS-UPLC (MM) m/z 511.1 [M+H]$^+$ vi. Preparation of S-13m

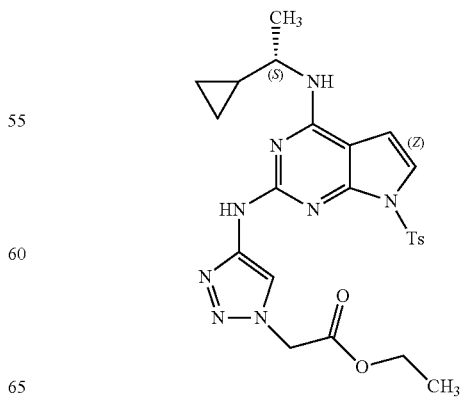

A solution of S-12 (0.30 g, 0.77 mmol), amine S-5m (0.12 g, 0.77 mmol), Cs$_2$CO$_3$ (0.50 g, 1.54 mmol) and 1,4-dioxane (3.0 mL) was charged into a microwave vial with stirrer bar. Argon gas was purged through septum and the reaction mixture was degassed for about 5 min. To this reaction mixture, xantphos (0.044 g, 0.077 mmol) and Pd$_2$(dba)$_3$ (0.07 g, 0.077 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 0-3% MeOH in CH$_2$Cl$_2$ as eluent to afford S-13m (0.15 g, 38%, AMRI lot # IN-CKB-G-140) as a yellow solid. The compound was characterized by UPLC-MS analysis. MS-UPLC (MM) m/z 511.2 [M+H]$^+$.

vii. Preparation of S-13s

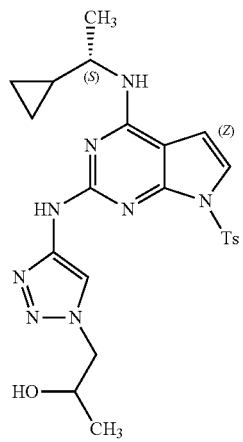

A solution of S-12 (0.30 g, 0.77 mmol), amine S-5s (0.13 g, 0.92 mmol), Cs$_2$CO$_3$ (0.50 g, 1.54 mmol) and 1,4-dioxane (3.0 mL) was charged into a microwave vial with stirrer bar. Argon gas was purged through septum and the reaction mixture was degassed for about 5 min. To this reaction mixture, xantphos (0.044 g, 0.077 mmol) and Pd$_2$(dba)$_3$ (0.07 g, 0.077 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 0-3% MeOH in CH$_2$Cl$_2$ as eluent to afford S-13s (0.20 g, 51%, AMRI lot # IN-CKB-G-150) as a yellow solid. The compound was characterized by UPLC-MS analysis. MS-UPLC (MM) m/z 497.1 [M+H]$^+$.

viii. Preparation of S-13t

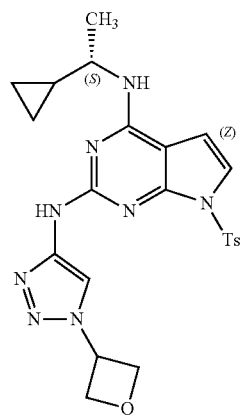

A stirred solution of S-12 (300 mg, 0.82 mmol) in 1,4-dioxane (3.0 mL) taken in a microwave vial was charged with amine S-5t (139 mg, 0.99 mmol) and Cs$_2$CO$_3$ (533 mg, 1.64 mmol). Argon gas was purged through septum and the reaction was degassed for about 5 min. To this reaction mixture, xantphos (47.0 mg, 0.082 mmol) followed by Pd$_2$(dba)$_3$ (75.0 mg, 0.082 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-3% MeOH in CH$_2$Cl$_2$ as eluent to afford S-13t (220 mg, 57%, AMRI lot # IN-AKK-I-190) as a green solid. The compound was characterized by $^1$H NMR analysis. $^1$H NMR (400 MHz, DMSO-d$_6$): δ 9.79 (s, 1H), 8.67 (bs, 1H), 7.93 (s, 2H), 7.58 (d, J=4.4 Hz, 1H), 7.38 (d, J=8.0 Hz, 2H), 7.24 (d, J=4.0 Hz, 1H), 6.82 (d, J=4.0 Hz, 1H), 5.88-5.81 (m, 1H), 5.12 (t, J=7.2 Hz, 2H), 4.88 (t, J=6.0 Hz, 2H), 3.79-3.75 (m, 1H), 2.32 (s, 3H), 1.23 (s, 3H), 0.99-0.93 (m, 1H), 0.47-0.33 (m, 3H), 0.18-0.14 (m, 1H).

ix. Preparation of S-13w

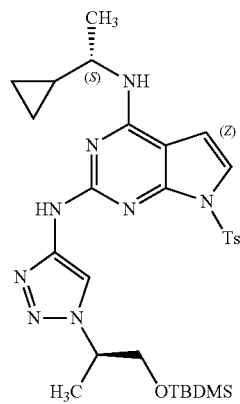

A stirred solution of S-12 (300 mg, 0.82 mmol) in 1,4-dioxane (3.0 mL) taken in a microwave vial was charged with amine S-5w (233 mg, 0.99 mmol) and Cs₂CO₃ (533 mg, 1.64 mmol). Argon gas was purged through septum and the reaction was degassed for about 5 min. To this reaction mixture, xantphos (47.0 mg, 0.082 mmol) followed by Pd₂(dba)₃ (75.0 mg, 0.082 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-3% MeOH in CH₂Cl₂ as eluent to afford S-13w (210 mg, 45%, AMRI lot # IN-AKK-I-194-1) as an off-white solid. The compound was characterized by ¹H NMR analysis. ¹H NMR (400 MHz, CD₃OD): δ 8.63 (s, 1H), 7.96 (d, J=8.0 Hz, 2H), 7.57 (s, 1H), 7.23 (d, J=8.0 Hz, 2H), 7.19 (d, J=4 Hz, 1H), 6.36 (d, J=4 Hz, 1H), 4.82-4.74 (m, 1H), 4.04-4.00 (m, 1H), 3.94-3.90 (m, 1H), 3.75-3.66 (m, 1H), 2.37 (s, 3H), 1.67 (d, J=6.8 Hz, 3H), 1.32 (d, J=6.4 Hz, 3H), 1.01-0.96 (m, 1H), 0.86 (s, 9H), 0.60-0.48 (m, 2H), 0.46-0.38 (m, 1H), 0.34-0.28 (m, 1H), 0.01 (s, 3H), 0.00 (s, 3H).

x. Preparation of S-13x

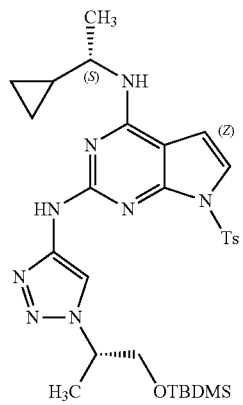

A stirred solution of S-12 (300 mg, 0.82 mmol) in 1,4-dioxane (3.0 mL) taken in a microwave vial was charged with amine S-5x (233 mg, 0.99 mmol) and Cs₂CO₃ (533 mg, 1.64 mmol). Argon gas was purged through septum and the reaction was degassed for about 5 min. To this reaction mixture, xantphos (47.0 mg, 0.082 mmol) followed by Pd₂(dba)₃ (75.0 mg, 0.082 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-3% MeOH in CH₂Cl₂ as eluent to afford S-13x (120 mg, 26%, AMRI lot # IN-AKK-I-200-1) as an off-white solid. The compound was characterized by ¹H NMR analysis. ¹H NMR (400 MHz, CD₃OD): δ 8.63 (s, 1H), 7.96 (d, J=8.0 Hz, 2H), 7.57 (s, 1H), 7.23 (d, J=8.0 Hz, 2H), 7.19 (d, J=4 Hz, 1H), 6.36 (d, J=4 Hz, 1H), 4.82-4.74 (m, 1H), 4.04-4.00 (m, 1H), 3.94-3.90 (m, 1H), 3.75-3.66 (m, 1H), 2.37 (s, 3H), 1.67 (d, J=6.8 Hz, 3H), 1.32 (d, J=6.4 Hz, 3H), 1.01-0.96 (m, 1H), 0.86 (s, 9H), 0.60-0.48 (m, 2H), 0.46-0.38 (m, 1H), 0.34-0.28 (m, 1H), 0.01 (s, 3H), 0.00 (s, 3H).

m. General Synthesis of (S)—N4-(1-cyclopropyl-ethyl)-N2-(1H-pyrazol-4-yl)-7-tosyl-7H-pyrrolo[2,3-d]pyrimidine-2,4-diamines (S-16)

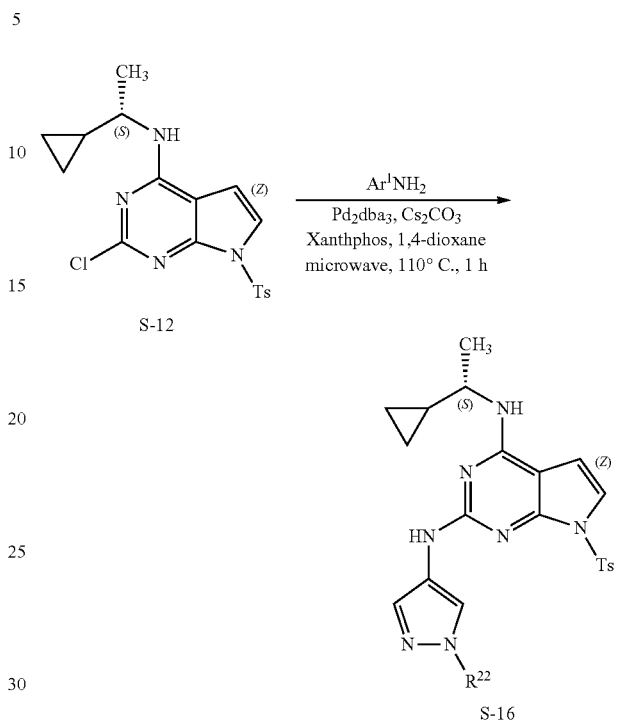

i. Preparation of S-16a

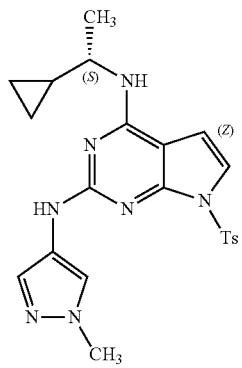

A stirred solution of S-12 (0.20 g, 0.51 mmol) in 1,4 dioxane taken in a microwave vial was charged with amine 1-methyl-1H-pyrazol-4-amine S-14a (0.059 g, 0.61 mmol) and Cs₂CO₃ (0.33 g, 102 mmol). Argon gas was purged through septum and the reaction was degassed for about 5 min. To this reaction mixture, Xantphos (0.029 g, 0.051 mmol) and Pd₂(dba)₃ (0.046 g, 0.051 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-16a (0.13 g, 56%, AMRI lot # IN-SKY-C-15) as an off-white solid. The compound was characterized by ¹H NMR analysis. ¹H NMR (400 MHz, CDCl₃): δ 7.96 (d, J=8.36 Hz, 2H), 7.49 (s, 1H), 7.22 (d, J=8.16 Hz, 2H), 7.16 (d, J=4 Hz, 1H), 6.56 (s, 1H), 6.29 (d, J=4 Hz, 1H), 4.79 (d, J=6.68 Hz, 1H), 3.93 (s, 3H), 3.69 (d, J=12.44 Hz, 1H), 2.35 (s, 3H), 1.28 (d, J=6.52 Hz, 3H), 0.96-0.80 (m, 1H), 0.57-0.47 (m, 2H), 0.39-0.26 (m, 2H).

ii. Preparation of S-16b

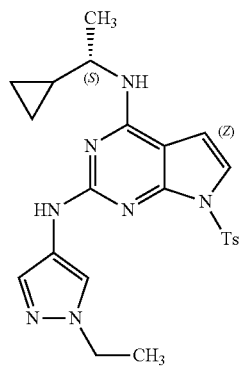

A stirred solution of S-12 (0.20 g, 0.51 mmol) in 1,4 dioxane taken in a microwave vial was charged with amine 1-ethyl-1H-pyrazol-4-amine S-14b (0.068 g, 0.61 mmol) and Cs$_2$CO$_3$ (0.33 g, 1.02 mmol). Argon gas was purged through septum and the reaction was degassed for about 5 min. To this reaction mixture, Xantphos (0.029 g, 0.051 mmol) and Pd$_2$(dba)$_3$ (0.046 g, 0.051 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-16b (0.16 g, 69%, AMRI lot # IN-SKY-C-16) as an off-white solid. The compound was characterized by $^1$H NMR analysis. $^1$H NMR (400 MHz, CDCl$_3$): δ 7.97 (d, J=8.36 Hz, 2H), 7.44 (s, 1H), 7.22 (s, 1H), 7.15 (d, J=4 Hz, 1H), 6.58 (s, 1H), 6.29 (d, J=4 Hz, 1H), 4.78 (d, J=7.52 Hz, 1H), 4.23-4.16 (m, 2H), 3.71-3.64 (m, 1H), 2.34 (s, 3H), 1.54-1.51 (m, 3H), 1.28 (d, J=6.52 Hz, 3H), 0.96-0.89 (m, 1H), 0.57-0.42 (m, 2H), 0.39-0.25 (m, 2H).

iii. Preparation of S-16d

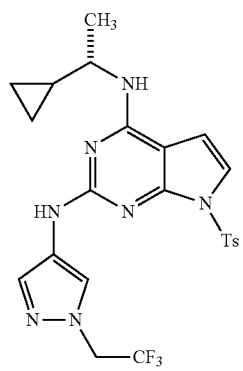 [SMILES: Cc1ccc(S(=O)(=O)n2ccc3c(N[C@@H](C)C4CC4)nc(Nc4cnn(CC(F)(F)F)c4)nc32)cc1]

A solution of S-12 (0.2 g, 0.512 mmol), amine 1-(2,2,2-trifluoroethyl)-1H-pyrazol-4-amine S-14d (0.101 g, 0.615 mmol), Cs$_2$CO$_3$ (0.332 g, 1.024 mmol) and 1,4-dioxane (3 mL) was charged into a microwave vial with stirrer bar. Argon gas was purged through septum and the reaction mixture was degassed for about 5 min. To this reaction mixture, Xantphos (0.029 g, 0.051 mmol) and Pd$_2$(dba)$_3$ (0.047 g, 0.051 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 0-60% EtOAc in hexanes as eluent to afford S-16d (0.11 g, 41%, AMRI lot # IN-CKB-G-20) as a brown solid. The compound was characterized by $^1$H NMR analysis. $^1$H-NMR (300 MHz, CDCl$_3$): δ 8.45 (bs, 1H), 7.89 (d, J=8.40 Hz, 2H), 7.45 (s, 1H), 7.16 (s, 1H), 7.12 (t, J=4.20 Hz, 2H), 6.60 (s, 1H), 6.24 (d, J=3.90 Hz, 1H), 4.76 (d, J=7.20 Hz, 1H), 4.68 (q, J=8.40 Hz, 2H), 3.63-3.54 (m, 1H), 2.28 (s, 3H), 1.21 (d, J=6.60 Hz, 3H), 0.90-0.78 (m, 1H), 0.50-0.34 (m, 2H), 0.30-0.17 (m, 2H); MS-UPLC (MM) m/z 520.2 [M+H]$^+$.

i. Preparation of S-16e

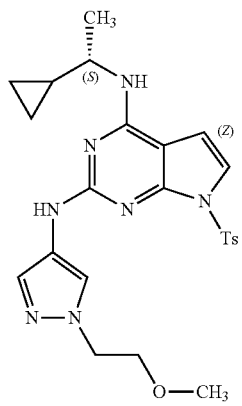

A stirred solution of S-12 (0.20 g, 0.51 mmol) in 1,4-dioxane taken in a microwave vial was charged with 1-(2-methoxyethyl)-1H-pyrazol-4-amine S-14e (0.086 g, 0.61 mmol) and Cs$_2$CO$_3$ (0.33 g, 1.02 mmol). Argon gas was purged through septum and the reaction was degassed for about 5 min. To this reaction mixture, Xantphos (0.029 g, 0.051 mmol) and Pd$_2$(dba)$_3$ (0.046 g, 0.051 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-16e (0.13 g, 51%, AMRI lot # IN-CKB-G-21) as an off-white solid. The compound was characterized by $^1$H NMR analysis. $^1$H-NMR (400 MHz, CDCl$_3$): δ 8.3 (bs, 1H), 7.98 (d, J=8.40 Hz, 2H), 7.48 (s, 1H), 7.21 (d, J=8.40 Hz, 1H), 7.16 (d, J=4.00 Hz, 2H), 6.54 (s, 1H), 6.29 (d, J=4.00 Hz, 1H), 4.77 (d, J=8.00 Hz, 1H), 4.30 (t, J=5.20 Hz, 2H), 3.81 (t, J=5.60 Hz, 2H), 3.35 (s, 3H), 2.35 (s, 3H), 1.28 (d, J=6.40 Hz, 3H), 0.95-0.88 (m, 1H), 0.55-0.42 (m, 2H), 0.38-0.26 (m, 2H); MS-UPLC (MM) m/z 496.2 [M+H]$^+$.

ii. Preparation of S-16f

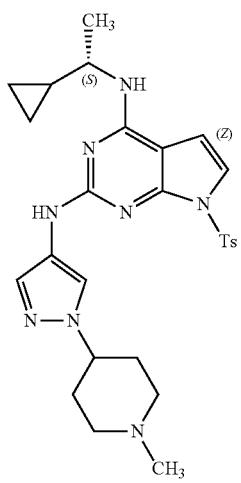

A stirred solution of S-12 (0.20 g, 0.51 mmol) in 1,4-dioxane taken in a microwave vial was charged with 1-(1-methylpiperidin-4-yl)-1H-pyrazol-4-amine S-14f (0.11 g, 0.61 mmol) and Cs$_2$CO$_3$ (0.33 g, 1.02 mmol). Argon gas was purged through septum and the reaction was degassed for about 5 min. To this reaction mixture, Xantphos (0.029 g, 0.051 mmol) and Pd$_2$(dba)$_3$ (0.046 g, 0.051 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-16f (0.12 g, 44%, AMRI lot # IN-CKB-G-31) as an off-white solid. The compound was characterized by $^1$H NMR analysis. $^1$H NMR (300 MHz, CDCl$_3$): δ 8.43 (bs, 1H), 7.96 (d, J=8.4 Hz, 2H), 7.45 (s, 1H), 7.19 (d, J=8.1 Hz, 2H), 7.14 (d, J=4.2 Hz, 1H), 6.61 (s, 1H), 6.29 (d, J=4.2 Hz, 1H), 7.80 (d, J=7.8 Hz, 1H), 4.13-4.11 (m, 1H), 3.71-3.64 (m, 1H), 2.98-2.95 (m, 2H), 2.34 (s, 3H), 2.31 (s, 3H), 2.17-2.14 (m, 6H), 1.27 (d, J=6.6 Hz, 3H), 0.95-0.85 (m, 1H), 0.55-0.25 (m, 4H).

iii. Preparation of S-16h

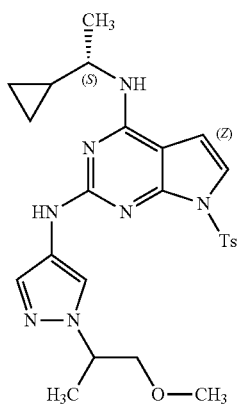

A stirred solution of S-12 (0.30 g, 0.76 mmol) in 1,4-dioxane taken in a microwave vial was charged with 1-(1-methoxypropan-2-yl)-1H-pyrazol-4-amine S-14h (0.143 g, 0.92 mmol) and Cs$_2$CO$_3$ (0.49 g, 1.52 mmol). Argon gas was purged through septum and the reaction was degassed for about 5 min. To this reaction mixture, xantphos (0.043 g, 0.076 mmol) and Pd$_2$(dba)$_3$ (0.069 g, 0.076 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-16h (0.15 g, 38%, AMRI lot # IN-CKB-G-65) as an off-white solid. The compound was characterized by $^1$H NMR and UPLC-MS analysis. $^1$H NMR (300 MHz, CDCl$_3$): δ 7.99 (d, J=8.40 Hz, 2H), 7.46 (s, 1H), 7.21 (d, J=8.40 Hz, 2H), 7.15 (d, J=4.20 Hz, 1H), 6.61 (s, 1H), 6.30 (d, J=3.90 Hz, 1H), 4.79 (d, J=7.80 Hz, 1H), 4.57 (q, J=6.30 Hz, 1H), 3.81-3.63 (m, 2H), 3.32 (s, 3H), 2.35 (s, 3H), 1.56 (d, J=6.90 Hz, 3H), 1.26 (d, J=3.90 Hz, 3H), 0.98-0.85 (m, 1H), 0.56-0.44 (m, 2H), 0.38-0.25 (m, 2H); MS-UPLC (MM) m/z 510.2 [M+H]$^+$.

n. Synthesis of 1-3, 5, and 11

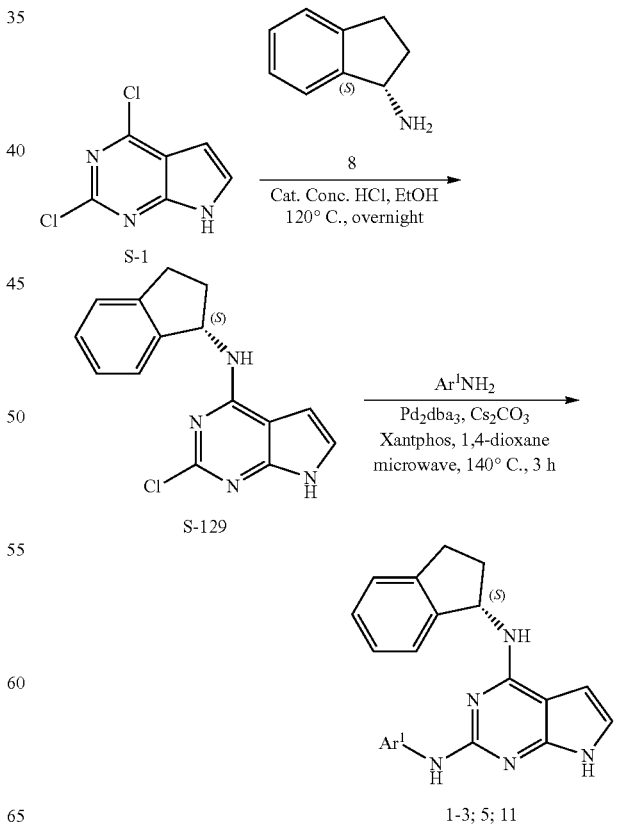

i. Preparation of S-129

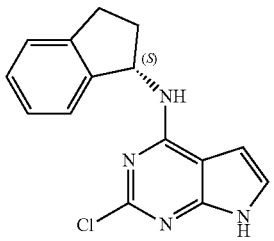

To a mixture of S-1 (1.2 g, 6.38 mmol), amine-8 (1.6 mL, 12.76 mmol) in ethanol (5 mL) in a sealed tube was added catalytic amount of Conc. HCl and reaction mixture was heated 120° C. overnight. Solvents were evaporated in vacuo to obtain a crude material. Two drops of 1 M NaOH was added to this crude material followed by 1 mL of water and ethyl acetate to it, layers were separated, organic layer was washed with brine, dried over sodium sulphate and solvents were evaporated in vacuo to afford S-129 (1.5 g, 83%) as white solid. $^1$H NMR (400 MHz, DMSO-$d_6$): δ 11.67 (bs, 1H), 8.15 (d, 1H, J=8 Hz), 7.29 (d, 1H, J=8 Hz), 7.21-7.24 (m, 2H), 7.18-7.15 (m, 1H), 7.07 (d, 1H, J=4 Hz), 6.61 (d, 1H, J=4 Hz), 5.79 (q, 1H, J=8 Hz), 3.05-2.98 (m, 1H), 2.92-2.82 (m, 1H), 2.57-2.51 (m, 1H), 2.02-1.88 (m, 1H). FABMS (M+H) calculated for $C_{15}H_{13}ClN_4$.H was 285.09015 found 285.08956.

i. Preparation of 1

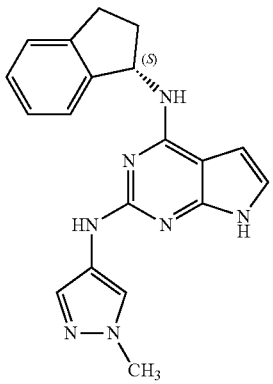

Coupling of 5-129 (75 mg, 0.26 mmol) to 1-methyl-1H-pyrazol-4-amine (51 mg, 0.52 mmol, CAS No. 69843-13-6) following the same procedure described for the synthesis of 21, after purification using MPLC and MDPS, afforded 1 (18 mg, 19.7%). $^1$H NMR (400 MHz, Chloroform-d) δ 8.41 (s, 1H), 7.83 (s, 1H), 7.49 (d, J=0.8 Hz, 1H), 7.40 (d, J=7.4 Hz, 1H), 7.34-7.26 (m, 2H), 7.26-7.18 (m, 1H), 6.72 (dd, J=2.1, 3.6 Hz, 1H), 6.42 (s, 1H), 6.21 (s, 1H), 5.86 (q, J=7.6 Hz, 1H), 5.06 (d, J=8.3 Hz, 1H), 3.84 (s, 3H), 3.13-2.88 (m, 2H), 2.79-2.65 (m, 1H), 2.00 (dq, J=8.2, 12.9 Hz, 1H). FABMS (M+H) calculated for $C_{19}H_{19}N_7$.H was 345.17747 found 345.17816. LCMS 100%, $t_R$=5.92 minutes.

ii. Preparation of 2

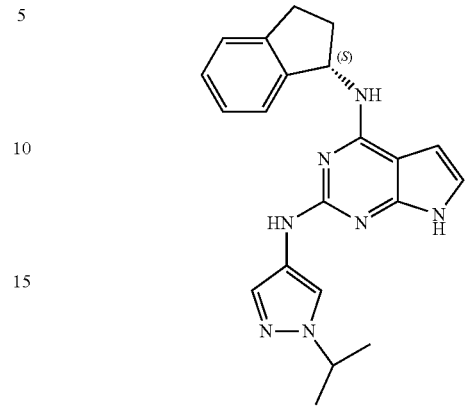

Buchwald Coupling of S-129 (75 mg, 0.26 mmol) and 1-isopropyl-1H-pyrazol-4-amine (66 mg, 0.52 mmol, CAS No. 977421-16-1) was done following same procedure as described in synthesis of SRI-35521 to afford 2 (10 mg, 10%). $^1$H NMR (400 MHz, Methanol-$d_4$) δ 7.94 (s, 1H), 7.61 (s, 1H), 7.36-7.25 (m, 2H), 7.25-7.15 (m, 2H), 6.90 (d, J=3.4 Hz, 1H), 6.65 (d, J=3.5 Hz, 1H), 5.94 (s, 1H), 4.46-4.37 (m, 1H), 3.37-3.27 (m, 1H), 3.18-3.06 (m, 1H), 3.02-2.89 (m, 1H), 2.64 (d, J=9.9 Hz, 1H), 1.35 (s, 6H). FABMS (M+H) calculated for $C_{21}H_{23}N_7$.H was 374.20877 found 374.20905. LCMS 100%, $t_R$=5.86 minutes.

iii. Preparation of 3

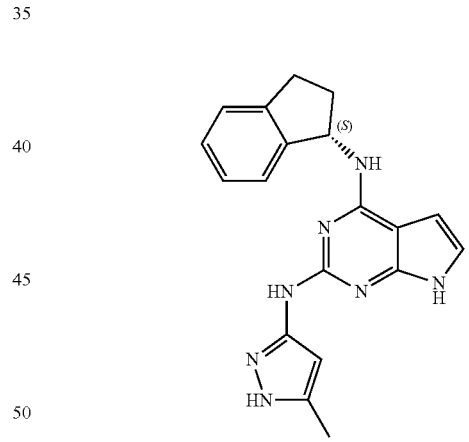

In a microwave vial (10 mL) was added S-129 (50 mg, 0.17 mmol), 5-methyl-1H-pyrazol-3-amine (34 mg, 0.35 mmol, CAS No. 31230-17-8), $K_3PO_4$ (74 mg, 0.35 mmol.) and DMSO (2 mL). The Argon was purged through septum and the reaction mixture was purged for about 10 min. To this mixture was added XPhos (8 mg, 0.018 mmol) followed by $Pd_2(dba)_3$ (16 mg, 0.018 mmol) and purged with Argon again for 5 min. Vial was sealed with the septum and irradiated at 150° C. for 1 h. After filtration through celite bed, solvents were removed in vacuo to obtain crude which was chromatographed on MPLC (DCM-MeOH: 2-15%) to afford 3 (10 mg, 16.4%). $^1$H NMR (400 MHz, Methanol-$d_4$) δ 7.36-7.11 (m, 5H), 6.79 (d, J=3.6 Hz, 1H), 6.44 (d, J=3.5 Hz, 1H), 5.89 (t, J=7.7 Hz, 1H), 3.07 (ddd, J=3.3, 8.7, 15.7 Hz, 1H), 2.92 (dt, J=8.4, 16.0 Hz, 1H), 2.65-2.6 (m, 1H), 2.19 (s, 3H), 2.05 (dq, J=8.5, 12.4 Hz, 1H). FABMS (M+H) calculated for C$_{19}$H$_{19}$N$_7$.H was 346.17747 found 346.17737. LCMS 98.13%, t$_R$=6.12 minutes.

iv. Preparation of 5

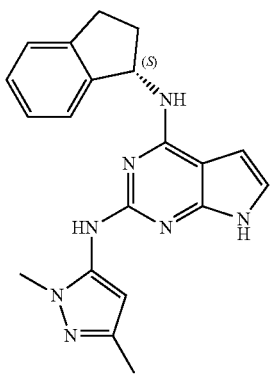

Buchwald Coupling of S-129 (100 mg, 0.35 mmol) and 1,3-dimethyl-1H-pyrazol-5-amine (78 mg, 0.70 mmol, CAS No. 3524-32-1) was done following same procedure as described in synthesis of 21 to afford 5 (15 mg, 11.8%). $^1$H NMR (400 MHz, Methanol-d$_4$) δ 7.30-7.09 (m, 4H), 6.76 (dd, J=0.7, 3.5 Hz, 1H), 6.42 (dd, J=0.7, 3.5 Hz, 1H), 6.17-6.05 (m, 1H), 5.85 (t, J=7.8 Hz, 1H), 3.65 (d, J=0.8 Hz, 3H), 3.09-2.95 (m, 1H), 2.86 (dt, J=8.3, 16.1 Hz, 1H), 2.57 (dtd, J=3.3, 7.7, 12.0 Hz, 1H), 2.17 (d, J=4.9 Hz, 3H), 2.08-1.92 (m, 1H). FABMS (M+H) calculated for C$_{20}$H$_{21}$N$_7$.H was 360.1931 found 360.19286. LCMS 96.88%, t$_R$=6.46 minutes.

v. Preparation of 11

SRI-32790

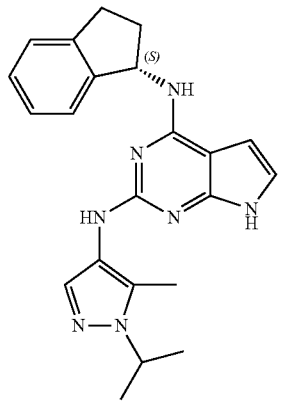

Buchwald Coupling of S-129 (200 mg, 0.7 mmol) and 1-isopropyl-5-methyl-1H-pyrazol-4-amine (196 mg, 1.45 mmol, CAS no. 1006495-81-3) was done following same procedure as described in synthesis of 21 to afford 11 (35 mg, 12.8%). $^1$H NMR (400 MHz, DMSO-d$_6$) δ 10.77 (s, 1H), 7.53 (d, J=39.4 Hz, 2H), 7.37 (d, J=8.6 Hz, 1H), 7.29-7.09 (m, 4H), 6.66 (dd, J=2.2, 3.4 Hz, 1H), 6.40 (dd, J=2.0, 3.4 Hz, 1H), 5.88 (q, J=8.2 Hz, 1H), 4.42 (p, J=6.6 Hz, 1H), 3.16-3.18 (m, 1H), 3.06-2.74 (m, 2H), 2.17 (s, 3H), 2.03-1.89 (m, 1H), 1.32 (dd, J=2.9, 6.6 Hz, 6H). FABMS (M+H) calculated for C$_{22}$H$_{25}$N$_7$.H was 388.22442 found 388.22438. LCMS 97.7%, t$_R$=1.72 minutes.

o. Synthesis of 4 and 17

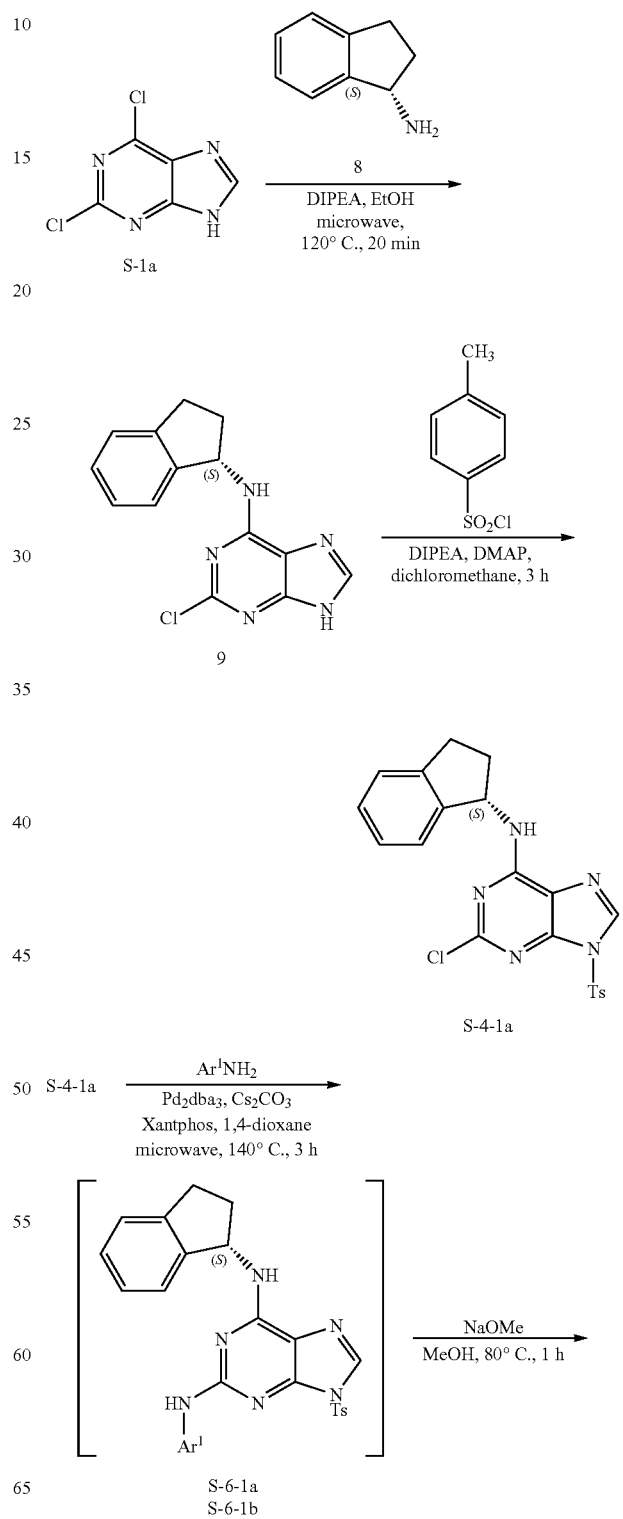

-continued

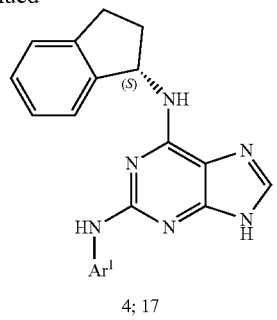

4; 17 i. Preparation of Intermediate 9

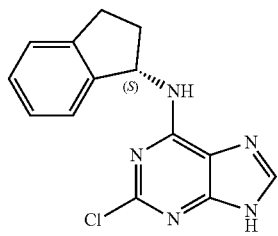

In a microwave vial (35 mL) was added 2,6-dichloro-9H-purine S-1a (0.5 g, 2.65 mmol) (S)-2,3-dihydro-1H-inden-1-amine 8 (0.423 g, 3.17 mmol, CAS #61341-864), N-ethyl-N-isopropylpropan-2-amine (0.513 g, 3.97 mmol) and ethanol (10 mL). The mixture was irradiated at 120° C. for 20 min and the vial was placed in an ice bath for 30 min. The desired intermediate 9 (0.67 g, 89%) was collected by filtration after several washes with cold ethanol. $^1$H NMR (400 MHz, DMSO-d$_6$): δ 13.03 (bs, 1H), 8.38 (bs, 1H), 8.13 (s, 1H), 7.35-7.14 (m, 4H), 5.77 (bs, 1H), 3.02-2.86 (m, 2H), 2.02-1.9 (bs, 1H), 1.05 (m, 1H). FABMS (M+H) calculated for $C_{14}H_{12}ClN_5$.H was 286.0854 found 286.0854. LCMS 100%, $t_R$=6.89 minutes.

ii. Preparation of S-4-1a

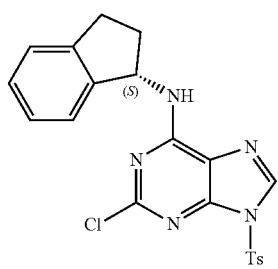

A solution of 9 (0.5 g, 1.750 mmol) in 20 mL of CH$_2$Cl$_2$-THF: 1/1 was treated with Et$_3$N (0.49 mL), tosyl chloride (0.667 g, 3.5 mmol) and then DMAP (43 mg, 0.352 mmol). The reaction mixture was stirred under argon stream for 3 hours at room temperature then filtered off and washed with THF. The evaporated filtrate (gummy residue) was chromatographed to afford S-6-1a (0.384 g, 50%). $^1$H NMR (400 MHz, DMSO-d$_6$): δ 9.02 (d, J=8.6 Hz, 1H), 8.64 (s, 1H), 8.07 (d, J=8.5 Hz, 2H), 7.54 (d, J=8.3 Hz, 2H), 7.55-7.13 (m, 4H), 5.78-5.72 (m, 1H), 3.04-2.97 (m, 1H), 2.87-2.79 (m, 1H), 2.45-2.37 (m, 1H), 2.41 (s, 3H), 2.15-2.08 (m, 1H). FABMS (M+H) calculated for $C_{21}H_{18}ClN_5O_2S$.H was 440.0942 found 440.0947.

iii. Preparation of 4

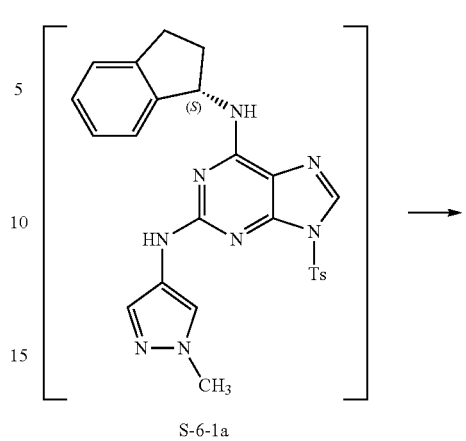

S-6-1a

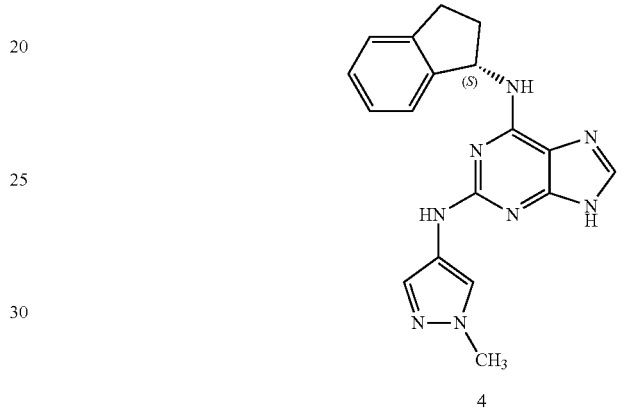

4

Coupling of S-4-1a (29 mg, 0.1 mmol) to 1-methyl-1H-pyrazol-4-amine (14 mg, 0.11 mmol, CAS #69843-13-6) following the same procedure described for the synthesis of 21 afforded, after purification using MDPS, 4 (7 mg, 20%). $^1$H NMR (400 MHz, DMSO-d$_6$) δ 13.91 (s, 1H), 8.42 (s, 1H), 7.96 (s, 1H), 7.52-6.70 (m, 6H), 6.37-6.11 (m, 1H), 5.88 (d, J=3.7 Hz, 1H), 3.90 (s, 3H), 3.12-2.79 (m, 2H), 2.74-2.51 (m, 2H). FABMS (M+H) calculated for $C_{18}H_{18}N_8O$.H was 347.1727 found 347.1729. LCMS 93%, $t_R$=1.37 minutes.

iv. Preparation of 17

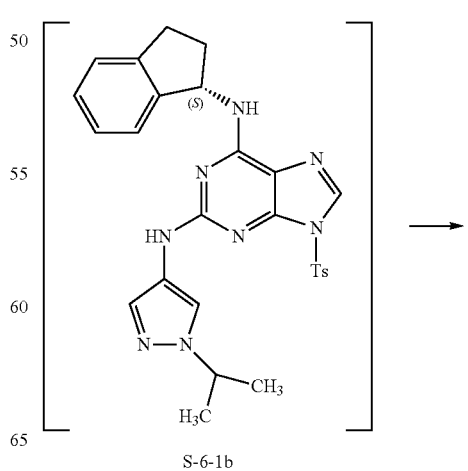

S-6-1b

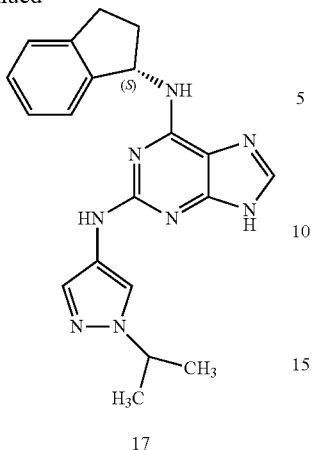

17

Coupling of S-4-1a to 1-isopropyl-5-methyl-1H-pyrazol-4-amine following the same procedure described for the synthesis of 21 afforded 17 (19 mg, 45%). $^1$H NMR (400 MHz, DMSO-$d_6$): δ 12.27 (bs, 1H), 8.61 (s, 1H), 7.89 (s, 1H), 7.74 (s, 1H), 7.58 (s, 1H), 7.43 (s, 1H), 7.31-7.16 (m, 4H), 7.13 (t, J=7.3 Hz, 1H), 5.87 (bs, 1H), 4.31 (bs, 1H), 3.02 (ddd, J=15.8, 8.7, 2.7 Hz, 1H), 2.84 (dt, J=16.2, 8.6 Hz, 1H), 2.17 (m, 1H), 1.27 (s, 6H). FABMS (M+H) calculated for $C_{20}H_{22}N_8$.H was 375.2040 found 375.2043. LCMS 100%, $t_R$=6.48 minutes.

p. Synthesis of 6

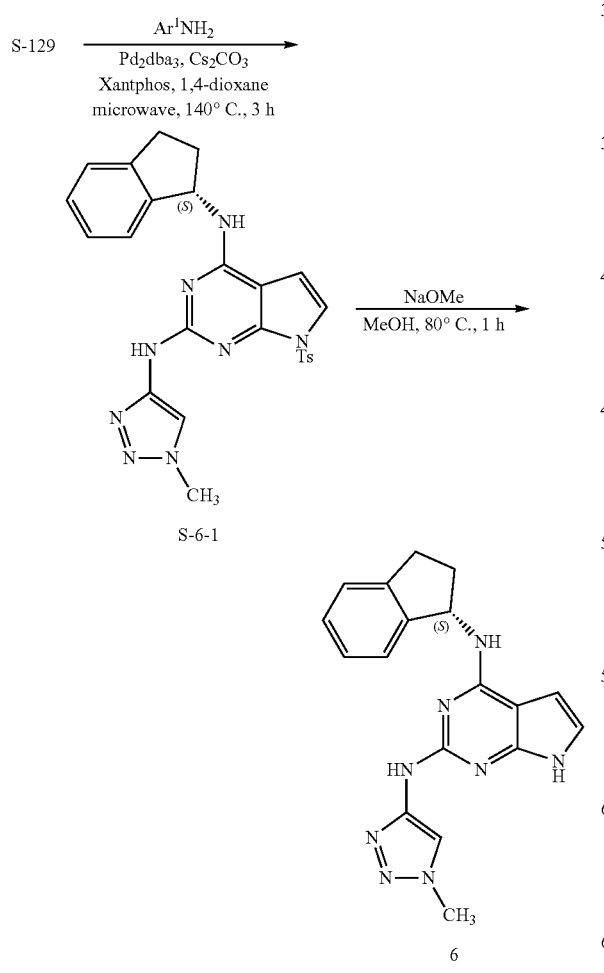

i. Preparation of S-6-1

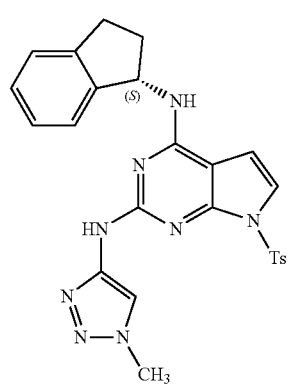

In a microwave vial (35 mL) was added S-129 (0.78 g, 1.82 mmol), amine 11 (0.18 g, 1.82 mmol), $Cs_2CO_3$ (1.18 g, 3.64 mmol.) and Dioxane (25 mL). The Argon was purged through septum and the reaction mixture was degassed for about 5 min. To this mixture was added Xantphos (103 mg, 0.2 mmol) followed by $Pd_2(dba)_3$ (162 mg, 0.2 mmol) and purged with Argon again for 5 min. Vial was sealed with the septum and irradiated at 140° C. for 3 h. After filtration, the obtained crude was chromatographed (Biotage, 25 g, eluent: DMC-EtOAc: 10-50%) to afford S-6-1 (390 mg, 44%). $^1$H NMR (400 MHz, DMSO-$d_6$): δ 9.61 (bs, 1H), 7.99 (d, J=7.8 Hz, 1H), 7.46-7.10 (m, 10H), 6.87 (d, J=3.9 Hz, 1H), 5.39 (m, 1H), 4.02 (s, 3H), 3.35-3.23 (m, 2H), 2.32 (s, 3H), 2.23 (m, 2H). FABMS (M+H) calculated for $C_{24}H_{24}N_8O_2S$.H was 489.1815 found 489.1813. LCMS 99%, $t_R$=7.37 minutes.

ii. Preparation of 6

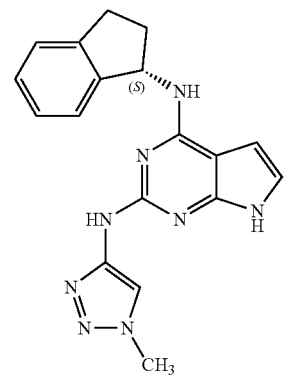

The tosylated intermediate S-6-1 (380 mg, 0.76 mmol) was treated with sodium methanolate (0.8 ml, 25%) in methanol (30 mL) at 70° C. for 1 h (TLC monitoring showed that the reaction was complete). The reaction mixture was pre-adsorbed on silica gel and chromatographed (Biotage, 25 g, eluent: DCM/MeOH: 2 to 10%) to afford 6 (185 mg, 70%). $^1$H NMR (400 MHz, DMSO-$d_6$): δ 10.96 (bs, 1H), 9.00 (s, 1H), 8.05 (s, 1H), 7.56 (d, J=8.4 Hz, 1H), 7.33-7.12 (m, 4H), 6.76 (dd, J=3.4, 2.2 Hz, 1H), 6.47 (dd, J=3.4, 2.0 Hz, 1H), 5.94-5.85 (m, 1H), 3.96 (s, 3H), 3.38-3.18 (m, 2H), 2.06-1.92 (m, 2H). FABMS (M+H) calculated for $C_{18}H_{18}N_8$·H was 347.1727 found 347.1727. LCMS 100%, $t_R$=6.13 minutes.

q. Synthesis of 7 and 8

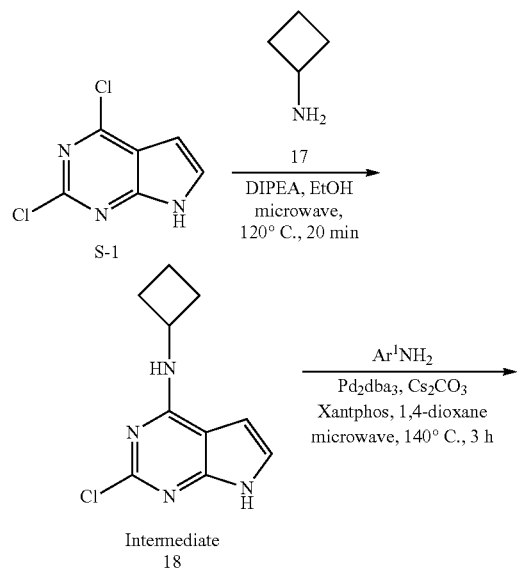

i. Preparation of 7

7 was prepared following the same procedure described for the synthesis of 1 (19 mg, 25%). FABMS (M+H) calculated for $C_{14}H_{17}N_7$·H was 284.1618 found 284.1617. LCMS 98%, $t_R$=5.55 minutes.

ii. Preparation of 8

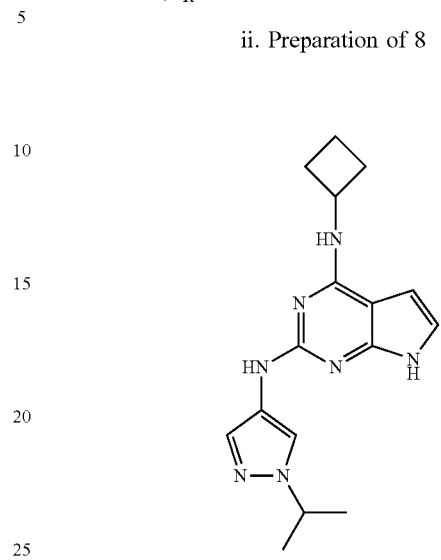

8 was prepared following the same procedure described for the synthesis of 1 (31 mg, 35%). FABMS (M+H) calculated for $C_{16}H_{21}N_7$·H was 312.1931 found 312.1927. LCMS 89%, $t_R$=5.99 minutes.

r. Synthesis of 9, 10, and 12

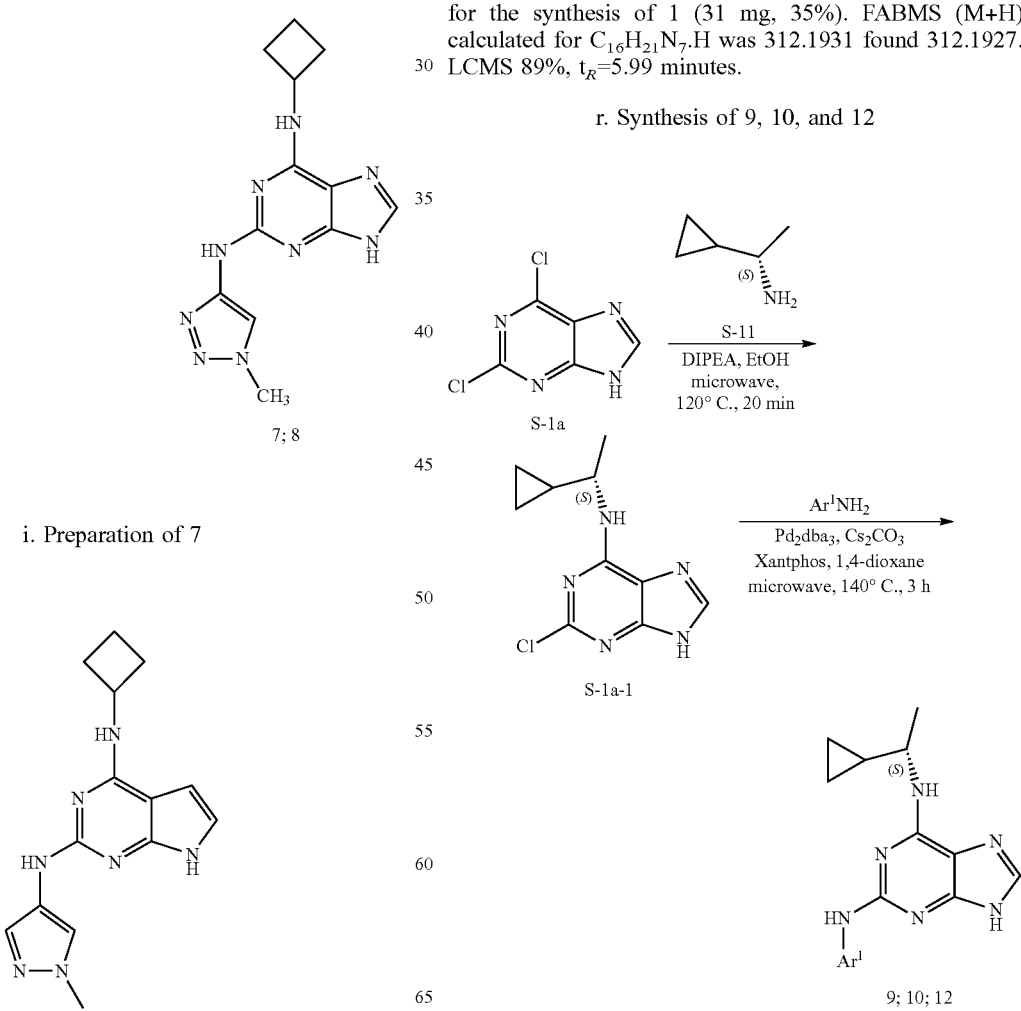

i. Preparation of 9

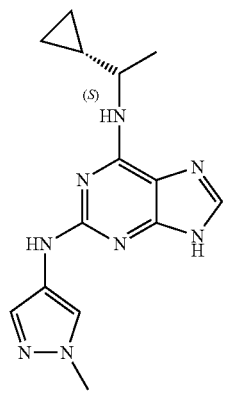

9 was prepared following the same procedure described for the synthesis of 1 (26 mg, 30%). FABMS (M+H) calculated for $C_{14}H_{18}N_8 \cdot H$ was 299.1727 found 299.1727. LCMS 96%, $t_R$=5.42 minutes.

ii. Preparation of 10

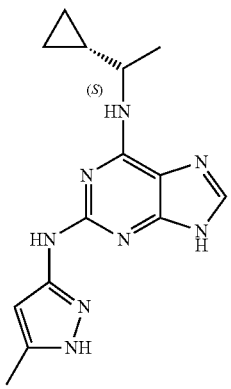

9 was prepared following the same procedure described for the synthesis of 1 (32 mg, 40%). FABMS (M+H) calculated for $C_{14}H_{18}N_8 \cdot H$ was 299.1727 found 299.1726. LCMS 99%, $t_R$=5.85 minutes.

iii. Preparation of 12

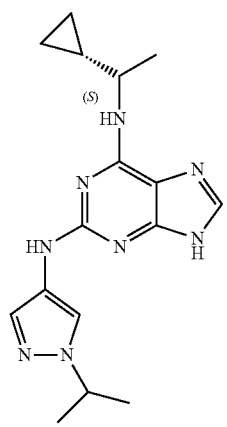

12 was prepared following the same procedure described for the synthesis of 1 (28 mg, 30%). FABMS (M+H) calculated for $C_{16}H_{22}N_8 \cdot H$ was 327.2040 found 327.2037. LCMS 81%, $t_R$=5.89 minutes.

s. Synthesis of 13

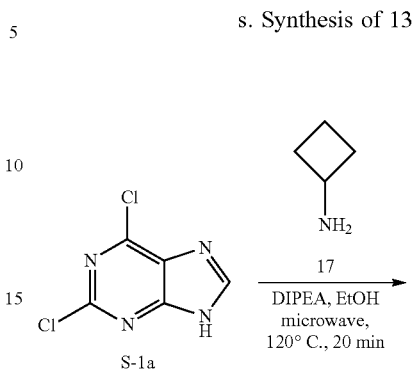

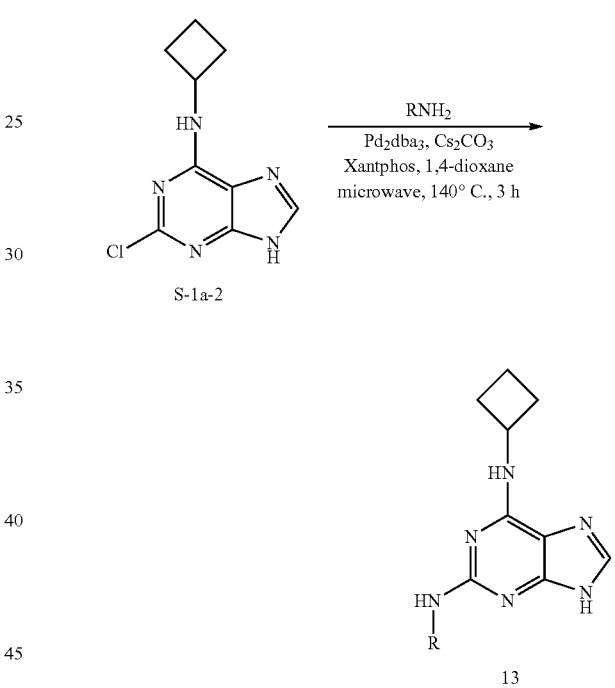

13 was prepared following the same procedure described for the synthesis of 1 (29 mg, 30%). FABMS (M+H) calculated for $C_{18}H_{20}N_8 \cdot H$ was 313.1887 found 313.1883. LCMS 94%, $t_R$=5.84 minutes.

t. Synthesis of 14

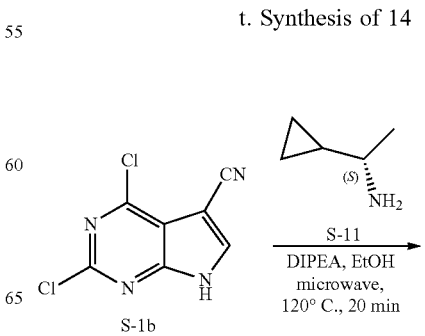

-continued

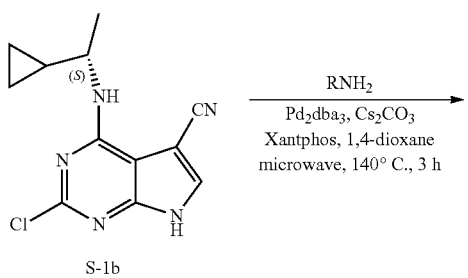

S-1b

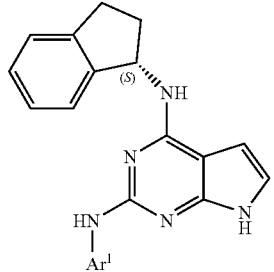

15; 16; 19; 20 i. Preparation of 15

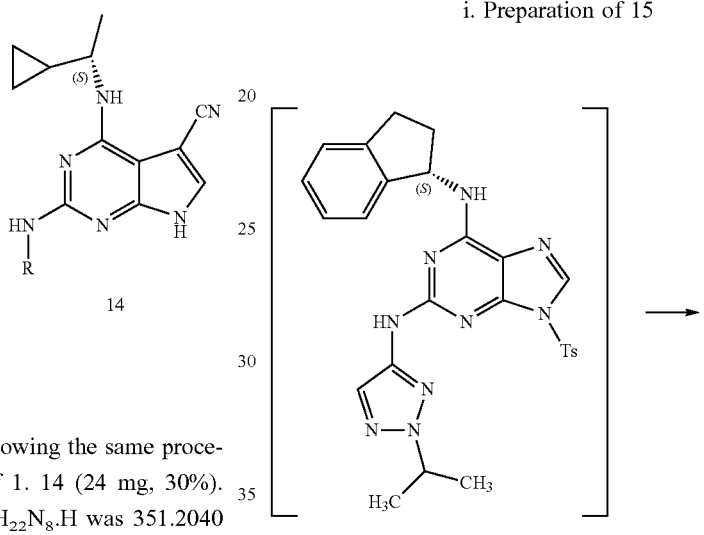

14

This compound was prepared following the same procedure described for the synthesis of 1. 14 (24 mg, 30%). FABMS (M+H) calculated for $C_{18}H_{22}N_8 \cdot H$ was 351.2040 found 351.2038. LCMS 93%, $t_R$=7 minutes.

u. Synthesis of 15, 16, 19, and 20

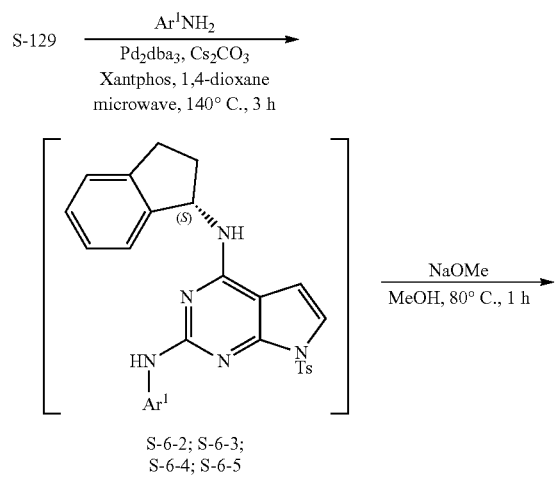

S-6-2; S-6-3;
S-6-4; S-6-5

Coupling of S-129 (43 mg, 0.098 mmol) to 2-isopropyl-2H-1,2,3-triazol-4-amine (21 mg, 0.098 mmol), following the same procedure described for the synthesis of 21 afforded, after purification using MDPS, 15 (18 mg, 49% from S5). $^1$H NMR (400 MHz, DMSO-$d_6$): δ 10.97 (bs, 1H), 9.09 (s, 1H), 7.99 (s, 1H), 7.58 (d, J=8.4 Hz, 1H), 7.33-7.10 (m, 4H), 6.77 (dd, J=3.4, 2.2 Hz, 1H), 6.46 (dd, J=3.4, 2.0 Hz, 1H), 4.62 (h, J=6.6 Hz, 1H), 3.28 (s, 1H), 3.08-2.89 (m, 2H), 2.01 (m, 2H), 1.43 (d, J=6.7 Hz, 6H). FABMS (M+H) calculated for $C_{20}H_{22}N_8 \cdot H$ was 374.2046 found 374.2046. LCMS 100%, $t_R$=5.54 minutes.

ii. Preparation of 16

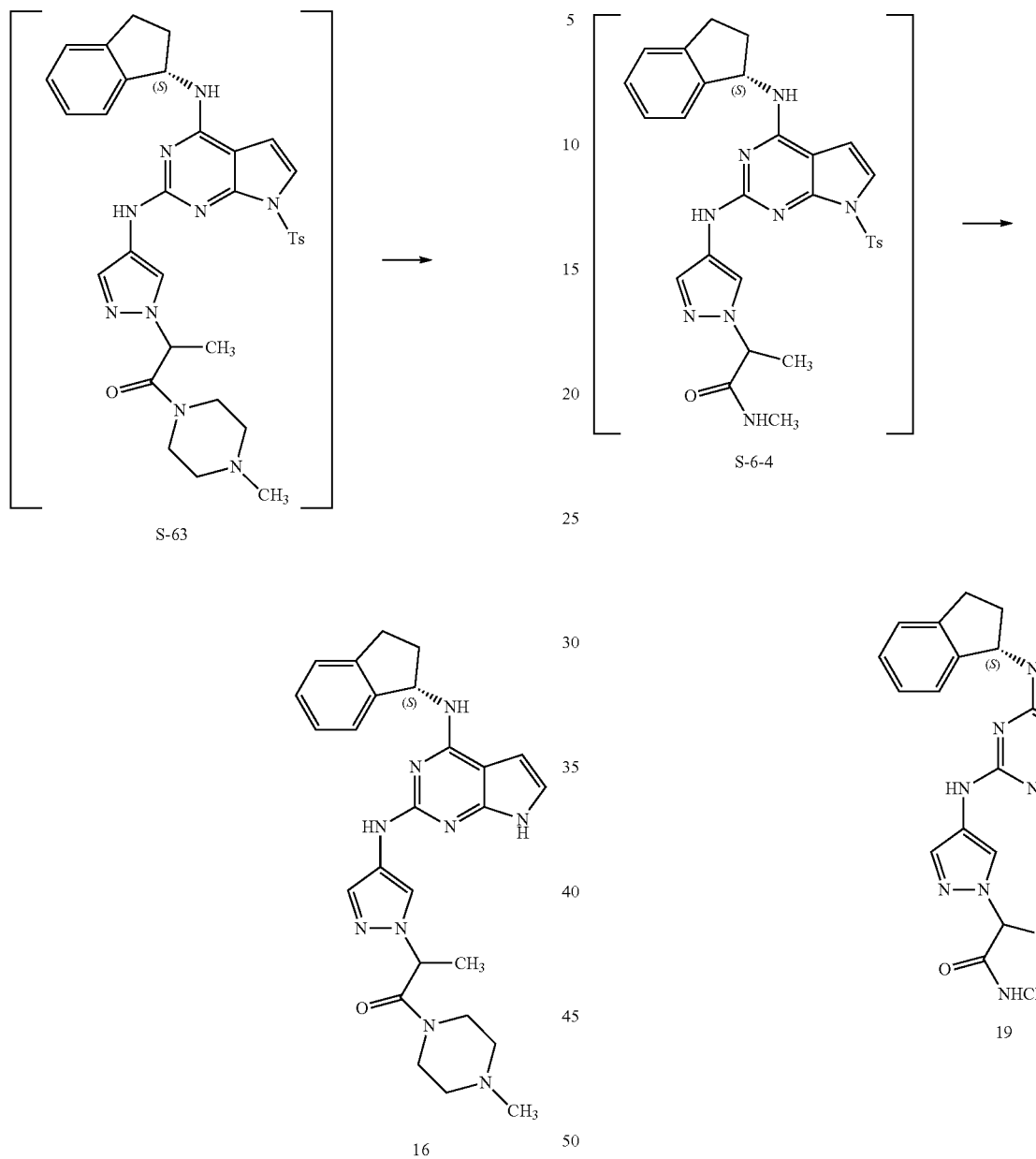

iii. Preparation of 19

Coupling of S-129 (88 mg, 0.2 mmol) to amine 13 (50 mg, 0.2 mmol), following the same procedure described for the synthesis of 21 afforded, after purification using MDPS, compound 16 (26 mg, 26%). $^1$H NMR (400 MHz, DMSO-$d_6$) δ 10.98 (bs, 1H), 8.60 (s, 1H), 7.54-7.43 (m, 4H), 7.32-7.21 (m, 2H), 7.24-7.18 (m, 1H), 7.20-7.07 (m, 3H), 6.75 (d, J=2.9 Hz, 1H), 6.59 (s, 1H), 6.44 (dd, J=3.4, 2.0 Hz, 1H), 5.87 (q, J=7.9 Hz, 1H), 5.29 (q, J=6.7 Hz, 1H), 3.51 (s, 1H), 3.43 (s, 1H), 3.19 (s, 1H), 3.03 (ddd, J=15.8, 8.7, 3.4 Hz, 1H), 2.87 (dt, J=16.1, 8.3 Hz, 1H), 2.56 (td, J=8.0, 3.8 Hz, 1H), 2.29 (s, 3H), 2.16 (s, 3H), 1.98 (dq, J=12.5, 8.5 Hz, 1H), 1.42 (d, J=6.7 Hz, 3H). FABMS (M+H) calculated for $C_{27}H_{33}N_9O$·H was 500.2878 found 500.2880. LCMS 99%, $t_R$=5.63 minutes.

Coupling of S-129 to amine 7, following the same procedure described for the synthesis of 21, afforded 19 (14 mg, 17%). $^1$H NMR (400 MHz, DMSO-$d_6$): δ 10.84 (bs, 1H), 8.46 (d, J=3.2 Hz, 1H), 7.99 (d, J=7.4 Hz, 1H), 7.83 (dd, J=9.7, 4.9 Hz, 1H), 7.54-7.43 (m, 2H), 7.32-7.10 (m, 4H), 6.71 (ddd, J=3.4, 2.2, 1.2 Hz, 1H), 6.47-6.41 (m, 1H), 5.96-5.83 (m, 1H), 4.86-4.75 (m, 1H), 3.02 (ddd, J=15.7, 8.7, 2.9 Hz, 1H), 2.88 (d, J=14.2 Hz, 1H), 2.55 (dd, J=8.2, 4.7 Hz, 3H), 2.07-1.91 (m, 1H), 1.47 (d, J=7.1 Hz, 3H), 0.85 (dt, J=10.4, 6.4 Hz, 1H). FABMS (M+H) calculated for $C_{22}H_{24}N_8O$·H was 417.2145 found 417.2144. LCMS 100%, $t_R$=6.04 minutes.

iv. Preparation of 20 v. Synthesis of 18

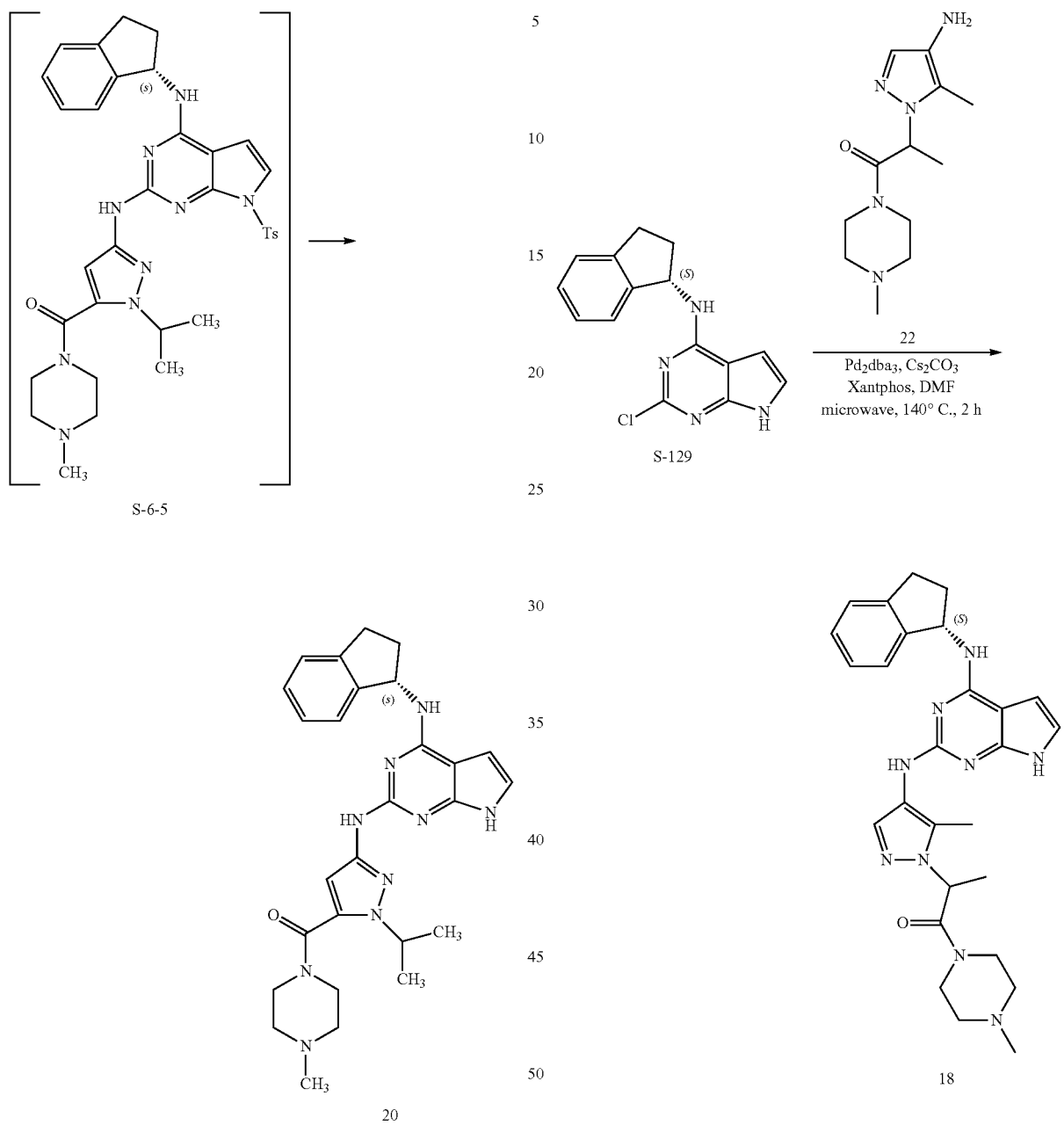

Coupling of S-129 to amine 16, following the same procedure described for the synthesis of 21, afforded 20 (15 mg, 15%). $^1$H NMR (400 MHz, DMSO-d$_6$): δ 10.95 (bs, 1H), 8.75 (s, 1H), 7.55 (d, J=8.4 Hz, 1H), 7.32-7.09 (m, 4H), 6.79-6.71 (m, 2H), 6.44 (dd, J=3.4, 2.0 Hz, 1H), 5.87 (q, J=8.1 Hz, 1H), 4.49 (hept, J=6.5 Hz, 1H), 3.6 (m, 6H), 3.05 (ddd, J=15.9, 9.0, 3.2 Hz, 1H), 2.86 (dt, J=16.1, 8.4 Hz, 1H), 2.63-2.51 (m, 2H), 2.05 (s, 3H), 2.07-1.94 (m, 2H), 1.35 (dd, J=6.6, 3.7 Hz, 6H). FABMS (M+H) calculated for C$_{27}$H$_{23}$N$_9$O.H was 500.2880 found 500.2879. LCMS 100%, $t_R$=5.65 minutes.

Buchwald Coupling of S-129 (75 mg, 0.26 mmol) and amine 22 (99 mg, 0.395 mmol) by following same procedure used in synthesis of 21 to afford 18 (4 mg, 3%). $^1$H NMR (400 MHz, Methanol-d$_4$) δ 7.69 (d, J=3.5 Hz, 1H), 7.30-7.10 (m, 4H), 6.71 (d, J=3.6 Hz, 1H), 6.38 (d, J=3.5 Hz, 1H), 5.86 (t, J=7.9 Hz, 1H), 5.38 (q, J=6.8 Hz, 1H), 3.69-3.5 (m, 1H), 3.25-3.29 (m, 1H), 3.03-2.84 (m, 3H), 2.59-2.43 (m, 3H), 2.3-2.24 (m, 2H), 2.23 (d, J=4.1 Hz, 3H), 2.18 (s, 3H), 2.08-1.89 (m, 2H), 1.54 (t, J=6.3 Hz, 3H). FABMS (M+H) calculated for C$_{27}$H$_{33}$N$_9$O.H was 500.28808 found 500.28844. LCMS 98.9%, $t_R$=5.3 minutes.

w. Synthesis of 21, 23, and 26

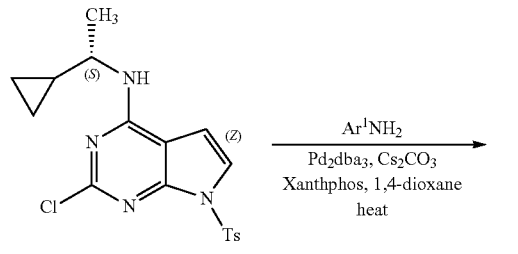

S-12

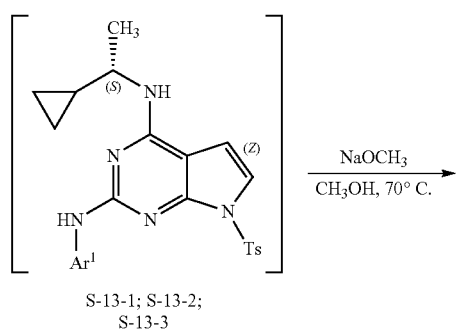

S-13-1; S-13-2; S-13-3

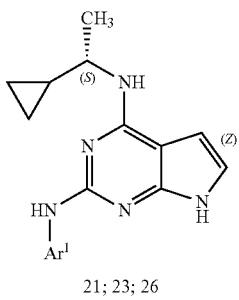

21; 23; 26 i. Preparation of 21

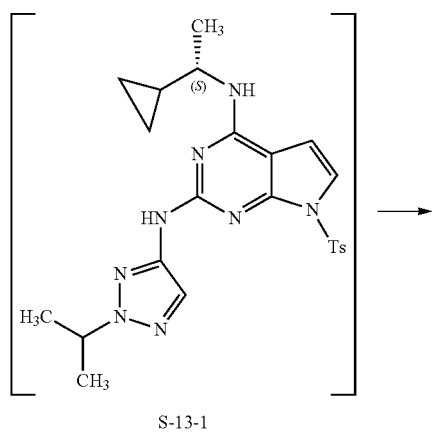

S-13-1

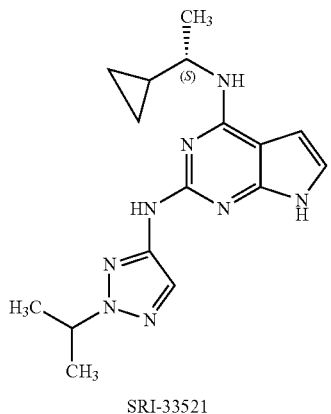

SRI-33521

In a microwave vial (35 mL) was added S-12 (87 mg, 0.2 mmol), 2-isopropyl-2H-1,2,3-triazol-4-amine (19.62 mg, 0.2 mmol, CAS #959237-97-9), $Cs_2CO_3$ (130 mg, 0.4 mmol.) and Dioxane (5 mL). The Argon was purged through septum and the reaction mixture was degassed for about 5 min. To this mixture was added Xantphos (11.65 mg, 0.02 mmol) followed by $Pd_2(dba)_3$ (18.3 mg, 0.02 mmol) and purged with Argon again for 5 min. Vial was sealed with the septum and irradiated at 140° C. for 3 h. After filtration, the obtained crude was chromatographed (DMC-EtOAc: 10-50%) to afford S-13-1 which was treated with NaOMe (0.3 mL) in MeOH (2 mL) at 70° C. for one hour. The reaction mixture was pre-absorbed on silica gel and chromatographed (DCM/MeOH: 2-10%) to give 21 (11 mg, 17%). $^1$H NMR (400 MHz, DMSO-$d_6$): δ 10.91 (bs, 1H), 8.98 (s, 1H), 7.96 (s, 1H), 7.09 (d, J=8.3 Hz, 1H), 6.75 (dd, J=3.4, 2.2 Hz, 1H), 6.46 (dd, J=3.4, 2.0 Hz, 1H), 4.64 (hept, J=6.6 Hz, 1H), 3.87 (h, J=7.0 Hz, 1H), 1.45 (d, J=6.7 Hz, 5H), 1.27 (d, J=6.6 Hz, 3H), 1.04 (qt, J=8.1, 5.0 Hz, 1H), 0.53-0.31 (m, 3H), 0.26-0.15 (m, 1H). FABMS (M+H) calculated for $C_{16}H_{22}N_8$·H was 327.2040 found 327.2039. LCMS 100%, $t_R$=6.28 minutes.

ii. Preparation of 23

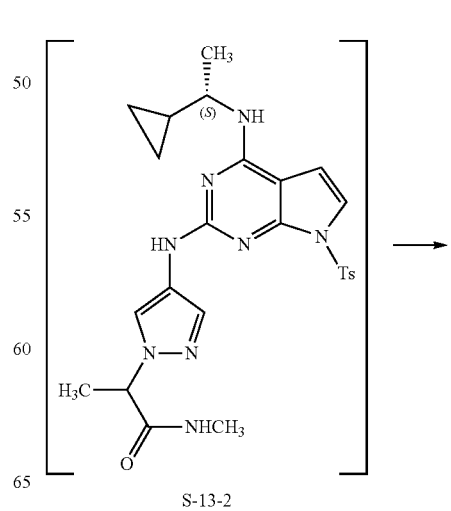

S-13-2

-continued

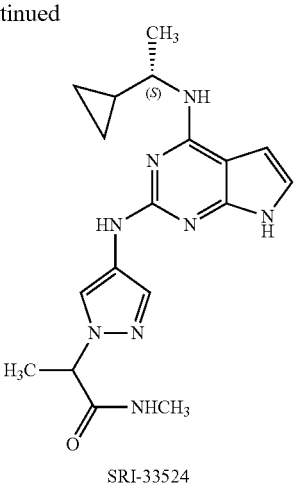

SRI-33524

Coupling of S-12 (85 mg, 0.2 mmol) to amine 7 (25 mg, 0.2 mmol) following the same procedure described for the synthesis of 21 afforded 23 (17 mg, 20%). $^1$H NMR (400 MHz, DMSO-d$_6$): δ 10.76 (bs, 1H), 8.34 (s, 1H), 7.96 (d, J=3.0 Hz, 1H), 7.88 (d, J=5.0 Hz, 1H), 7.47 (s, 1H), 6.98 (d, J=8.3 Hz, 1H), 6.69 (dd, J=3.4, 2.2 Hz, 1H), 6.43 (dd, J=3.5, 1.9 Hz, 1H), 4.85 (q, J=7.1 Hz, 1H), 2.59 (d, J=4.6 Hz, 3H), 1.55 (d, J=7.1 Hz, 3H), 1.27 (d, J=6.6 Hz, 3H), 1.09-0.98 (m, 1H), 0.85 (dt, J=10.8, 6.7 Hz, 1H), 0.53-0.32 (m, 3H), 0.24 (s, 1H). FABMS (M+H) calculated for C$_{18}$H$_{24}$N$_8$O.H was 369.2145 found 369.2146. LCMS 98%, t$_R$=5.64 minutes.

iii. Preparation of 26

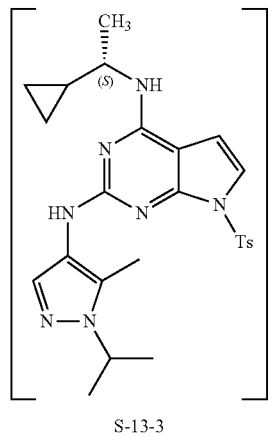

S-13-3

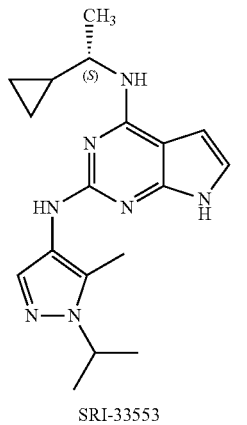

SRI-33553

Buchwald coupling of S-12 (0.2, 0.512 mmol) and 1-isopropyl-5-methyl-1H-pyrazol-4-amine (107 mg, 0.767 mmol, CAS No. 1000495-81-3) to S-13-3 (185 mg, 0.375 mmol) following the same procedure described for the synthesis of 21 afforded 26 (65 mg, 37% from S-12). $^1$H NMR (400 MHz, DMSO-d$_6$) δ 10.70 (s, 1H), 7.51 (s, 1H), 7.32 (s, 1H), 6.84 (d, J=8.5 Hz, 1H), 6.64 (dd, J=2.2, 3.4 Hz, 1H), 6.38 (dd, J=2.0, 3.4 Hz, 1H), 4.43 (hept, J=6.7 Hz, 1H), 3.82 (h, J=7.0 Hz, 1H), 2.15 (s, 3H), 1.35 (d, J=6.5 Hz, 6H), 1.22 (d, J=6.7 Hz, 3H), 1.03-0.94 (m, 1H), 0.43 (ddt, J=3.1, 5.8, 11.3 Hz, 1H), 0.34 (q, J=6.8, 7.3 Hz, 2H), 0.19-0.09 (m, 1H). FABMS (M+H) calculated for C$_{18}$H$_{25}$N$_7$.H was 340.22442 found 340.22445. LCMS 98.3%, t$_R$=5.88 minutes.

x. Synthesis of 22 and 24

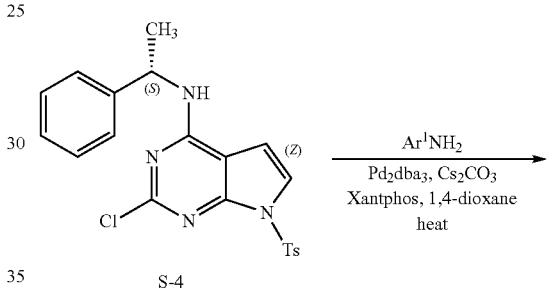

S-4

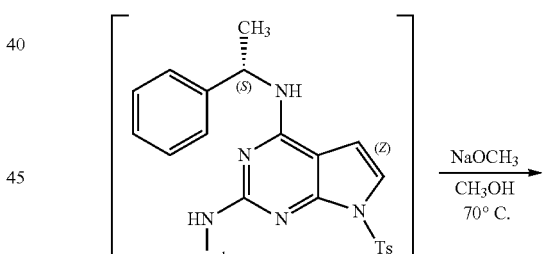

S-6-6a; S-6-6b

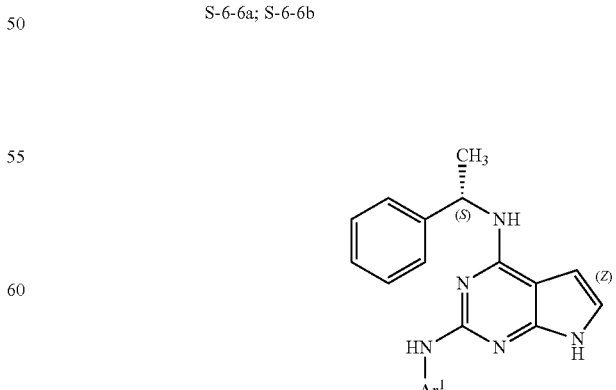

22; 24 i. Preparation of 22

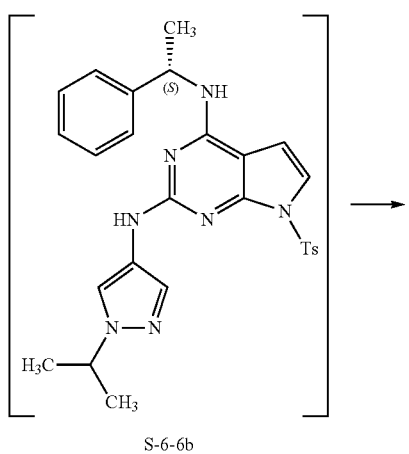

S-6-6b

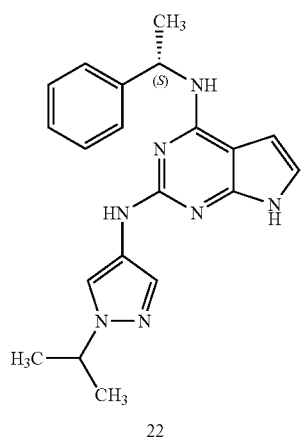

22

Coupling of S-4 (85 mg, 0.2 mmol) to 1-isopropyl-1H-pyrazol-4-amine (25 mg, 0.2 mmol, CAS #97421-16-4) following the same procedure described for the synthesis of 21 afforded 22 (17 mg, 23%). $^1$H NMR (400 MHz, DMSO-d$_6$): δ 10.79 (bs, 1H), 8.25 (s, 1H), 7.78 (s, 1H), 7.47-7.37 (m, 4H), 7.31 (dd, J=8.4, 6.9 Hz, 2H), 7.27-7.15 (m, 1H), 6.71 (dd, J=3.5, 2.2 Hz, 1H), 6.51 (dd, J=3.5, 2.0 Hz, 1H), 5.51 (p, J=7.2 Hz, 1H), 4.36 (hept, J=6.7 Hz, 1H), 1.54 (d, J=7.0 Hz, 3H), 1.37 (dd, J=6.7, 4.9 Hz, 6H). FABMS (M+H) calculated for C$_{20}$H$_{23}$N$_7$.H was 362.2087 found 362.2087. LCMS 99%, t$_R$=6.23 minutes.

ii. Preparation of 24

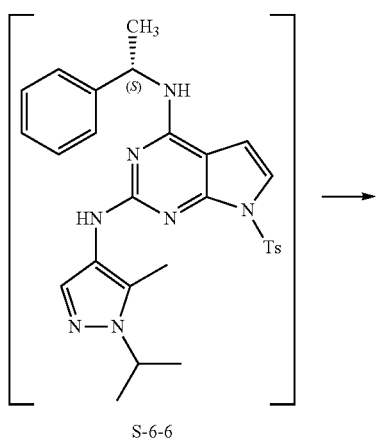

S-6-6

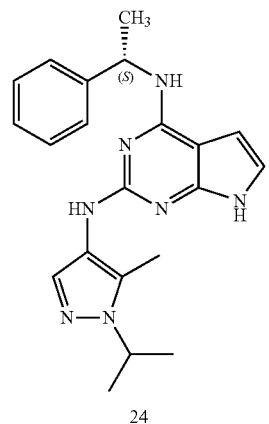

24

Buchwald coupling of S-4 (100 mg, 0.23 mmol) with 1-isopropyl-5-methyl-1H-pyrazol-4-amine (50 mg, 0.35 mmol, CAS No. 1006495-81-3) was performed following procedure used in synthesis of 21 to afford S-6-6 which was treated with NaOMe (0.05 mL) in MeOH (2 mL) at 90° C. for 3 h. The solvents were removed in vacuo and obtained residue was chromatographed (DCM/MeOH: 0-15%) to give 24 (15 mg, 17% from S-4). $^1$H NMR (400 MHz, Methanol-d$_4$) δ 7.50 (s, 1H), 7.38-7.31 (m, 2H), 7.31-7.23 (m, 2H), 7.22-7.12 (m, 1H), 6.69 (d, J=3.6 Hz, 1H), 6.44 (d, J=3.6 Hz, 1H), 5.40 (q, J=7.0 Hz, 1H), 4.51 (p, J=6.7 Hz, 1H), 2.11 (s, 3H), 1.54 (d, J=7.1 Hz, 3H), 1.46 (t, J=6.8 Hz, 7H). FABMS (M+H) calculated for C$_{21}$H$_{25}$N$_7$.H calc.—376.22442 found 376.22459. LCMS 99.42%, t$_R$=6.08 minutes.

y. Synthesis of 25

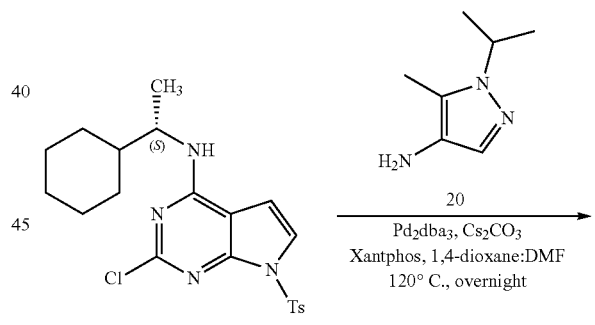

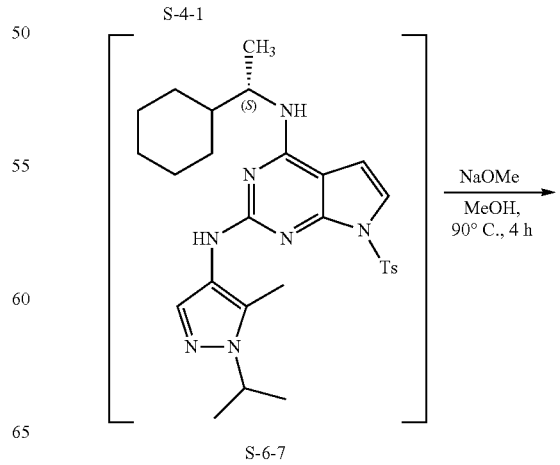

S-6-7

183
-continued

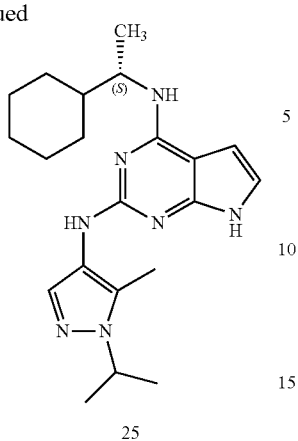

25

In a sealed tube was added S-4-1 (200 mg, 0.46 mmol), 1-isopropyl-5-methyl-1H-pyrazol-4-amine 20 (129 mg, 0.92 mmol, CAS No. 1006.495-81-3), $Cs_2CO_3$ (452 mg, 1.3 mmol.) and Dioxane:DMF (5 mL, 4:1). The Argon was purged through septum and the reaction mixture was purged for about 5 min. To this mixture was added XPhos (22 mg, 0.04 mmol) followed by $Pd_2(dba)_3$ (42 mg, 0.04 mmol) and purged with Argon again for 5 min. Tube was sealed and irradiated at 120° C. overnight. After filtration through celite bed, filterate solvents were removed in vacuo to obtain crude which was chromatographed on MPLC (DCM-MeOH: 0-10%) to afford S-6-7 (0.2, 81%) which was treated with NaOMe (0.3 mL) in MeOH (3 mL) at 90° C. for 4 h. The solvents were removed in vacuo and obtained residue was chromatographed (DCM/MeOH: 0-20%) to give 25 (62 mg, 35% from S-4-1). $^1$H NMR (400 MHz, Methanol-$d_4$) δ 7.60 (s, 1H), 6.68 (d, J=3.6 Hz, 1H), 6.39 (d, J=3.5 Hz, 1H), 4.53 (hept, J=6.7 Hz, 1H), 4.13 (p, J=6.8 Hz, 1H), 2.22 (s, 3H), 1.87-1.79 (m, 2H), 1.75-1.71 (m, 3H), 1.67-1.64 (m, 1H), 1.53-1.48 (m, 1H), 1.46 (d, J=6.6 Hz, 6H), 1.31-1.11 (m, 5H), 1.03 (qd, J=3.5, 12.0 Hz, 2H). FABMS (M+H) calculated for $C_{21}H_{31}N_7$.H was 382.2713 found 382.2717. LCMS 96.6%, $t_R$=6.5 minutes.

z. Synthesis of 27-34, 37, 39, 40, 52-54, 56, and 58

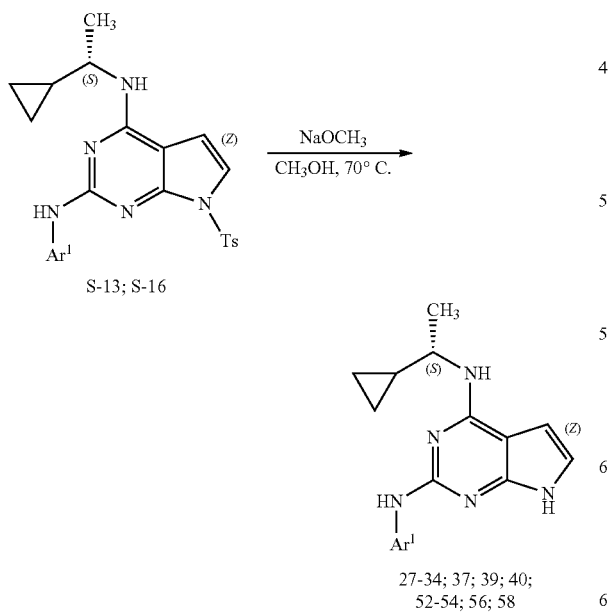

27-34; 37; 39; 40;
52-54; 56; 58

184
i. Preparation of 27

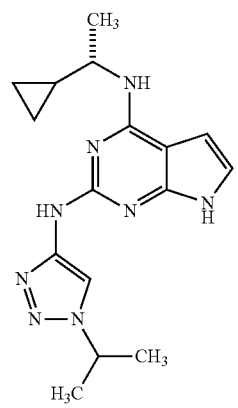 [SMILES: CC(C)n1cc(Nc2nc(N[C@@H](C)C3CC3)c3cc[nH]c3n2)nn1]

Compound S-13a (0.16 g, 0.33 mmol) was treated with NaOMe (0.3 mL, 25%) in MeOH at 70° C. for 2 h. The reaction mixture was cooled to room temperature and concentrated under reduced pressure. The residue was diluted with water (10 mL) and extracted with EtOAc (2×10 mL). The combined organic layers were washed with water (20 mL). The organic layers were dried over anhydrous $Na_2SO_4$ and concentrated under reduced pressure. The crude product was purified by column chromatography on silica gel using 1-3% MeOH in $CH_2Cl_2$ as eluent to afford 27 (0.045 g, 41%, UPLC 99.8%, AMRI lot # IN-AKK-I-28) as a white solid. The compound was characterized by $^1$H, $^{13}$C NMR and MS analyses. $^1$H NMR (300 MHz, DMSO-$d_6$): δ 10.98 (bs, 1H), 9.11 (bs, 1H), 8.05 (s, 1H), 7.15 (d, J=8.1 Hz, 1H), 6.77-6.75 (dd, J=3.3, 3.3 Hz, 1H), 6.47-6.45 (dd, J=3.3, 3.3 Hz, 1H), 4.80-4.71 (m, 1H), 3.87-3.79 (m, 1H), 1.47 (d, J=6.9 Hz, 6H), 1.28 (d, J=6.6 Hz, 3H), 1.11-1.00 (m, 1H), 0.53-0.42 (m, 4H); $^{13}$C NMR (100 MHz, DMSO-$d_6$): δ 156.08, 154.78, 151.97, 146.43, 117.69, 108.94, 99.09, 96.82, 52.20, 49.12, 22.62, 22.55, 20.48, 17.32, 3.09, 2.90; MS-UPLC (MM) m/z 327.2 [M+H]$^+$; UPLC Purity>99 (% AUC).

ii. Preparation of 28

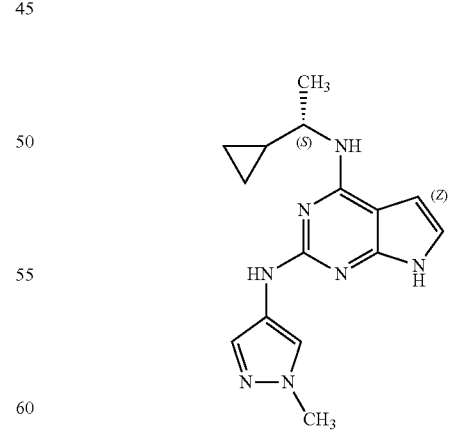

Compound S-16a (0.13 g, 0.28 mmol) was treated with NaOMe (0.5 M in MeOH, 1.3 mL) at 70° C. for 2 h. The reaction mixture was pre-absorbed on silica gel and purified by column chromatography on silica gel using 0-5% MeOH in $CH_2Cl_2$ as eluent to afford 28 (0.053 g, 63%, AMRI lot #

IN-SKY-C-17) as an off-white solid. The compound was characterized by $^1$H, $^{13}$C NMR and MS analyses. $^1$H NMR (300 MHz, CD$_3$OD): δ 7.84 (s, 1H), 7.54 (s, 1H), 6.71 (d, J=3.54 Hz, 1H), 6.40 (d, J=3.51 Hz, 1H), 3.86-3.81 (m, 4H), 1.34 (d, J=6.63 Hz, 3H), 1.11-0.99 (m, 1H), 0.58-0.49 (m, 1H), 0.47-0.40 (m, 2H), 0.30-0.22 (m, 1H); $^{13}$C NMR (100 MHz, CD$_3$OD): 158.28, 158.06, 153.12, 131.71, 126.38, 122.42, 118.58, 99.97, 98.17, 51.26, 38.93, 20.89, 18.50, 3.71, 3.61; MS-UPLC (MM) m/z 298.2 [M+H]$^+$; UPLC Purity>94 (% AUC).

iii. Preparation of 29

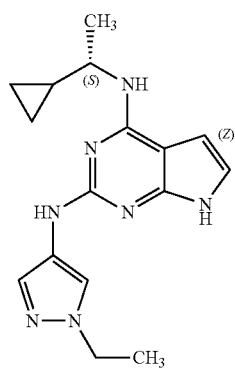

Compound S-16b (0.16 g, 0.34 mmol) was treated with NaOMe (0.5 M in MeOH, 1.6 mL) at 70° C. for 2 h. The reaction mixture was pre-absorbed on silica gel and purified by column chromatography on silica gel using 0-5% MeOH in CH$_2$Cl$_2$ as eluent to afford 29 (0.054 g, 50%, AMRI lot # IN-SKY-C-18) as an off-white solid. The compound was characterized by $^1$H, $^{13}$C NMR and MS analyses. $^1$H NMR (400 MHz, CD$_3$OD): δ 7.79 (s, 1H), 7.45 (s, 1H), 6.62 (d, J=3.56 Hz, 1H), 6.31 (d, J=3.56 Hz, 1H), 4.05-3.99 (m, 2H), 3.74 (q, J=8 Hz, 1H), 1.5 (t, J=7.28 Hz, 3H), 1.24 (d, J=6.68 Hz, 3H), 1.00-0.91 (m, 1H), 0.47-0.40 (m, 1H), 0.38-0.29 (m, 2H), 0.19-0.13 (m, 1H); $^{13}$C NMR (100 MHz, CD$_3$OD): δ 158.28, 158.07, 153.12, 131.54, 126.17, 120.80, 118.58, 99.96, 98.17, 51.30, 47.90, 20.89, 18.48, 15.95, 3.73, 3.64; MS-UPLC (MM) m/z 312.2 [M+H]$^+$; UPLC Purity>93 (% AUC).

iv. Preparation of 30

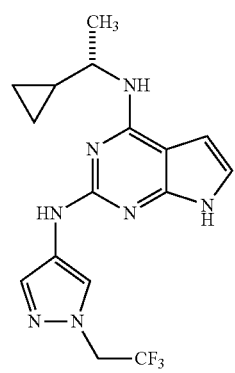 [SMILES: C[C@H](Nc1nc(Nc2cnn(CC(F)(F)F)c2)nc2[nH]ccc12)C1CC1]

Compound S-16d (110 mg, 0.21 mmol) was treated with NaOMe (0.6 mL, 25%) in MeOH at 70° C. for 2 h. When TLC showed complete consumption of the starting material, the reaction mixture was cooled to room temperature and concentrated under reduced pressure. The residue was diluted with the water (10 mL) and extracted with EtOAc (2×10 mL). The combined organic layer was washed with water (20 mL). The organic layer was dried over anhydrous Na$_2$SO$_4$ and concentrated under reduced pressure. The crude product was purified by column chromatography on silica gel using 1-3% MeOH in CH$_2$Cl$_2$ as eluent to afford 30 (0.059 g, 72%, AMRI lot # IN-CKB-G-26) as an off-white solid. The compound was characterized by $^1$H NMR, UPLC analysis. $^1$H NMR (400 MHz, CDCl$_3$): δ 8.67 (s, 1H), 8.00 (s, 1H), 7.57 (s, 1H), 6.71 (d, J=4.00 Hz, 1H), 6.58 (s, 1H), 6.26 (s, 1H), 4.90 (d, J=6.8 Hz, 1H), 4.65-4.59 (q, J=8.00 Hz, 2H), 3.82-3.78 (m, 1H), 1.34 (d, J=6.40 Hz, 3H), 1.05-0.94 (m, 1H), 0.60-0.30 (m, 4H); $^{13}$C NMR (100 MHz, CDCl$_3$): δ 156.60, 156.36, 152.47, 132.68, 125.56, 120.56, 117.57, 98.72, 96.91, 53.49, 53.15, 50.45, 20.50, 17.61, 3.10, 2.97; MS-UPLC (MM) m/z 366.2 [M+H]$^+$; UPLC purity>98 (% AUC).

v. Preparation of 31

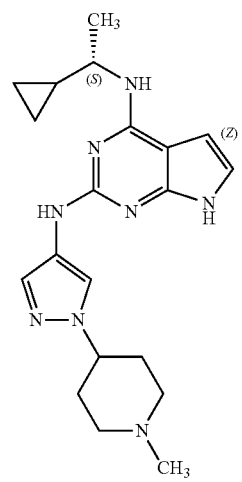

Compound S-16f (0.20 g, 0.37 mmol) was treated with NaOMe (0.5 M in MeOH, 1.3 mL) at 70° C. for 2 h. The reaction mixture was adsorbed on silica gel and purified by column chromatography on silica gel using 0-5% MeOH in CH$_2$Cl$_2$ as eluent to afford 31 (0.045 g, 31%, AMRI lot # IN-AKK-I-45) as an off-white solid. The compound was characterized by $^1$H NMR, UPLC-MS analysis. $^1$H NMR (400 MHz, CH$_3$OD): δ 7.82 (bs, 1H), 7.64 (s, 1H), 6.80 (d, J=3.2 Hz, 1H), 6.55 (d, J=3.6 Hz, 1H), 4.43-4.40 (m, 1H), 3.59 (d, J=8.4 Hz, 2H), 3.15-3.12 (m, 2H), 2.85 (s, 3H), 2.27-2.23 (m, 4H), 1.30 (d, J=6.8 Hz, 3H), 1.05-1.0 (m, 1H), 0.55-0.19 (m, 4H); MS-UPLC (MM) m/z 380.2 [M+H]$^+$; UPLC purity>98 (% AUC).

vi. Preparation of 32

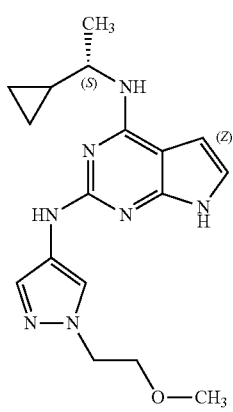

The tosylated compound S-16e (0.13 g, 0.26 mmol) was treated with NaOMe (0.5 M in MeOH, 1.3 mL) at 70° C. for 2 h. The reaction mixture was adsorbed on silica gel and purified by column chromatography on silica gel using 0-5% MeOH in $CH_2Cl_2$ as eluent to afford 32 (0.053 g, 55%, AMRI lot # IN-CKB-G-28) as an off-white solid. The compound was characterized by $^1$H NMR, UPLC-MS analysis. $^1$H-NMR (400 MHz, $CDCl_3$): δ 8.59 (s, 1H), 7.86 (s, 1H), 7.53 (s, 1H), 6.68 (d, J=3.60 Hz, 1H), 6.38 (s, 1H), 6.23 (d, J=3.60 Hz, 1H), 4.86 (d, J=7.60 Hz, 1H), 4.24 (t, J=5.60 Hz, 2H), 3.74 (t, J=5.20 Hz, 2H), 3.33 (s, 3H), 1.34 (s, 3H), 1.01-0.94 (m, 1H), 0.57-0.30 (m, 4H); $^{13}$C NMR (100 MHz, $CDCl_3$): δ 156.78, 156.61, 152.59, 131.43, 123.85, 121.09, 117.40, 98.70, 96.73, 71.43, 59.00, 52.37, 50.35, 20.58, 17.71, 3.13, 2.97; MS-UPLC (MM) m/z 342.2 [M+H]$^+$; UPLC purity>99 (% AUC).

vii. Preparation of 33

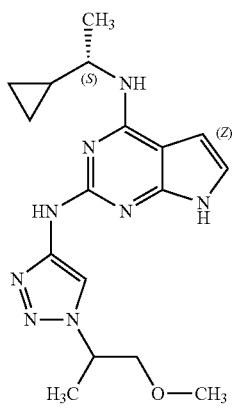

Compound S-13g (0.14 g, 0.27 mmol) was treated with NaOMe (0.5 M in MeOH, 1.4 mL) at 70° C. for 2 h. When TLC showed complete consumption of the starting material, the reaction mixture was cooled to room temperature and concentrated under reduced pressure. The residue was diluted with water (10 mL) and extracted with EtOAc (2×10 mL). The combined organic layer was washed with water (20 mL). The organic layer was dried over anhydrous $Na_2SO_4$ and concentrated under reduced pressure. The crude product was purified by column chromatography on silica gel using 1-3% MeOH in $CH_2Cl_2$ as eluent to afford 33 (0.048 g, 49%, AMRI lot # IN-SKY-C-67) as an off-white solid. The compound was characterized by $^1$H NMR, UPLC analysis. $^1$H NMR (300 MHz, $CD_3OD$): δ 8.10 (s, 1H), 6.68 (d, J=3.6 Hz, 1H), 6.35 (d, J=3.6 Hz, 1H), 4.71 (s, 1H), 3.76 (q, J=7.8 Hz, 1H), 3.64-3.61 (m, 2H), 3.25 (s, 3H), 1.50 (d, J=7.2 Hz, 3H), 1.29-1.26 (m, 3H), 1.04-0.96 (m, 1H), 0.48-0.28 (m, 3H), 0.24-0.18 (m, 1H); MS-UPLC (MM) m/z 357.2 [M+H]$^+$; UPLC purity>92 (% AUC).

viii. Preparation of 34

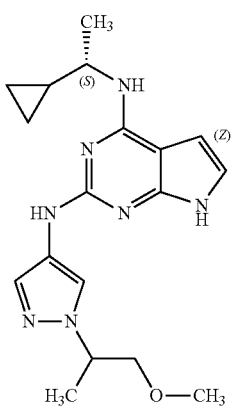

Compound S-16h (0.15 g, 0.29 mmol) was treated with NaOMe (0.5 M in MeOH, 1.3 mL) at 70° C. for 2 h. When TLC showed complete consumption of the starting material, the reaction mixture was cooled to room temperature and concentrated under reduced pressure. The residue was diluted with the water (10 mL) and extracted with EtOAc (2×10 mL). The combined organic layer was washed with water (20 mL). The organic layer was dried over anhydrous $Na_2SO_4$ and concentrated under reduced pressure. The crude product was purified by mass triggered preparative HPLC to afford 34 (0.05 g, 47%, AMRI lot # IN-CKB-G-72) as an off-white semi solid. The compound was characterized by $^1$H NMR, UPLC-MS analysis. $^1$H NMR (400 MHz, $CDCl_3$): δ 7.83 (s, 1H), 7.54 (s, 1H), 6.79 (d, J=3.20 Hz, 1H), 6.55 (d, J=3.60 Hz, 1H), 4.46-4.43 (m, 1H), 3.75 (s, 1H), 3.61-3.54 (m, 2H), 1.40 (d, J=6.80 Hz, 3H), 1.30 (dd, J=2.80, 6.80 Hz, 3H), 1.06-0.97 (m, 1H), 0.52-0.22 (m, 4H); MS-UPLC (MM) m/z 356.2 [M+H]$^+$; UPLC purity>97 (% AUC).

ix. Preparation of 37

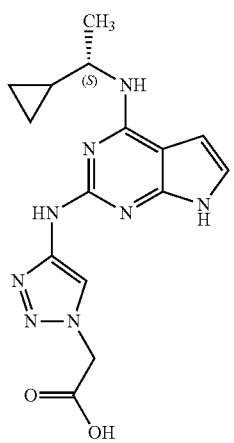

Compound S-13j (0.18 g, 0.34 mmol) was treated with NaOMe (0.5 M in MeOH, 1.3 mL) at 70° C. for 2 h. When TLC showed complete consumption of the starting material, the reaction mixture was cooled to room temperature and concentrated under reduced pressure. The residue was diluted with the water (10 mL) and extracted with EtOAc (2×10 mL). The combined organic layer was washed with water (20 mL). The organic layer was dried over anhydrous Na$_2$SO$_4$ and concentrated under reduced pressure. The crude product was purified by MS-triggered preparative HPLC to afford 37 (0.048 g, 42%, AMRI lot # IN-AKK-I-119-1) as an off-white solid. The compound was characterized by $^1$H NMR, UPLC analysis. $^1$H NMR (400 MHz, DMSO-d$_6$): δ 13.48 (bs, 1H), 11.54 (s, 1H), 10.27 (bs, 1H), 8.52 (bs, 1H), 8.05 (s, 1H), 6.96 (s, 1H), 6.67 (s, 1H), 5.32 (s, 2H), 1.32 (d, J=10.4 Hz, 3H), 1.09-1.07 (m, 1H), 0.53-0.30 (m, 4H); MS-UPLC (MM) m/z 342.2 [M+H]$^+$; UPLC purity>97 (% AUC).

x. Preparation of 39

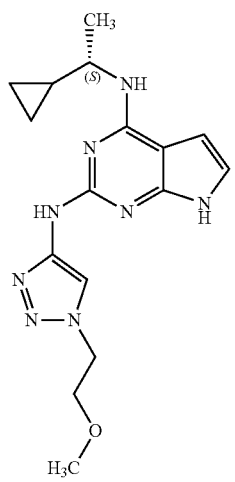

Compound S-13i (0.11 g, 0.22 mmol) was treated with NaOMe (0.5 M in MeOH, 1.3 mL) at 70° C. for 2 h. When TLC showed complete consumption of the starting material, the reaction mixture was cooled to room temperature and concentrated under reduced pressure. The residue was diluted with water (10 mL) and extracted with EtOAc (2×10 mL). The combined organic layer was washed with water (20 mL). The organic layer was dried over anhydrous Na$_2$SO$_4$ and concentrated under reduced pressure. The crude product was purified by column chromatography on silica gel using 1-3% MeOH in CH$_2$Cl$_2$ as eluent to afford 39 (0.035 g, 46%, AMRI lot # IN-AKK-I-111-1) as an off-white solid. The compound was characterized by $^1$H NMR analysis. $^1$H NMR (300 MHz, DMSO-d$_6$): δ 11.36 (s, 1H), 9.79 (bs, 1H), 8.09 (s, 1H), 7.23 (d, J=8.1 Hz, 1H), 6.83 (s, 1H), 6.50 (s, 1H), 4.52-4.50 (m, 2H), 3.91-3.84 (m, 1H), 3.74 (t, J=4.5 Hz, 2H), 3.35 (s, 3H), 1.31 (d, J=6.6 Hz, 3H), 1.10-1.06 (m, 1H), 0.51-0.22 (m, 4H); $^{13}$C NMR (75 MHz, DMSO-d$_6$): δ 156.15, 154.66, 151.90, 146.62, 117.76, 111.58, 99.19, 96.82, 70.43, 58.03, 49.74, 49.08, 20.56, 17.44, 3.05, 2.88; MS-UPLC (MM) m/z 342.2 [M+H]$^+$; UPLC purity>97 (% AUC).

xi. Preparation of 40

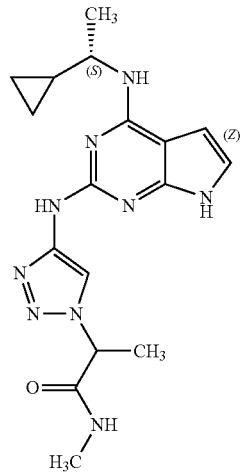

Compound S-13h (140 mg, 0.26 mmol) was treated with NaOMe (0.5 M in MeOH, 1.3 mL) at 70° C. for 2 h. When TLC showed complete consumption of the starting material, the reaction mixture was cooled to room temperature and concentrated under reduced pressure. The residue was diluted with the water (10 mL) and extracted with EtOAc (2×10 mL). The combined organic layer was washed with water (20 mL). The organic layer was dried over anhydrous Na$_2$SO$_4$ and concentrated under reduced pressure. The crude product was purified by column chromatography on silica gel using 1-3% MeOH in CH$_2$Cl$_2$ as eluent to afford 40 (0.047 g, 47%, AMRI lot # IN-AKK-I-116-1) as an off-white solid. The compound was characterized by $^1$H NMR, UPLC analysis. $^1$H NMR (400 MHz, DMSO-d$_6$): δ 10.94 (bs, 1H), 9.01 (s, 1H), 8.29 (d, J=4.4 Hz, 1H), 8.13 (d, J=6.8 Hz, 1H), 7.14-7.11 (dd, J=5.2, 2.8 Hz, 1H), 6.75 (t, J=2.8 Hz, 1H), 6.46 (s, 1H), 5.28-5.23 (m, 1H), 3.86-3.76 (m, 1H), 2.63 (d, J=4.8 Hz, 3H), 1.64 (d, J=1.6 Hz, 3H), 1.29 (d, J=6.4 Hz, 3H), 1.09-1.03 (m, 1H), 0.48-0.26 (m, 4H); MS-UPLC (MM) m/z 369.2 [M+H]$^+$; UPLC purity>97 (% AUC).

xii. Preparation of 52

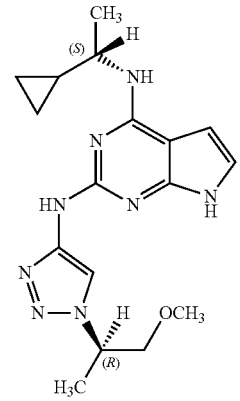

Compound S-13m (0.165 g, 0.29 mmol) was charged with NaOMe (0.3 mL, 25%) in MeOH at 70° C. for 2 h. The reaction mixture was cooled to room temperature and concentrated under reduced pressure. The residue was diluted with water (10 mL) and extracted with EtOAc (2×10 mL). The combined organic layers were washed with water (20 mL). The organic layers were dried over anhydrous Na$_2$SO$_4$ and concentrated under reduced pressure. The crude product was purified by column chromatography on silica gel using 1-3% MeOH in CH$_2$Cl$_2$ as eluent to afford 52 (0.04 g, 38%, AMRI lot # IN-CKB-G-143) as an off-white semi solid. The compound was characterized by $^1$H, $^{13}$C NMR and MS analyses. $^1$H NMR (400 MHz, CD$_3$OD): δ 8.10 (s, 1H), 6.69 (d, J=3.60 Hz, 1H), 6.35 (d, J=3.60 Hz, 1H), 4.78 (s, 1H) 3.82-3.76 (m, 1H), 3.67-3.59 (m, 2H), 3.25 (s, 3H), 1.50 (d, J=6.80 Hz, 3H), 1.29 (d, J=6.40 Hz, 3H), 1.02-0.97 (m, 1H), 0.49-0.30 (m, 3H), 0.24-0.18 (m, 1H); $^{13}$C NMR (100 MHz, CD$_3$OD): δ 158.21, 156.26, 147.85, 119.13, 111.98, 99.95, 76.43, 59.10, 51.37, 20.95, 18.41, 3.60; MS-UPLC (MM) m/z 356.2 [M+H]$^+$; UPLC Purity>99 (% AUC).

xiii. Preparation of 53

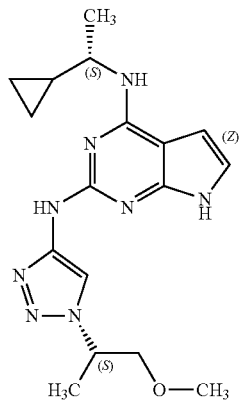

Compound S-13l (0.15 g, 0.29 mmol) was charged with NaOMe (0.3 mL, 25%) in MeOH at 70° C. for 2 h. The reaction mixture was cooled to room temperature and concentrated under reduced pressure. The residue was diluted with water (10 mL) and extracted with EtOAc (2×10 mL). The combined organic layers were washed with water (20 mL). The organic layers were dried over anhydrous Na$_2$SO$_4$ and concentrated under reduced pressure. The crude product was purified by column chromatography on silica gel using 1-3% MeOH in CH$_2$Cl$_2$ as eluent to afford 53 (0.05 g, 48%, AMRI lot # IN-CKB-G-145) as a gummy material. The compound was characterized by $^1$H, $^{13}$C NMR and MS analyses. $^1$H NMR (400 MHz, CD$_3$OD): δ 7.92 (s, 1H), 6.99 (d, J=3.60 Hz, 1H), 6.71 (d, J=3.20 Hz, 1H), 4.99 (s, 1H), 3.78-3.70 (m, 3H), 3.34 (s, 3H), 1.60 (d, J=7.20 Hz, 3H), 1.42 (d, J=6.40 Hz, 3H), 1.19-1.10 (m, 1H), 0.67-0.51 (m, 2H), 0.45-0.32 (m, 2H); $^{13}$C NMR (100 MHz, CD$_3$OD): δ 145.0, 113.41, 102.24, 76.15, 59.23, 20.27, 17.56, 4.04; MS-UPLC (MM) m/z 356.2 [M+H]$^+$; UPLC Purity>98 (% AUC).

xiv. Preparation of 54

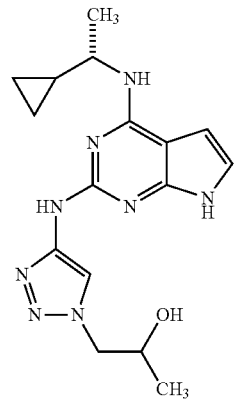 [SMILES: CC(O)Cn1cc(Nc2nc(N[C@@H](C)C3CC3)c3cc[nH]c3n2)nn1]

Compound S-13s (0.20 g, 0.4 mmol) was charged with NaOMe (0.3 mL, 25%) in MeOH at 70° C. for 2 h. The reaction mixture was cooled to room temperature and concentrated under reduced pressure. The residue was diluted with water (10 mL) and extracted with EtOAc (2×10 mL). The combined organic layers were washed with water (20 mL). The organic layers were dried over anhydrous Na$_2$SO$_4$ and concentrated under reduced pressure. The crude product was purified by MS triggered preparative HPLC to afford 54 (0.06 g, 32%, AMRI lot # IN-CKB-G-152) as a gummy liquid. The compound was characterized by $^1$H NMR and UPLC-MS analysis. $^1$H NMR (400 MHz, CD$_3$OD): δ 7.95 (s, 1H), 6.98 (d, J=3.60 Hz, 1H), 6.70 (d, J=3.60 Hz, 1H), 4.47 (dd, J=3.60, 13.80 Hz, 1H), 4.32 (dd, J=7.60, 13.80 Hz, 1H), 4.21-4.16 (m, 1H), 3.78 (s, 1H), 1.42 (d, J=6.40 Hz, 3H), 1.22 (d, J=6.40 Hz, 3H), 1.16-1.09 (m, 1H), 0.65-0.53 (m, 2H), 0.43-0.35 (m, 2H); MS-UPLC (MM) m/z 343.2 [M+H]$^+$; UPLC Purity>95 (% AUC).

xv. Preparation of 56

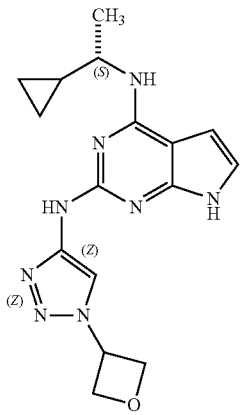

Compound S-13t (220 g, 0.441 mmol) was treated with NaOMe (0.5 M in MeOH, 2.0 mL) at 70° C. for 2 h. The reaction mixture was adsorbed on silica gel and purified by column chromatography on silica gel using 0-5% MeOH in CH₂Cl₂ as eluent to afford 56 (100 mg, 66%, AMRI lot # IN-AKK-I-196-2) as an off-white solid. The compound was characterized by ¹H NMR and MS analysis. ¹H NMR (400 MHz, DMSO-d₆): δ 10.97 (s, 1H), 9.17 (s, 1H), 8.33 (s, 1H), 7.15 (d, J=8.1 Hz, 1H), 6.77 (d, J=3.3 Hz, 1H), 6.45 (d, J=3.3 Hz, 1H), 5.83-5.74 (m, 1H), 5.07 (t, J=7.2 Hz, 2H), 4.87 (t, J=6.1 Hz, 2H), 3.88-3.81 (m, 1H), 1.29 (d, J=6.6 Hz, 3H), 1.14-0.99 (m, 1H), 0.52-0.35 (m, 3H), 0.27-0.19 (m, 1H); MS-UPLC (MM) m/z 340.3 [M+H]⁺; UPLC purity>98 (% AUC).

xvi. Preparation of 58

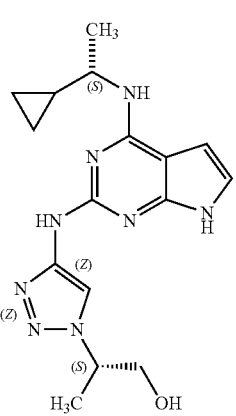

Compound S-13x (120 mg, 0.19 mmol) was charged with NaOMe (0.5 M in MeOH, 2.0 mL) at 70° C. for 2 h. The reaction mixture was adsorbed on silica gel and purified by column chromatography on silica gel using 0-2% MeOH in CH₂Cl₂ as eluent to afford 58 (23.0 mg, 32%, AMRI lot # IN-AKK-I-201-1) as a brown liquid. The compound was characterized by ¹H NMR and MS analysis. ¹H NMR (400 MHz, CD₃OD): δ 8.15 (s, 1H), 6.69 (d, J=3.6 Hz, 1H), 6.34 (d, J=3.6 Hz, 1H), 4.65-4.58 (m, 1H), 3.80-3.71 (m, 3H), 1.49 (d, J=7.2 Hz, 3H), 1.29 (d, J=6.8 Hz, 3H), 1.04-0.95 (m, 1H), 0.50-0.20 (m, 4H); MS-UPLC (MM) m/z 342.3 [M+H]⁺; UPLC purity>94 (% AUC).

aa. Synthesis of 35

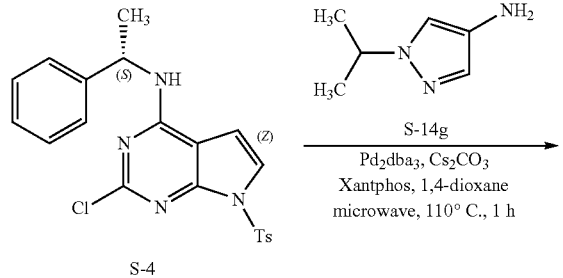

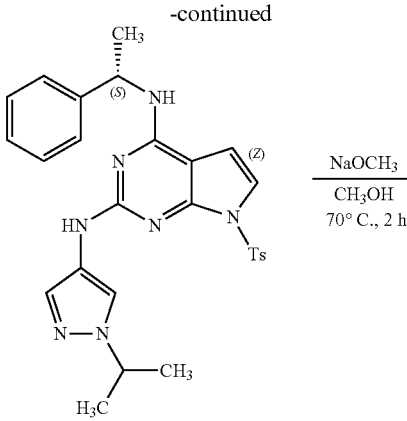

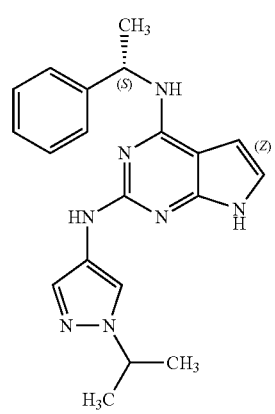

35 i. Preparation of S-57

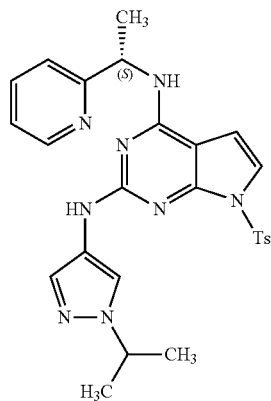

A stirred solution of S-56 (0.30 g, 0.7 mmol) in 1,4-dioxane taken in a microwave vial was charged with 1-isopropyl-1H-pyrazol-4-amine S-14g (0.105 g, 0.84 mmol) and Cs₂CO₃ (0.45 g, 1.4 mmol). Argon gas was purged through septum and the reaction was degassed for about 5 min. To this reaction mixture, xantphos (0.04 g, 0.07 mmol) and Pd₂(dba)₃ (0.064 g, 0.07 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-5% MeOH in CH₂Cl₂ as eluent to afford S-57 (0.20 g, 55%, AMRI lot # IN-CKB-G-62) as an off-white solid. The compound was characterized by ¹H NMR and UPLC-MS analysis. ¹H NMR (400 MHz, CDCl₃): δ 8.56 (d, J=4.80 Hz, 1H), 7.97 (d, J=8.40 Hz, 2H), 7.66-7.62 (m, 1H), 7.43 (s, 1H), 7.19 (d, J=8.40 Hz, 3H), 7.15 (d, J=4.00 Hz, 1H), 6.66 (s, 1H), 6.40 (d, J=4.00 Hz, 1H), 6.26 (d, J=6.80 Hz, 1H), 5.38 (t, J=6.80 Hz, 1H), 4.57-4.50 (m, 1H), 2.33 (s, 3H), 1.57-1.55 (m, 9H); MS-UPLC (MM) m/z 517.2 [M+H]⁺.

ii. Preparation of 35

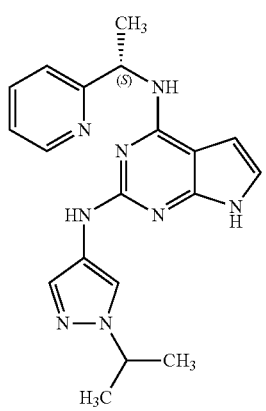

Compound S-57 (0.20 g, 0.38 mmol) was treated with NaOMe (0.5 M in MeOH, 2 mL) at 70° C. for 2 h. When TLC showed complete consumption of the starting material, the reaction mixture was cooled to room temperature and concentrated under reduced pressure. The residue was diluted with water (10 mL) and extracted with EtOAc (2×10 mL). The combined organic layer was washed with water (20 mL). The organic layer was dried over anhydrous Na₂SO₄ and concentrated under reduced pressure. The crude product was purified by mass triggered preparative HPLC to afford 35 (0.135 g, 95%, AMRI lot # IN-CKB-G-71) as an off-white semi solid. The compound was characterized by ¹H, ¹³C NMR and UPLC-MS analysis. ¹H-NMR (400 MHz, CD₃OD): δ 8.56 (d, J=5.20 Hz, 1H), 8.13 (d, J=7.20 Hz, 2H), 7.70-7.57 (m, 3H), 7.30 (s, 1H), 6.85 (d, J=3.60 Hz, 2H), 6.66 (s, 1H), 5.48 (q, J=6.80 Hz, 1H), 4.45-4.38 (m, 1H), 1.67 (d, J=7.20 Hz, 3H), 1.40 (d, J=6.80 Hz, 3H); ¹³C NMR (100 MHz, CDCl₃): δ 161.67, 146.65, 125.35, 123.73, 121.16, 102.28, 98.98, 55.59, 52.55, 23.02, 20.90; MS-UPLC (MM) m/z 363.2 [M+H]⁺; UPLC purity>99 (% AUC).

bb. Synthesis of 36, 44, 50, and 51

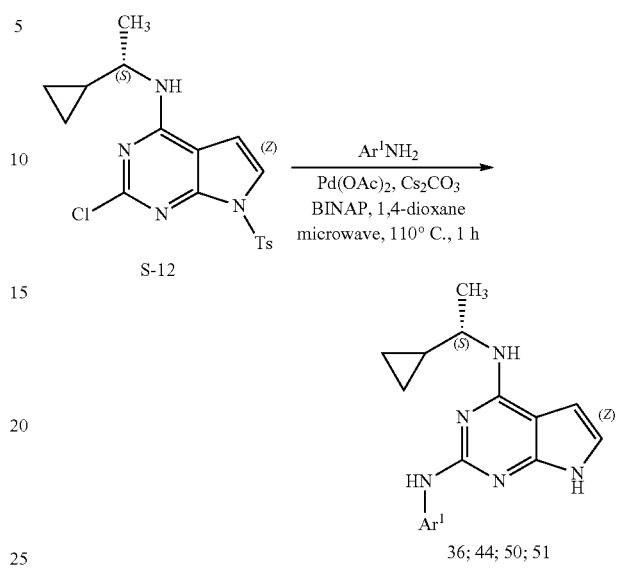

i. Preparation of 36

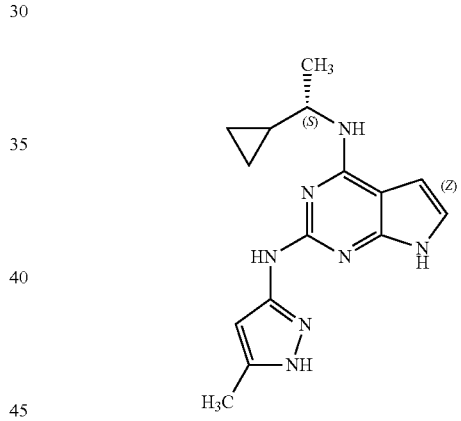

A solution of S-12 (0.30 g, 0.77 mmol), 5-methyl-1H-pyrazol-3-amine S-14c (0.11 g, 1.4 mmol), Cs₂CO₃ (0.45 g, 1.4 mmol) and 1,4-dioxane (3 mL) was charged into a microwave vial with stirrer bar. Argon gas was purged through septum and the reaction mixture was degassed for about 5 min. To this reaction mixture, BINAP (0.047 g, 0.077 mmol) and Pd(OAc)₂ (0.018 g, 0.077 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified MS triggered preparative HPLC to afford 36 (0.044 g, 19%, AMRI lot # IN-SKY-C-82) as an off-white solid. The compound was characterized by ¹H NMR, UPLC analysis. ¹H NMR (400 MHz, CD₃OD): δ 6.87 (d, J=3.6 Hz, 1H), 6.58 (d, J=3.6 Hz, 1H), 5.72 (s, 1H), 3.69-3.62 (m, 1H), 2.21 (s, 3H), 1.32 (d, J=6.4 Hz, 3H), 1.05-1.01 (m, 1H), 0.55-0.50 (m, 1H), 0.46-0.33 (m, 2H), 0.27-0.22 (m, 1H); ¹³C NMR (400 MHz, CD₃OD): δ 149.89, 142.29, 121.20, 102.13, 94.30, 53.41, 20.32, 18.07, 10.64, 4.03, 3.94; MS-UPLC (MM) m/z 298.2 [M+H]⁺; UPLC purity>99 (% AUC).

ii. Synthesis of 44

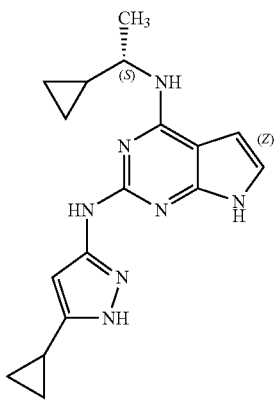

A stirred solution of S-12 (0.30 g, 0.76 mmol) in 1,4-dioxane taken in a microwave vial was charged with 5-cyclopropyl-1H-pyrazol-3-amine S-96 (0.11 g, 0.92 mmol) and Cs₂CO₃ (0.49 g, 1.52 mmol). Argon gas was purged through septum and the reaction was degassed for about 5 min. To this reaction mixture, xantphos (0.044 g, 0.076 mmol) and Pd₂(dba)₃ (0.069 g, 0.076 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by Mass triggered preparative HPLC to afford 44 (0.07 g, 28%, AMRI lot # IN-SKY-C-119) as an off-white solid. The compound was characterized by ¹H NMR and UPLC analysis. ¹H NMR (400 MHz, CD₃OD): δ 6.87 (d, J=3.6 Hz, 1H), 6.58 (d, J=3.6 Hz, 1H), 5.57 (s, 1H), 3.63 (s, 1H), 1.86-1.81 (m, 1H), 1.32 (d, J=6.4 Hz, 3H), 1.05-1.01 (m, 1H), 0.96-0.91 (m, 2H), 0.67-0.64 (m, 2H), 0.53-0.52 (m, 1H), 0.47-0.42 (m, 1H), 0.40-0.34 (m, 1H), 0.33-0.23 (m, 1H); MS-UPLC (MM) m/z 324.2 [M+]⁺; UPLC purity>98 (% AUC).

iii. Preparation of 51

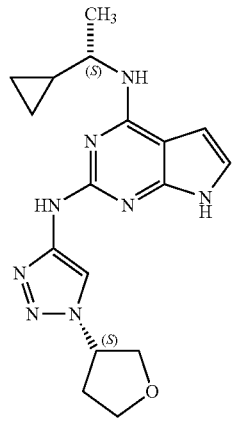

A stirred solution of S-12 (240 mg, 0.61 mmol) in 1,4-dioxane (3.0 mL) taken in a microwave vial was charged with amine S-5p (104 mg, 0.67 mmol) and Cs₂CO₃ (396 mg, 1.22 mmol). Argon gas was purged through septum and the reaction was degassed for about 5 min. To this reaction mixture, xantphos (29.0 mg, 0.061 mmol) followed by Pd₂(dba)₃ (55.0 mg, 0.061 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-3% MeOH in CH₂Cl₂ as eluent to afford 51 (42.0 mg, 20%, AMRI lot # IN-AKK-I-167) as an off-white solid. The compound was characterized by ¹H NMR analysis. ¹H NMR (300 MHz, CD₃OD): δ 8.13 (s, 1H), 6.84 (d, J=3.6 Hz, 1H), 6.51 (d, J=3.3 Hz, 1H), 5.37-5.33 (m, 1H), 4.21-3.74 (m, 5H), 2.69-2.57 (m, 1H), 2.36-2.26 (m, 1H), 1.39 (d, J=6.6 Hz, 3H), 1.15-1.04 (m, 1H), 0.59-0.32 (m, 4H); MS-UPLC (MM) m/z 354.1 [M+H]⁺; UPLC purity>94 (% AUC).

iv. Preparation of 50

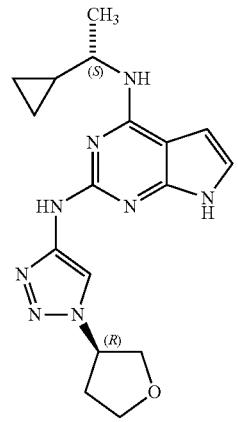

A stirred solution of S-12 (340 mg, 0.87 mmol) in 1,4-dioxane (3.0 mL) taken in a microwave vial was charged with amine S-5q (147 mg, 0.95 mmol) and Cs₂CO₃ (565 mg, 1.74 mmol). Argon gas was purged through septum and the reaction was degassed for about 5 min. To this reaction mixture, xantphos (41.0 mg, 0.087 mmol) followed by Pd₂(dba)₃ (79.0 mg, 0.087 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-3% MeOH in CH₂Cl₂ as eluent to afford 50 (43.0 mg, 20%, AMRI lot # IN-AKK-I-166) as an off-white solid. The compound was characterized by ¹H NMR analysis. ¹H NMR (400 MHz, CD₃OD): δ 8.00 (s, 1H), 6.98 (d, J=3.2 Hz, 1H), 6.70 (d, J=3.2 Hz, 1H), 5.40-5.37 (m, 1H), 4.18-3.91 (m, 4H), 3.76-3.72 (m, 1H), 2.69-2.59 (m, 1H), 2.39-2.32 (m, 1H), 1.42 (d, J=6.4 Hz, 3H), 1.19-1.10 (m, 1H), 0.66-0.53 (m, 2H), 0.44-0.34 (m, 2H); MS-UPLC (MM) m/z 354.2 [M+H]⁺; UPLC purity>99 (% AUC).

cc. Synthesis of 38

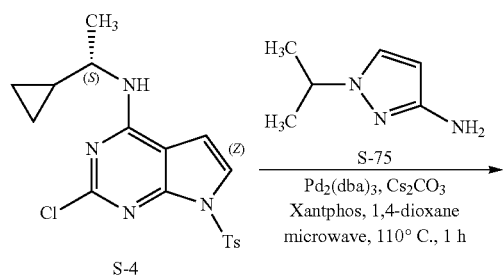

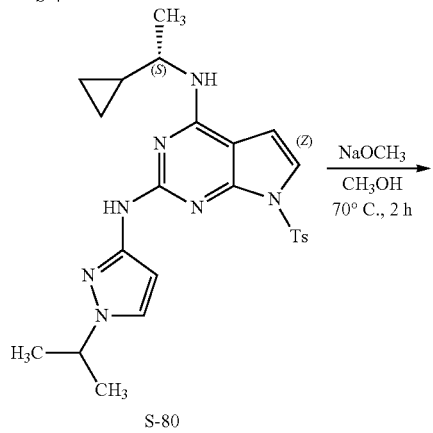

i. Preparation of S-80

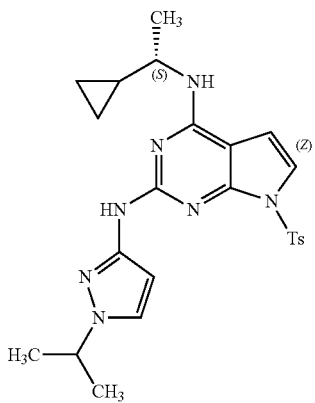

A solution of S-12 (0.30 g, 0.76 mmol), 1-isopropyl-1H-pyrazol-3-amine S-75 (0.11 g, 0.92 mmol), Cs$_2$CO$_3$ (0.49 g, 1.52 mmol) and 1,4-dioxane (3 mL) was charged into a microwave vial with stirrer bar. Argon gas was purged through septum and the reaction mixture was degassed for about 5 min. To this reaction mixture, xantphos (0.044 g, 0.076 mmol) and Pd$_2$(dba)$_3$ (0.070 g, 0.076 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 20-60% EtOAc in hexanes as eluent to afford S-80 (0.16 g, 66%, AMRI lot # IN-SKY-C-98) as a brown solid. The compound was characterized by $^1$H NMR analysis. $^1$H NMR (300 MHz, CD$_3$OD): δ 7.85 (d, J=8.1 Hz, 2H), 7.44 (d, J=2.4 Hz, 1H), 7.18 (d, J=8.1 Hz, 2H), 7.04 (d, J=4.2 Hz, 1H), 6.83 (d, J=1.8 Hz, 1H), 6.54 (d, J=3.9 Hz, 1H), 4.32-4.25 (m, 1H), 3.69-3.59 (m, 1H), 2.24 (s, 3H), 1.38 (d, J=6.9 Hz, 6H), 1.16 (d, J=3 Hz, 3H), 0.93-0.79 (m, 1H), 0.45-0.34 (m, 1H), 0.32-0.22 (m, 2H), 0.17-0.08 (m, 1H).

ii. Preparation of 38

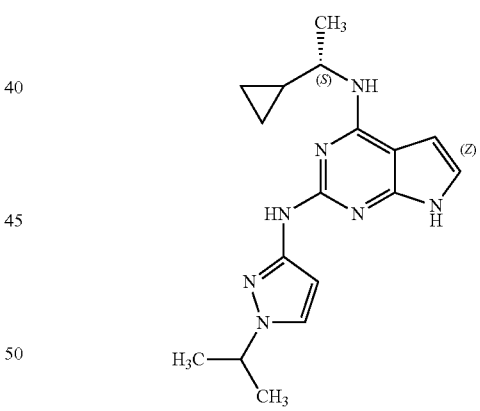

Compound S-80 (165 mg, 0.34 mmol) was treated with NaOMe (0.5 M, in MeOH, 1.7 mL) at 70° C. for 2 h. When TLC showed complete consumption of the starting material, the reaction mixture was cooled to room temperature and concentrated under reduced pressure. The residue was diluted with water (10 mL) and extracted with EtOAc (2×10 mL). The combined organic layer was washed with water (20 mL). The organic layer was dried over anhydrous Na$_2$SO$_4$ and concentrated under reduced pressure. The crude product was purified by column chromatography on silica gel using 0-3% MeOH in CH$_2$Cl$_2$ as eluent to afford compound 38 (0.053 g, 48%, AMRI lot # IN-SKY-C-99) as an off-white solid. The compound was characterized by $^1$H NMR, UPLC analysis. $^1$H NMR (300 MHz, CD$_3$OD): δ 7.39 (d, J=2.4 Hz, 1H), 6.65 (d, J=6 Hz, 1H), 6.53 (d, J=2.1 Hz, 1H), 4.32-4.24 (m, 1H), 3.79-3.69 (m, 1H), 1.37 (d, J=6.6 Hz, 6H), 1.24 (d, J=2.4 Hz, 3H), 1.01-0.89 (m, 1H), 0.48-0.20 (m, 3H), 0.18-0.12 (m, 1H); $^{13}$C NMR (100 MHz, CDCl$_3$): δ 149.77, 148.75, 129.95, 121.10, 102.24, 95.21 55.31, 53.25, 22.93, 22.91, 20.30, 17.98, 4.04, 3.94; MS-UPLC (MM) m/z 326.2 [M+H]$^+$; UPLC purity>96 (% AUC).

dd. Synthesis of 41

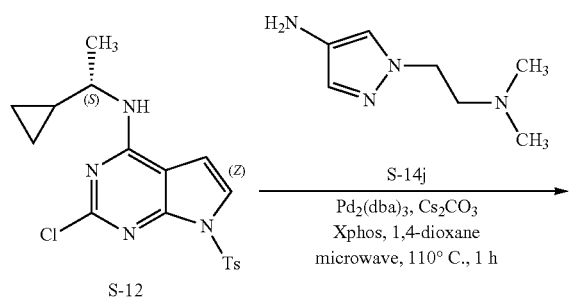

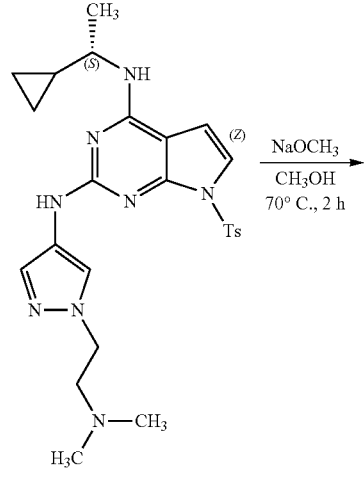

i. Preparation of S-81

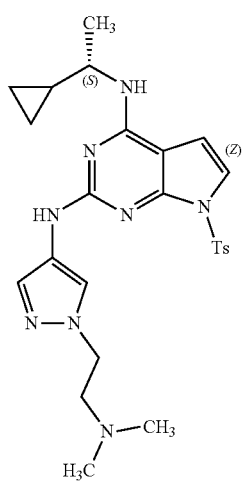

A solution of S-12 (0.30 g, 0.76 mmol), amine S-14j (0.15 g, 0.92 mmol), Cs$_2$CO$_3$ (0.49 g, 1.52 mmol) and 1,4-dioxane (3 mL) was charged into a microwave vial with stirrer bar. Argon gas was purged through septum and the reaction mixture was degassed for about 5 min. To this reaction mixture, xantphos (0.034 g, 0.076 mmol) and Pd$_2$(dba)$_3$ (0.070 g, 0.076 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude product was purified by column chromatography on silica gel using 0-3% MeOH in CH$_2$Cl$_2$ as eluent to afford S-81 (0.20 g, 51%, AMRI lot # IN-CKB-G-84) as a brown solid. The compound was characterized by $^1$H NMR analysis. $^1$H NMR (400 MHz, CDCl$_3$): δ 7.98 (d, J=8.40 Hz, 2H), 7.44 (t, J=2.80 Hz, 1H), 7.21 (d, J=8.00 Hz, 2H), 7.15 (d, J=4.00 Hz, 1H), 6.55 (s, 1H), 6.29 (d, J=4.00 Hz, 1H), 4.77 (d, J=7.20 Hz, 1H), 4.25-4.27 (m, 2H), 2.84-2.76 (m, 2H), 2.35 (s, 3H), 2.28 (s, 6H), 1.26 (d, J=5.20 Hz, 3H), 0.97-0.88 (m, 1H), 0.56-0.45 (m, 2H), 0.39-0.24 (m, 2H).

ii. Preparation of 41

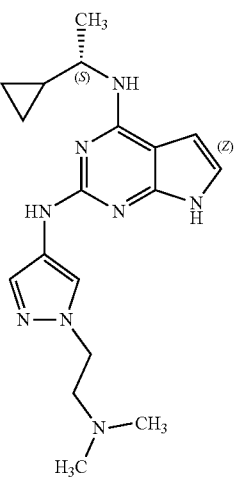

Compound S-81 (200 mg, 0.39 mmol) was treated with NaOMe (0.5 M in MeOH, 1.3 mL) at 70° C. for 2 h. When TLC showed complete consumption of the starting material, the reaction mixture was cooled to room temperature and concentrated under reduced pressure. The residue was diluted with water (10 mL) and extracted with EtOAc (2×10 mL). The combined organic layer was washed with water (20 mL). The organic layer was dried over anhydrous Na$_2$SO$_4$ and concentrated under reduced pressure. The crude product was purified by Mass triggered preparative HPLC to afford 41 (0.087 g, 62%, AMRI lot # IN-CKB-G-85) as an off-white semi solid. The compound was characterized by $^1$H NMR, UPLC analysis. $^1$H-NMR (400 MHz, CD$_3$OD): δ 7.87 (s, 1H), 7.69 (s, 1H), 6.81 (d, J=3.20 Hz, 1H), 6.56 (d, J=3.60 Hz, 1H), 4.49 (t, J=5.60 Hz, 2H), 3.71 (s, 1H), 3.60 (t, J=5.60 Hz, 2H), 2.88 (s, 6H), 1.30-1.32 (m, 2H), 1.06-0.98 (m, 1H), 0.54-0.42 (m, 2H), 0.30-0.22 (m, 2H); MS-UPLC (MM) m/z 355.2 [M+H]$^+$; UPLC purity>99 (% AUC).

ee. Synthesis of 42

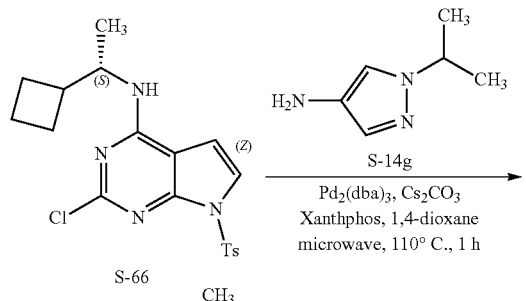

S-66

S-67

42 i. Preparation of S-67

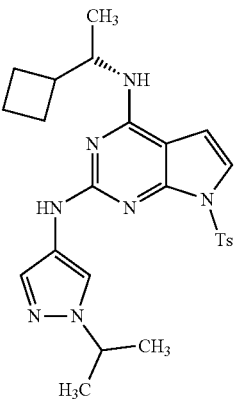

A stirred solution of S-66 (0.30 g, 0.74 mmol) in 1,4-dioxane taken in a microwave vial was charged with 1-isopropyl-1H-pyrazol-4-amine S-14g (0.11 g, 0.89 mmol) and Cs$_2$CO$_3$ (0.48 g, 1.48 mmol). Argon gas was purged through septum and the reaction was degassed for about 5 min. To this reaction mixture, xantphos (0.042 g, 0.074 mmol) and Pd$_2$(dba)$_3$ (0.067 g, 0.074 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-67 (0.16 g, 44%, AMRI lot # IN-SKY-C-103) as an off-white solid. The compound was characterized by $^1$H NMR analysis. $^1$H NMR (300 MHz, CD$_3$OD): δ 8.39 (bs, 1H), 7.50 (d, J=3.54 Hz, 2H), 7.46 (s, 1H), 7.16 (d, J=3.54 Hz, 2H), 6.99 (d, J=3.9 Hz, 1H), 6.50 (d, J=4.2 Hz, 1H), 4.44-4.35 (m, 1H), 4.26-4.22 (m, 1H), 2.34-2.27 (m, 1H), 1.97-1.84 (m, 2H), 1.78-1.64 (m, 4H), 1.43 (dd, J=6.9 Hz, 6H), 1.99 (d, J=6.6 Hz, 3H).

ii. Preparation of 42

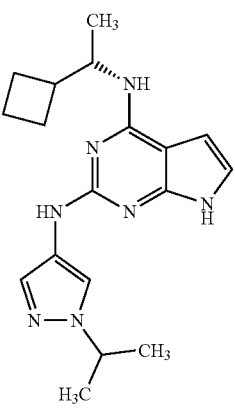

Compound S-67 (0.16 g, 0.32 mmol) was treated with NaOMe (0.5 M, in MeOH, 1.6 mL) at 70° C. for 2 h. When TLC showed complete consumption of the starting material, the reaction mixture was cooled to room temperature and concentrated under reduced pressure. The residue was diluted with water (10 mL) and extracted with EtOAc (2×10 mL). The combined organic layer was washed with water (20 mL). The organic layer was dried over anhydrous Na$_2$SO$_4$ and concentrated under reduced pressure. The crude product was purified by column chromatography on silica gel using 0-3% MeOH in CH$_2$Cl$_2$ as eluent to afford 42 (0.061 g, 55%, AMRI lot # IN-SKY-C-106) as an off-white solid. The compound was characterized by $^1$H, $^{13}$C NMR and UPLC analysis. $^1$H NMR (300 MHz, CD$_3$OD): δ 7.89 (s, 1H), 7.47 (s, 1H), 6.60 (d, J=3.6 Hz, 1H), 6.29 (d, J=3.6 Hz, 1H), 4.41-4.34 (m, 1H), 4.32-4.27 (m, 1H), 2.44-2.34 (m, 1H), 2.04-1.99 (m, 2H), 1.96-1.70 (m, 4H), 1.41 (dd, J=1.2, 6.9 Hz, 6H), 1.07 (d, J=6.3 Hz, 3H); $^{13}$C NMR (100 MHz, CDCl$_3$): δ 158.75, 158.05, 153.07, 131.09, 125.97, 118.82, 118.54, 99.95, 98.18, 55.08, 52.19, 42.92, 26.86, 26.60, 23.16, 18.46, 18.40; MS-UPLC (MM) m/z 340.2 [M+H]$^+$; UPLC purity>96 (% AUC).

ff. Synthesis of 45

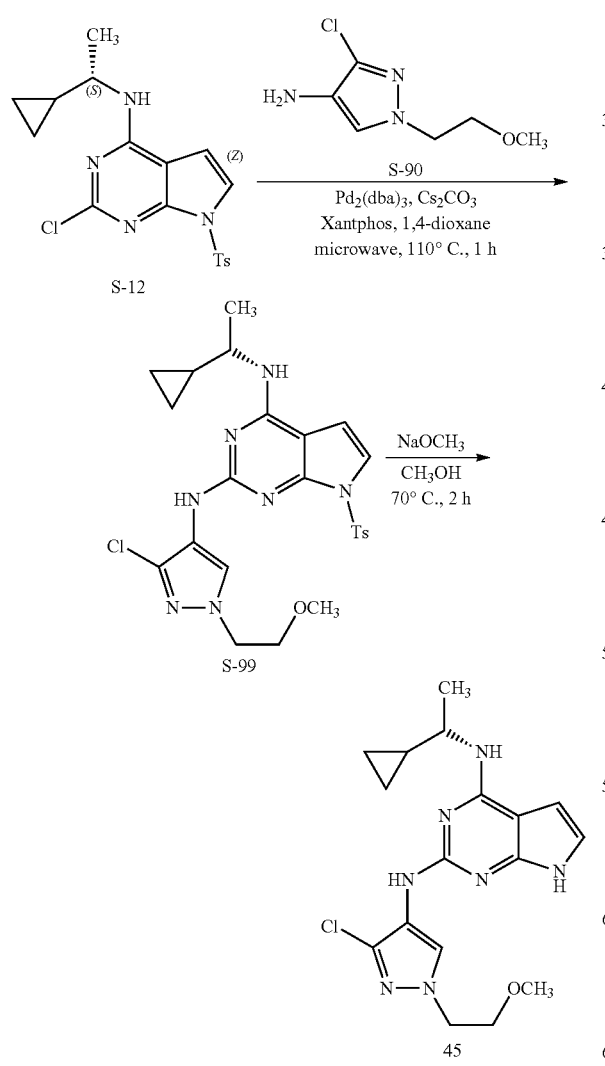

i. Preparation of S-99

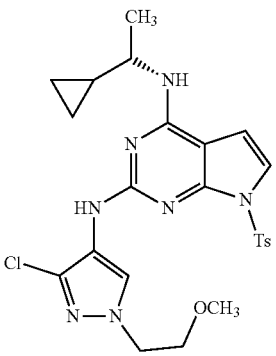

A stirred solution of S-12 (0.30 g, 0.76 mmol) in 1,4 dioxane taken in a microwave vial was charged with S-90 (0.092 g, 0.92 mmol) and Cs$_2$CO$_3$ (0.49 g, 1.52 mmol). Argon gas was purged through septum and the reaction was degassed for about 5 min. To this reaction mixture, xantphos (0.044 g, 0.076 mmol) followed by Pd$_2$(dba)$_3$ (0.069 g, 0.076 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-99 (0.18 g, 44%, AMRI lot # IN-SKY-C-130) as an off-white solid. The compound was characterized by $^1$H NMR analysis. $^1$H NMR (300 MHz, DMSO-d$_6$): δ 9.61 (s, 1H), 8.43 (bs, 1H), 7.93 (d, J=6.6 Hz, 2H), 7.58 (d, J=8.4 Hz, 1H), 7.37 (d, J=8.1 Hz, 2H), 7.33 (d, J=4 Hz, 1H), 7.22 (d, J=3.9 Hz, 1H), 6.82 (d, J=3.9 Hz, 1H), 4.87-4.74 (m, 1H), 3.44-3.36 (q, J=15.9, 8.4 Hz, 1H), 2.31 (s, 3H), 1.53 (d, J=6.6 Hz, 6H), 1.12-1.01 (m, 2H), 0.53-0.44 (m, 2H), 0.36-0.21 (m, 6H).

ii. Preparation of 45

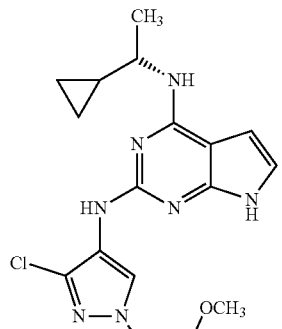

Compound S-99 (0.18 g, 0.34 mmol) was treated with NaOMe (0.5 M in MeOH, 1.8 mL) at 70° C. for 2 h. When TLC showed complete consumption of the starting material, the reaction mixture was cooled to room temperature and concentrated under reduced pressure. The residue was diluted with water (10 mL) and extracted with EtOAc (2×10 mL). The combined organic layers were washed with water (20 mL). The organic layers were dried over anhydrous Na₂SO₄ and concentrated under reduced pressure. The crude product was purified by Mass triggered preparative HPLC to afford 45 (0.080 g, 63%, AMRI lot # IN-SKY-C-133) as an off-white solid. The compound was characterized by ¹H NMR, UPLC analysis. ¹H NMR (400 MHz, CD₃OD): δ 7.94 (s, 1H), 6.87 (d, J=3.2 Hz, 1H), 6.62 (d, J=3.2 Hz, 1H), 4.22-4.21 (m, 2H), 3.73-3.71 (m, 2H), 3.69-3.64 (m, 1H), 3.27-3.26 (m, 3H), 1.34 (d, J=6.4 Hz, 3H), 1.06-1.03 (m, 1H), 0.58-0.53 (m, 1H), 0.47-0.46 (m, 1H), 0.36-0.32 (m, 1H), 0.27-0.25 (m, 1H); MS-UPLC (MM) m/z 376.2 [M+]⁺; UPLC purity>98 (% AUC).

gg. Synthesis of 46

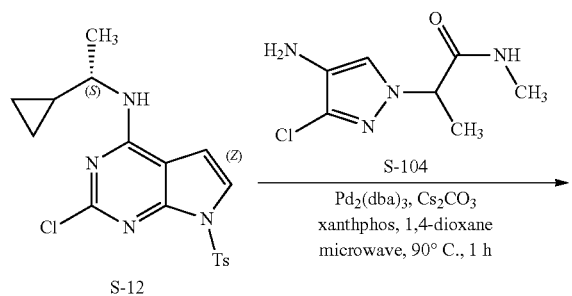

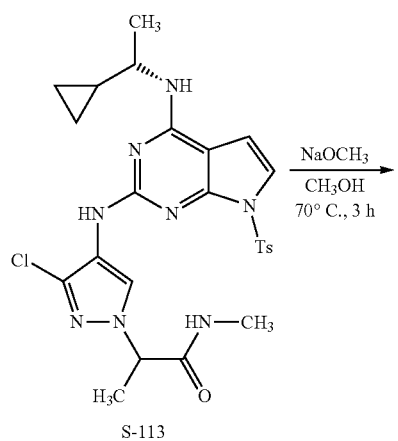

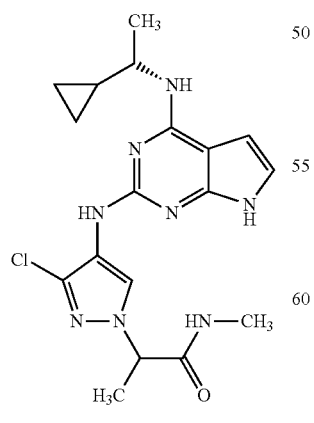

i. Preparation of S-113

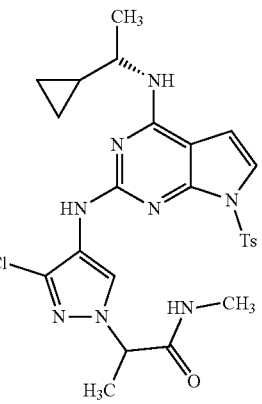

A stirred solution of S-12 (0.30 g, 0.76 mmol) in 1,4-dioxane (3.0 mL) taken in a microwave vial was charged with amine S-104 (0.18 g, 0.92 mmol) and Cs₂CO₃ (0.49 g, 1.52 mmol). Argon gas was purged through septum and the reaction was degassed for about 5 min. To this reaction mixture, xantphos (0.043 g, 0.07 mmol) and Pd₂(dba)₃ (0.069 g, 0.07 mmol) were added under inert atmosphere. This reaction mixture was purged with argon gas again for 5 min. The microwave vial was sealed and irradiated at 90° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-113 (0.16 g, 37%, AMRI lot # IN-SKY-C-146) as an off-white solid. The compound was characterized by ¹H NMR analysis. ¹H NMR (300 MHz, CD₃OD): δ 8.70 (s, 1H), 7.91 (d, J=8.4 Hz, 2H), 7.32 (d, J=8.4 Hz, 2H), 7.15 (d, J=3.9 Hz, 1H), 6.66 (d, J=3.9 Hz, 1H), 4.94-4.89 (m, 1H), 3.75-3.69 (m, 1H), 2.74 (s, 3H), 2.35 (s, 3H), 1.77 (d, J=7.2 Hz, 3H), 1.30-1.28 (m, 3H), 1.06-0.96 (m, 1H), 0.53-0.41 (m, 2H), 0.38-0.23 (m, 2H).

ii. Preparation of 46

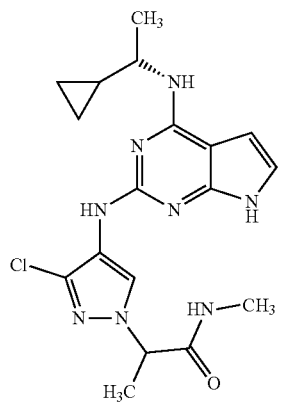

Compound S-113 (0.16 g, 0.28 mmol) was charged with NaOMe (0.5 M in MeOH, 1.6 mL) at 70° C. for 3 h. The crude product was purified by mass triggered preparative HPLC to afford 46 (0.043 g, 36%, AMRI lot # IN-SKY-C-149) as an off-white solid. The compound was characterized by ¹H NMR and MS analysis. ¹H NMR (400 MHz, CD₃OD): δ 8.11 (s, 1H), 6.91 (s, 1H), 6.67 (d, J=3.6 Hz, 1H), 5.0-4.95 (m, 1H), 3.85-3.71 (m, 1H), 2.78 (s, 3H), 1.73 (d, J=7.2 Hz, 3H), 1.39 (d, J=6.4 Hz, 3H), 1.13-1.07 (m, 1H), 0.63-0.58 (m, 1H), 0.55-0.49 (m, 1H), 0.42-0.30 (m, 2H); MS-UPLC (MM) m/z 403.2 [M+H]⁺; UPLC purity>98 (% AUC).

hh. Synthesis of 47

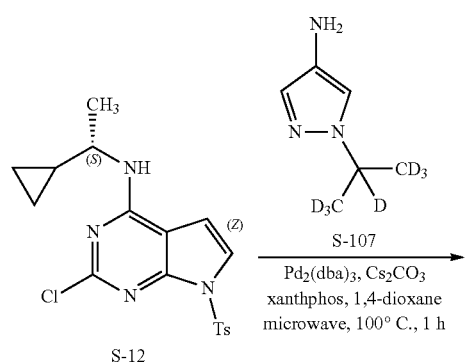

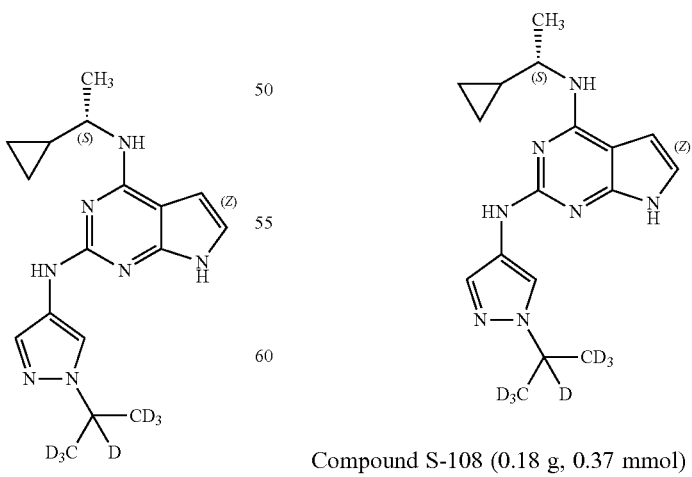

i. Preparation of S-108

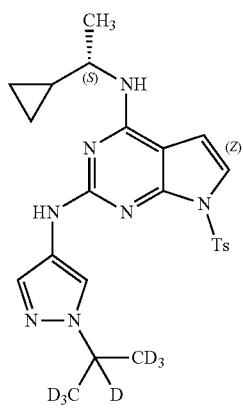

A stirred solution of S-12 (0.30 g, 0.76 mmol) in 1,4-dioxane (3.0 mL) taken in a microwave vial was charged with amine S-107 (0.12 g, 0.92 mmol) and Cs₂CO₃ (0.49 g, 1.52 mmol). Argon gas was purged through septum and the reaction was degassed for about 5 min. To this reaction mixture, xantphos (0.043 g, 0.07 mmol) and Pd₂(dba)₃ (0.069 g, 0.07 mmol) were added under inert atmosphere. This reaction mixture was purged with argon gas again for 5 min. The microwave vial was sealed and irradiated at 100° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-108 (0.18 g, 48%, AMRI lot # IN-SKY-C-147) as an off-white solid. The compound was characterized by ¹H NMR analysis. ¹H NMR (400 MHz, CD₃OD): δ 8.45-8.39 (m, 1H), 7.94 (d, J=8.4 Hz, 2H), 7.53 (s, 1H), 7.27 (d, J=7.8 Hz, 2H), 7.10 (d, J=4 Hz, 1H), 6.62 (d, J=4 Hz, 1H), 3.78-3.71 (m, 1H), 2.33 (s, 3H), 1.28 (d, J=6.4 Hz, 3H), 1.04-0.96 (m, 1H), 0.51-0.47 (m, 1H), 0.43-0.34 (m, 2H), 0.23-0.18 (m, 1H).

ii. Preparation of 47

Compound S-108 (0.18 g, 0.37 mmol) was charged with NaOMe (0.5 M in MeOH, 1.8 mL) at 70° C. for 5 h. The crude product was purified by mass triggered preparative HPLC to afford 47 (0.07 g, 57%, AMRI lot # IN-SKY-C-

148) as an off-white solid. The compound was characterized by ¹H, ¹³C NMR and MS analysis. ¹H NMR (400 MHz, CD₃OD): δ 7.89 (s, 1H), 7.60 (d, 1H), 6.88 (s, 1H), 6.65 (d, J=3.2 Hz, 1H), 3.81 (s, 1H), 1.39 (d, J=6.8 Hz, 3H), 1.12-1.08 (m, 1H), 0.64-0.59 (m, 1H), 0.54-0.50 (m, 1H), 0.42-0.36 (m, 1H), 0.30-0.26 (m, 1H); MS-UPLC (MM) m/z 332.2 [M+H]⁺; UPLC purity>99 (% AUC).

ii. Synthesis of 48, 49, and 63

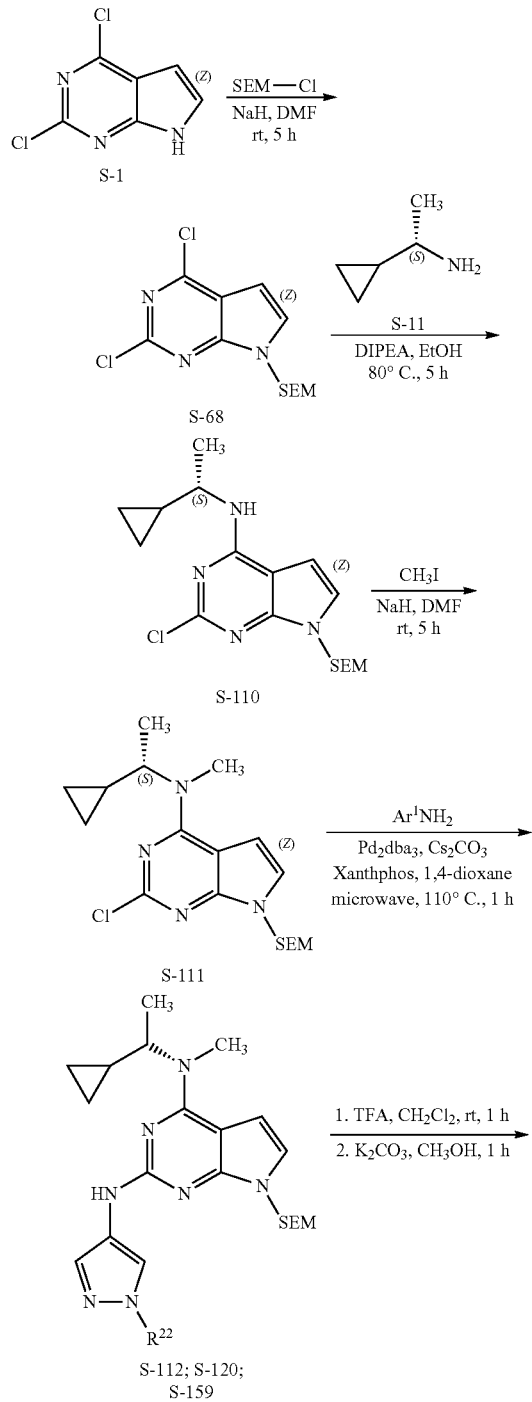

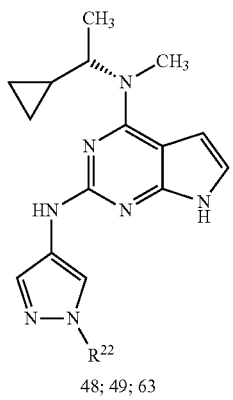

48; 49; 63 i. Preparation of S-111

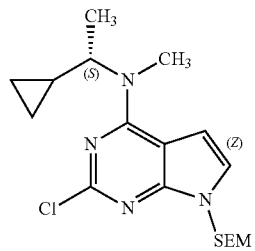

A stirred solution of S-110 (0.40 g, 1.09 mmol) in DMF (10 mL) taken in a round-bottom flask was charged with NaH (0.05 g, 1.09 mmol) and CH₃I (0.23 g, 1.63 mmol) successively at 0° C. under nitrogen atmosphere. The reaction mixture was stirred for 5 h at room temperature. To the reaction mixture, ice cold water (30 mL) was added and extracted with EtOAc (50 mL). The organic layer was washed with brine (1×30 mL). The organic layer was dried over anhydrous Na₂SO₄ and was concentrated under reduced pressure. The crude compound was purified by column chromatography on silica gel using 5-40% EtOAc in hexanes as eluent to afford S-111 (0.30 g, 72%, AMRI lot # IN-SKY-C-140) as an off-white solid. The compound was characterized by ¹H NMR analysis. ¹H NMR (400 MHz, CDCl₃): δ 7.02 (d, J=3.6 Hz, 1H), 6.57 (s, 1H), 5.55 (s, 2H), 4.42-4.32 (m, 1H), 3.56 (t, J=8 Hz, 2H), 3.34 (s, 3H), 1.34 (d, J=6.4 Hz, 3H), 1.07-1.01 (m, 1H), 0.97-0.92 (m, 2H), 0.69-0.64 (m, 1H), 0.52-0.42 (m, 2H), 0.36-0.32 (m, 1H), 0.0 (s, 9H).

ii. Synthesis of 48

(1) Preparation of S-112

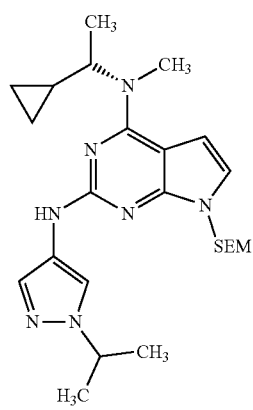

A stirred solution of S-111 (0.30 g, 0.78 mmol) in 1,4-dioxane (3.0 mL) taken in a microwave vial was charged with 1-isopropyl-1H-pyrazol-4-amine S-14g (0.11 g, 0.94 mmol) and Cs$_2$CO$_3$ (0.50 g, 1.56 mmol). Argon gas was purged through septum and the reaction was degassed for about 5 min. To this reaction mixture, xantphos (0.045 g, 0.078 mmol) and Pd$_2$(dba)$_3$ (0.071 g, 0.078 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford S-112 (0.15 g, 40%, AMRI lot # IN-SKY-C-150) as an off-white solid. The compound was characterized by $^1$H NMR analysis. $^1$H NMR (400 MHz, CD$_3$OD): δ 8.05 (s, 1H), 7.66 (s, 1H), 6.95 (d, J=3.6 Hz, 1H), 6.61 (d, J=3.6 Hz, 1H), 5.57 (s, 2H), 4.63-4.52 (m, 1H), 4.44 (s, 1H), 3.66 (t, J=8 Hz, 2H), 3.41 (s, 3H), 1.59 (d, J=6.4 Hz, 6H), 1.42 (d, J=6.8 Hz, 3H), 1.25-1.19 (m, 1H), 0.97 (t, J=8 Hz, 2H), 0.78-0.73 (m, 1H), 0.59-0.52 (m, 1H), 0.49-0.44 (m, 1H), 0.37-0.31 (m, 1H), 0.0 (s, 9H).

(2) Preparation of 48

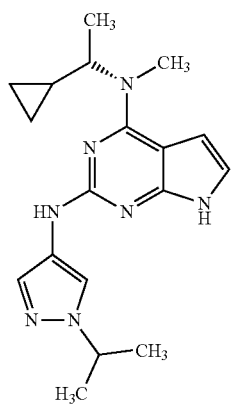

Compound S-112 (0.15 g, 0.31 mmol) was charged with trifluoroacetic acid (1.5 mL) and CH$_2$Cl$_2$ (5.0 mL) at room temperature for 1 h. When TLC showed complete consumption of the starting material, the reaction mixture was concentrated under reduced pressure. The residue was diluted with the MeOH (1.2 mL), pH was adjusted to ~10 with K$_2$CO$_3$ and was stirred at room temperature for 30 min. The reaction mixture was concentrated under reduced pressure, diluted with water and extracted with EtOAc (2×10 mL). The combined organic layer was washed with water (20 mL). The organic layer was dried over anhydrous Na$_2$SO$_4$ and concentrated under reduced pressure. The crude product was purified by mass triggered preparative HPLC to afford 48 (0.04 g, 37%, AMRI lot # IN-SKY-C-151) as an off-white solid. The compound was characterized by $^1$H, $^{13}$C NMR and MS analysis. $^1$H NMR (400 MHz, CD$_3$OD): δ 7.82 (s, 1H), 7.57 (s, 1H), 6.93 (d, J=3.6 Hz, 1H), 6.72 (s, 1H), 4.56-4.47 (m, 2H), 3.45 (s, 3H), 1.51 (d, J=6.8 Hz, 6H), 1.36 (s, 3H), 1.19-1.15 (m, 1H), 0.75-0.68 (m, 1H), 0.54-0.49 (m, 1H), 0.38-0.34 (m, 1H), 0.24-0.22 (m, 1H); $^{13}$C NMR (400 MHz, CD$_3$OD): 162.70, 150.06, 133.99, 122.51, 120.96, 120.04, 105.70, 98.20, 59.11, 55.61, 33.05, 23.08, 17.29, 15.62, 5.82, 3.89; MS-UPLC (MM) m/z 340.2 [M+H]$^+$; UPLC purity>99 (% AUC).

iii. Preparation of 49

(1) Preparation of S-120

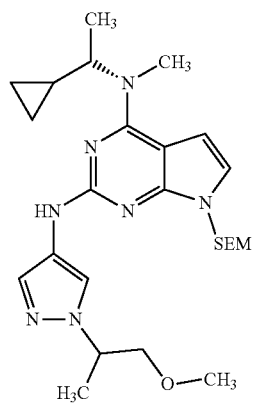

A stirred solution of S-111 (0.30 g, 0.79 mmol) in 1,4-dioxane (3.0 mL) taken in a microwave vial was charged with 1-(1-methoxypropan-2-yl)-1H-pyrazol-4-amine S-14h (0.147 g, 0.95 mmol) and Cs$_2$CO$_3$ (0.51 g, 1.58 mmol). Argon gas was purged through septum and the reaction was degassed for about 5 min. To this reaction mixture, xantphos (0.045 g, 0.079 mmol) and Pd$_2$(dba)$_3$ (0.072 g, 0.079 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-5% MeOH in CH$_2$Cl$_2$ as eluent to afford S-120 (0.15 g, 39%, AMRI lot # IN-CKB-G-121) as a yellow solid. The compound was characterized by UPLC-MS analysis. MS-UPLC (MM) m/z 499.2 [M+H]$^+$.

(2) Preparation of 49

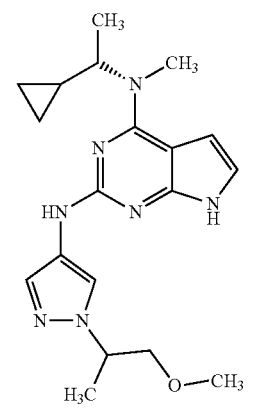

215

Compound S-120 (0.15 g, 0.30 mmol) taken in $CH_2Cl_2$ (10 mL) was charged with trifluoroacetic acid (2.0 mL) at room temperature for 1 h. When TLC showed complete consumption of the starting material, the reaction mixture was concentrated under reduced pressure. The residue was diluted with MeOH (1.0 mL), pH was adjusted to ~10 with $K_2CO_3$ and was stirred at room temperature for 30 min. The reaction mixture was concentrated under reduced pressure, diluted with water and extracted with EtOAc (2×10 mL). The combined organic layer was washed with water (20 mL). The organic layer was dried over anhydrous $Na_2SO_4$ and concentrated under reduced pressure. The crude product was purified by mass triggered preparative HPLC to afford 49 (0.065 g, 45%, AMRI lot # IN-CKB-G-122) as a gummy liquid. The compound was characterized by $^1H$ NMR and UPLC-MS analysis. $^1H$ NMR (400 MHz, $CD_3OD$): δ 7.83 (s, 1H), 7.60 (s, 1H), 6.93 (d, J=3.60 Hz, 1H), 6.73 (s, 1H), 4.59-4.51 (m, 1H), 3.74-3.62 (m, 2H), 3.46 (s, 3H), 3.35 (s, 3H), 1.50 (d, J=7.20 Hz, 3H), 1.37 (s, 3H), 1.24-1.18 (m, 1H), 0.76-0.72 (m, 1H), 0.52-0.41 (m, 2H), 0.23-0.14 (m, 1H); MS-UPLC (MM) m/z 370.2 $[M+H]^+$; UPLC purity>97 (% AUC).

iv. Synthesis of 63

(1) Preparation of 63a

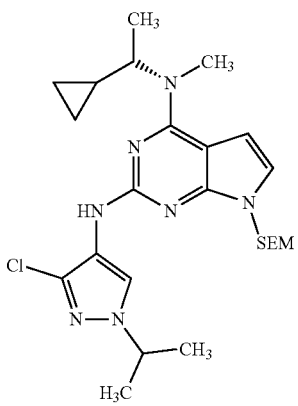

A stirred solution of S-111 (300 mg, 0.79 mmol) in 1,4-dioxane (3.0 mL) taken in a microwave vial was charged with amine S-159 (119 mg, 0.95 mmol) and $Cs_2CO_3$ (510 mg, 1.58 mmol). Argon gas was purged through septum and the reaction was degassed for about 5 min. To the reaction mixture, Xantphos (45.0 mg, 0.079 mmol) and $Pd_2(dba)_3$ (72.0 mg, 0.0479 mmol) were added under inert atmosphere. The reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-60% EtOAc in hexanes as eluent to afford 63a (130 mg, 32%, AMRI lot # IN-CKB-H-11) as a brown solid. The compound was characterized by UPLC-MS analysis. MS-UPLC (MM) m/z 505.1 $[M+H]^+$.

216

(2) Preparation of 63

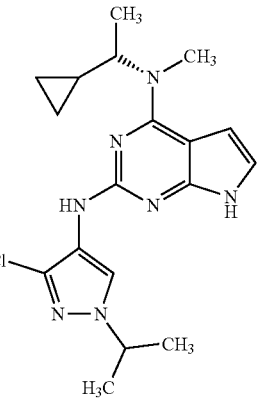

Compound S-126a (150 mg, 0.32 mmol) taken in $CH_2Cl_2$ (10 mL) was charged with trifluoroacetic acid (2.0 mL) at room temperature for 1 h. Upon complete consumption of the starting material by TLC, the reaction mixture was concentrated under reduced pressure. The residue was diluted with MeOH (1.0 mL) and pH was adjusted to ~10 with $K_2CO_3$ and stirred at room temperature for 30 min. The reaction mixture was concentrated under reduced pressure, diluted with water and extracted with EtOAc (2×10 mL). The combined organic layer was washed with water (20 mL). The organic layer was dried over anhydrous $Na_2SO_4$ and concentrated under reduced pressure. The crude product was purified by mass triggered preparative HPLC to afford 63 (17.0 mg, 17%, AMRI lot # IN-CKB-H-14-2) as an off-white gummy solid. The compound was characterized by $^1H$ NMR and UPLC-MS analysis. $^1H$ NMR (300 MHz, MeOD): δ 7.91 (s, 1H), 6.95 (d, J=3.60 Hz, 1H), 6.70 (s, 1H), 4.52-4.46 (m, 1H), 4.43 (s, 1H), 3.43 (s, 3H), 1.51 (d, J=6.60 Hz, 6H), 1.34 (s, 3H), 1.26-1.01 (m, 1H), 0.80-0.31 (m, 2H), 0.24-0.18 (m, 2H); MS-UPLC (MM) m/z 374.1 $[M+]+$; UPLC purity>98 (% AUC).

jj. Synthesis of 55

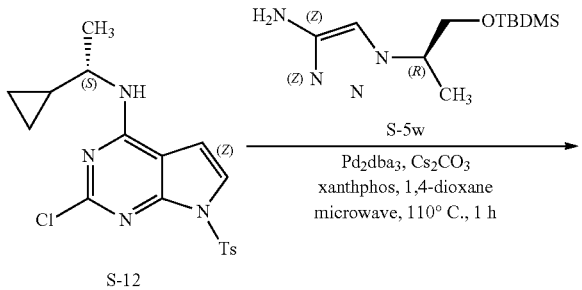

-continued

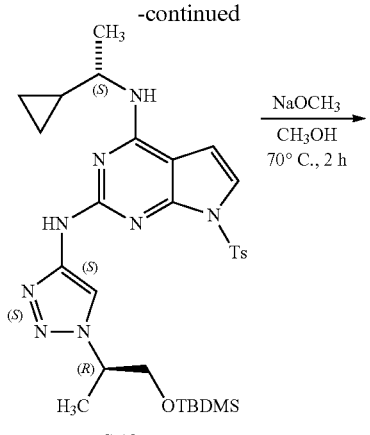

S-13w

NaOCH₃
CH₃OH
70° C., 2 h

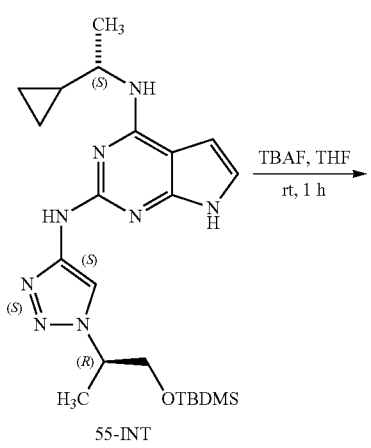

55-INT

TBAF, THF
rt, 1 h

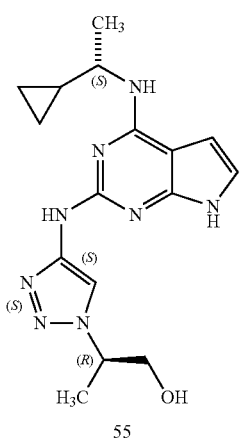

55 i. Preparation of 55-INT

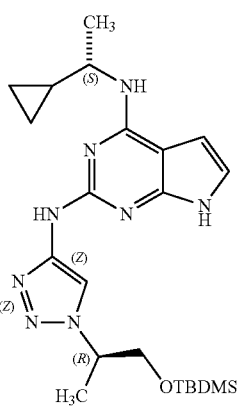

Compound S-13w (210 mg, 0.34 mmol) was charged with NaOMe (0.5 M in MeOH, 2.0 mL) at 70° C. for 2 h. The reaction mixture was adsorbed on silica gel and purified by column chromatography on silica gel using 0-2% MeOH in CH₂Cl₂ as eluent to afford 55-INT (130 mg, 83%, AMRI lot # IN-AKK-I-195-1) as a white solid. The compound was characterized by MS analysis. MS (MM) m/z 456.9 [M+H]⁺ ii. Preparation of 55

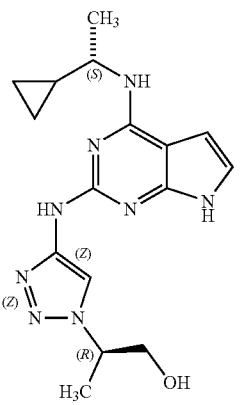

Compound 55-INT (130 mg, 0.28 mmol) in THF (4.0 mL) was charged with Tetrabutylammonium fluoride (1.0 M in THF, 0.6 mL) at room temperature for 1 h. The reaction mixture was diluted with EtOAc (20 mL) and washed with water (50 mL). The obtained was dried over anhydrous Na₂SO₄ and concentrated under reduced pressure followed by purification of the crude product by column chromatography on silica gel using 0-2% MeOH in CH₂Cl₂ as eluent to afford 55 (88.0 mg, 90%, AMRI lot # IN-AKK-I-197-2) as a brown solid. The compound was characterized by $^1$H NMR and MS analysis. $^1$H NMR (400 MHz, DMSO-d₆): δ 8.27 (s, 1H), 6.81 (d, J=3.6 Hz, 1H), 6.45 (d, J=3.6 Hz, 1H), 4.76-4.68 (m, 1H), 3.93-3.86 (m, 3H), 1.60 (d, J=6.8 Hz, 3H), 1.39 (d, J=6.8 Hz, 3H), 1.15-1.06 (m, 1H), 0.59-0.29 (m, 4H); MS-UPLC (MM) m/z 342.3 [M+H]⁺; UPLC purity>95 (% AUC).

kk. Synthesis of 57

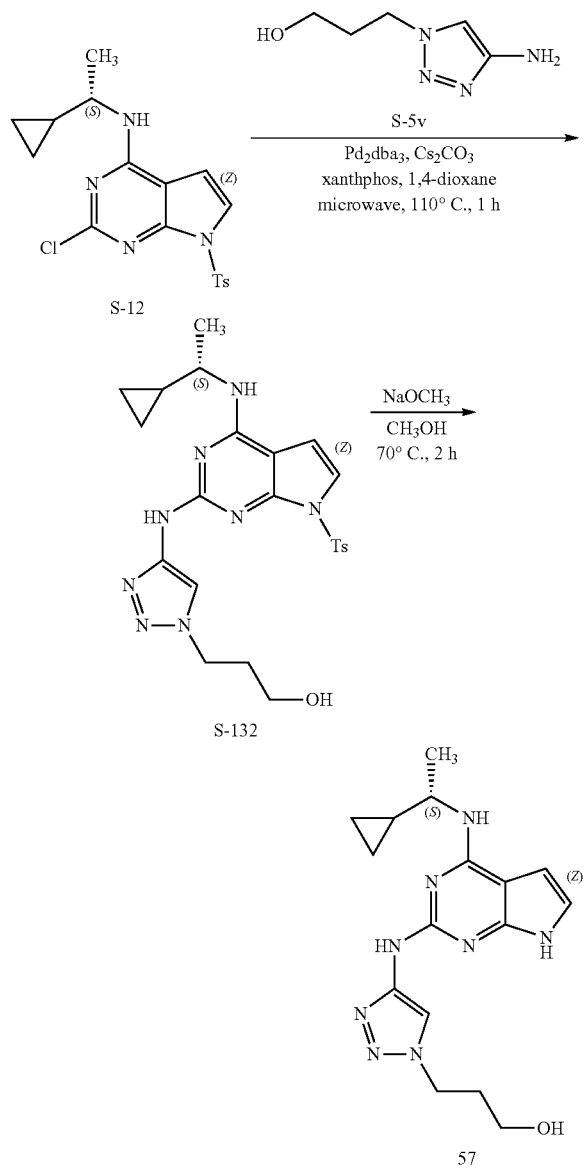

i. Preparation of S-132

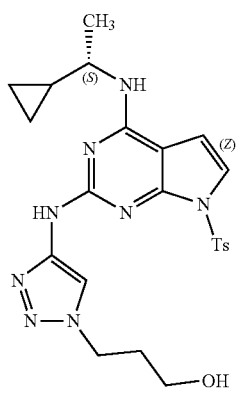

A stirred solution of S-12 (0.20 g, 0.51 mmol) in 1,4-dioxane (3.0 mL) taken in a microwave vial was charged with amine S-5v (0.086 g, 0.61 mmol) and Cs$_2$CO$_3$ (0.33 g, 1.02 mmol). Argon gas was purged through septum and the reaction was degassed for about 5 min. To this reaction mixture, xantphos (0.029 g, 0.051 mmol) and Pd$_2$(dba)$_3$ (0.046 g, 0.051 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was directly used to next step without further purification to afford S-132 (0.11 g, 43%, AMRI lot # IN-SKY-C-181) as an off-white solid. The compound was characterized by UPLC-MS analysis. MS-UPLC (MM) m/z 497.2 [M+H]$^+$.

ii. Preparation of 57

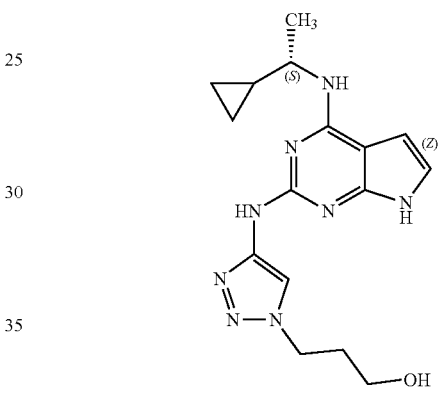

Compound S-132 (0.11 g, 0.22 mmol) was charged with NaOMe (0.5 M in MeOH, 1.1 mL) at 70° C. for 3 h. The crude product was purified by mass triggered preparative HPLC to afford 57 (0.019 g, 25%, AMRI lot # IN-SKY-C-183) as an off-white solid. The compound was characterized by $^1$H NMR and UPLC-MS analysis. $^1$H NMR (400 MHz, CD$_3$OD): δ 7.90 (s, 1H), 6.98 (d, J=2.8 Hz, 1H), 6.69 (d, J=3.6 Hz, 1H), 4.54 (t, J=6.8 Hz, 2H), 3.76 (s, 1H), 3.59 (t, J=6.0 Hz, 2H), 2.15-2.01 (m, 2H), 1.42 (d, J=6.4 Hz, 3H), 1.13-1.12 (m, 1H), 0.64-0.60 (m, 1H), 0.54-0.51 (m, 1H), 0.46-0.42 (m, 1H), 0.35-0.33 (m, 1H); MS-UPLC (MM) m/z 343.1 [M+H]$^+$; UPLC Purity>92 (% AUC).

ll. Synthesis of 59 and 60

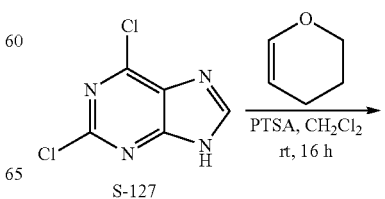

i. Synthesis of 59

(3) Preparation of 59a

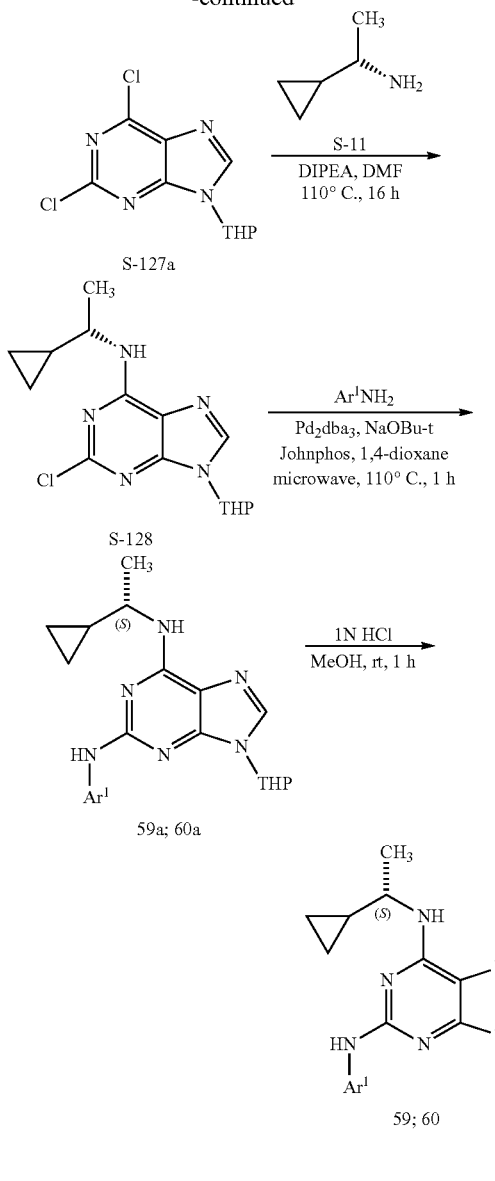

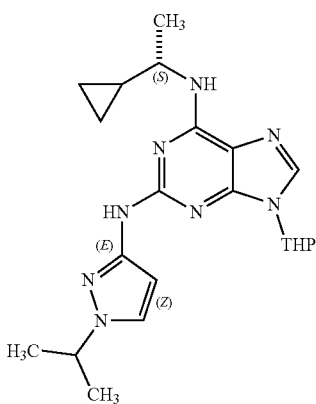

A stirred solution of S-128 (200 mg, 0.62 mmol) in 1,4-dioxane (3.0 mL) taken in a microwave vial was charged with 1-isopropyl-1H-pyrazol-3-amine S-75 (85.0 mg, 0.68 mmol) and NaOBu-t (120 mg, 1.24 mmol). Argon gas was purged through septum and the reaction was degassed for about 5 min. To this reaction mixture, johnphos (18.0 mg, 0.062 mmol) followed by $Pd_2(dba)_3$ (56.0 mg, 0.062 mmol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-2% MeOH in $CH_2Cl_2$ as eluent to afford 59a (130 mg, 52%, AMRI lot # IN-AKK-I-202-1) as an off-white solid. The compound was characterized by $^1$H NMR analysis. $^1$H NMR (400 MHz, $CDCl_3$): δ 7.71 (s, 1H), 7.30 (d, J=2.4 Hz, 1H), 7.24 (s, 1H), 6.76 (d, J=2.4 Hz, 1H), 5.62-5.53 (m, 2H), 4.39-4.38 (m, 1H), 4.17-4.13 (m, 1H), 3.82-3.72 (m, 2H), 2.08-2.04 (m, 3H), 1.77-1.61 (m, 6H), 1.47 (d, J=6.6 Hz, 6H), 1.32 (d, J=6.6 Hz, 3H), 1.00-0.91 (m, 1H), 0.56-0.30 (m, 4H).

(4) Preparation of 59

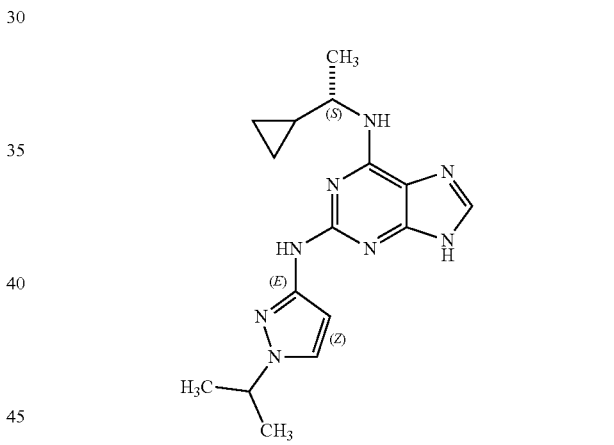

Compound 59a (130 mg, 0.19 mmol) in MeOH (3.0 mL) was charged with HCl (1 N, 0.5 mL) at room temperature. The reaction mixture was stirred at room temperature for 1 h. The reaction mixture was concentrated under reduced pressure, diluted with EtOAc (20 mL) and washed with saturated $NaHCO_3$ (10 mL), water (10 mL) and brine (10 mL). The obtained was dried over anhydrous $Na_2SO_4$ and concentrated under reduced pressure followed by purification by column chromatography on silica gel and purified by column chromatography on silica gel using 0-2% MeOH in $CH_2Cl_2$ as eluent to afford 59 (90.0 mg, 87%, AMRI lot # IN-AKK-I-204-2) as an off-white solid. The compound was characterized by $^1$H NMR and MS analysis. $^1$H NMR (400 MHz, $CDCl_3$): δ 13.81 (s, 1H), 11.6 (s, 1H), 7.56 (s, 1H), 7.26 (d, J=1.8 Hz, 1H), 6.84 (d, J=1.8 Hz, 1H), 5.94 (d, J=6.3 Hz, 1H), 4.39-4.30 (m, 1H), 3.99-3.91 (m, 1H), 1.48 (d, J=6.6 Hz, 6H), 1.30 (d, J=6.6 Hz, 3H), 0.99-0.90 (m, 1H), 0.50-0.25 (m, 4H); MS-UPLC (MM) m/z 326.40 $[M+H]^+$; UPLC purity>95 (% AUC).

223 ii. Synthesis of 60

(1) Preparation of 60a

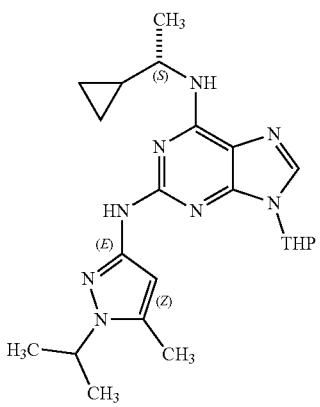

A stirred solution of S-128 (200 mg, 0.62 mmol) in 1,4-dioxane (3.0 mL) taken in a microwave vial was charged with amine S-5j (94.0 mg, 0.68 mmol) and NaOBu-t (120 mg, 1.24 mmol). Argon gas was purged through septum and the reaction was degassed for about 5 min. To this reaction mixture, johnphos (18.0 mg, 0.062 m mol) followed by $Pd_2(dba)_3$ (56.0 mg, 0.062 m mol) were added under inert atmosphere. This reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-2% MeOH in $CH_2Cl_2$ as eluent to afford 60a (140 mg, 53%, AMRI lot # IN-AKK-I-203-1) as an off-white solid. The compound was characterized by $^1H$ NMR analysis. $^1H$ NMR (400 MHz, $CDCl_3$): δ 7.70 (s, 1H), 7.20 (s, 1H), 6.53 (s, 1H), 5.59-5.54 (m, 2H), 4.37-4.28 (m, 1H), 4.17-4.11 (m, 1H), 3.79-3.72 (m, 3H), 2.28 (s, 3H), 2.06-2.04 (m, 3H), 1.77-1.65 (m, 8H), 1.42 (d, J=6.6 Hz, 6H), 1.32 (d, J=6.6 Hz, 3H), 1.00-0.91 (m, 1H), 0.56-0.30 (m, 4H).

(2) Preparation of 60

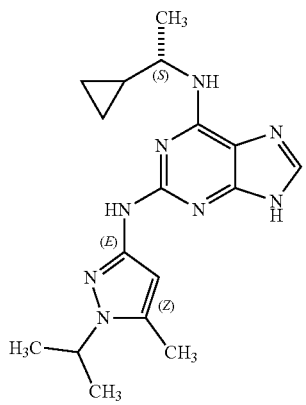

224

Compound 60a (140 mg, 0.33 mmol) in MeOH (3.0 mL) was charged with HCl (1 N, 0.5 mL) at room temperature. The reaction mixture was stirred at room temperature for 1 h. The reaction mixture was concentrated under reduced pressure, diluted with EtOAc (20 mL) and washed with saturated $NaHCO_3$ (10 mL), water (10 mL) and brine (10 mL). The obtained was dried over anhydrous $Na_2SO_4$ and concentrated under reduced pressure followed by purification by column chromatography on silica gel and purified by column chromatography on silica gel using 0-2% MeOH in $CH_2Cl_2$ as eluent to afford 60 (46.0 mg, 41%, AMRI lot # IN-AKK-I-205-2) as an off-white liquid. The compound was characterized by $^1H$ NMR and MS analysis. $^1H$ NMR (400 MHz, DMSO-$d_6$): δ 1088 (s, 1H), 8.93 (s, 1H), 8.28 (s, 1H), 5.96 (s, 1H), 4.58 (m, 1H), 3.79-3.76 (m, 1H), 2.29 (s, 3H), 1.40 (d, J=6.4 Hz, 6H), 1.33 (d, J=6.6 Hz, 3H), 1.16-1.09 (m, 1H), 0.59-0.24 (m, 4H); MS-UPLC (MM) m/z 340.2 $[M+H]^+$; UPLC purity>94 (% AUC).

mm. Synthesis of 61

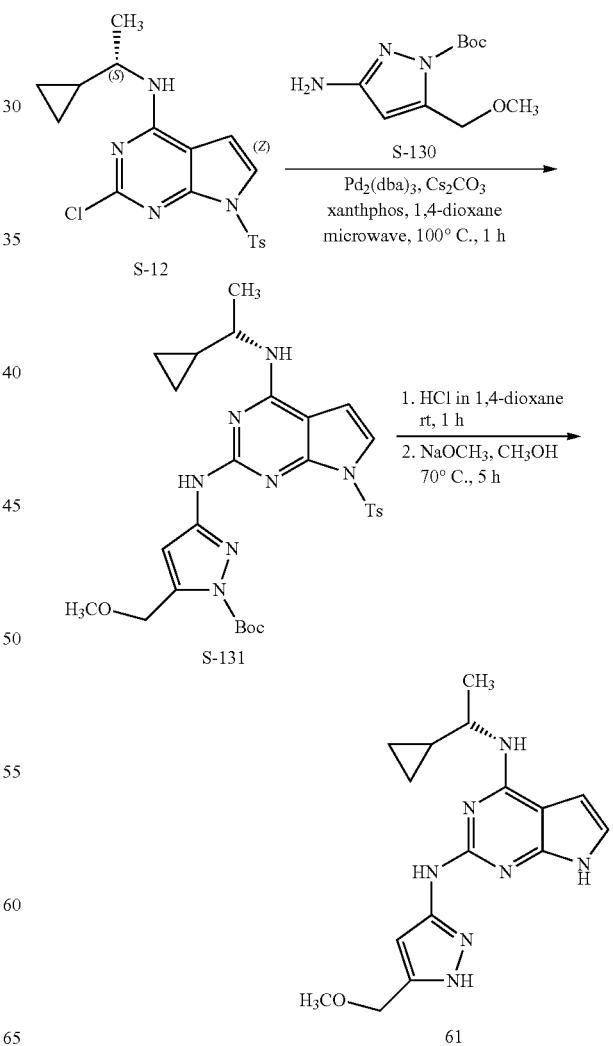

i. Preparation of S-131

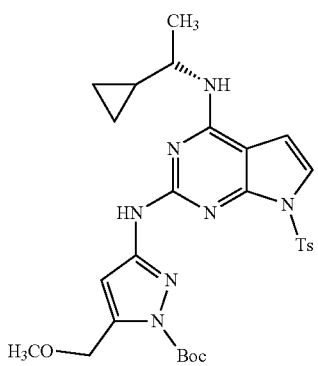

A stirred solution of S-12 (0.10 g, 0.25 mmol) in 1,4-dioxane (3.0 mL) taken in a microwave vial was charged with amine S-130 (0.068 g, 0.30 mmol) and Cs$_2$CO$_3$ (0.16 g, 0.51 mmol). Argon gas was purged through septum and the reaction was degassed for about 5 min. To this reaction mixture, xantphos (0.014 g, 0.025 mmol) and Pd$_2$(dba)$_3$ (0.022 g, 0.025 mmol) were added under inert atmosphere. This reaction mixture was purged with argon gas again for 5 min. The microwave vial was sealed and irradiated at 100° C. for 1 h in CEM-microwave instrument. The reaction mixture was filtered, washed with EtOAc (30 mL) and the filtrate was concentrated under reduced pressure. The crude compound was directly used in next step without further purification to afford S-131 (0.04 g, 28%, AMRI lot # IN-SKY-C-192) as an off-white solid. The compound was characterized by UPLC-MS analysis. MS-UPLC (MM) m/z 582.1 [M+H]$^+$.

ii. Preparation of 61

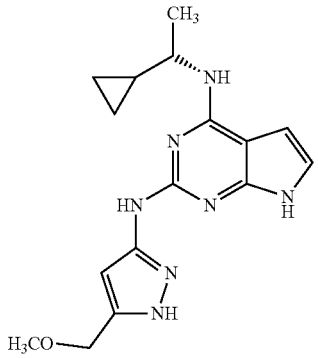

Compound S-131 (0.04 g, 0.06 mmol) was charged with HCl in 1,4-dioxane (0.04 mL) at room temperature for 1 h. The reaction mixture was concentrated under reduced pressure. The crude product was treated with NaOMe (0.5 M in MeOH, 0.08 mL) at 70° C. for 5 h. The reaction mixture was concentrated under reduced pressure and the crude product was purified by mass triggered preparative HPLC to afford 61 (0.004 g, 28%, AMRI lot # IN-SKY-C-199) as an off-white solid. The compound was characterized by $^1$H NMR and UPLC analysis. $^1$H NMR (400 MHz, CD$_3$OD): δ 6.99 (d, J=3.2 Hz, 1H), 6.69 (d, J=3.6 Hz, 1H), 5.99 (s, 1H), 4.62 (s, 2H), 3.89 (s, 3H), 3.29-3.27 (m, 1H), 1.41 (s, 3H), 1.14-1.11 (m, 1H), 0.64-0.60 (m, 1H), 0.55-0.51 (m, 1H), 0.47-0.44 (m, 1H), 0.33-0.31 (m, 1H); MS-UPLC (MM) m/z 328.2 [M+H]$^+$; UPLC Purity>92 (% AUC).

nn. Synthesis of 62

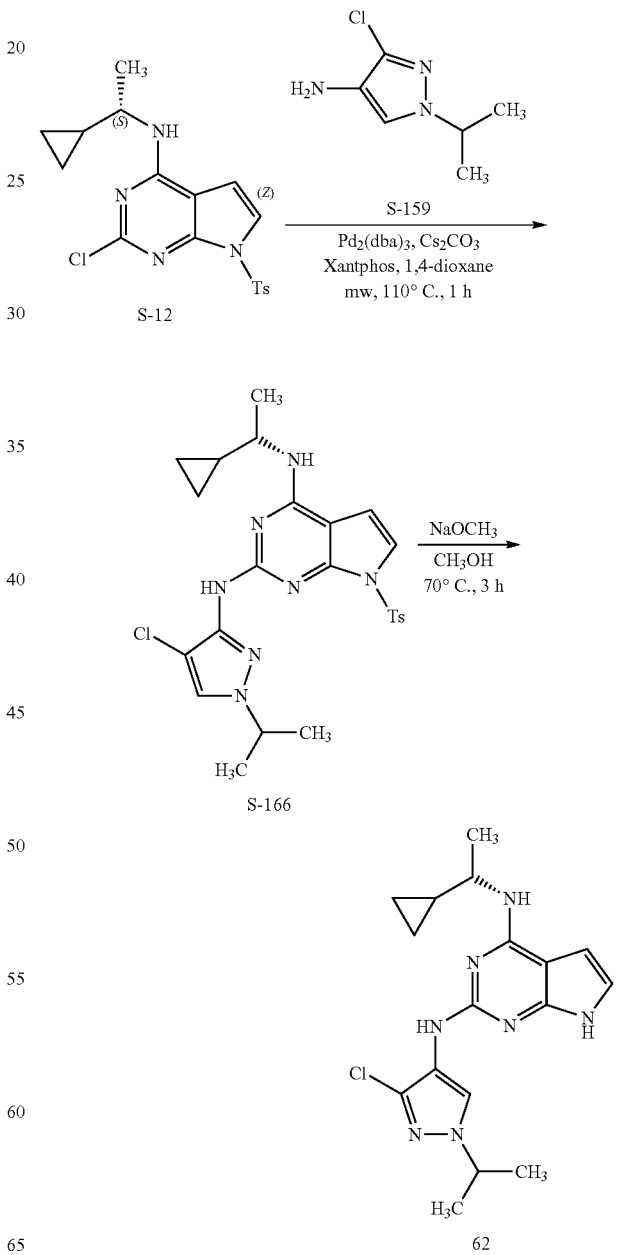

i. Preparation of S-166

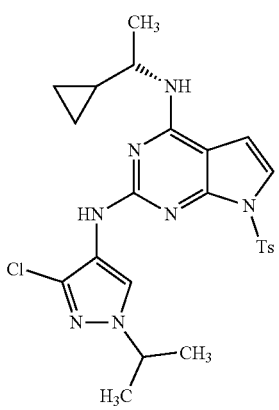

A stirred solution of S-12 (300 mg, 0.77 mmol) in 1,4-dioxane (3.0 mL) taken in a microwave vial was charged with amine S-159 (140 mg, 0.92 mmol) and $Cs_2CO_3$ (490 mg, 1.53 mmol). Argon gas was purged through septum and the reaction was degassed for about 5 min. To the reaction mixture, Xantphos (44.0 mg, 0.077 mmol) and $Pd_2(dba)_3$ (69.0 mg, 0.077 mmol) were added under inert atmosphere. The reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-50% EtOAc in hexanes as eluent to afford S-166 (220 mg, 56%, AMRI lot # IN-SKY-D-36) as an off-white solid. The compound was characterized by UPLC-MS analysis. MS-UPLC (MM) m/z 514.1 $[M+H]^+$.

ii. Preparation of 62

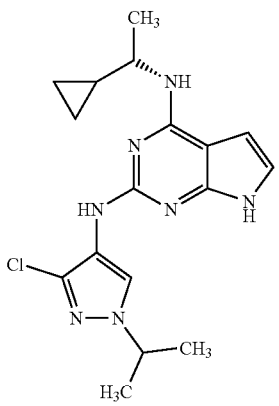

Compound S-166 (220 mg, 0.42 mmol) was charged with NaOMe (0.5 M in MeOH, 2.2 mL) at 70° C. for 3 h. The reaction mixture was concentrated under reduced pressure. The crude product was purified by mass triggered preparative HPLC to afford 62 (120 mg, 78%, AMRI lot # IN-SKY-D-38) as an off-white semi solid. The compound was characterized by $^1$H NMR and UPLC-MS analysis. $^1$H NMR (400 MHz, $CD_3OD$): δ 8.00 (s, 1H), 6.93 (d, J=3.2 Hz, 1H), 6.68 (d, J=3.6 Hz, 1H), 4.52-4.46 (m, 1H), 3.70 (t, J=7.6 Hz, 1H), 1.52 (d, J=6.8 Hz, 6H), 1.39 (d, J=6.8 Hz, 3H), 1.13-1.07 (m, 1H), 0.65-0.58 (m, 1H), 0.55-0.48 (m, 1H), 0.41-0.35 (m, 1H), 0.28-0.26 (m, 1H); MS-UPLC (MM) m/z 360.2 $[M+H]^+$; UPLC purity>96 (% AUC).

oo. Synthesis of 64

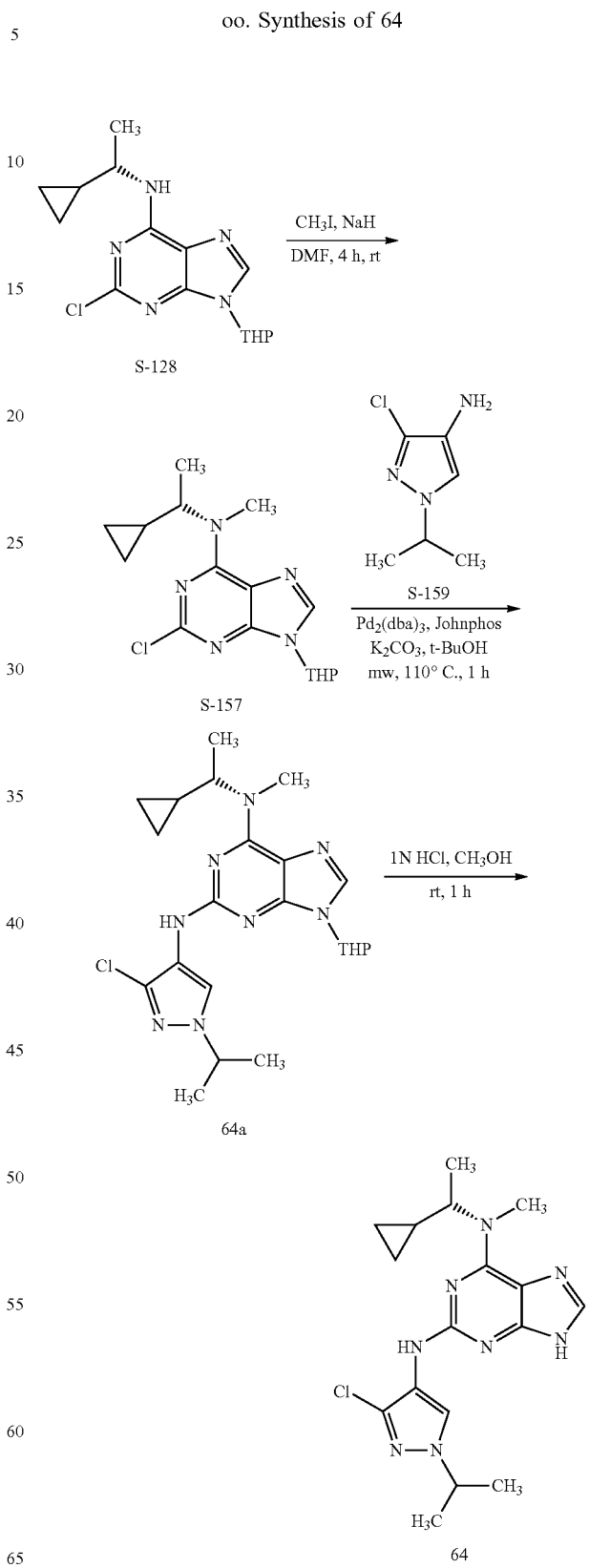

229
i. Preparation of S-157

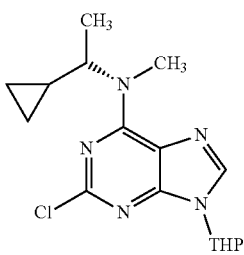

A stirred solution of S-128 (600 mg, 1.86 mmol) in DMF (20 mL) taken in a round-bottom flask was charged with NaH (112 mg, 2.79 mmol) and methyl iodide (318 mg, 2.24 mmol) successively at 0° C. under nitrogen atmosphere. The reaction mixture was stirred for 4 h at ambient temperature. The reaction mixture was diluted with MTBE (100 mL) and washed with water (40 mL). The organic layer was separated and washed with brine (1×50 mL). The organic layer was dried over anhydrous $Na_2SO_4$ and was concentrated under reduced pressure. The crude compound was purified by column chromatography on silica gel using 20-50% EtOAc in hexanes as eluent to afford S-157 (500 mg, 80%, AMRI lot # IN-CKB-H-6) as an off-white gummy. The compound was characterized by UPLC-MS analysis. MS-UPLC (MM) m/z 336.2 [M+]$^+$.

ii. Preparation of 64a

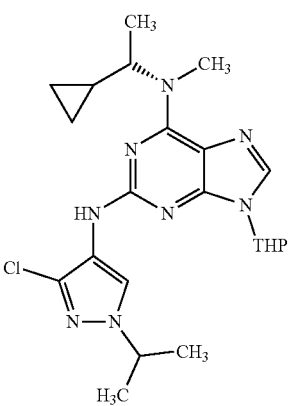

A stirred solution of S-157 (200 mg, 0.59 mmol) in t-BuOH (3.0 mL) taken in a microwave vial was charged with S-159 (115 mg, 0.71 mmol) and $K_2CO_3$ (162 mg, 1.18 mmol). Argon gas was purged through septum and the reaction was degassed for about 5 min. To the reaction mixture, Johnphos (70.0 mg, 0.23 mmol) and $Pd_2(dba)_3$ (54.0 mg, 0.059 mmol) were added under inert atmosphere. The reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-5% MeOH in $CH_2Cl_2$ as eluent to afford S-133a (70.0 mg, 17%, AMRI lot # IN-CKB-H-20) as an off-white liquid. The compound was characterized by UPLC-MS analysis. MS-UPLC (MM) m/z 459.2 [M+]$^+$.

230
iii. Preparation of 64

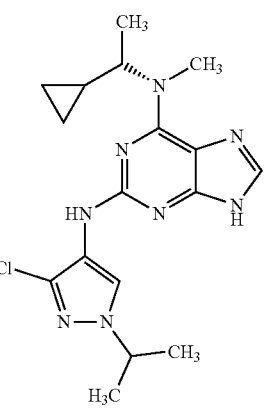

Compound 64a (70.0 mg, 0.19 mmol) in MeOH (3.0 mL) was charged with HCl (1 N, 0.5 mL) at room temperature. The reaction mixture was stirred at room temperature for 1 h. The reaction mixture was concentrated under reduced pressure, diluted with EtOAc (20 mL) and washed with saturated $NaHCO_3$ (10 mL), water (10 mL) and brine (10 mL). The obtained was dried over anhydrous $Na_2SO_4$ and concentrated under reduced pressure. The crude compound was purification by MS triggered preparative HPLC to afford 64 (15.0 mg, 26%, AMRI lot # IN-CKB-H-23-2) as an off-white gummy. The compound was characterized by $^1$H NMR and MS analysis. $^1$H NMR (300 MHz, MeOD): δ 8.08 (s, 1H), 7.93 (s, 1H), 4.55-4.46 (m, 1H), 4.34 (s, 1H), 3.61 (s, 3H), 1.53 (d, J=6.60 Hz, 6H), 1.38 (s, 3H), 1.26-1.19 (m, 1H), 0.71 (m, 2H), 0.41 (m, 2H); MS-UPLC (MM) m/z 375.20 [M+H]$^+$; UPLC purity>97 (% AUC).

pp. Synthesis of 65

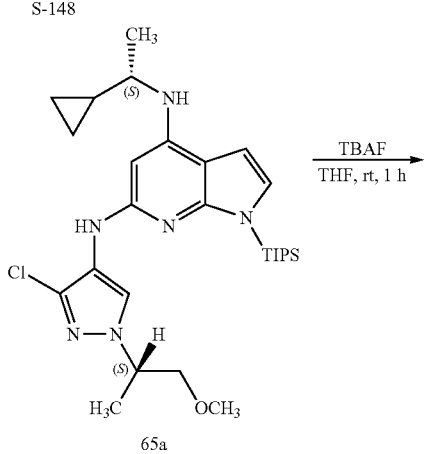

-continued

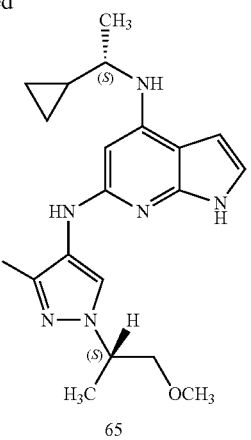

65 i. Preparation of 65a

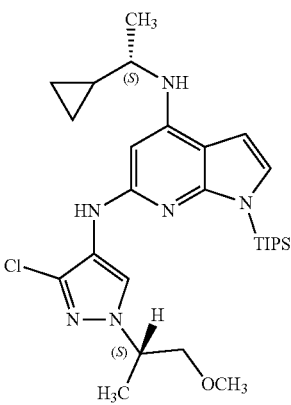

A stirred solution of S-148 (200 mg, 0.51 mmol) in t-BuOH (4.0 mL) taken in a microwave vial was charged with (S)-3-chloro-1-(1-methoxypropan-2-yl)-1H-pyrazol-4-amine S-165 (110 mg, 0.61 mmol) and K$_2$CO$_3$ (210 mg, 1.53 mmol). Argon gas was purged through septum and the reaction was degassed for about 5 min. To the reaction mixture, Xantphos (29.0 mg, 0.051 mmol) and Pd$_2$(dba)$_3$ (46.0 mg, 0.051 mmol) were added under inert atmosphere. The reaction mixture was purged with argon gas again for 5 min. The microwave vial was sealed and irradiated at 110° C. for 1 h in CEM-microwave instrument. The reaction mixture was filtered, washed with EtOAc (50 mL) and the filtrate was concentrated under reduced pressure. The crude compound was purified by column chromatography on silica gel using 0-50% EtOAc in hexanes as eluent to afford 65a (80.0 mg, 28%, AMRI lot # IN-SKY-D-41) as an off-white solid. The compound was characterized by UPLC-MS analysis. MS-UPLC (MM) m/z 545.3 [M+H]$^+$.

ii. Preparation of 65

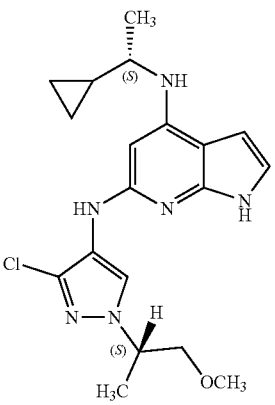

A stirred solution of 65a (80.0 mg, 0.147 mmol) in THF (2.0 mL) taken in a round-bottom flask was charged with TBAF (0.8 mL) at room temperature for 1 h. The reaction mixture was diluted with EtOAc (30 mL), washed with saturated NaHCO$_3$ (10 mL), water (10 mL) and brine (10 mL). The obtained was dried over anhydrous Na$_2$SO$_4$ and concentrated under reduced pressure. The crude product was purified by mass triggered preparative HPLC to afford 65 (18.0 mg, 31%, AMRI lot # IN-SKY-D-42) as an off-white solid. The compound was characterized by $^1$H NMR and UPLC-MS analysis. $^1$H NMR (300 MHz, CD$_3$OD): δ 7.60 (s, 1H), 6.79 (d, J=3.6 Hz, 1H), 6.59 (d, J=3.3 Hz, 1H), 5.46 (s, 1H), 4.73-4.70 (m, 1H), 3.76 (t, J=9.7 Hz, 1H), 3.53 (dd, J=10.2, 4.2 Hz, 1H), 3.24 (s, 3H), 3.11-2.98 (m, 1H), 1.37 (d, J=6.9 Hz, 3H), 1.25 (d, J=6.3 Hz, 3H), 1.05-0.92 (m, 1H), 0.52-0.40 (m, 2H), 0.26-0.13 (m, 2H); MS-UPLC (MM) m/z 390.2 [M+H]$^+$; UPLC purity>95 (% AUC).

3. Characterization of Exemplary Compounds

The compounds below in Table 1 were synthesized with methods identical or analogous to those described herein. The requisite starting materials were commercially available, described in the literature, or readily synthesized by one skilled in the art of organic synthesis.

TABLE 1

| No. | Structure | Name |
|---|---|---|
| 1 | 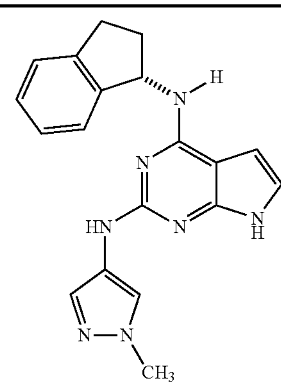 | (S)-N4-(2,3-dihydro-1H-inden-1-yl)-N2-(1-methyl-1H-pyrazol-4-yl)-7H-pyrrolo[2,3-d]pyrimidine-2,4-diamine |

TABLE 1-continued

| No. | Structure | Name |
|---|---|---|
| 2 | 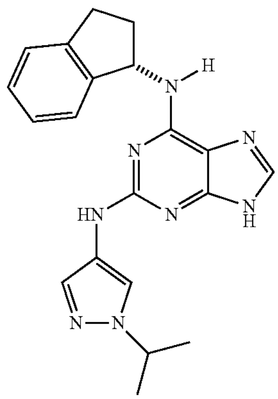 | (S)-N6-(2,3-dihydro-1H-inden-1-yl)-N2-(1-isopropyl-1H-pyrazol-4-yl)-9H-purine-2,6-diamine |
| 3 | 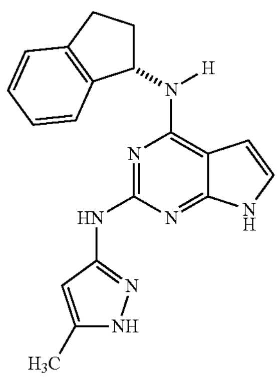 | (S)-N4-(2,3-dihydro-1H-inden-1-yl)-N2-(5-methyl-1H-pyrazol-3-yl)-7H-pyrrolo[2,3-d]pyrimidine-2,4-diamine |
| 4 | 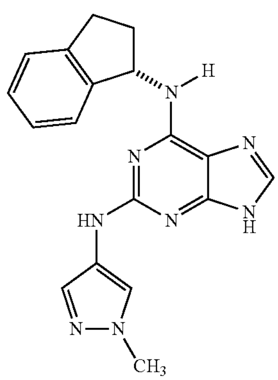 | (S)-N6-(2,3-dihydro-1H-inden-1-yl)-N2-(1-methyl-1H-pyrazol-4-yl)-9H-purine-2,6-diamine |
| 5 | 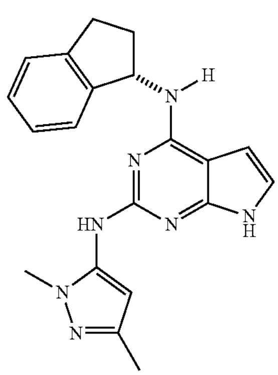 | (S)-N4-(2,3-dihydro-1H-inden-1-yl)-N2-(1,3-dimethyl-1H-pyrazol-5-yl)-7H-pyrrolo[2,3-d]pyrimidine-2,4-diamine |

TABLE 1-continued
| No. | Structure | Name |
|---|---|---|
| 6 | 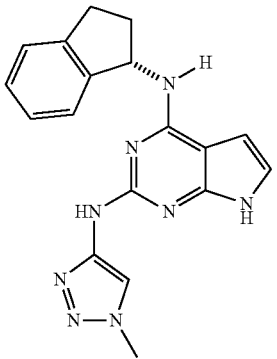 | (S)-N4-(2,3-dihydro-1H-inden-1-yl)-N2-(1-methyl-1H-1,2,3-triazol-4-yl)-7H-pyrrolo[2,3-d]pyrimidine-2,4-diamine |
| 7 | 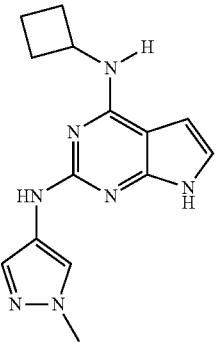 [SMILES: Cn1cc(Nc2nc(NC3CCC3)c3cc[nH]c3n2)cn1] | N4-cyclobutyl-N2-(1-methyl-1H-pyrazol-4-yl)-7H-pyrrolo[2,3-d]pyrimidine-2,4-diamine |
| 8 | 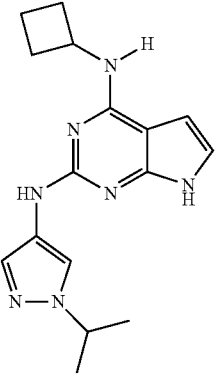 [SMILES: CC(C)n1cc(Nc2nc(NC3CCC3)c3cc[nH]c3n2)cn1] | N4-cyclobutyl-N2-(1-isopropyl-1H-pyrazol-4-yl)-7H-pyrrolo[2,3-d]pyrimidine-2,4-diamine |
| 9 | 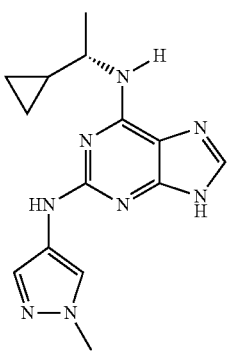 [SMILES: C[C@H](Nc1nc(Nc2cnn(C)c2)nc2[nH]cnc12)C1CC1] | (S)-N6-(1-cyclopropylethyl)-N2-(1-methyl-1H-pyrazol-4-yl)-9H-purine-2,6-diamine |

TABLE 1-continued

| No. | Structure | Name |
| --- | --- | --- |
| 10 | 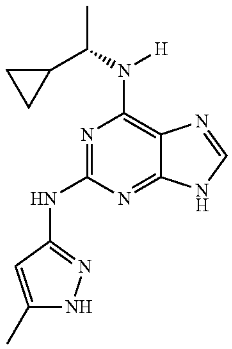 [SMILES: Cc1cc(Nc2nc(N[C@@H](C)C3CC3)c3nc[nH]c3n2)n[nH]1] | (S)-N6-(1-cyclopropylethyl)-N2-(5-methyl-1H-pyrazol-3-yl)-9H-purine-2,6-diamine |
| 11 | 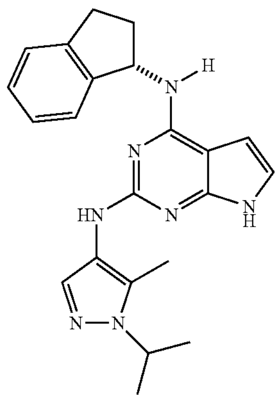 | (S)-N4-(2,3-dihydro-1H-inden-1-yl)-N2-(1-isopropyl-5-methyl-1H-pyrazol-4-yl)-7H-pyrrolo[2,3-d]pyrimidine-2,4-diamine |
| 12 | 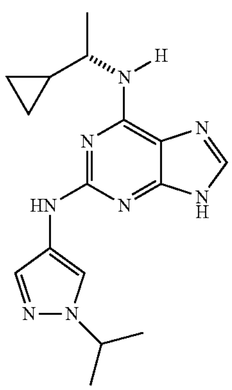 | (S)-N6-(1-cyclopropylethyl)-N2-(1-isopropyl-1H-pyrazol-4-yl)-9H-purine-2,6-diamine |
| 13 | 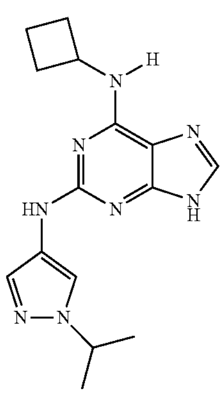 [SMILES: CC(C)n1cc(Nc2nc(NC3CCC3)c3nc[nH]c3n2)cn1] | N6-cyclobutyl-N2-(1-isopropyl-1H-pyrazol-4-yl)-9H-purine-2,6-diamine |

TABLE 1-continued

| No. | Structure | Name |
|---|---|---|
| 14 | 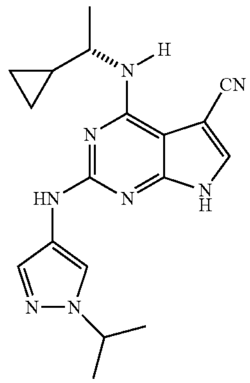 | (S)-4-((1-cyclopropylethyl)amino)-2-((1-isopropyl-1H-pyrazol-4-yl)amino)-7H-pyrrolo[2,3-d]pyrimidine-5-carbonitrile |
| 15 | 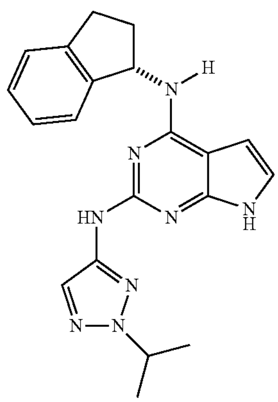 | (S)-N4-(2,3-dihydro-1H-inden-1-yl)-N2-(2-isopropyl-2H-1,2,3-triazol-4-yl)-7H-pyrrolo[2,3-d]pyrimidine-2,4-diamine |
| 16 | 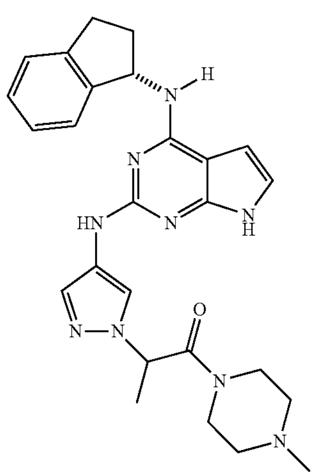 | 2-(4-((4-(((S)-2,3-dihydro-1H-inden-1-yl)amino)-7H-pyrrolo[2,3-d]pyrimidin-2-yl)amino)-1H-pyrazol-1-yl)-1-(4-methylpiperazin-1-yl)propan-1-one |

TABLE 1-continued

| No. | Structure | Name |
|---|---|---|
| 17 | 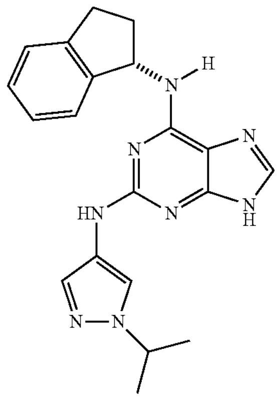 | (S)-N6-(2,3-dihydro-1H-inden-1-yl)-N2-(1-isopropyl-1H-pyrazol-4-yl)-9H-purine-2,6-diamine |
| 18 | 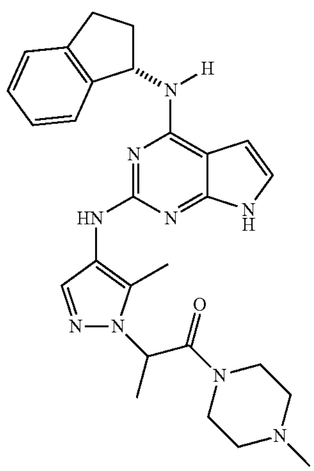 | 2-(4-((4-(((S)-2,3-dihydro-1H-inden-1-yl)amino)-7H-pyrrolo[2,3-d]pyrimidin-2-yl)amino)-5-methyl-1H-pyrazol-1-yl)-1-(4-methylpiperazin-1-yl)propan-1-one |
| 19 | 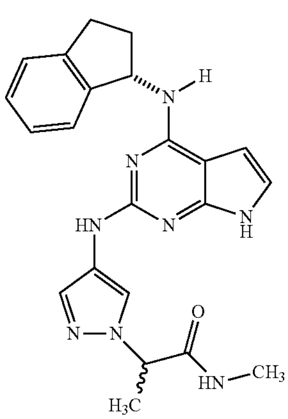 | 2-(4-((4-(((S)-2,3-dihydro-1H-inden-1-yl)amino)-7H-pyrrolo[2,3-d]pyrimidin-2-yl)amino)-1H-pyrazol-1-yl)-N-methylpropanamide |

TABLE 1-continued

| No. | Structure | Name |
|---|---|---|
| 20 | 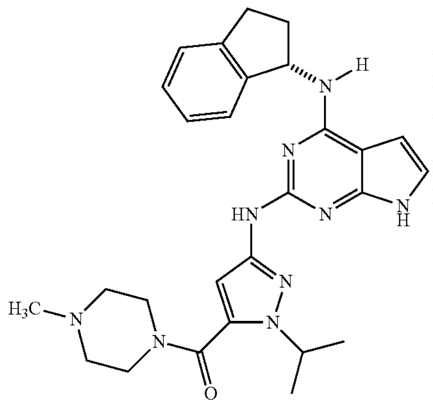 | (S)-(3-((4-((2,3-dihydro-1H-inden-1-yl)amino)-7H-pyrrolo[2,3-d]pyrimidin-2-yl)amino)-1-isopropyl-1H-pyrazol-5-yl)(4-methylpiperazin-1-yl)methanone |
| 21 | 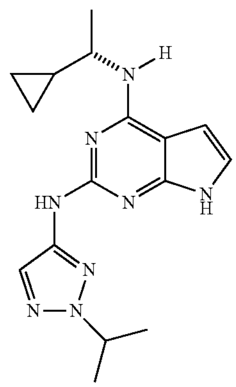 | (S)-N4-(1-cyclopropylethyl)-N2-(2-isopropyl-2H-1,2,3-triazol-4-yl)-7H-pyrrolo[2,3-d]pyrimidine-2,4-diamine |
| 22 | 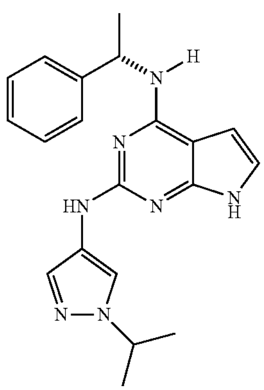 | (S)-N2-(1-isopropyl-1H-pyrazol-4-yl)-N4-(1-phenylethyl)-7H-pyrrolo[2,3-d]pyrimidine-2,4-diamine |
| 23 | 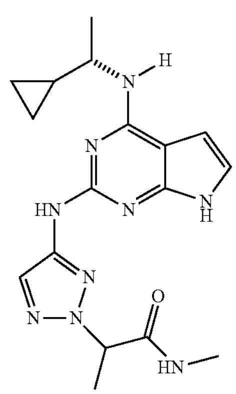 | 2-(4-((4-(((S)-1-cyclopropylethyl)amino)-7H-pyrrolo[2,3-d]pyrimidin-2-yl)amino)-1H-pyrazol-1-yl)-N-methylpropanamide |

TABLE 1-continued

| No. | Structure | Name |
|---|---|---|
| 24 | 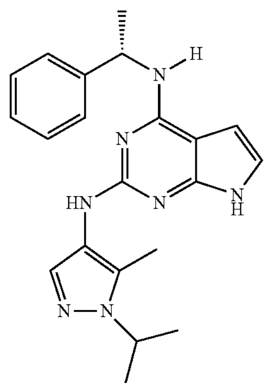 [SMILES: Cc1c(Nc2nc(N[C@@H](C)c3ccccc3)c3cc[nH]c3n2)cnn1C(C)C] | (S)-N2-(1-isopropyl-5-methyl-1H-pyrazol-phenylethyl)-7H-pyrrolo[2,3-d]pyrimidine-2,4-diamine |
| 25 | 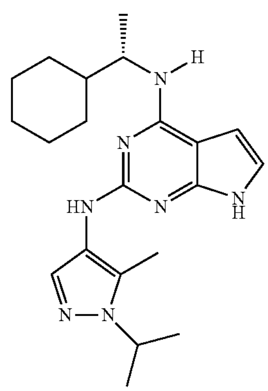 [SMILES: Cc1c(Nc2nc(N[C@@H](C)C3CCCCC3)c3cc[nH]c3n2)cnn1C(C)C] | (S)-N4-(1-cyclohexylethyl)-N2-(1-isopropyl-5-methyl-1H-pyrazol-4-yl)-7H-pyrrolo[2,3-d]pyrimidine-2,4-diamine |
| 26 | 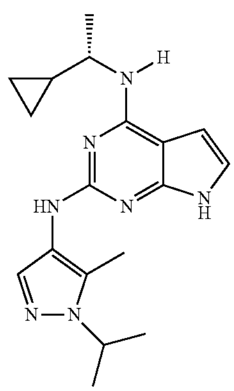 [SMILES: Cc1c(Nc2nc(N[C@@H](C)C3CC3)c3cc[nH]c3n2)cnn1C(C)C] | (S)-N4-(1-cyclopropylethyl)-N2-(1-isopropyl-5-methyl-1H-pyrazol-4-yl)-7H-pyrrolo[2,3-d]pyrimidine-2,4-diamine |
| 27 | 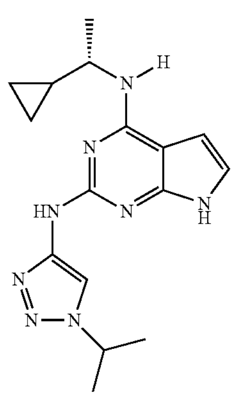 [SMILES: CC(C)n1cc(Nc2nc(N[C@@H](C)C3CC3)c3cc[nH]c3n2)nn1] | (S)-N4-(1-cyclopropylethyl)-N2-(1-isopropyl-1H-1,2,3-triazol-4-yl)-7H-pyrrolo[2,3-d]pyrimidine-2,4-diamine |

TABLE 1-continued

| No. | Structure | Name |
|---|---|---|
| 28 | 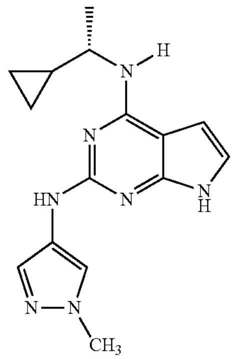 [SMILES: C[C@H](Nc1nc(Nc2cnn(C)c2)nc2[nH]ccc12)C1CC1] | (S)-N4-(1-cyclopropylethyl)-N2-(1-methyl-1H-pyrazol-4-yl)-7H-pyrrolo[2,3-d]pyrimidine-2,4-diamine |
| 29 | 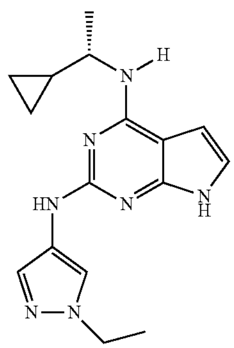 [SMILES: CCn1cc(Nc2nc(N[C@@H](C)C3CC3)c3cc[nH]c3n2)cn1] | (S)-N4-(1-cyclopropylethyl)-pyrazol-4-yl)-7H-pyrrolo[2,3-d]pyrimidine-2,4-diamine |
| 30 | 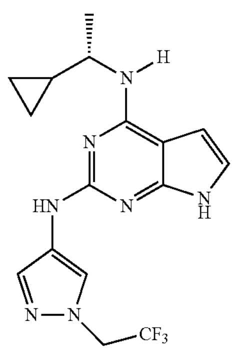 [SMILES: C[C@H](Nc1nc(Nc2cnn(CC(F)(F)F)c2)nc2[nH]ccc12)C1CC1] | (S)-N4-(1-cyclopropylethyl)-N2-(1-(2,2,2-trifluoroethyl)-1H-pyrazol-4-yl)-7H-pyrrolo[2,3-d]pyrimidine-2,4-diamine |
| 31 | 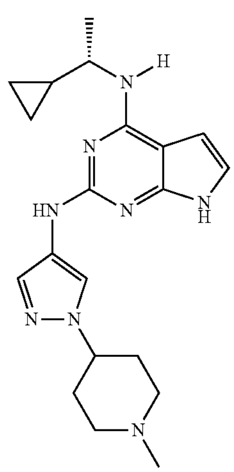 [SMILES: C[C@H](Nc1nc(Nc2cnn(C3CCN(C)CC3)c2)nc2[nH]ccc12)C1CC1] | (S)-N4-(1-cyclopropylethyl)-N2-(1-(1-methylpiperidin-4-yl)-1H-pyrazol-4-yl)-7H-pyrrolo[2,3-d]pyrimidine-2,4-diamine |

TABLE 1-continued

| No. | Structure | Name |
|---|---|---|
| 32 | 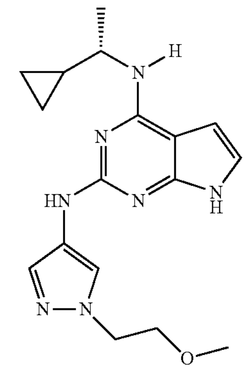 [SMILES: COCCn1cc(Nc2nc(N[C@@H](C)C3CC3)c3cc[nH]c3n2)cn1] | (S)-N4-(1-cyclopropylethyl)-N2-(1-(2-methoxyethyl)-1H-pyrazol-4-yl)-7H-pyrrolo[2,3-d]pyrimidine-2,4-diamine |
| 33 | 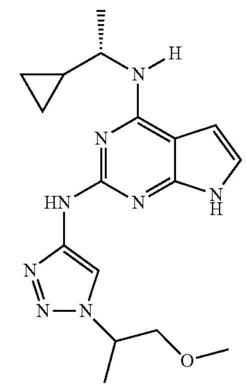 [SMILES: COCC(C)n1cc(Nc2nc(N[C@@H](C)C3CC3)c3cc[nH]c3n2)nn1] | N4-((S)-1-cyclopropylethyl)-N2-(1-(1-methoxypropan-2-yl)-1H-1,2,3-triazol-4-yl)-7H-pyrrolo[2,3-d]pyrimidine-2,4-diamine |
| 34 | 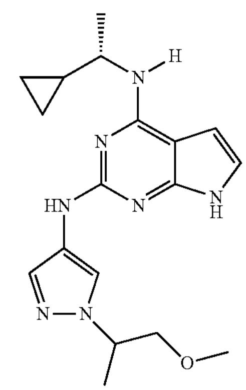 [SMILES: COCC(C)n1cc(Nc2nc(N[C@@H](C)C3CC3)c3cc[nH]c3n2)cn1] | N4-((S)-1-cyclopropylethyl)-N2-(1-(1-methoxypropan-2-yl)-1H-pyrazol-4-yl)-7H-pyrrolo[2,3-d]pyrimidine-2,4-diamine |
| 35 | 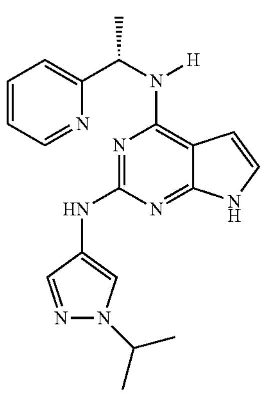 [SMILES: CC(C)n1cc(Nc2nc(N[C@@H](C)c3ccccn3)c3cc[nH]c3n2)cn1] | (S)-N2-(1-isopropyl-1H-pyrazol-4-yl)-N4-(1-(pyridin-2-yl)ethyl)-7H-pyrrolo[2,3-d]pyrimidine-2,4-diamine |

TABLE 1-continued

| No. | Structure | Name |
|---|---|---|
| 36 | 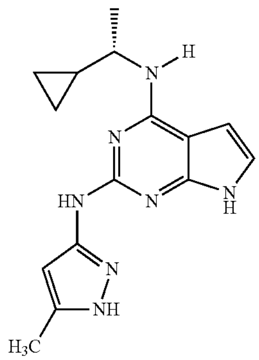 [SMILES: Cc1cc(Nc2nc(N[C@@H](C)C3CC3)c3cc[nH]c3n2)n[nH]1] | (S)-N4-(1-cyclopropylethyl)-N2-(5-methyl-1H-pyrazol-3-yl)-7H-pyrrolo[2,3-d]pyrimidine-2,4-diamine |
| 37 | 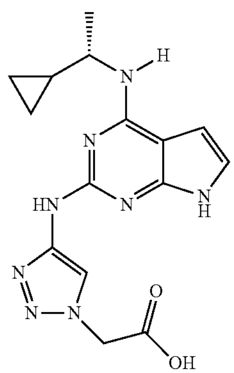 [SMILES: C[C@H](Nc1nc(Nc2cn(CC(=O)O)nn2)nc2[nH]ccc12)C1CC1] | (S)-2-(4-((4-((1-cyclopropylethyl)amino)-7H-pyrrolo[2,3-d]pyrimidin-2-yl)amino)-1H-1,2,3-triazol-1-yl)acetic acid |
| 38 | 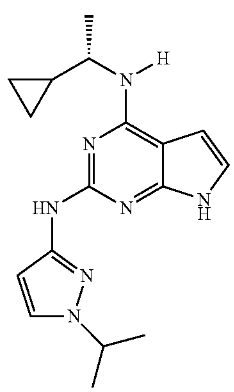 [SMILES: CC(C)n1ccc(Nc2nc(N[C@@H](C)C3CC3)c3cc[nH]c3n2)n1] | (S)-N4-(1-cyclopropylethyl)-N2-(1-isopropyl-1H-pyrazol-3-yl)-7H-pyrrolo[2,3-d]pyrimidine-2,4-diamine |
| 39 | 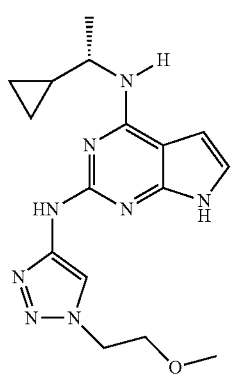 | (S)-N4-(1-cyclopropylethyl)-N2-(1-(2-methoxyethyl)-1H-1,2,3-triazol-4-yl)-7H-pyrrolo[2,3-d]pyrimidine-2,4-diamine |

TABLE 1-continued

| No. | Structure | Name |
|---|---|---|
| 40 | 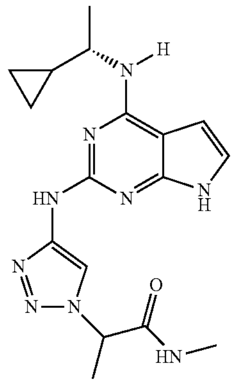 [SMILES: CNC(=O)C(C)n1cc(Nc2nc(N[C@@H](C)C3CC3)c3cc[nH]c3n2)nn1] | 2-(4-((4-(((S)-1-cyclopropylethyl)amino)-7H-pyrrolo[2,3-d]pyrimidin-2-yl)amino)-1H-1,2,3-triazol-1-yl)-N-methylpropanamide |
| 41 | 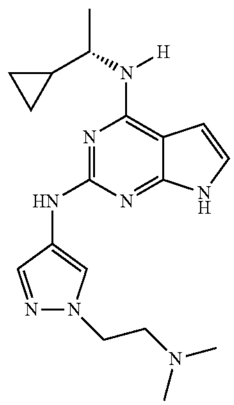 [SMILES: C[C@H](Nc1nc(Nc2cnn(CCN(C)C)c2)nc2[nH]ccc12)C1CC1] | (S)-N4-(1-cyclopropylethyl)-N2-(1-(2-(dimethylamino)ethyl)-1H-pyrazol-4-yl)-7H-pyrrolo[2,3-d]pyrimidine-2,4-diamine |
| 42 | 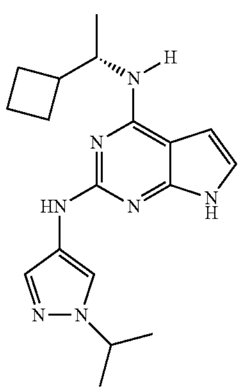 [SMILES: CC(C)n1cc(Nc2nc(N[C@@H](C)C3CCC3)c3cc[nH]c3n2)cn1] | (S)-N4-(1-cyclobutylethyl)-N2-(1-isopropyl-1H-pyrazol-4-yl)-7H-pyrrolo[2,3-d]pyrimidine-2,4-diamine |
| 43 | 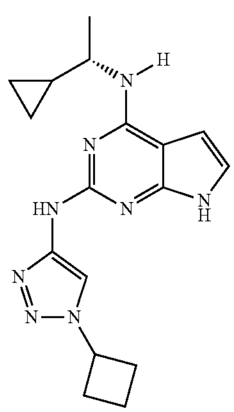 [SMILES: C[C@H](Nc1nc(Nc2cn(C3CCC3)nn2)nc2[nH]ccc12)C1CC1] | (S)-N2-(1-cyclobutyl-1H-pyrazol-4-yl)-N4-(1-cyclopropylethyl)-7H-pyrrolo[2,3-d]pyrimidine-2,4-diamine |

TABLE 1-continued

| No. | Structure | Name |
|---|---|---|
| 44 | 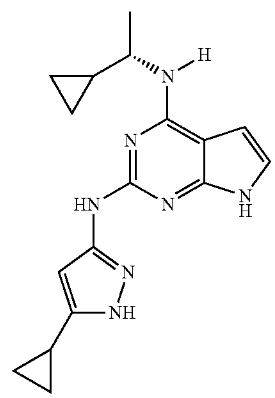 [SMILES: C[C@H](Nc1nc(Nc2cc(C3CC3)[nH]n2)nc2[nH]ccc12)C1CC1] | (S)-N2-(5-cyclopropyl-1H-pyrazol-3-yl)-N4-(1-cyclopropylethyl)-7H-pyrrolo[2,3-d]pyrimidine-2,4-diamine |
| 45 | 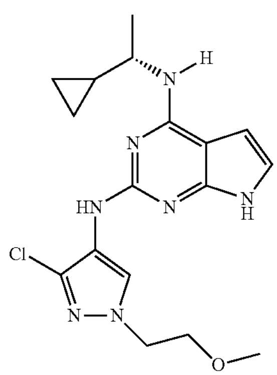 [SMILES: COCCn1cc(Nc2nc(N[C@@H](C)C3CC3)c3cc[nH]c3n2)c(Cl)n1] | (S)-N2-(3-chloro-1-(2-methoxyethyl)-1H-pyrazol-4-yl)-N4-(1-cyclopropylethyl)-7H-pyrrolo[2,3-d]pyrimidine-2,4-diamine |
| 46 | 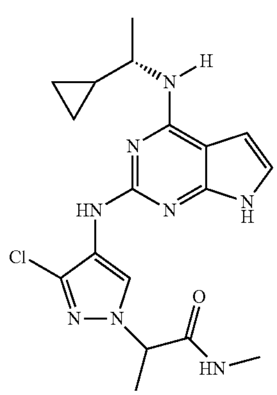 [SMILES: CNC(=O)C(C)n1cc(Nc2nc(N[C@@H](C)C3CC3)c3cc[nH]c3n2)c(Cl)n1] | 2-(3-chloro-4-((4-(((S)-1-cyclopropylethyl)amino)-7H-pyrrolo[2,3-d]pyrimidin-2-yl)amino)-1H-pyrazol-1-yl)-N-methylpropanamide |
| 47 | 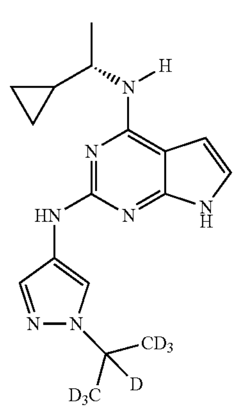 [SMILES: [2H]C([2H])([2H])C([2H])(n1cc(Nc2nc(N[C@@H](C)C3CC3)c3cc[nH]c3n2)cn1)C([2H])([2H])[2H]] | (S)-N4-(1-cyclopropylethyl)-N2-(1-(propan-2-yl-d7)-1H-pyrazol-4-yl)-7H-pyrrolo[2,3-d]pyrimidine-2,4-diamine |

TABLE 1-continued

| No. | Structure | Name |
|---|---|---|
| 48 | 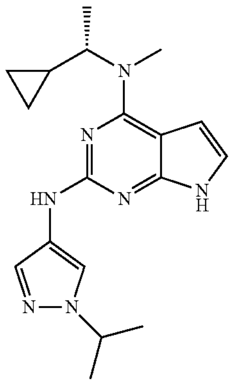 [SMILES: CC(C)n1cc(Nc2nc(N(C)[C@@H](C)C3CC3)c3cc[nH]c3n2)cn1] | (S)-N4-(1-cyclopropylethyl)-N2-(1-isopropyl-1H-pyrazol-4-yl)-N4-methyl-7H-pyrrolo[2,3-d]pyrimidine-2,4-diamine |
| 49 | 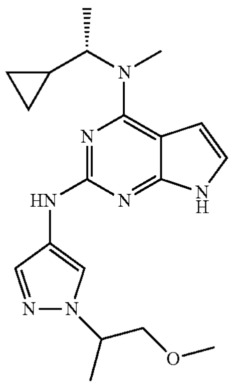 [SMILES: COCC(C)n1cc(Nc2nc(N(C)[C@@H](C)C3CC3)c3cc[nH]c3n2)cn1] | N4-((S)-1-cyclopropylethyl)-N2-(1-(1-methoxypropan-2-yl)-1H-pyrazol-4-yl)-N4-methyl-7H-pyrrolo[2,3-d]pyrimidine-2,4-diamine |
| 50 | 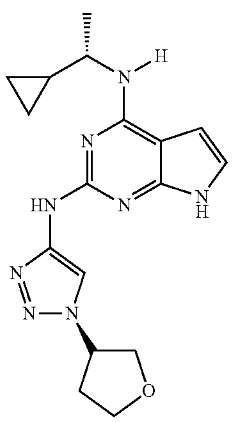 | N4-((S)-1-cyclopropylethyl)-N2-(1-((S)-tetrahydrofuran-3-yl)-1H-1,2,3-triazol-4-yl)-7H-pyrrolo[2,3-d]pyrimidine-2,4-diamine |
| 51 | 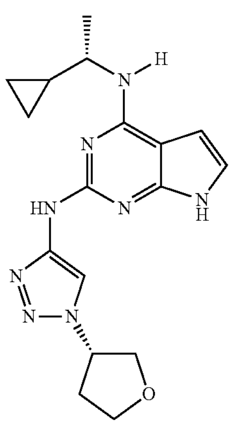 [SMILES: C[C@H](Nc1nc(Nc2cn([C@H]3CCOC3)nn2)nc2[nH]ccc12)C1CC1] | N4-((S)-1-cyclopropylethyl)-N2-(1-((S)-tetrahydrofuran-3-yl)-1H-1,2,3-triazol-4-yl)-7H-pyrrolo[2,3-d]pyrimidine-2,4-diamine |

TABLE 1-continued

| No. | Structure | Name |
|---|---|---|
| 52 | 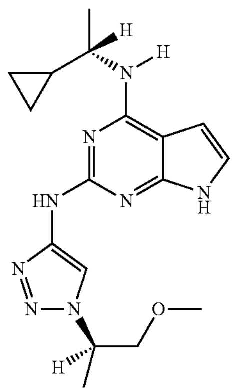 [SMILES: COC[C@@H](C)n1cc(Nc2nc(N[C@@H](C)C3CC3)c3cc[nH]c3n2)nn1] | N4-((S)-1-cyclopropylethyl)-N2-(1-((R)-1-methoxypropan-2-yl)-1H-1,2,3-triazol-4-yl)-7H-pyrrolo[2,3-d]pyrimidine-2,4-diamine |
| 53 | 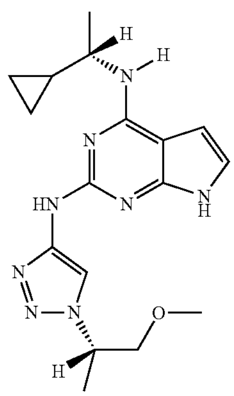 [SMILES: COC[C@H](C)n1cc(Nc2nc(N[C@@H](C)C3CC3)c3cc[nH]c3n2)nn1] | N4-((S)-1-cyclopropylethyl)-N2-(1-((S)-1-methoxypropan-2-yl)-1H-1,2,3-triazol-4-yl)-7H-pyrrolo[2,3-d]pyrimidine-2,4-diamine |
| 54 | 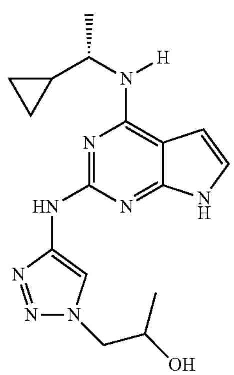 [SMILES: CC(O)Cn1cc(Nc2nc(N[C@@H](C)C3CC3)c3cc[nH]c3n2)nn1] | 1-(4-((4-(((S)-1-cyclopropylethyl)amino)-7H-pyrrolo[2,3-d]pyrimidin-2-yl)amino)-1H-1,2,3-triazol-1-yl)propan-2-ol |
| 55 | 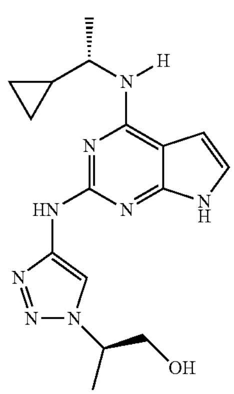 [SMILES: C[C@H](Nc1nc(Nc2cn([C@H](C)CO)nn2)nc2[nH]ccc12)C1CC1] | (R)-2-(4-((4-(((S)-1-cyclopropylethyl)amino)-7H-pyrrolo[2,3-d]pyrimidin-2-yl)amino)-1H-1,2,3-triazol-1-yl)propan-1-ol |

TABLE 1-continued

| No. | Structure | Name |
|---|---|---|
| 56 | 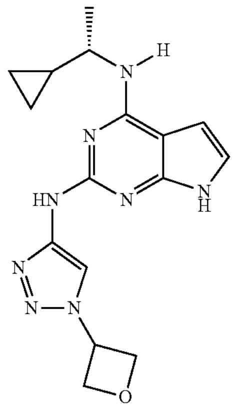 [SMILES: C[C@H](Nc1nc(Nc2cn(C3COC3)nn2)nc2[nH]ccc12)C1CC1] | (S)-N4-(1-cyclopropylethyl)-N2-(1-(oxetan-3-yl)-1H-1,2,3-triazol-4-yl)-7H-pyrrolo[2,3-d]pyrimidine-2,4-diamine |
| 57 | 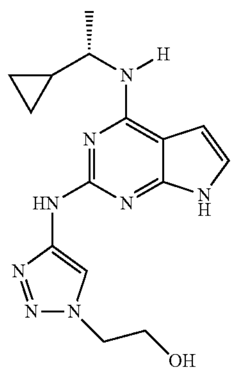 [SMILES: C[C@H](Nc1nc(Nc2cn(CCO)nn2)nc2[nH]ccc12)C1CC1] | (S)-2-(4-((4-((1-cyclopropylethyl)amino)-7H-pyrrolo[2,3-d]pyrimidin-2-yl)amino)-1H-1,2,3-triazol-1-yl)ethan-1-ol |
| 58 | 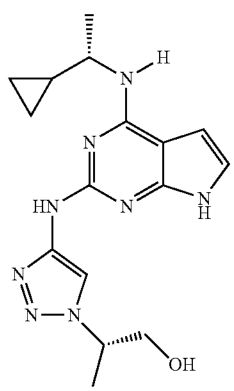 [SMILES: C[C@H](Nc1nc(Nc2cn([C@@H](C)CO)nn2)nc2[nH]ccc12)C1CC1] | (S)-2-(4-((4-(((S)-1-cyclopropylethyl)amino)-7H-pyrrolo[2,3-d]pyrimidin-2-yl)amino)-1H-1,2,3-triazol-1-yl)propan-1-ol |
| 59 | 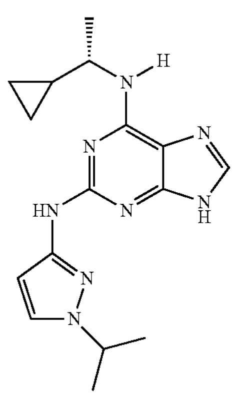 [SMILES: CC(C)n1ccc(Nc2nc(N[C@@H](C)C3CC3)c3nc[nH]c3n2)n1] | (S)-N6-(1-cyclopropylethyl)-N2-(1-isopropyl-1H-pyrazol-3-yl)-9H-purine-2,6-diamine |

TABLE 1-continued

| No. | Structure | Name |
|---|---|---|
| 60 | 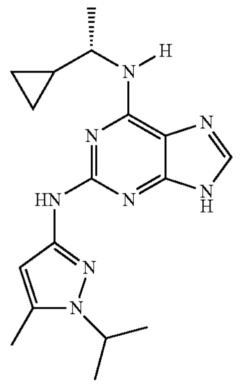 [SMILES: Cc1cc(Nc2nc(N[C@@H](C)C3CC3)c3nc[nH]c3n2)nn1C(C)C] | (S)-N6-(1-cyclopropylethyl)-N2-(1-isopropyl-5-methyl-1H-pyrazol-3-yl)-9H-purine-2,6-diamine |
| 61 | 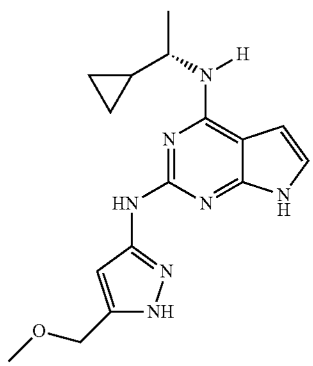 [SMILES: COCc1cc(Nc2nc(N[C@@H](C)C3CC3)c3cc[nH]c3n2)n[nH]1] | (S)-N4-(1-cyclopropylethyl)-N2-(5-(methoxymethyl)-1H-pyrazol-3-yl)-7H-pyrrolo[2,3-d]pyrimidine-2,4-diamine |
| 62 | 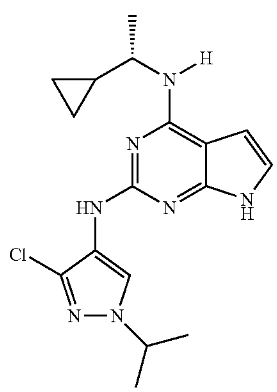 [SMILES: CC(C)n1cc(Nc2nc(N[C@@H](C)C3CC3)c3cc[nH]c3n2)c(Cl)n1] | (S)-N2-(3-chloro-1-isopropyl-1H-pyrazol-4-yl)-N4-(1-cyclopropylethyl)-7H-pyrrolo[2,3-d]pyrimidine-2,4-diamine |
| 63 | 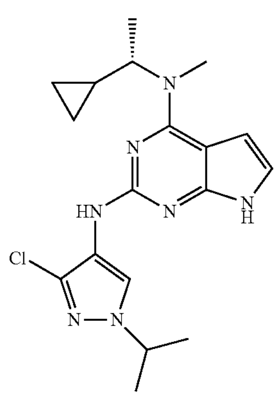 [SMILES: CC(C)n1cc(Nc2nc(N(C)[C@@H](C)C3CC3)c3cc[nH]c3n2)c(Cl)n1] | (S)-N2-(3-chloro-1-isopropyl-1H-pyrazol-4-yl)-N4-(1-cyclopropylethyl)-N4-methyl-7H-pyrrolo[2,3-d]pyrimidine-2,4-diamine |

TABLE 1-continued

| No. | Structure | Name |
|---|---|---|
| 64 | 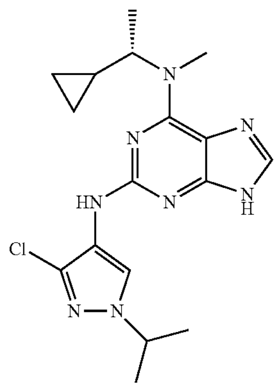 [SMILES: CC(C)n1cc(Nc2nc(N(C)[C@@H](C)C3CC3)c3nc[nH]c3n2)c(Cl)n1] | (S)-N2-(3-chloro-1-isopropyl-1H-pyrazol-4-yl)-N6-(1-cyclopropylethyl)-N6-methyl-9H-purine-2,6-diamine |
| 65 | 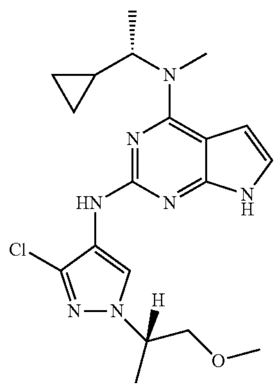 [SMILES: COC[C@H](C)n1cc(Nc2nc(N(C)[C@@H](C)C3CC3)c3cc[nH]c3n2)c(Cl)n1] | N2-(3-chloro-1-((S)-1-methoxypropan-2-yl)-1H-pyrazol-4-yl)-N4-((S)-1-cyclopropylethyl)-N4-methyl-7H-pyrrolo[2,3-d]pyrimidine-2,4-diamine |
| 66 | | |

4. Evaluation of Inhibitory Activity Against LRRK2

Compounds were assessed for inhibition of LRRK2 inhibition using the following procedure. Recombinant GST-LRRK2 (delta970) purified from baculovirus infected insect cells (SF9), at least 90% pure and either wild-type sequence or bearing the pathogenic G2019S mutation, was combined into a kinase buffer at 30 nM concentration. Kinase buffer consists of 50 mM Tris HCl pH 7.4, 1 mM EDTA, and 50 µM peptide substrate (amino acid sequence RLGAW-RFYTLRRARQGNTKQR). Experimental compounds or control (no compound) were added at desired concentrations in DMSO and water, where final concentration of DMSO in kinase reactions was 0.1% for all drug concentrations. Activation buffer that consists of a final concentration in the reactions of 10 mM $MgCl_2$ and ATP (~92 µM for WT-LRRK2 reactions and ~52 µM for G2019S-LRRK2, which represent respective Km ATP concentrations) were added to each reaction, in addition to 0.5 µCi of gamma-32-P-dATP per reaction. Reactions were incubated at 1400 RPM at 30° C. for 30 min. and then spotted in triplicate directly onto a slot-blot apparatus fitted with phospho-cellulose paper and allowed to dry. Each slot was then washed with 10 mM phosphoric acid buffer until beta-radiation could not be detected in eluted wash buffer, usually ~1 mL per slot. Paper within each slot were excised and radiation measured by liquid scintillation. Raw CPM were input into GraphPad, and IC-50 values calculated using non-linear regression analysis, where 100% activity is defined by reactions with control (no) inhibitor compounds, and baseline activity is defined by control reactions that did not include LRRK2 enzyme.

Table 2 below contains the data for the compounds of the invention.

TABLE 2

| No. | LRRK2 Assay G2019S ($IC_{50}$ µM) | LRRK2 Assay WT ($IC_{50}$ µM) |
|---|---|---|
| 1 | 0.004 | 0.001 |
| 2 | 0.0008 | 0.006 |
| 3 | 0.027 | 0.02 |
| 4 | 0.103 | 0.081 |
| 5 | 0.043 | 0.034 |
| 6 | 0.050 | 0.036 |
| 7 | 0.019 | 0.008 |
| 8 | 0.009 | 0.005 |
| 9 | 0.100 | 0.038 |
| 10 | 0.048 | 0.019 |
| 11 | 0.013 | 0.008 |
| 12 | 0.022 | 0.010 |
| 13 | 0.015 | 0.007 |
| 14 | 0.011 | 0.006 |
| 15 | 0.066 | 0.047 |
| 16 | 0.020, 0.027 | 0.014, 0.022 |
| 17 | 0.008 | 0.006 |
| 18 | 0.049 | 0.037 |
| 19 | 0.014 | 0.011 |
| 20 | 0.045 | 0.031 |
| 21 | 0.026 | 0.019 |
| 22 | 0.056 | 0.037 |
| 23 | 0.009 | 0.008 |

TABLE 2-continued

| No. | LRRK2 Assay G2019S (IC$_{50}$ μM) | LRRK2 Assay WT (IC$_{50}$ μM) |
|---|---|---|
| 24 | 0.063 | 0.055 |
| 25 | 0.043 | 0.042 |
| 26 | 0.008 | 0.006 |
| 27 | 0.077 | 0.060 |
| 28 | 0.030 | 0.020 |
| 29 | 0.017 | 0.012 |
| 30 | 0.011 | 0.007 |
| 31 | 0.023 | 0.020 |
| 32 | 0.011 | 0.011 |
| 33 | 0.014, 0.033, 0.167 | 0.012, 0.024, 0.09 |
| 34 | 0.015 | 0.011 |
| 35 | 0.097 | 0.066 |
| 36 | 0.044 | 0.038 |
| 37 | 0.059 | 0.044 |
| 38 | 0.056 | 0.072 |
| 39 | 0.058, 0.113, 0.088 | 0.043, 0.74, 0.057 |
| 40 | 0.032 | 0.025 |
| 41 | 0.065 | 0.050 |
| 42 | 0.078 | 0.067 |
| 43 | 0.019 | 0.013 |
| 44 | 0.010 | 0.007 |
| 45 | 0.036 | 0.025 |
| 46 | 0.017 | 0.012 |
| 47 | 0.009 | 0.006 |
| 48 | 0.044 | 0.019 |
| 49 | 0.069 | 0.027 |
| 50 | 0.061 | 0.040 |
| 51 | 0.102 | 0.066 |
| 52 | 0.060 | 0.038 |
| 53 | 0.071 | 0.042 |
| 54 | 0.027 | 0.021 |
| 55 | 0.013, 0.032 | 0.009, 0.019 |
| 56 | 0.115 | 0.073 |
| 57 | 0.014, 0.034 | 0.009, 0.02 |
| 58 | 0.101 | 0.072 |
| 59 | 0.115 | 0.051 |
| 60 | 0.065 | 0.032 |
| 61 | 0.099 | 0.064 |

What is claimed is:

1. A compound having a structure represented by a formula:

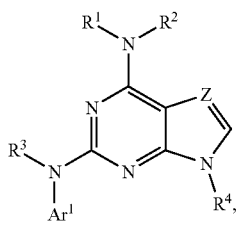

wherein Z is selected from N and $CR^{20}$,
wherein each occurrence of $R^{20}$, when present, is independently selected from hydrogen, —CN, —CF$_3$, and C1-C4 alkyl;
wherein $R^1$ is selected from $Cy^1$, $Ar^2$, —$CR^{21a}R^{21b}Cy^2$, and —$CR^{21a}R^{21b}Ar^2$;
wherein each of $R^{21a}$ and $R^{21b}$, when present, are independently selected from hydrogen and C1-C4 alkyl;
wherein $Cy^1$, when present, is selected from C3-C5 cycloalkyl and 2,3-dihydroindene and is substituted with 0, 1, or 2 groups independently selected from halogen, C1-C4 alkyl, C1-C4 monohaloalkyl, and C1-C4 polyhaloalkyl;
wherein $Cy^2$, when present, is selected from C3-C6 cycloalkyl, C2-C5 heterocycloalkyl, and 2,3-dihydroindene and is substituted with 0, 1, or 2 groups independently selected from halogen, C1-C4 alkyl, C1-C4 monohaloalkyl, and C1-C4 polyhaloalkyl;
wherein $Ar^2$, when present, is selected from C5-C6 aryl and C4-C5 heteroaryl and is substituted with 0, 1, or 2 groups independently selected from halogen, C1-C4 alkyl, C1-C4 monohaloalkyl, and C1-C4 polyhaloalkyl; and
wherein each of $R^2$, $R^3$, and $R^4$ are independently selected from hydrogen and C1-C4 alkyl;
wherein $Ar^1$ is a structure selected from:

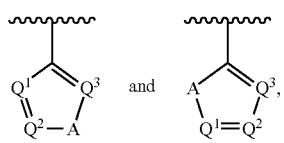

wherein A is selected from $NR^{22}$ and $CR^{23a}R^{23b}$;
wherein $R^{22}$, when present, is selected from hydrogen, halogen, C1-C8 alkyl, C1-C8 monohaloalkyl, C1-C8 polyhaloalkyl, C1-C8 hydroxyalkyl, C1-C8 alkoxyalkyl, —(C1-C8 alkyl)NH$_2$, —(C1-C8 alkyl)NH(C1-C8alkyl), —(C1-C8 alkyl)N(C1-C8 alkyl)(C1-C8 alkyl), C1-C8 alkylacid, —(C1-C4 alkyl)CONH$_2$, —(C1-C4 alkyl)CONH(C1-C4 alkyl), —(C1-C4 alkyl)CON(C1-C4 alkyl)(C1-C4 alkyl), —(C1-C4 alkyl)(C=O)Cy$^3$, and Cy$^3$;
wherein each occurrence of Cy$^3$, when present, is independently selected from C3-C6 cycloalkyl and C2-C5 heterocycloalkyl and is substituted with 0, 1, or 2 groups independently selected from halogen, C1-C4 alkyl, C1-C4 monohaloalkyl, and C1-C4 polyhaloalkyl;
wherein each of $R^{23a}$ and $R^{23b}$, when present, is independently selected from hydrogen, halogen, C1-C8 alkyl, C1-C8 monohaloalkyl, C1-C8 polyhaloalkyl, C1-C8 hydroxyalkyl, C1-C8 alkoxyalkyl, C1-C8 alkylacid, —(C1-C4 alkyl)(C=O)Cy$^1$, —(C1-C4 alkyl)CONH$_2$, —(C1-C4 alkyl)CONH(C1-C4 alkyl), —(C1-C4 alkyl)CON(C1-C4 alkyl)(C1-C4 alkyl), and Cy$^3$;
wherein each of $Q^1$, $Q^2$, and $Q^3$ is independently selected from N and $CR^{24}$; and
wherein each occurrence of $R^{24}$, when present, is independently selected from hydrogen, halogen, C1-C8 alkyl, C1-C8 monohaloalkyl, C1-C8 polyhaloalkyl, C1-C8 alkoxyalkyl, —(C1-C4 alkyl)CONH$_2$, —(C1-C4 alkyl)CONH(C1-C4 alkyl), —(C1-C4 alkyl)CON(C1-C4 alkyl)(C1-C4 alkyl),
provided that two or three of A, $Q^1$, $Q^2$, and $Q^3$ are N, and
provided that if $Ar^1$ is a structure represented by a formula:

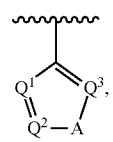

wherein each of Z, $Q^1$, and $Q^3$ are CH, $Q^2$ is N, A is $NR^{22}$, $R^{22}$ is C1-C8 alkyl, and each of $R^2$, $R^3$, and $R^4$ are hydrogen, then R¹ is selected from Ar², —CR²¹ᵃR²¹ᵇCy², and —CR²¹ᵃR²¹ᵇAr²;

or a pharmaceutically acceptable salt thereof.

2. The compound of claim 1, wherein R¹ is selected from Ar², —CR²¹ᵃR²¹ᵇCy², and —CR²¹ᵃR²¹ᵇAr².

3. The compound of claim 1, wherein R¹ is Cy¹.

4. The compound of claim 1, wherein each of R², R³, and R⁴ are hydrogen.

5. The compound of claim 1, wherein Ar¹ is a structure having a formula:

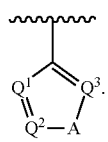

6. The compound of claim 1, wherein the compound has a structure:

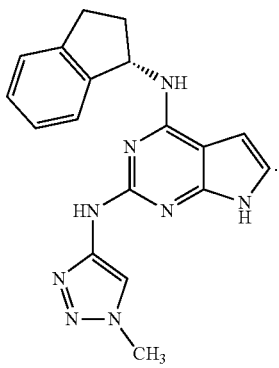 [SMILES: Cn1cc(Nc2nc(N[C@H]3CCc4ccccc43)c3cc[nH]c3n2)nn1]

7. The compound of claim 1, wherein the compound has a structure represented by a formula:

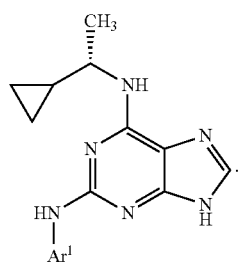

8. The compound of claim 1, wherein the compound has a structure selected from:

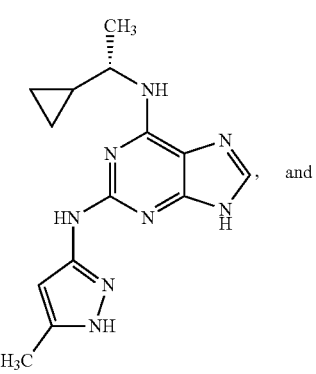

and

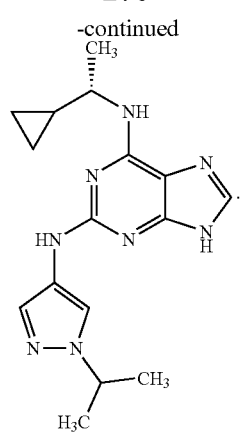

9. A pharmaceutical composition comprising at least one compound of claim 1, or a pharmaceutically acceptable salt thereof, and a pharmaceutically acceptable carrier.

10. A method for the treatment of a disorder associated with LRRK2 kinase dysfunction in a mammal having the disorder, the method comprising the step of administering to the mammal an effective amount of at least one compound of claim 1, or a pharmaceutically acceptable salt thereof.

11. A compound having a structure represented by a formula:

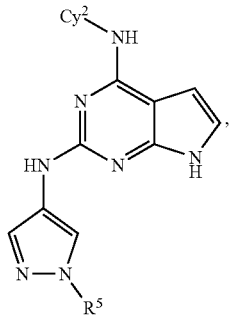

wherein Cy² is selected from C3-C5 cycloalkyl and 2,3-dihydroindene and is substituted with 0, 1, or 2 groups independently selected from halogen, C1-C4 alkyl, C1-C4 monohaloalkyl, and C1-C4 polyhaloalkyl; and wherein R⁵ is C1-C8 alkyl, or a pharmaceutically acceptable salt thereof.

12. The compound of claim 11, wherein R⁵ is C1-C4 alkyl.

13. The compound of claim 11, wherein the compound has a structure represented by a formula:

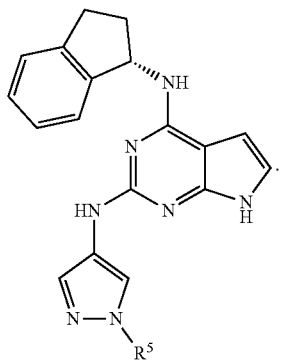

14. A pharmaceutical composition comprising at least one compound of claim 11, or a pharmaceutically acceptable salt thereof, and a pharmaceutically acceptable carrier.

15. A method for the treatment of a disorder associated with LRRK2 kinase dysfunction in a mammal having the disorder, the method comprising the step of administering to the mammal an effective amount of at least one compound of claim 11, or a pharmaceutically acceptable salt thereof.

16. The method of claim 15, wherein the disorder is a neurodegenerative disorder, a cancer, an autoimmune disorder, or leprosy.

17. The method of claim 16, wherein the neurodegenerative disorder is Parkinson's disease.

18. The method of claim 16, wherein the cancer is selected from renal cancer and thyroid cancer.

19. The method of claim 16, wherein the autoimmune disorder is selected from Crohn's disease, rheumatoid arthritis, and psoriasis.

20. A method for the treatment of a disorder associated with LRRK2 kinase dysfunction in a mammal having the disorder, the method comprising the step of administering to the mammal an effective amount of at least one compound having a structure represented by a formula:

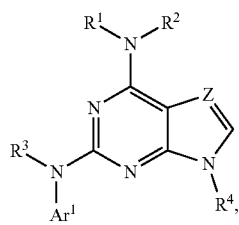

wherein Z is selected from N and $CR^{20}$,
  wherein each occurrence of $R^{20}$, when present, is independently selected from hydrogen, —CN, —$CF_3$, and C1-C4 alkyl;
wherein $R^1$ is selected from $Cy^1$, $Ar^2$, —$CR^{21a}R^{21b}Cy^2$, and —$CR^{21a}R^{21b}Ar^2$;
  wherein each of $R^{21a}$ and $R^{21b}$, when present, are independently selected from hydrogen and C1-C4 alkyl;
  wherein $Cy^1$, when present, is selected from C3-C5 cycloalkyl and 2,3-dihydroindene and is substituted with 0, 1, or 2 groups independently selected from halogen, C1-C4 alkyl, C1-C4 monohaloalkyl, and C1-C4 polyhaloalkyl;
  wherein $Cy^2$, when present, is selected from C3-C6 cycloalkyl, C2-C5 heterocycloalkyl, and 2,3-dihydroindene and is substituted with 0, 1, or 2 groups independently selected from halogen, C1-C4 alkyl, C1-C4 monohaloalkyl, and C1-C4 polyhaloalkyl;
  wherein $Ar^2$, when present, is selected from C5-C6 aryl and C4-C5 heteroaryl and is substituted with 0, 1, or 2 groups independently selected from halogen, C1-C4 alkyl, C1-C4 monohaloalkyl, and C1-C4 polyhaloalkyl; and
wherein each of $R^2$, $R^3$, and $R^4$ are independently selected from hydrogen and C1-C4 alkyl;

wherein $Ar^1$ is a structure selected from:

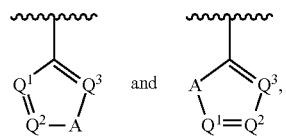

wherein A is selected from $NR^{22}$ and $CR^{23a}R^{23b}$;
  wherein $R^{22}$, when present, is selected from hydrogen, halogen, C1-C8 alkyl, C1-C8 monohaloalkyl, C1-C8 polyhaloalkyl, C1-C8 hydroxyalkyl, C1-C8 alkoxyalkyl, —(C1-C8 alkyl)$NH_2$, —(C1-C8 alkyl)NH (C1-C8alkyl), —(C1-C8 alkyl)N(C1-C8 alkyl)(C1-C8 alkyl), C1-C8 alkylacid, —(C1-C4 alkyl) $CONH_2$, —(C1-C4 alkyl)CONH(C1-C4 alkyl), —(C1-C4 alkyl)CON(C1-C4 alkyl)(C1-C4 alkyl), —(C1-C4 alkyl)(C═O)$Cy^3$, and $Cy^3$;
    wherein each occurrence of $Cy^3$, when present, is independently selected from C3-C6 cycloalkyl and C2-C5 heterocycloalkyl and is substituted with 0, 1, or 2 groups independently selected from halogen, C1-C4 alkyl, C1-C4 monohaloalkyl, and C1-C4 polyhaloalkyl;
  wherein each of $R^{23a}$ and $R^{23b}$, when present, is independently selected from hydrogen, halogen, C1-C8 alkyl, C1-C8 monohaloalkyl, C1-C8 polyhaloalkyl, C1-C8 hydroxyalkyl, C1-C8 alkoxyalkyl, C1-C8 alkylacid, —(C1-C4 alkyl)(C═O)$Cy^1$, —(C1-C4 alkyl)$CONH_2$, —(C1-C4 alkyl)CONH(C1-C4 alkyl), —(C1-C4 alkyl)CON(C1-C4 alkyl)(C1-C4 alkyl), and $Cy^3$;
  wherein each of $Q^1$, $Q^2$, and $Q^3$ is independently selected from N and $CR^{24}$; and
  wherein each occurrence of $R^{24}$, when present, is independently selected from hydrogen, halogen, C1-C8 alkyl, C1-C8 monohaloalkyl, C1-C8 polyhaloalkyl, C1-C8 alkoxyalkyl, —(C1-C4 alkyl)$CONH_2$, —(C1-C4 alkyl)CONH(C1-C4 alkyl), —(C1-C4 alkyl)CON(C1-C4 alkyl)(C1-C4 alkyl),
  provided that two or three of A, $Q^1$, $Q^2$, and $Q^3$ are N, or a pharmaceutically acceptable salt thereof,
wherein the disorder is selected from a neurodegenerative disorder and leprosy.

21. The method of claim 20, wherein the disorder is a neurodegenerative disorder.

22. The method of claim 21, wherein the neurodegenerative disorder is Parkinson's disease.

23. The method of claim 21, wherein the neurodegenerative disorder is selected from Alzheimer's disease, Parkinson's disease, Huntington's disease, Amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia and Lewy body disease.

24. The method of claim 20, wherein the disorder is leprosy.

25. The method of claim 10, wherein the disorder is a neurodegenerative disorder, a cancer, an autoimmune disorder, or leprosy.

26. The method of claim 25, wherein the neurodegenerative disorder is Parkinson's disease.

27. The method of claim 25, wherein the cancer is selected from renal cancer and thyroid cancer.

28. The method of claim 25, wherein the autoimmune disorder is selected from Crohn's disease, rheumatoid arthritis, and psoriasis.

29. The compound of claim 1, selected from
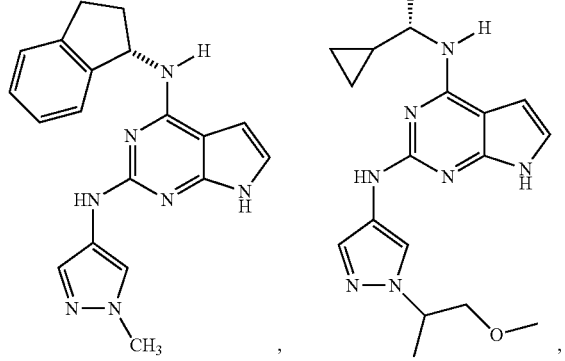
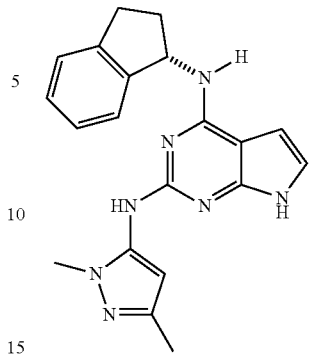
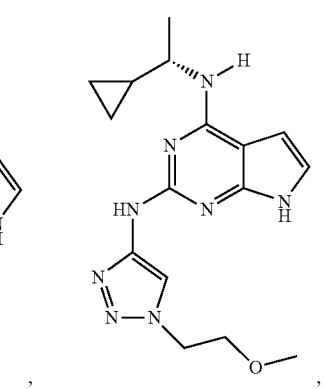
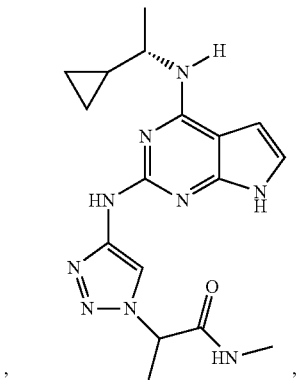
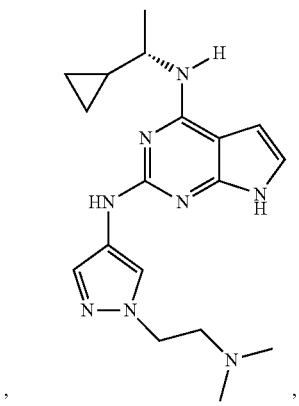

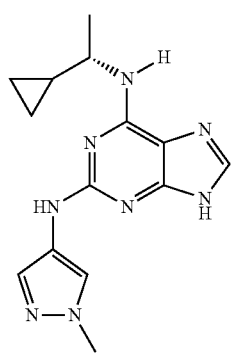 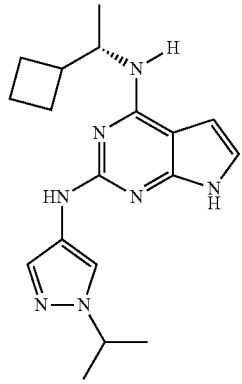 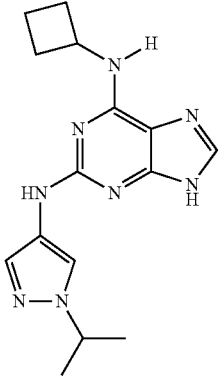 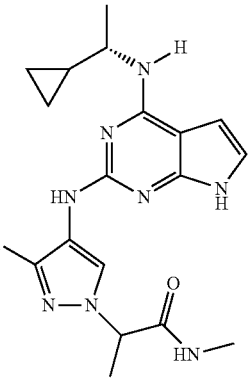
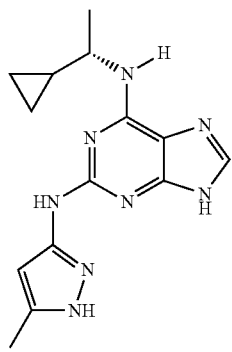 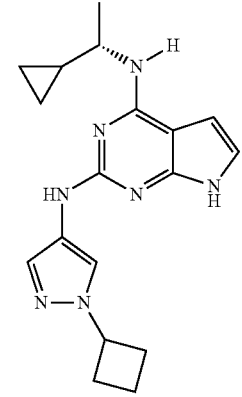 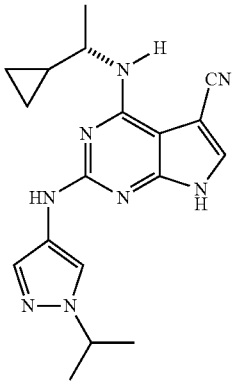 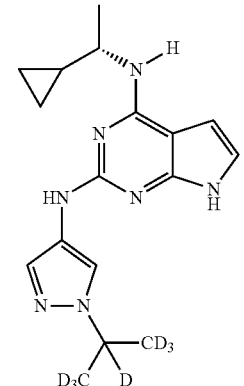
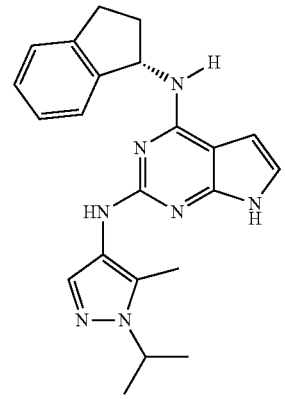 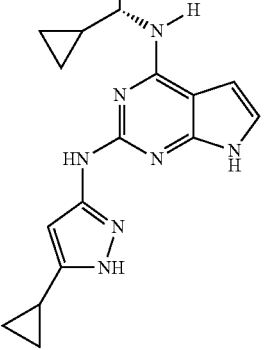 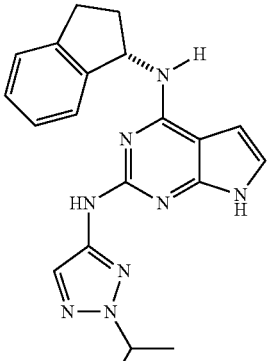 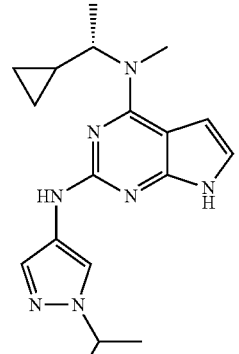
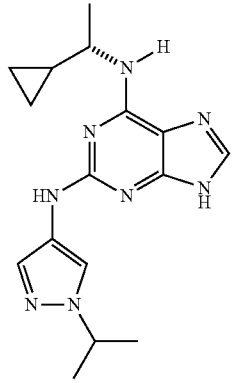 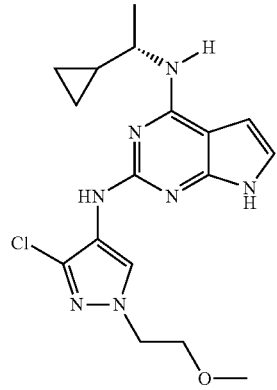 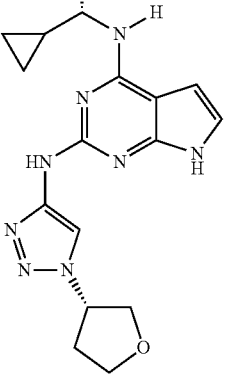 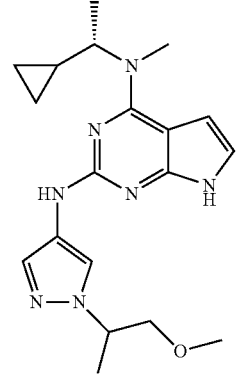

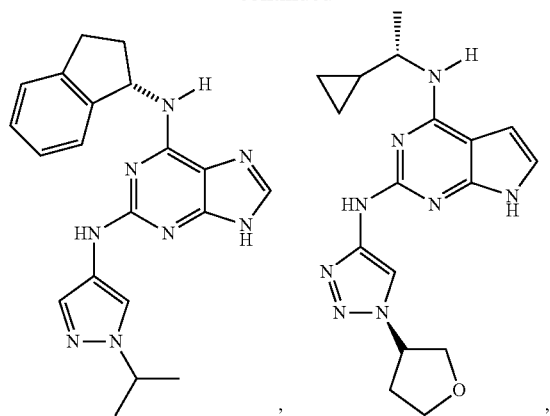

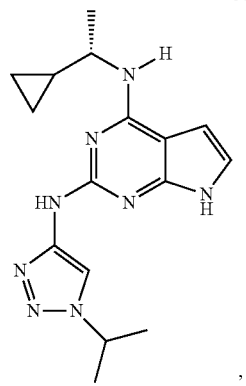 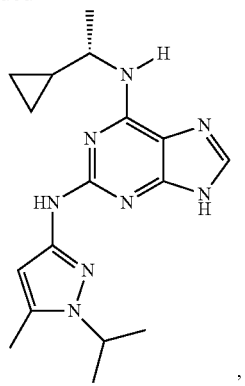 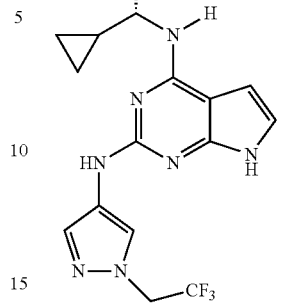 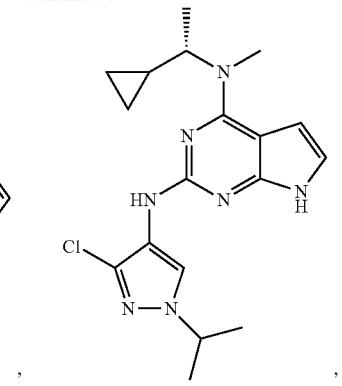
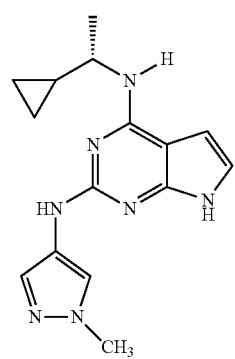 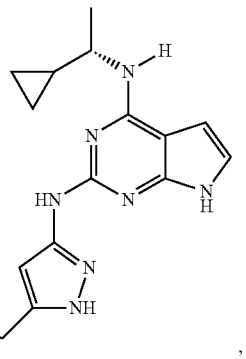 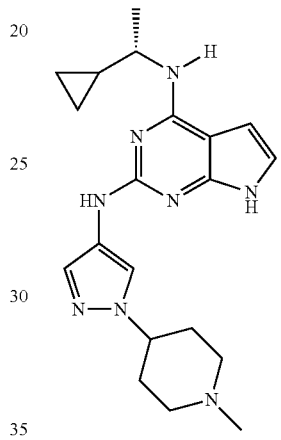 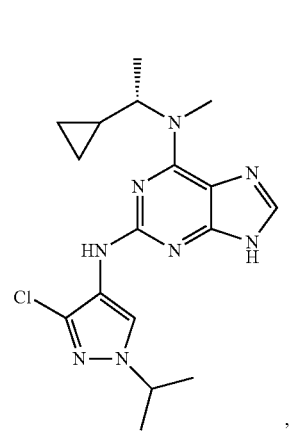
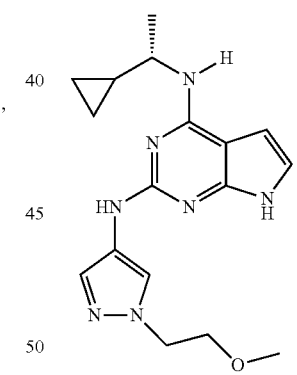 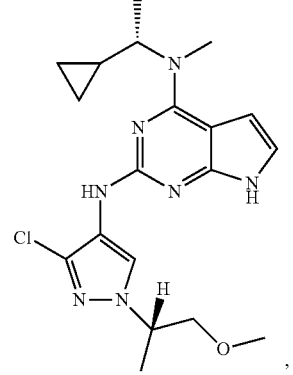
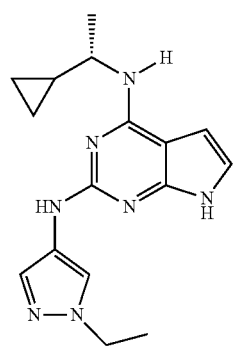 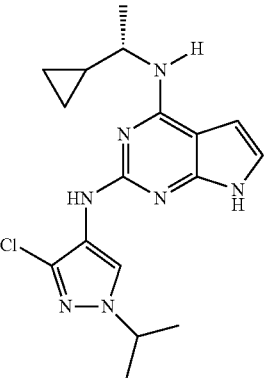 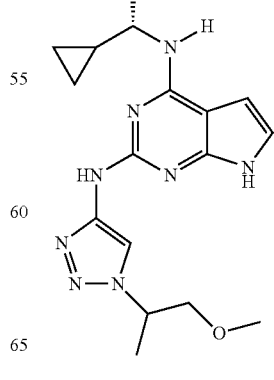 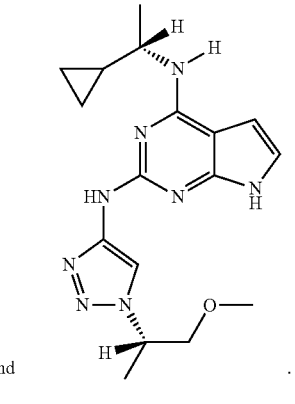

30. The compound of claim 11, selected from:
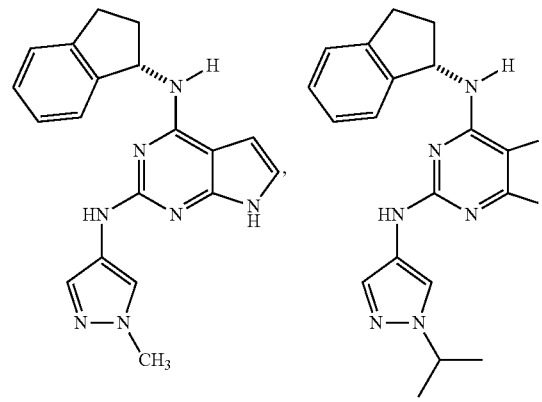 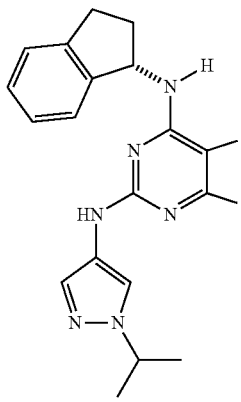
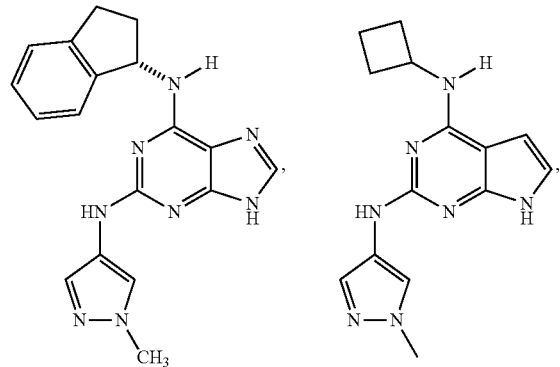 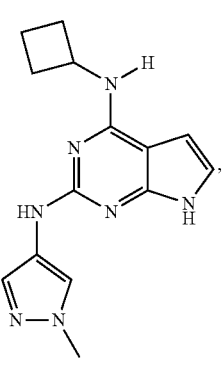
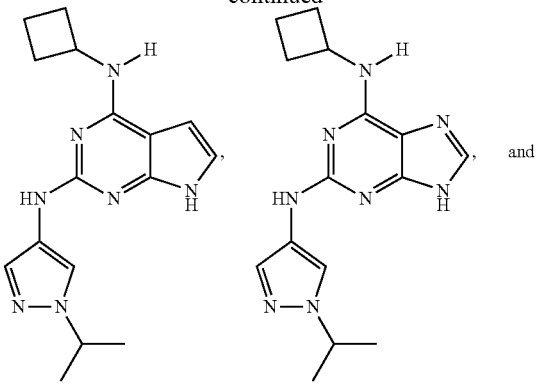 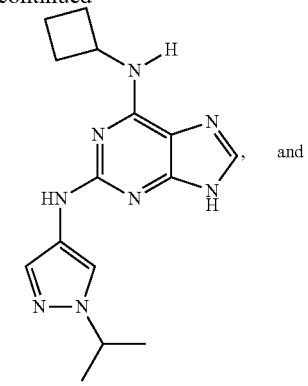
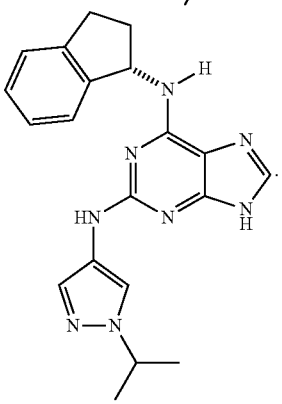
* * * * *